(12) United States Patent
Bombardieri et al.

(10) Patent No.: US 10,590,188 B2
(45) Date of Patent: Mar. 17, 2020

(54) ANTIBODY

(71) Applicant: Queen Mary University of London, London (GB)

(72) Inventors: Michele Bombardieri, London (GB); Constantino Pitzalis, London (GB); Elisa Corsiero, London (GB)

(73) Assignee: Queen Mary University of London, London (GB)

( * ) Notice: Subject to any disclaimer, the term of this patent is extended or adjusted under 35 U.S.C. 154(b) by 0 days.

(21) Appl. No.: 15/317,340

(22) PCT Filed: Jun. 12, 2015

(86) PCT No.: PCT/GB2015/051737
§ 371 (c)(1),
(2) Date: Dec. 8, 2016

(87) PCT Pub. No.: WO2015/189638
PCT Pub. Date: Dec. 17, 2015

(65) Prior Publication Data
US 2017/0129948 A1 May 11, 2017

(30) Foreign Application Priority Data
Jun. 12, 2014 (GB) .................................. 1410520.9

(51) Int. Cl.
| | |
|---|---|
| *G01N 33/53* | (2006.01) |
| *C07K 16/18* | (2006.01) |
| *C07K 16/44* | (2006.01) |
| *G01N 33/564* | (2006.01) |

(52) U.S. Cl.
CPC .............. *C07K 16/18* (2013.01); *C07K 16/44* (2013.01); *G01N 33/564* (2013.01); *C07K 2317/21* (2013.01); *C07K 2317/565* (2013.01); *G01N 2496/00* (2013.01); *G01N 2800/105* (2013.01)

(58) Field of Classification Search
CPC .... C07K 16/18; C07K 16/44; C07K 2317/21; C07K 2317/565; G01N 33/564; G01N 2496/00; G01N 2800/105
See application file for complete search history.

(56) References Cited

FOREIGN PATENT DOCUMENTS

WO    WO20090115612    *    9/2009    ............. C07K 16/00

OTHER PUBLICATIONS

Stavnezer et al Annu Rev Innnnunol 2008; 26:261-292.*
Humby et al., Ectopic Lymphoid Structures Support Ongoing Production of Class-Switched Autoantibodies in Rheumatoid Synovium, PLoS Med. 6(1):0059-0075 (2009).

* cited by examiner

*Primary Examiner* — Julie Wu
*Assistant Examiner* — Carmencita M Belei
(74) *Attorney, Agent, or Firm* — Grimes & Yvon LLP

(57) ABSTRACT

The present invention provides an antibody which comprises a variable heavy (VH) chain comprising CDR1, CDR2 and CDR3, and/or a variable light (VL) chain comprising CDR1, CDR2 and CDR3, wherein the CDRs have the same amino acid sequence as those from a complete antibody isolated from a synovial tissue sample of rheumatoid arthritis patients, as listed in Tables 1 and 2 or Tables 1 A and 2 A.

10 Claims, 17 Drawing Sheets

Specification includes a Sequence Listing.

Figure 2
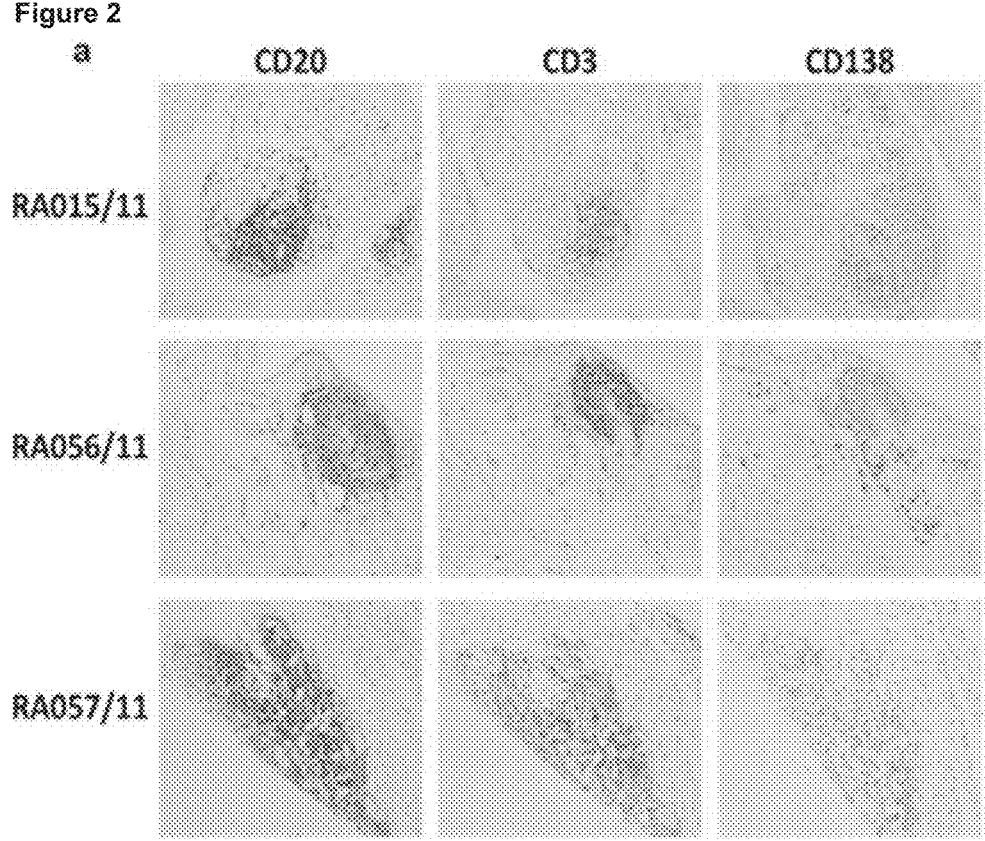
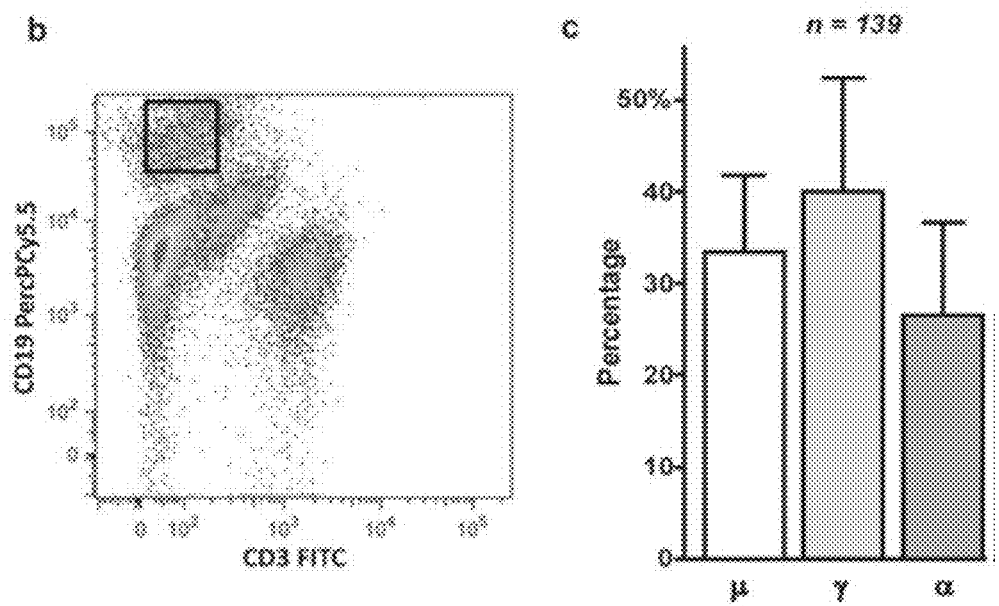

Figure 2 (continued)
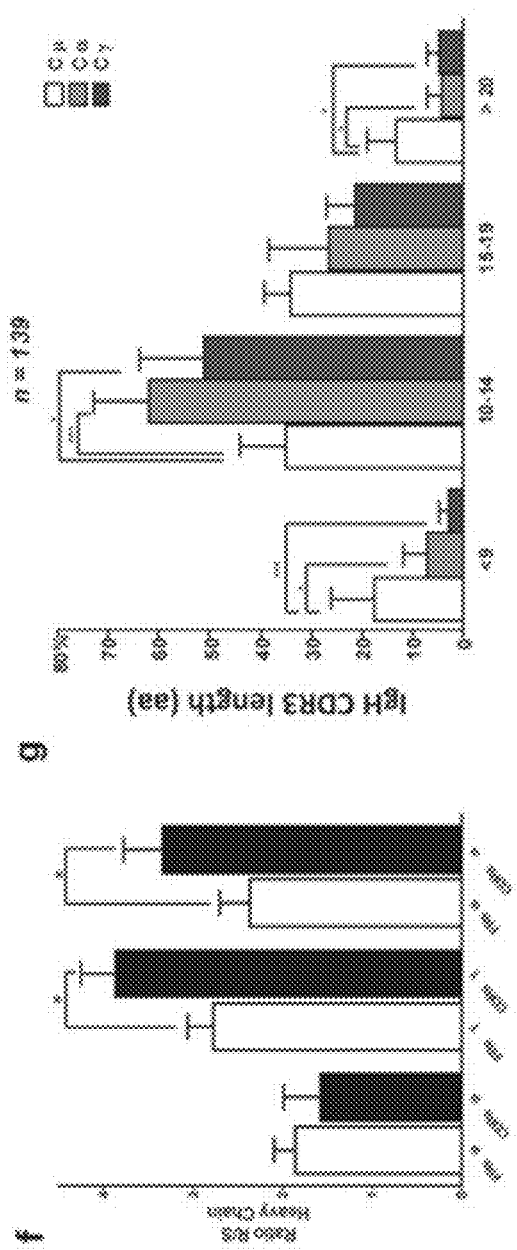
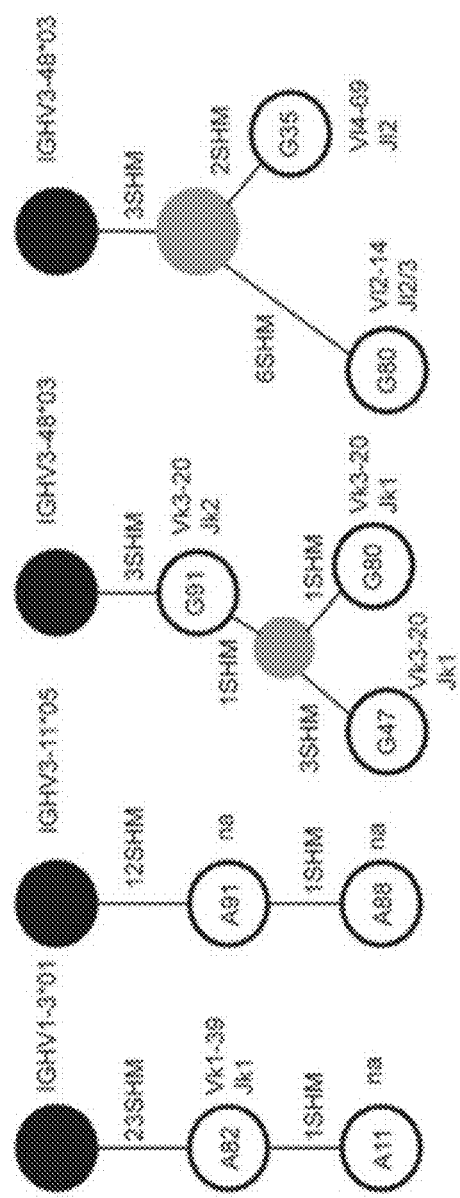

Figure 3 (continued)
C
Histone2A Cit
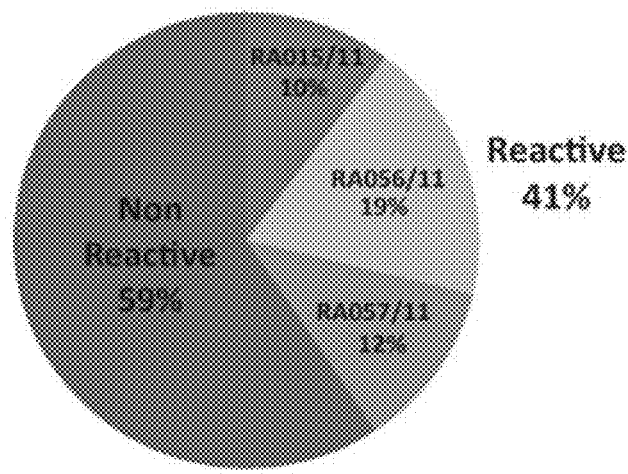
Histone2B Cit
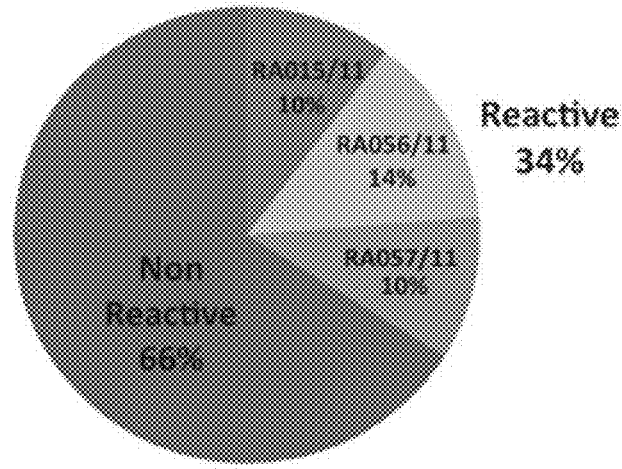

| Clone | Isotype | Luminex | | Anti-NETs | Highest histone epitope binding |
|---|---|---|---|---|---|
| | | H2A Cit | H2Bcit | | |
| RA015/11.58 | γ | | | | H4 cit (14-34) |
| RA015/11.68 | γ | | | | |
| RA015/11.81 | α | | | | H2A 1-21 |
| RA015/11.88 | μ | | | | H2A 69-90 |
| RA015/11.91 | α | | | | |
| RA015/11.94 | μ | | | | |
| RA015/11.95 | α | | | | |
| RA015/11.12.2 | μ | | | | H2A 1-21 |
| RA015/11.17.2 | α | | | | |
| RA015/11.19.2 | μ | | | | H2A 79-98 |
| RA015/11.66.2 | α | | | | |
| RA015/11.83.2 | μ | | | | |
| RA056/11.29.1 | γ | | | | |
| RA056/11.33.1 | γ | | | | |
| RA056/11.35.1 | γ | | | | |
| RA056/11.56.1 | γ | | | | H2A 1-21 |
| RA056/11.66.1 | γ | | | | H4 cit (14-34) |
| RA056/11.68.1 | γ | | | | H4 cit (14-34) |
| RA056/11.76.1 | γ | | | | |
| RA056/11.80.1 | γ | | | | |
| RA056/11.95.1 | α | | | | |
| RA056/11.96.1 | α | | | | |
| RA056/11.9.2 | μ | | | | |
| RA056/11.12.2 | γ | | | | |
| RA056/11.23.2 | γ | | | | H2A 69-90 |
| RA056/11.34.2 | μ | | | | |
| RA056/11.36.2 | γ | | | | |
| RA056/11.38.2 | μ | | | | |
| RA056/11.39.2 | γ | | | | |
| RA056/11.41.2 | μ | | | | |
| RA056/11.45.2 | γ | | | | |
| RA056/11.48.2 | μ | | | | |
| RA056/11.54.2 | γ | | | | |
| RA056/11.56.2 | γ | | | | |
| RA056/11.75.2 | γ | | | | |
| RA056/11.81.2 | μ | | | | H2A 27-47 |
| RA056/11.93.2 | α | | | | |
| RA056/11.95.2 | γ | | | | |
| RA057/11.25.1 | α | | | | |
| RA057/11.28.1 | μ | | | | |
| RA057/11.35.1 | μ | | | | |
| RA057/11.44.1 | μ | | | | |
| RA057/11.47k.1 | α | | | | |
| RA057/11.50.1 | γ | | | | |
| RA057/11.51.1 | μ | | | | |
| RA057/11.61.1 | μ | | | | |
| RA057/11.62k.1 | μ | | | | |
| RA057/11.67.1 | μ | | | | |
| RA057/11.71.1 | μ | | | | |
| RA057/11.72.1 | γ | | | | |
| RA057/11.78.1 | γ | | | | |
| RA057/11.89.1 | μ | | | | |
| RA057/11.93.1 | γ | | | | |
| RA057/11.2.1 | μ | | | | |
| RA057/11.17.1 | μ | | | | |
| RA057/11.80.1 | γ | | | | |
| RA057/11.47L.1 | α | | | | |
| RA057/11.62L.1 | μ | | | | |
| RA057/11.82L.1 | μ | | | | |

High/Medium Reactivity

Low Reactivity

Representative micrographs showing reactivity of recombinant antibodies (specified to the left of the micrographs).

ANTIBODY

CROSS-REFERENCE TO RELATED APPLICATIONS

This application is the National Stage of International Application No. PCT/GB2015/051737, filed on Jun. 12, 2015, and claims the benefit of priority to GB Application No. 1410520.9, filed on Jun. 12, 2014, both of which are hereby incorporated by referenced in their entireties for all purposes.

SEQUENCE LISTING

The instant application contains a Sequence Listing which has been submitted electronically in ASCII format and is hereby incorporated by reference in its entirety. Said ASCII copy was created on Sep. 5, 2017, is named DYC_007_US1_SL.txt and is 434,264 bytes in size.

FIELD OF THE INVENTION

The present invention relates to antibodies relevant to rheumatoid arthritis.

BACKGROUND TO THE INVENTION

Inflammatory arthritis is a prominent clinical manifestation in diverse autoimmune disorders including rheumatoid arthritis (RA), psoriatic arthritis (PsA), systemic lupus erythematosus (SLE), Sjogren's syndrome and polymyositis.

Rheumatoid arthritis (RA) is a chronic inflammatory disease that affects approximately 0.5 to 1% of the adult population in northern Europe and North America. It is a systemic inflammatory disease characterized by chronic inflammation in the synovial membrane of affected joints, which ultimately leads to loss of daily function due to chronic pain and fatigue. The majority of patients also experience progressive deterioration of cartilage and bone in the affected joints, which may eventually lead to permanent disability. The long-term prognosis of RA is poor, with approximately 50% of patients experiencing significant functional disability within 10 years from the time of diagnosis. Life expectancy is reduced by an average of 3-10 years.

Inflammatory bone diseases, such as RA, are accompanied by bone loss around affected joints due to increased osteoclastic resorption. This process is mediated largely by increased local production of pro-inflammatory cytokines, of which tumor necrosis factor-$\alpha$ (TNF-$\alpha$) is a major effector.

In RA specifically, an immune response is thought to be initiated/perpetuated by one or several antigens presenting in the synovial compartment, producing an influx of acute inflammatory cells and lymphocytes into the joint. Successive waves of inflammation lead to the formation of an invasive and erosive tissue called pannus. This contains proliferating fibroblast-like synoviocytes and macrophages that produce proinflammatory cytokines such as TNF-$\alpha$ and interleukin-1 (IL-1). Local release of proteolytic enzymes, various inflammatory mediators, and osteoclast activation contribute to much of the tissue damage. There is loss of articular cartilage and the formation of bone erosion. Surrounding tendons and bursa may become affected by the inflammatory process. Ultimately, the integrity of the joint structure is compromised, producing disability.

B cells are thought to contribute to the immunopathogenesis of RA, predominantly by serving as the precursors of autoantibody-producing cells but also as antigen presenting cells (APC) and pro-inflammatory cytokine producing cells. Autoantibodies such as rheumatoid factor (RF) are detected in the serum and synovial fluid of RA patients. Although the sensitivity of RF in diagnosing RA is 30%-70% in early cases and 80%-85% in progressive cases, the specificity of RF is only ~40%. The presence of serum anti-immunoglobulin binding protein (BiP) antibodies has been reported in RA sera, and anti-BiP antibodies showed similar sensitivity and specificity as RF. BiP concentrations are elevated in the synovial fluid of RA patients and BiP-responsive T cells are also detected in RA patients. Anti-citrullinated protein/peptide antibodies (ACPAs) have been reported to be specific in the diagnosis of RA and the sensitivity and specificity of anti-CCP antibodies in the diagnosis of RA are 60%-80% and 95%-98%, respectively. A number of additional autoantibody specificities have also been associated with RA, including antibodies to Type II collagen and proteoglycans. The generation of large quantities of these antibodies may lead to immune complex formation and the activation of the complement cascade. This in turn amplifies the immune response and may culminate in local cell lysis.

Current standard therapies for RA which are used to modify the disease process and to delay joint destruction are known as disease modifying anti-rheumatic drugs (DMARDs). Examples of DMARDs include methotrexate, leflunomide and sulfasalazine.

Biologic agents designed to target specific components of the immune system that play role in RA are also used as therapeutics. There are various groups of biologic treatments for RA including: TNF-$\alpha$ inhibitors (etanercept, infliximab and adalimumab), B cell targeted therapy (Rituximab), human IL-1 receptor antagonist (anakinra) and selective co-stimulation modulators (abatacept).

Despite the identification of a number of auto-antibodies associated with RA and improved knowledge of the aetiology of the disease, there remains a subset of patients who do not respond adequately to current therapies.

Further understanding of the molecular mechanisms underlying RA is required. Thus there is a need for the provision of relevant autoantibodies associated with RA.

DESCRIPTION OF THE FIGURES

FIG. 6—A Table summarising the reactivity of each antibody to citH2A-H2B in Luminex and to NETs in immunofluorescence. The additional column on the right indicates for which of several citrullinated peptides in H2A and H4 each antibody displayed the strongest binding.

SUMMARY OF ASPECTS OF THE INVENTION

Figure 1:
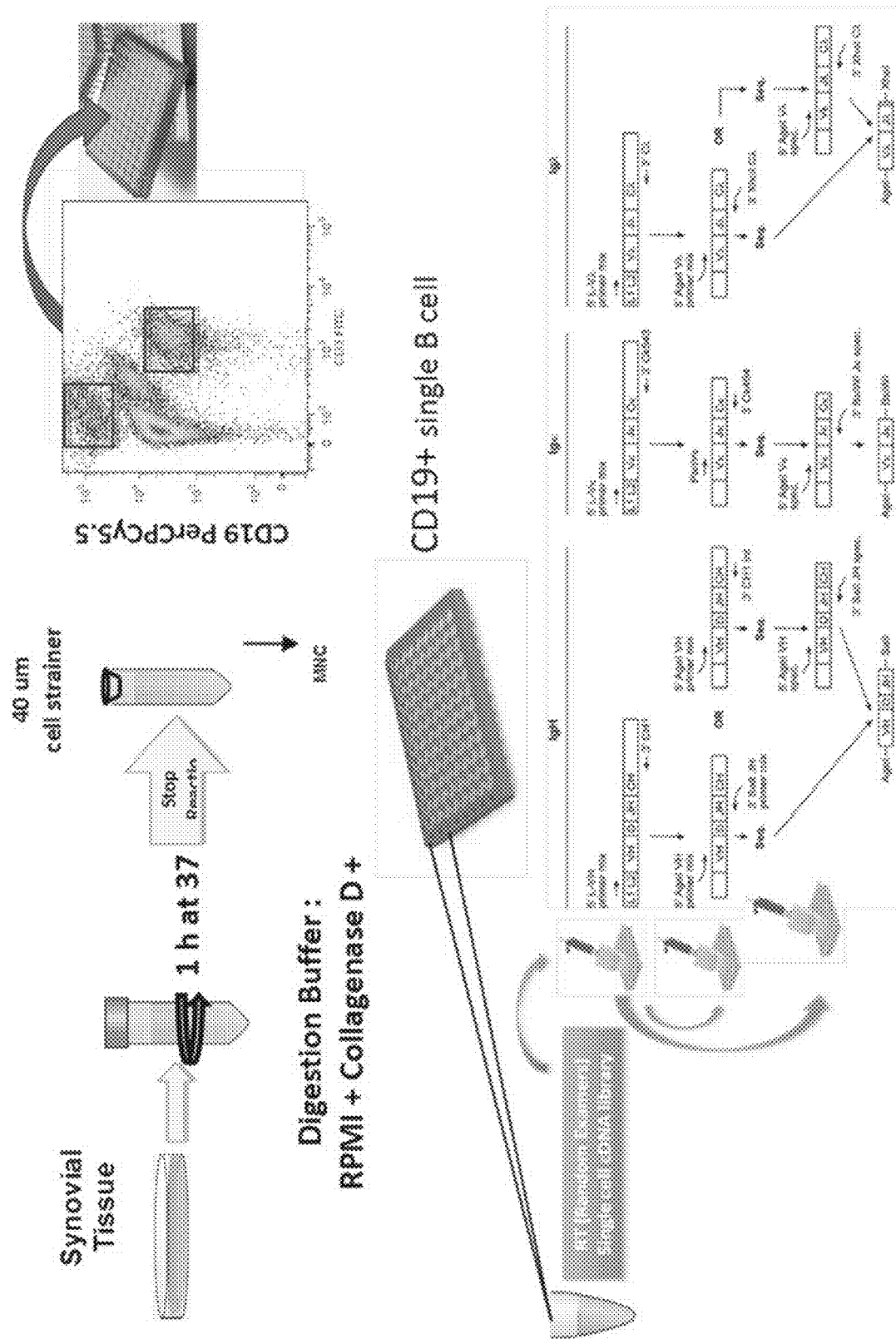
FIG. 1—A diagram showing the strategy to prepare mononuclear cells from synovial tissue and to generate human monoclonal antibodies from single FACS sorted CD19+ B cell.
Figure 1:
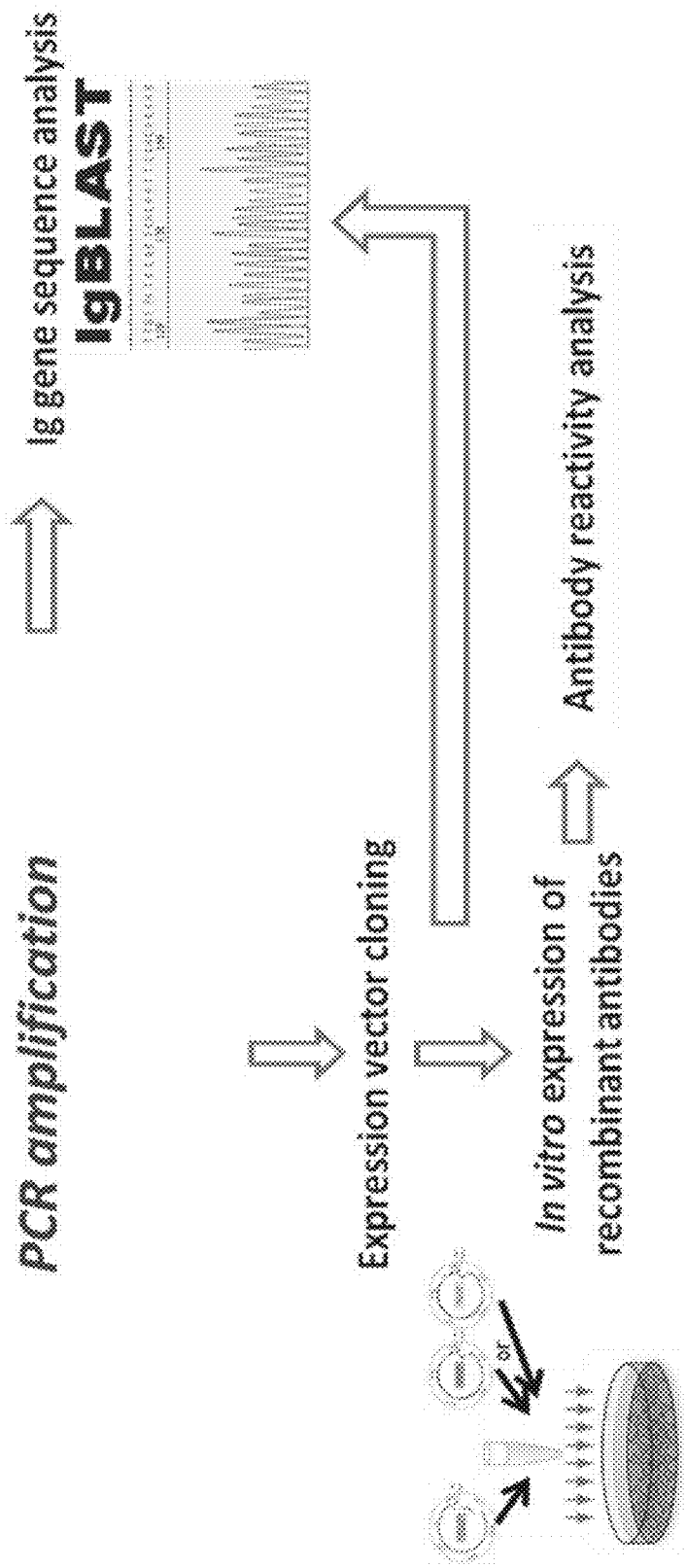

The present invention provides antibodies which are relevant to RA. In particular, provided herein are the variable heavy (VH) and variable light (VL) chain sequences which include both the complementarity determining regions (CDRs) and framework regions sequences, derived from full antibody molecules isolated from synovial tissue samples comprising ectopic germinal centres.

Thus in a first aspect the present invention provides an antibody which comprises a variable heavy (VH) chain comprising CDR1, CDR2 and CDR3, and/or a variable light (VL) chain comprising CDR1, CDR2 and CDR3, wherein the CDRs have the same amino acid sequence as those from a complete antibody isolated from a synovial tissue sample, as listed in Tables 1 and 2.

In a related aspect, the present invention provides an antibody which comprises a variable heavy (VH) chain comprising CDR1, CDR2 and CDR3, and/or a variable light (VL) chain comprising CDR1, CDR2 and CDR3, wherein the CDRs have the same amino acid sequence as those from a complete antibody isolated from a synovial tissue sample, as listed in Tables 1 and 2 or Tables 1A and 2A.

The antibody may comprise a VH and VL sequence as shown in Table 3 and Table 4; or a sequence which has at least 90% sequence identity thereto.

The antibody may comprise a VH and VL sequence as shown in Tables 3 and 4 or Tables 3A and 4A; or a sequence which has at least 90% sequence identity thereto.

The antibody may bind Neutrophil extracellular traps (NETs).

The antibody may bind citrullinated histone 2 A (cit-H2A) and/or cit-H2B.

The antibody may be selected from the group consisting of a full length antibody, a single chain antibody, a single-chain variable fragment, a bispecific antibody, a minibody, a domain antibody, a synthetic antibody and an antibody fusion.

In a second aspect, the present invention provides a nucleotide sequence encoding an antibody according to the first aspect of the present invention.

In a third aspect, the present invention provides the use of an antibody according to the first aspect of the invention as a positive control in a diagnostic test for rheumatoid arthritis.

The diagnostic test may be an ELISA assay.

In a fourth aspect, the present invention provides the use of an antibody according to the first aspect of the invention to exacerbate arthritis symptoms in an animal model of rheumatoid arthritis.

DETAILED DESCRIPTION

In a first aspect, the present invention provides antibodies relevant to RA. In particular the present invention relates to VH/VL sequences including CDRs identified from full antibody molecules isolated from synovial tissue samples comprising ectopic germinal centres.

Rheumatoid Arthritis (RA)

RA is a chronic, systemic inflammatory disorder that may affect many tissues and organs, but principally affects synovial joints. It is a disabling and painful condition, which can lead to substantial loss of functioning and mobility if not adequately treated.

The disease process involves an inflammatory response of the synovium, secondary to massive immune cell infiltrate and proliferation of synovial cells, excess synovial fluid, and the development of fibrous tissue (pannus) in the synovium that attacks the cartilage and sub-chondral bone. This often leads to the destruction of articular cartilage and the formation of bone erosions with secondary ankylosis (fusion) of the joints. RA can also produce diffuse inflammation in the lungs, the pericardium, the pleura, the sclera, and also nodular lesions, most commonly in subcutaneous tissue. RA is considered a systemic autoimmune disease as autoimmunity plays a pivotal role in its chronicity and progression.

A number of cell types are involved in the aetiology of RA, including T cells, B cells, monocytes, macrophages, dendritic cells and synovial fibroblasts.

As discussed above, numerous autoantibodies are associated with the RA aetiology and RA is considered to be an autoimmune condition.

Autoantibodies such as rheumatoid factor (RF) are detected in the serum and synovial fluid of RA patients. Although the sensitivity of RF in diagnosing RA is 30%-70% in early cases and 80%-85% in progressive cases, the specificity of RF is only ~40%. The presence of serum anti-immunoglobulin binding protein (BiP) antibodies has been reported in RA sera, and anti-BiP antibodies showed similar sensitivity and specificity as RF. BiP concentrations are elevated in the synovial fluid of RA patients and BiP-responsive T cells are also detected in RA patients. Anti-citrullinated protein/peptide antibodies (ACPAs) have been reported to be specific in the diagnosis of RA and the sensitivity and specificity of anti-CCP antibodies in the diagnosis of RA are 60%-80% and 95%-98%, respectively. A number of additional autoantibody specificities have also been associated with RA, including antibodies to Type II collagen and proteoglycans. The generation of large quantities of these antibodies may lead to immune complex formation and the activation of the complement cascade. This in turn amplifies the immune response and may culminate in local cell lysis.

The antibodies of the present invention comprise one or more CDR sequences identified from a full antibody molecule isolated from a synovial tissue sample comprising ectopic germinal centres.

Germinal centres are sites where mature B cells rapidly proliferate, differentiate, and undergo somatic hypermutation and class switch recombination during an immune response. During this process of rapid division and selection, B cells are known as centroblasts, and once they have stopped proliferating they are known as centrocytes. B cells within germinal centres typically express CD138 and activation-induced-cytidine-deaminase (AID). Germinal centres develop dynamically after the activation of B cells by T-cell dependent antigen.

As used herein, the term germinal centre refers to an ectopic or tertiary lymphatic structure that forms in non-lymphoid tissues and may develop to become a place of autoantibody generation. In the context of RA, germinal centres form in the synovium and are typically characterised by the presence of aggregated T and/or B lymphocytes alongside follicular dendritic cells (FDCs).

FDCs have high expression of complement receptors CR1 and CR2 (CD35 and CD21 respectively) and Fc-receptor FcγRIIb (CD32). Further FDC specific molecular markers include FDC-M1, FDC-M2 and C4.

The identification of germinal centres in a synovial sample of a RA patient may therefore involve determining the presence of cells positive for one or more of the above markers. For example it may involve determining the presence of plasma cells (CD138$^+$) or FDCs (CD35$^+$-CD21$^+$).

Determining the presence of germinal centre in a synovial sample of a RA patient may involve identifying FDCs within B cell aggregates using one or more of the above markers. Determining the presence of germinal centres may involve the identification of CD21$^+$ cells within B cell aggregates in a synovial sample from a RA patient.

Identification of germinal centres may be performed using standard methods which are known in the art. Such methods include, but are not limited to, immunohistochemistry and fluorescence microscopy.

In the context of the present invention, the germinal centres are present in the synovial tissue of a patient suffering from RA. The synovial tissue sample may be isolated from any joint. In particular the synovial tissue sample may be isolated from the hip or knee joint of a patient suffering from RA.

Antibody

The term "antibody" is used herein to relate to an antibody or a functional fragment thereof. By functional fragment, it is meant any portion of an antibody which retains the ability to bind to the same antigen target as the parental antibody.

Binding of the antibody to the antigen is facilitated by the Fab (fragment, antigen binding) region at the N-terminal domain of the antibody. The Fab is composed of one constant and one variable domain from each heavy and light chain of the antibody. The diversity of the antibody repertoire is based on the somatic recombination of variable (V), diversity (D) and joining (J) gene segments. In humans, Ig genes are randomly assembled from about 50 V, 25 D and 6 J gene segments for heavy chains and over 30 potentially functional Vκ and Vλ light chain genes and 5 Jκ and 4 Jλ genes, respectively.

Variable loops, three each on the VL and VH chains are responsible for binding to the antigen. These loops are referred to as the complementarity determining regions (CDRs). The CDRs (CDR1, CDR2 and CDR3) of each of the VH and VL are arranged non-consecutively. Within the variable domain, CDR1 and CDR2 are found in the V region of the polypeptide chain, and CDR3 includes some of V, all of D (heavy chains only) and J regions. Since most sequence variation associated with immunoglobulins is found in the CDRs, these regions may be referred to as hypervariable regions. Among these, CDR3 shows the greatest variability as it is encoded by a recombination of the VJ in the case of a light chain region and VDJ in the case of heavy chain regions. Regions between CDRs in the variable domain of an immunoglobulin are known as framework regions. These are important for establishing the structure of the VH and VL domains. The variable domains of the VH and VL chains constitute an Fv unit and can interact closely to form a single chain Fv (ScFv) unit.

References to "VH" refer to the variable region of an immunoglobulin heavy chain References to "VL" refer to the variable region of an immunoglobulin light chain The C-terminal domain of an antibody is called the constant region. In most H chains, a hinge region is found. This hinge region is flexible and allows the Fab binding regions to move freely relative to the rest of the molecule. The hinge region is also the place on the molecule most susceptible to the action of proteases which can split the antibody into the antigen binding site (Fab) and the effector (Fc) region.

The domain structure of the antibody molecule is favourable to protein engineering, facilitating the exchange between molecules of functional domains carrying antigen-binding activities (Fabs and Fvs) or effector functions (Fcs).

The structure of the antibody also makes it easy to produce antibodies with an antigen recognition capacity joined to molecules such as toxins, lymphocytes, growth factors and detectable or therapeutic agents.

As used herein, "antibody" means a polypeptide having an antigen binding site which comprises at least one complementarity determining region (CDR). The antibody may comprise 3 CDRs and have an antigen binding site which is equivalent to that of a domain antibody (dAb). The antibody may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'2, Fv, single chain Fv (ScFv) fragment or Nanobody. The antibody may be a conjugate of the antibody and another agent or antibody, for example the antibody may be conjugated to a polymer (eg PEG), toxin or label. The antibody may be a bifunctional antibody. The antibody may be non-human, chimeric, humanised or fully human.

Fab, Fv and ScFv fragments with VH and VL joined by a polypeptide linker exhibit specificities and affinities for antigen similar to the original monoclonal antibodies. The ScFv fusion proteins can be produced with a non-antibody molecule attached to either the amino or the carboxy terminus. In these molecules, the Fv can be used for specific targeting of the attached molecule to a cell expressing the appropriate antigen. Bifunctional antibodies can also be created by engineering two different binding specificities into a single antibody chain. Bifunctional Fab, Fv and ScFv antibodies may comprise engineered domains such as CDR grafted or humanised domains.

The antigen-binding domain may be comprised of the heavy and light chains of an immunoglobulin, expressed from separate genes, or may use the light chain of an immunoglobulin and a truncated heavy chain to form a Fab and a F(ab)'2 fragment. Alternatively, truncated forms of both heavy and light chains may be used which assemble to form a Fv fragment. An engineered svFv fragment may also be used, in which case, only a single gene is required to encode the antigen-binding domain.

The present invention provides antibodies as defined in Tables 1 to 4.

TABLE 1

VH CDR and FR amino acid sequences

| Ab identifier | FR1 | CDR1 | FR2 | CDR2 |
|---|---|---|---|---|
| RA015-11_88.1 | EVQLEESGPGLVKPSETL SLTCTVS (SEQ ID NO: 1) | GGSISSY Y (SEQ ID NO: 2) | WSWIRQPAGKGLE WIGR (SEQ ID NO: 3) | IYTSGST (SEQ ID NO: 4) |
| RA015-11_94.1 | QVQLVESGAEVKKPGAS VKVSCKAS (SEQ ID NO: 5) | GYSFTSY A (SEQ ID NO: 6) | MHWVRQAPGQRL EWMGW (SEQ ID NO: 7) | INDGNG NT (SEQ ID NO: 8) |
| RA015-11_12.2 | EVQLVESGGGLVKPGGS LRLSCAAS (SEQ ID NO: 9) | GFTFSNA W (SEQ ID NO: 10) | MSWVRQAPGKGL EWVGR (SEQ ID NO: 11) | EKSKAN GETI (SEQ ID NO: 12) |
| RA015-11_19.2 | QVQLVQSGAEVKKPGAS VKVSCKAS (SEQ ID NO: 13) | GYTFTG YY (SEQ ID NO: 14) | MITWVRQAPGQGL EWMGW (SEQ ID NO: 15) | INPNSG DT (SEQ ID NO: 16) |

TABLE 1-continued

VH CDR and FR amino acid sequences

| | | | | |
|---|---|---|---|---|
| RA015-11_83.2 | EVQLVESGGGLVQPGGS LRLSCTAS (SEQ ID NO: 17) | GFTFSSY E (SEQ ID NO: 18) | MNWVRQAPGKGL EWVSY (SEQ ID NO: 19) | ISSSGTT I (SEQ ID NO: 20) |
| RA015-11_58.1 | QVQLVESGGGLVQSGGS LRLSCSAS (SEQ ID NO: 21) | GFRFSGH A (SEQ ID NO: 22) | MHWVRQPAGKGL EYISA (SEQ ID NO: 23) | ISGNGE AT (SEQ ID NO: 24) |
| RA015-11_68.1 | EVQLEESGPGLVKPSQTL SLTCTVS (SEQ ID NO: 25) | GGSISSG DYY (SEQ ID NO: 26) | WSWIRQHPGKGLE WIGY (SEQ ID NO: 27) | IYYSGS T (SEQ ID NO: 28) |
| RA015-11_81.1 | EVQLVESGAEVKKPGAS VKVSCKAS (SEQ ID NO: 29) | GYTFSD YF (SEQ ID NO: 30) | IHWVRQAPGQGLE WMGW (SEQ ID NO: 31) | INPHSD DT (SEQ ID NO: 32) |
| RA015-11_91.1 | EVQLVESGGGLVKPGGS LRLSCAAS (SEQ ID NO: 33) | GFTFSTY T (SEQ ID NO: 34) | MIWVRQAPGKGL EWVSS (SEQ ID NO: 35) | ISGSGSY I (SEQ ID NO: 36) |
| RA015-11_95.1 | EVQLVQSGPEVKKPGTS VKVSCKAS (SEQ ID NO: 37) | GFTSSRS A (SEQ ID NO: 38) | VQWLRQTRGQRL EWIGG (SEQ ID NO: 39) | IVVGSG NT (SEQ ID NO: 40) |
| RA015-11_17.2 | EVQLVESGGGFVQPGGS LRLSCAAS (SEQ ID NO: 41) | GFSIGNY A (SEQ ID NO: 42) | LTWVRQAPGKRL EWVSS (SEQ ID NO: 43) | ITGSGG DT (SEQ ID NO: 44) |
| RA015-11_64.2 | EVQLVESGGDLVQPGRS LRLSCAAS (SEQ ID NO: 45) | GFTFDD YD (SEQ ID NO: 46) | MHWVRQAPGKGL EWVSG (SEQ ID NO: 47) | IRWNSD TI (SEQ ID NO: 48) |
| RA015-11_66.2 | EVQLQESGPGLVKPSGTL SLTCAVS (SEQ ID NO: 49) | GGSISIT NW (SEQ ID NO: 50) | WTWVRQPPGKGL EWIGE (SEQ ID NO: 51) | IYHSGY T (SEQ ID NO: 52) |
| RA056-11_9.2 | EVQLLESGGGLVQPGGS LRLSCAAS (SEQ ID NO: 53) | GFTFSSY A (SEQ ID NO: 54) | MSWVRQAPGKGL EWVSA (SEQ ID NO: 55) | ISGSGGS T (SEQ ID NO: 56) |
| RA056-11_34.2 | EVQLVESGGGLVKPGGS LRLSCAAS (SEQ ID NO: 57) | GFTFSSY S (SEQ ID NO: 58) | MNWVRQAPGKGL EWVSS (SEQ ID NO: 59) | ISSSSYI (SEQ ID NO: 60) |
| RA056-11_38.2 | EVQLEESGGGVVQPGRS LRLSCAAS (SEQ ID NO: 61) | GFTFSRN G (SEQ ID NO: 62) | MHWVRQAPGKGL EWVAV (SEQ ID NO: 63) | IWYDGS NR (SEQ ID NO: 64) |
| RA056-11_41.2 | EVQLLESGGGLVQPGGS LRLSCAAS (SEQ ID NO: 65) | GFTFSSY A (SEQ ID NO: 66) | MSWVRQAPGKGL EWVSA (SEQ ID NO: 67) | ISGSGGS T (SEQ ID NO: 68) |
| RA056-11_48.2 | QVQLQESGPGLVKPSQT LSLTCTVS (SEQ ID NO: 69) | GGSISSG GYY (SEQ ID NO: 70) | WSWIRQIIPGKGLE WIGY (SEQ ID NO: 71) | IYYSGS T (SEQ ID NO: 72) |
| RA056-11_81.2 | EVQLVESGGGLVQPGGS LRLSCSAS (SEQ ID NO: 73) | GFTFSSY A (SEQ ID NO: 74) | MHWVRQAPGKGL EYVSA (SEQ ID NO: 75) | ISSNGGS T (SEQ ID NO: 76) |
| RA056-11_29.1 | EVQLVESGAEVKKPGAS VKVSCKAS (SEQ ID NO: 77) | GYTFNT YE (SEQ ID NO: 78) | INWVRQATGQGLE WMGW (SEQ ID NO: 79) | MNPNSG DT (SEQ ID NO: 80) |
| RA056-11_33.1 | EVQLVESGGGLVKPGGS LRLSCAAS (SEQ ID NO: 81) | GFTFSNA W (SEQ ID NO: 82) | MSWVRQAPGKGL EWVGR (SEQ ID NO: 83) | IKSKAN GETI (SEQ ID NO: 84) |
| RA056-11_35.1 | QVQLVESGGGLVQPGGS LRLSCAAS (SEQ ID NO: 85) | GFTFSSY E (SEQ ID NO: 86) | MNWVRQAPGKGL EWVSY (SEQ ID NO: 87) | ICSSGST I (SEQ ID NO: 88) |
| RA056-11_45.1 | EVQLVESGGGVVQPGRS LRLSCGAT (SEQ ID NO: 89) | GFTFSSH A (SEQ ID NO: 90) | MHWVRQVAGKG LEWVAV (SEQ ID NO: 91) | ISDDSSE K (SEQ ID NO: 92) |

TABLE 1-continued

VH CDR and FR amino acid sequences

| | | | | |
|---|---|---|---|---|
| RA056-11_56.1 | QVQLVESGGGLVQPGESLRLSCAAS (SEQ ID NO: 93) | GFTFGNYA (SEQ ID NO: 94) | MSWVRQAPGKGLAWVAA (SEQ ID NO: 95) | TSGSGGST (SEQ ID NO: 96) |
| RA056-11_66.1 | EVQLQESGPRLVKPSETLSLTCTVS (SEQ ID NO: 97) | GGSISSSDRY (SEQ ID NO: 98) | WAWIRQPPGKGLAYIGI (SEQ ID NO: 99) | IYYTGST (SEQ ID NO: 100) |
| RA056-11_68.1 | EVQLVESGPGLVRPSQTLSLTCTVA (SEQ ID NO: 101) | GGSVSSGSYH (SEQ ID NO: 102) | WSWIRQPPGKGLEWIGY (SEQ ID NO: 103) | LFYSGTT (SEQ ID NO: 104) |
| RA056-11_76.1 | QVQLVESGAEVKKPGSSVKVSCKAS (SEQ ID NO: 105) | GGTFSSYA (SEQ ID NO: 106) | ISWVRQAPGQGLEWMGG (SEQ ID NO: 107) | IIPIFGTA (SEQ ID NO: 108) |
| RA056-11_80.1 | EVQLVESGGGLVQPGGSLRLSCAAS (SEQ ID NO: 109) | GFTFSSYE (SEQ ID NO: 110) | MNWVRQAPGKGLEWVSY (SEQ ID NO: 111) | IICSDGVI (SEQ ID NO: 112) |
| RA056-11_12.2 | EVQLVESGPGLVKPSETLSLTCTVS (SEQ ID NO: 113) | GGSISPYY (SEQ ID NO: 114) | WNWIRQPPGKRLEWIGY (SEQ ID NO: 115) | VYYNGNT (SEQ ID NO: 116) |
| RA056-11_20.2 | QVQLVQSGAEVKKSGESLWISCKGS (SEQ ID NO: 117) | GYSFTRYW (SEQ ID NO: 118) | IGWVRQMPGKGLEWMGI (SEQ ID NO: 119) | ISPGDSNT (SEQ ID NO: 120) |
| RA056-11_23.2 | EVQLVESGGGVVKPGRSLRLSCAAS (SEQ ID NO: 121) | GFNLSSYG (SEQ ID NO: 122) | MHWVRQAPGKGLEWVAV (SEQ ID NO: 123) | VWYDGRNK (SEQ ID NO: 124) |
| RA056-11_36.2 | EVQLQESGPRLVKPSETLSLTCTVS (SEQ ID NO: 125) | GGSISSSDHY (SEQ ID NO: 126) | WAWIRQPPGKGLAYIGI (SEQ ID NO: 127) | IYYTGST (SEQ ID NO: 128) |
| RA056-11_39.2 | QVQLVESGGDLVQPGRSLRLSCAAS (SEQ ID NO: 129) | GFTFDDYD (SEQ ID NO: 130) | MHWVRQAPGKGLEWVSG (SEQ ID NO: 131) | IRWNSDTI (SEQ ID NO: 132) |
| RA056-11_45.2 | QVQLVESGGGVVQPGRSLRLSCAAS (SEQ ID NO: 133) | GFTFSNYG (SEQ ID NO: 134) | IHWVRQAPGKGLEWMAF (SEQ ID NO: 135) | ISHDGSKK (SEQ ID NO: 136) |
| RA056-11_54.2 | QVQLVESGAEVKTPGASVKVSCKTS (SEQ ID NO: 137) | GYTFTSYY (SEQ ID NO: 138) | IHWVRQAPGQGLEWMGI (SEQ ID NO: 139) | INPSAGST (SEQ ID NO: 140) |
| RA056-11_56.2 | QVQLQQWGAGLLKPSETLSLTCVVY (SEQ ID NO: 141) | GGSFSGYY (SEQ ID NO: 142) | WSWIRQSPGKGLEWIGE (SEQ ID NO: 143) | VNHSGSS (SEQ ID NO: 144) |
| RA056-11_75.2 | EVQLQQSGPGLVKPSETLSLTCTVS (SEQ ID NO: 145) | GGSISSYY (SEQ ID NO: 146) | WSWIRQPPGKGLEWIGY (SEQ ID NO: 147) | IHHSGSA (SEQ ID NO: 148) |
| RA056-11_94.2 | QVQLVQSGGGVVQPGRSLRLSCAAS (SEQ ID NO: 149) | GFTFSGYG (SEQ ID NO: 150) | MHWVRQAPGKGLEWVAF (SEQ ID NO: 151) | ISFDGSDK (SEQ ID NO: 152) |
| RA056-11_95.2 | EVQLVESGGGLVQPGGSLRLSCAAS (SEQ ID NO: 153) | GFTFTDNA (SEQ ID NO: 154) | MTWVRQAPGKGLEWVST (SEQ ID NO: 155) | IRNNGQNT (SEQ ID NO: 156) |
| RA056-11_95.1 | EVQLVESGGGLVQPGGSLRLSCAVS (SEQ ID NO: 157) | GFTFRNYA (SEQ ID NO: 158) | MSWVRQAPGKGLEWVSS (SEQ ID NO: 159) | ISDTGFST (SEQ ID NO: 160) |
| RA056-11_96.2 | VQLVEMGGGRIVQPGRSLSLSCAAS (SEQ ID NO: 161) | GFSFSSHA (SEQ ID NO: 162) | MHWVRQAPGKGLEWVAV (SEQ ID NO: 163) | ISYDGGDK (SEQ ID NO: 164) |
| RA056-11_58.2 | QVQLVQSGADVKKPGASVKISCKAS (SEQ ID NO: 165) | GYTFTAYA (SEQ ID NO: 166) | IHWVRQAPGQRLEWMGW (SEQ ID NO: 167) | INAGNGNT (SEQ ID NO: 168) |

TABLE 1-continued

VH CDR and FR amino acid sequences

| | | | | |
|---|---|---|---|---|
| RA056-11_93.2 | EVQLQESGPGLVEPSGTLSLTCVVS (SEQ ID NO: 169) | GGSITSSNW (SEQ ID NO: 170) | WSWVRQPPGKGPEWIGE (SEQ ID NO: 171) | IYHIGDS (SEQ ID NO: 172) |
| RA057.11_2.1 | QVQLVESGAEVKKPGASVKVSCKAS (SEQ ID NO: 173) | GYTFTSYY (SEQ ID NO: 174) | MHWVRQAPGQGLEWMGI (SEQ ID NO: 175) | INPSGGST (SEQ ID NO: 176) |
| RA057.11_17.1 | QVQLVESGPGLVKPSQTLSLTCTVS (SEQ ID NO: 177) | GGSISSGGYY (SEQ ID NO: 178) | WSWIRQHPGKGLEWIGY (SEQ ID NO: 179) | IYYSGST (SEQ ID NO: 180) |
| RA057.11_28.1 | QVQLVESGGGLVKPGGSLRLSCAAS (SEQ ID NO: 181) | GFTFSSYS (SEQ ID NO: 182) | MNWVRQAPGKGLEWVSS (SEQ ID NO: 183) | ISSSSSYI (SEQ ID NO: 184) |
| RA057.11_35.1 | QVQLVEWGAGLLKPSETLSLTCAVY (SEQ ID NO: 185) | GGSFSGYY (SEQ ID NO: 186) | WSWIRQPPGKGLEWIGE (SEQ ID NO: 187) | INHSGST (SEQ ID NO: 188) |
| RA057.11_44.1 | QVQLVQSGAEVKKPGASVKVSCKAS (SEQ ID NO: 189) | GYTFTSYY (SEQ ID NO: 190) | MHWVRQAPGQGLEWMGI (SEQ ID NO: 191) | INPSGGST (SEQ ID NO: 192) |
| RA057.11_51.1 | EVQLEESGPGLVKPSETLSLTCTVS (SEQ ID NO: 193) | GGSISSYY (SEQ ID NO: 194) | WSWIRQPPGKGLEWIGY (SEQ ID NO: 195) | IYYSGST (SEQ ID NO: 196) |
| RA057.11_56.1 | QVQLVESGAEVKKPGESLKISCKGS (SEQ ID NO: 197) | GYSFTSYW (SEQ ID NO: 198) | IGWVRQMPGKGLEWMGI (SEQ ID NO: 199) | IYPGDSDT (SEQ ID NO: 200) |
| RA057.11_61.1 | QVQLVESGGGLVKPGGSLRLSCAAS (SEQ ID NO: 201) | GFTFSSYS (SEQ ID NO: 202) | MNWVRQAPGKGLEWVSS (SEQ ID NO: 203) | ISSSSSYI (SEQ ID NO: 204) |
| RA057.11_62.1 | QVQLVESGGGLVQPGGSLRLSCAAS (SEQ ID NO: 205) | GFTFSSYW (SEQ ID NO: 206) | MSWVRQAPGKGLEWVAN (SEQ ID NO: 207) | IKQDGSEK (SEQ ID NO: 208) |
| RA057.11_67.1 | EVQLQESGPGLVKPSETLSLTCTVS (SEQ ID NO: 209) | GGSISSYY (SEQ ID NO: 210) | WSWIRQPPGKGLEWIGY (SEQ ID NO: 211) | IYYSGST (SEQ ID NO: 212) |
| RA057.11_71.1 | QVQLVQSGAEVKKPGASVKVSCKAS (SEQ ID NO: 213) | GYTFTSYG (SEQ ID NO: 214) | ISWVRQAPGQGLEWMGW (SEQ ID NO: 215) | ISAYNGNT (SEQ ID NO: 216) |
| RA057.11_82.1 | QVQLVESGAEVKKPGASVKVSCKVS (SEQ ID NO: 217) | GYTLTELS (SEQ ID NO: 218) | MHWVRQAPGKGLEWMGG (SEQ ID NO: 219) | FDPEDGET (SEQ ID NO: 220) |
| RA057.11_89.1 | QVQLVQSGAEVKKPGASVKVSCKAS (SEQ ID NO: 221) | GYTFTSYG (SEQ ID NO: 222) | ISWVRQAPGQGLEWMGW (SEQ ID NO: 223) | ISAYNGNT (SEQ ID NO: 224) |
| RA057.11_50.1 | QVQLVESGGGLVQPGRSLRLSCAAS (SEQ ID NO: 225) | GFTFEDYA (SEQ ID NO: 226) | MHWVRQVPGKGLEWVSS (SEQ ID NO: 227) | ISWNSVTI (SEQ ID NO: 228) |
| RA057.11_72.1 | QVQLVESGGGLVQPGGSLRLSCAAS (SEQ ID NO: 229) | GFTFYDYD (SEQ ID NO: 230) | MSWVRQAPGKGLQWVST (SEQ ID NO: 231) | ITLSGVTA (SEQ ID NO: 232) |
| RA057.11_78.1 | QVQLVESGGGLVICPGGSLRLSCAAS (SEQ ID NO: 233) | GFTFSSYS (SEQ ID NO: 234) | MNWVRQAPGKGLEWVSF (SEQ ID NO: 235) | ISSSSSYM (SEQ ID NO: 236) |
| RA057.11_80.1 | QVQLVESGGGLVQPGGSLRLSCAAS (SEQ ID NO: 237) | GFTFSSYE (SEQ ID NO: 238) | MNWVRQAPGKGLEWVSY (SEQ ID NO: 239) | ICSSGSTI (SEQ ID NO: 240) |
| RA057.11_93.1 | QVQLVESGGGLVQPGGSLRLSCAAS (SEQ ID NO: 241) | GFTFSSYW (SEQ ID NO: 242) | MHWVRQAPGKGLVWVAR (SEQ ID NO: 243) | IKTDGSIT (SEQ ID NO: 244) |

TABLE 1-continued

VH CDR and FR amino acid sequences

| Ab identifier | FR1 | CDR1 | FR2 | CDR2 |
|---|---|---|---|---|
| RA057.11_25.1 | EVQLVESGGGLVQPGGSLRLSCAAP (SEQ ID NO: 245) | GFSFSSHW (SEQ ID NO: 246) | MSWVRQAPGKGLEWVAN (SEQ ID NO: 247) | IKADGSEK (SEQ ID NO: 248) |
| RA057.11_47.1 | QVQLVQSGGGLVQPGGSLRLSCAAS (SEQ ID NO: 249) | GFTFSNYW (SEQ ID NO: 250) | MTWVRQAPGKGLEWVAN (SEQ ID NO: 251) | IKQDGSQK (SEQ ID NO: 252) |

| Ab identifier | FR3 | CDR3 |
|---|---|---|
| RA015-11_88.1 | NYNPSLKSRVTMSVDTSKNQFSLKLSSVTAADTAVYYC (SEQ ID NO: 253) | EVPTPYFDL (SEQ ID NO: 254) |
| RA015-11_94.1 | KYSQKFQGRVTITRDTSASTAYMGLSSLRSEDTAVYYC (SEQ ID NO: 255) | GGEDGYGDSYNAFDL (SEQ ID NO: 256) |
| RA015-11_12.2 | DYAAPVKGRFTISRDDSKNTLYLQMNSLKTEDTAVYYC (SEQ ID NO: 257) | HFESCGGDCSNW (SEQ ID NO: 258) |
| RA015-11_19.2 | NYAQKFQGRVEVITRDTSISAAYMELSSLRSDDTAVYYC (SEQ ID NO: 259) | VGGGRQLWLKDNYDYFYMDV (SEQ ID NO: 260) |
| RA015-11_83.2 | YYADSVKGRFTISRDNAKNSLYLQ1VIHSLRAEDTAVYYC (SEQ ID NO: 261) | DMPHFLYSSRWYPFDY (SEQ ID NO: 262) |
| RA015-11_58.1 | YYAGSVKGRFTISRDNFICNTLYLQMTSLRPEDTAVYYC (SEQ ID NO: 263) | EIVGANRWVPVGP (SEQ ID NO: 264) |
| RA015-11_68.1 | YYNPSLKSRVTISVDTSKNQFSLKLSSVTAADTAVYYC (SEQ ID NO: 265) | AISWADGYYMDV (SEQ ID NO: 266) |
| RA015-11_81.1 | NIAQKFQGRVTLPMDTSISTAYMEITRLESDDTAIYYC (SEQ ID NO: 267) | GAYGDPLHI (SEQ ID NO: 268) |
| RA015-11_91.1 | FYADSVKGRFTISRDNPKNSLYLQMNSLRADDTAVYYC (SEQ ID NO: 269) | WRAGVPSYFDY (SEQ ID NO: 270) |
| RA015-11_95.1 | NYAPNFQDRVTITWDMSTRTAYMELSSLRSEDTAVYYC (SEQ ID NO: 271) | GGSYVDY (SEQ ID NO: 272) |
| RA015-11_17.2 | YNADFMKGRFTMSRDLYICNTLYLffMNSLRAEDTAIYYC (SEQ ID NO: 273) | SPTDFWDDYLYYFDS (SEQ ID NO: 274) |
| RA015-11_64.2 | GYADSVKGRFTISRDNARNSLYLQMNSLRAEDTALYYC (SEQ ID NO: 275) | DISSYDDTSGYYYN (SEQ ID NO: 276) |
| RA015-11_66.2 | NYNPSLKTRVTISVDKSKNHLSLKLSFVTAADTAVYYC (SEQ ID NO: 277) | KGTYSTDSYDGFDI (SEQ ID NO: 278) |
| RA056-11_9.2 | YYADSVKGRFTISRDNSKNTLYLQMNSLRAEDTAVYYC (SEQ ID NO: 279) | CETGERRWYYYGSGTIREAFDI (SEQ ID NO: 280) |
| RA056-11_34.2 | YYADSVKGRFTISRDNAKNSLYLQMNSLRAEDTAVYYC (SEQ ID NO: 281) | PRQLGSVWFDP (SEQ ID NO: 282) |
| RA056-11_38.2 | YYTDSVKGRFTISRDNSRNTLYLQMDSLKPEDTALYYC (SEQ ID NO: 283) | DRSSSWYFDH (SEQ ID NO: 284) |
| RA056-11_41.2 | YYADSVKGRFTISRDNSICNTLYLQMNSLRAEDTAVYYC (SEQ ID NO: 285) | GSGTFDY (SEQ ID NO: 286) |
| RA056-11_48.2 | YYNPSLKSRVTISVDTSKNQFSLKLSSVTAADTAVYYC (SEQ ID NO: 287) | VSLNSSSSLIHYYYYMDV (SEQ ID NO: 288) |
| RA056-11_81.2 | YYADSVKGRFTISRDNSKNTLYLQMSSLRAEDTAVYYC (SEQ ID NO: 289) | VKEYDFWSGYYYRGATRTTPNFDY (SEQ ID NO: 290) |
| RA056-11_29.1 | VYAQKCQGRVSMTRHTSTSTASMELISLIFEDTAVYYC (SEQ ID NO: 291) | AAGVGVALDY (SEQ ID NO: 292) |
| RA056-11_33.1 | DYAAPVKGRLTISRDDSKNTLYLQMNSLKTEDTAVYYC (SEQ ID NO: 293) | FIFESCGGDCSNW (SEQ ID NO: 294) |
| RA056-11_35.1 | YYADSVKGRFTISRDNAKNSLYLQMNSLRAEDTAVYYC (SEQ ID NO: 295) | VHMYYYDSSGYYYDDY (SEQ ID NO: 296) |

TABLE 1-continued

VH CDR and FR amino acid sequences

| | | |
|---|---|---|
| RA056-11_45.1 | YYADSVRGRFIISRDNAKDTVYLQMNSLRPDDTAVYYC (SEQ ID NO: 297) | PHRLLDSCSSTSCYVVAFDL (SEQ ID NO: 298) |
| RA056-11_56.1 | YYAGSVK*CFTISRDNSKITLYLQVHSLRPEDTAVYYC (SEQ ID NO: 299) | GTLSGFATTFDY (SEQ ID NO: 300) |
| RA056-11_66.1 | YYNPSLKSRVSISVDTSKNQFSLNVNSVTAADTGVYYC (SEQ ID NO: 301) | RHIGRHYYFDY (SEQ ID NO: 302) |
| RA056-11_68.1 | KYNPSLKSRVTISTDVSKNQFSLKLKSVTAADTAVYYC (SEQ ID NO: 303) | DASIAARPPWGMDV (SEQ ID NO: 304) |
| RA056-11_76.1 | NYAQKFQGRVTITADESTSTAYMELSSLRSEDTAVYYC (SEQ ID NO: 305) | VRITIFGVVMVKSDNWFDP (SEQ ID NO: 306) |
| RA056-11_80.1 | YYADSVKGRFTISRDNAKNSLYLQMNSLRAEDTAVYYC (SEQ ID NO: 307) | VHLYYYDSSGYYYDDY (SEQ ID NO: 308) |
| RA056-11_12.2 | NYNPSLKSRVTISVDTPKNQFSLRLSSVTAADTAVYYC (SEQ ID NO: 309) | YGVDYFDY (SEQ ID NO: 310) |
| RA056-11_20.2 | RYSPSFQGQVTISADKSISTAYLQLSSLKASDIATYYC (SEQ ID NO: 311) | QGYYDRSPRPHYMDV (SEQ ID NO: 312) |
| RA056-11_23.2 | FYTDSVKGRFTISRDNSINSVYLQMNSLRAEDTAIYYC (SEQ ID NO: 313) | VTSRVVAAAGGYFDH (SEQ ID NO: 314) |
| RA056-11_36.2 | YYNPSLKSRVSISVDTSKNQFSLNVNSVTAADTGVYYC (SEQ ID NO: 315) | RITIGRHYYFDY (SEQ ID NO: 316) |
| RA056-11_39.2 | GYADSVKGRFTISRDNARNSLYLQMNSLRAEDTALYYC (SEQ ID NO: 317) | DISSYDDTSGYYYN (SEQ ID NO: 318) |
| RA056-11_45.2 | NYADSVKGRFTISRDNSKNTLYLQMNRLRVEDTAIYHC (SEQ ID NO: 319) | DIVVVPAATSLLGGYYYYYMDV (SEQ ID NO: 320) |
| RA056-11_54.2 | TYPQKFQGRVTMTRDRSTSTVYMELSSLRSEDTAVYYC (SEQ ID NO: 321) | DGLEARRTTSSHPHYYMDV (SEQ ID NO: 322) |
| RA056-11_56.2 | YYNPSLKSRVTISVDTSKDQFSLKLTSVTAADTAVYYC (SEQ ID NO: 323) | KKGRVGIAYMEV (SEQ ID NO: 324) |
| RA056-11_75.2 | DYNPSLKGRVTISLDTSKKQFSLKLRFVTTADTALYYC (SEQ ID NO: 325) | TPYPPLDWYFDL (SEQ ID NO: 326) |
| RA056-11_94.2 | YYAASVKGRFTLSRDNSICNTLYLKINSLRTEDTAVYYC (SEQ ID NO: 327) | EVREYTDY (SEQ ID NO: 328) |
| RA056-11_95.2 | YYTDSVKGRFTISRDNFNNMVYLQMSSLRAEDTAVYYC (SEQ ID NO: 329) | LVGITHLSAAPWT (SEQ ID NO: 330) |
| RA056-11_95.1 | YYADSVKGRFAISRDNSKNRLYLEMNSLRADDTAIYYC (SEQ ID NO: 331) | VPHQLVPIWFDP (SEQ ID NO: 332) |
| RA056-11_96.2 | NYADSVRGRFTISRDNSEDTLYLQMNGLRTEDTAMYFC (SEQ ID NO: 333) | DARGVRNAFDL (SEQ ID NO: 334) |
| RA056-11_58.2 | KYSQKFQGRVTITRDTSANTSYMDLSSLRSEDTAVYFC (SEQ ID NO: 335) | SLYCSTHSCSFLIILY (SEQ ID NO: 336) |
| RA056-11_93.2 | NYNPSLKSRVTMSVDKSKNQFSLKLRSVTAADTAIYYC (SEQ ID NO: 337) | TFWSGSYSRYFDS (SEQ ID NO: 338) |
| RA057.11_2.1 | SYAQKFQGRVTMTRDTSTSTVYMELSSLRSEDTAVYYC (SEQ ID NO: 339) | FGRHDYGGKDDY (SEQ ID NO: 340) |
| RA057.11_17.1 | YYNPSLKSRVTISVDTSKNQFSLKLSSVTAADTAVYYC (SEQ ID NO: 341) | DQITMVRGGDGQNYYYYYMDV (SEQ ID NO: 342) |
| RA057.11_28.1 | YYADSVKGRFTISRDNAKNSLYLQMNSLRAEDTAVYYC (SEQ ID NO: 343) | DVGDIVVVTASLDY (SEQ ID NO: 344) |
| RA057.11_35.1 | NYNPSLKSRVTISVDTSKNQFSLKLSSVTAADTAVYYC (SEQ ID NO: 345) | GWAYSSSWYRRMISFDY (SEQ ID NO: 346) |

TABLE 1-continued

VH CDR and FR amino acid sequences

| | | |
|---|---|---|
| RA057.11_44.1 | SYAQKFQGRVTMTRDTSTSTVYMELSSL RSEDTAVYYC (SEQ ID NO: 347) | VGGGYYDSSGGALDY (SEQ ID NO: 348) |
| RA057.11_51.1 | NYNPSLKSRVTISVDTSKNQFSLKLSSVT AADTAVYYC (SEQ ID NO: 349) | RVGSPYCGGDCYPAFDI (SEQ ID NO: 350) |
| RA057.11_56.1 | RYSPSFQGQVTISADKSISTAYLQWSSLK ASDTAMYYC (SEQ ID NO: 351) | ILVDCSSTSCYYYYYYMD V (SEQ ID NO: 352) |
| RA057.11_61.1 | YYADSVKGRFTISRDNAKNSLYLQMNSL RAEDTAVYYC (SEQ ID NO: 353) | GGSSWYYFDY (SEQ ID NO: 354) |
| RA057.11_62.1 | YYVDSVKGRFTISRDNAKNSLYLQMNSL RAEDTAVYYC (SEQ ID NO: 355) | ELFHILSY (SEQ ID NO: 356) |
| RA057.11_67.1 | NYNPSLKSRVTISVDTSKNQFSLKLSSVT AADTAVYYC (SEQ ID NO: 357) | RESSRLGNAFDI (SEQ ID NO: 358) |
| RA057.11_71.1 | NYAQKLQGRVTMTTDTSTSTAYMELRSL RSDDTAVYYC (SEQ ID NO: 359) | DLNSYYFDY (SEQ ID NO: 360) |
| RA057.11_82.1 | IYAQKFQGRVTMTEDTSTDTAYMELSSL RSEDTAVYYC (SEQ ID NO: 361) | PIVLGAFDI (SEQ ID NO: 362) |
| RA057.11_89.1 | NYAQKLQGRVTMTTDTSTSTAYMELRSL RSDDTAVYYC (SEQ ID NO: 363) | RYCSSTSCYKGSYYYYY YYMDV (SEQ ID NO: 364) |
| RA057.11_50.1 | DYADSVKGRFTISRDNARNSLYLQMNSL RPEDTALYYC (SEQ ID NO: 365) | GSYRYYYYCIDV (SEQ ID NO: 366) |
| RA057.11_72.1 | YYADSVKGRFTISRDNSKNMVYLQMNSL RAEDTAVYYC (SEQ ID NO: 367) | HWDS (SEQ ID NO: 368) |
| RA057.11_78.1 | HYADSVKDRFTISRDNANNSLYLQMNSL TAEDTGVYYC (SEQ ID NO: 369) | LGYDFWSGFIRH (SEQ ID NO: 370) |
| RA057.11_80.1 | YYADSVKGRFTISRDNAKNSLYLQMNSL RAEDTAVYYC (SEQ ID NO: 371) | VHLYYYDSSGYYYDDY (SEQ ID NO: 372) |
| RA057.11_93.1 | GHADSVKGRFSVSRDNAKNTLYLQMNS LRAEDTGVYFC (SEQ ID NO: 373) | DGGEAYDFWSDNFIRFYF YYYMDV (SEQ ID NO: 374) |
| RA057.11_25.1 | YYIDSVKGRFSISRDNAKKSLYLQMNSLR AEDTAVYYC (SEQ ID NO: 375) | DQVEQQLVLGYFYYYYM DV (SEQ ID NO: 376) |
| RA057.11_47.1 | YYVDSVKGRFTISRDNAENSLYLQMNGL RAEDTAVYYC (SEQ ID NO: 377) | DPRAYDYWSGYYEGYFD Y (SEQ ID NO: 378) |

TABLE 1A

VH CDR and FR amino acid sequences

| Ab identifier | FR1 | CDR1 | FR2 | CDR2 |
|---|---|---|---|---|
| RA061.11_G29.1 | QVQLQESGSGLVRSSQN LSLTCSVS (SEQ ID NO: 379) | GGSVSR GGAS (SEQ ID NO: 380) | WGWVRQPPGQG LEWIGY (SEQ ID NO: 381) | ITHSGT T (SEQ ID NO: 382) |
| RA061.11_G35.1 | EVQLVESGGGSVQPGGS LRLSCAAS (SEQ ID NO: 383) | GFTFSSH W (SEQ ID NO: 384) | IHWVRQAPGKGL VCVSR (SEQ ID NO: 385) | INSDG SST (SEQ ID NO: 386) |
| RA061.11_G40.1 | QVQLVESGGGLVQPGGS LRLSCATS (SEQ ID NO: 387) | RFTFSNY A (SEQ ID NO: 388) | MNWVRQAPGKG LEWVSA (SEQ ID NO: 389) | ISGSG GTT (SEQ ID NO: 390) |
| RA061.11_M43.1 | EVQLQESGPGLVKPSETL SLTCTVS (SEQ ID NO: 391) | GGSITSD TFY (SEQ ID NO: 392) | WGWVRQPPGKG LEWIAS (SEQ ID NO: 393) | ISYSGS T (SEQ ID NO: 394) |
| RA061.11_M44.1 | EVQLVQSGAEVKKPGAS VKVSCKAS (SEQ ID NO: 395) | GYTFTSY G (SEQ ID NO: 396) | ISWVRQAPGQGL EWMGW (SEQ ID NO: 397) | ISAYN GNT (SEQ ID NO: 398) |

TABLE 1A-continued

VH CDR and FR amino acid sequences

| Ab identifier | FR1 | CDR1 | FR2 | CDR2 |
|---|---|---|---|---|
| RA061.11_M47.1 | QVQLVQSGAEVKKPGASVKVSCKAS (SEQ ID NO: 399) | GYTFTSYY (SEQ ID NO: 400) | MHWVRQAPGQGLEWMGI (SEQ ID NO: 401) | INPSGGST (SEQ ID NO: 402) |
| RA061.11_G65.1 | QVQLVESGGVVVQPGGSLRLSCAAS (SEQ ID NO: 403) | GFTFDDYA (SEQ ID NO: 404) | IHWVRQAPGKGLEWVSL (SEQ ID NO: 405) | ISWDGGST (SEQ ID NO: 406) |
| RA061.11_G66.1 | QVQLVESGGGLIQPGGSLRLSCAAS (SEQ ID NO: 407) | GFTVSGNY (SEQ ID NO: 408) | MSWVRQAPGRGLEWVSV (SEQ ID NO: 409) | IYSTGDT (SEQ ID NO: 410) |
| RA061.11_G67.1 | QVQLVQSGAEVKKPGESLKISCHGS (SEQ ID NO: 411) | GYTFSNYW (SEQ ID NO: 412) | IGWVRQMPGKGLEWMGI (SEQ ID NO: 413) | IYTGDSYS (SEQ ID NO: 414) |
| RA061.11_M71.1 | EVQLQESGPGLVKPSETLSLTCTVS (SEQ ID NO: 415) | GGSISSSSYY (SEQ ID NO: 416) | WGWIRQPPGKGLEWIGS (SEQ ID NO: 417) | IYYSGST (SEQ ID NO: 418) |
| RA061.11_M72.1 | EVQLVESGGGLVQPGGSLRLSCAAS (SEQ ID NO: 419) | GFTFSSYA (SEQ ID NO: 420) | MSWVRQAPGKGLEWVSA (SEQ ID NO: 421) | ISGSGGST (SEQ ID NO: 422) |
| RA061.11_M80.1 | EVQLVESGGGLVQPGGSLRLSCAAS (SEQ ID NO: 423) | GFTFSSYW (SEQ ID NO: 424) | MHWVRQAPGKGLVWVSR (SEQ ID NO: 425) | INSDGSST (SEQ ID NO: 426) |
| RA061.11_M82.1 | QVQLVESGGGLVQPGGSLRLSCAAS (SEQ ID NO: 427) | GFTFSSYS (SEQ ID NO: 428) | MNWVRQAPGKGLEWVSY (SEQ ID NO: 429) | ISSSSSTI (SEQ ID NO: 430) |
| RA061.11_A89.1 | QVQLVQSGGGLVQPGGSLTLSCAVS (SEQ ID NO: 431) | GFTVRSSY (SEQ ID NO: 432) | VSWLRQTPGKGLEWVSV (SEQ ID NO: 433) | LFSGGST (SEQ ID NO: 434) |
| RA061.11_A90.1 | EVQLVESGGGLVQPGGSLRLSCEAS (SEQ ID NO: 435) | GFNFENYA (SEQ ID NO: 436) | MDWVRQAPGKGLEWVSG (SEQ ID NO: 437) | ITWNSGKI (SEQ ID NO: 438) |
| RA061.11_A95.1 | QVQLVESGGCVVQPGRSLRLSCAAS (SEQ ID NO: 439) | GFTFSTYA (SEQ ID NO: 440) | MYWVRQAPGEGLEWVAV (SEQ ID NO: 441) | ISYHGSNK (SEQ ID NO: 442) |

| Ab identifier | FR3 | CDR3 |
|---|---|---|
| RA061.11_29.1 | GFSNPSLKSRVMISKDKSQNHFSLSLTSVTVADTAVYFC (SEQ ID NO: 443) | ARWSTAFDR (SEQ ID NO: 444) |
| RA061.11_35.1 | GSYADSVKGRFTISRDNAKNMVYLQMNSLRAEDTAVDLG (SEQ ID NO: 445) | TSDRRSQFRRSGRAPWDAFDI (SEQ ID NO: 446) |
| RA061.11_40.1 | GYYADSVKGRFTISRDNSRNSLYLQMNSLRGEDTAVYYC (SEQ ID NO: 447) | VKESVGALLWEIDDWQFFDY (SEQ ID NO: 448) |
| RA061.11_43.1 | MFYNPSLKSRVTMSVDTSKNQFSLHLNSVTAADTAVFYC (SEQ ID NO: 449) | AKHGGGMATSFDY (SEQ ID NO: 450) |
| RA061.11_44.1 | MNYAQKLQGRVTMTTDTSTSTAYMELRSLRSDDTAVYYC (SEQ ID NO: 451) | ARDTDHYFDY (SEQ ID NO: 452) |
| RA061.11_47.1 | MSYAQKFQGRVTMTRDTSTSTVYMELSSLRSEDTAVYYC (SEQ ID NO: 453) | AREGAIAAAGFDY (SEQ ID NO: 454) |
| RA061.11_65.1 | GYYADSVKGRFTISRDNSKNSLYLQMNSLRTEDTALYYC (SEQ ID NO: 455) | AKDTAILFGGSSFDY (SEQ ID NO: 456) |
| RA061.11_66.1 | GYYAESVKGRFTVSRDDNSKSSVKVVVEQTESRGHGRVL (SEQ ID NO: 457) | LCERKGQWLVQRYGR (SEQ ID NO: 458) |
| RA061.11_67.1 | GRYSPSFQGLGDVAVDESLSTAYLEWSSLKASDTAMYYC (SEQ ID NO: 459) | VRQWENRGWSIAY (SEQ ID NO: 460) |
| RA061.11_71.1 | MYYNPSLKSRVTISVDTSKNQFSLKLSSVTAADTAVYYC (SEQ ID NO: 461) | ARHLRYNWFDP (SEQ ID NO: 462) |

TABLE 1A-continued

VH CDR and FR amino acid sequences

RA061.11_ MYYADSVKGRFTISRDNSKNTLYLQMNSLR    AKMLFTPWEVTWLRP
72.1     AEDTAVYYC (SEQ ID NO: 463)        YFDY (SEQ ID NO: 464)

RA061.11_ MSYADSVKGRFTISRDNAKNTLYLQMNSLR    ASLVPAAGGDY
80.1     AEDTAVYYC (SEQ ID NO: 465)        (SEQ ID NO: 466)

RA061.11_ MYYADSVKGRFTISRDNAKNSLYLQMNSLR    ARGSPYSSSSSVRGM
82.1     AEDTAVYYC (SEQ ID NO: 467)        DV (SEQ ID NO: 468)

RA061.11_ ASYADFVKGRFTMSRDNSKNTLYLQMDSLR    AKGGWELTNWFDP
89.1     SDDTAVYYC (SEQ ID NO: 469)        (SEQ ID NO: 470)

RA061.11_ AHYADSVKGRFTISRDNAKNSLFLQMNNLR    AKASGEDFPDY
90.1     HEDTALYYC (SEQ ID NO: 471)        (SEQ ID NO: 472)

RA061.11_ AYYADSVKGRFTISRDNSKNTLYLLMNSLR    ARDPGWSGSLMDYYY
95.1     AEDTAVYYC (SEQ ID NO: 473)        GMDV (SEQ ID NO: 474)

TABLE 2

VL CDR and FR amino acid sequences

| Ab identifier | FR1 | CDR1 | FR2 | CDR2 |
|---|---|---|---|---|
| RA015.11_ KC88.1 | FVSQTPATLSASVGDRV TITCRAS (SEQ ID NO: 475) | QSISSY (SEQ ID NO: 476) | LNWYQQKPGKV PKLLIY (SEQ ID NO: 477) | AAS |
| RA015.11_ KC94.1 | MTPTIPVTLSASVGDRV TITCRAS (SEQ ID NO: 478) | QSISNW (SEQ ID NO: 479) | LAWYQQKPGKA PKLLIY (SEQ ID NO: 480) | KAS |
| RA015.11_L C12.2 | QSELTQPPSVSVAPGQT ARITCGGN (SEQ ID NO: 481) | NIGSKS (SEQ ID NO: 482) | VHWYQQKPGQA PVLVVY (SEQ ID NO: 483) | DDS |
| RA015.11_ KC19.2 | YHDPQAPLTLSLSPGER ATLSCRAS (SEQ ID NO: 484) | QSVSSSY (SEQ ID NO: 485) | LAWYQQKPGQA PRLLIY (SEQ ID NO: 486) | GAS |
| RA015.11_ KC83.2 | HDPQAPATLSASVGDR VTITCRAS (SEQ ID NO: 487) | QGISSY (SEQ ID NO: 488) | LAWYQQKPGKA PNLLIY (SEQ ID NO: 489) | AAS |
| RA015.11_ KC58.1 | MTLIIPVTLSLSPGERAT LSCRAS (SEQ ID NO: 490) | QSIRSN (SEQ ID NO: 491) | LAWYQQKPGQA PRLLIH (SEQ ID NO: 492) | GAS |
| RA015.11_L C68.1 | QFVLTQPPSVSGAPGQR VTISCTGS (SEQ ID NO: 493) | SSNIGAGY D (SEQ ID NO: 494) | VHWYQQLPGTA PKLLIY (SEQ ID NO: 495) | GNS |
| RA015.11_L C81.1 | QSVLTQTPSVSVAPGQT AIITCGGH (SEQ ID NO: 496) | SIGNRA (SEQ ID NO: 497) | VHWYQQKPGQA PVVVVY (SEQ ID NO: 498) | DDS |
| RA015.11_ KC91.1 | LLSLHIPVTLSASVGDR VTITCQAS (SEQ ID NO: 499) | QDITKY (SEQ ID NO: 500) | LNWYQQKPGKA PKLLIY (SEQ ID NO: 501) | DVS |
| RA015.11_ KC95.1 | SSHIPVTLAVSLGERATI NCKSS (SEQ ID NO: 502) | QSVLYYSN SKNY (SEQ ID NO: 503) | LTWYQQKPGQPP KLLIY (SEQ ID NO: 504) | WAS |
| RA015.11_ KC17.2 | YDPTAPATLSLSPGERA TLSCRAS (SEQ ID NO: 505) | QSVRSSY (SEQ ID NO: 506) | LAWYQQKPGQA PRLLIY (SEQ ID NO: 507) | GAS |
| RA015.11_ KC64.2 | LPQAPATLSLSPGERAT LSCRAS (SEQ ID NO: 508) | QSVSSY (SEQ ID NO: 509) | LAWYQQKPGQA PRLLIY (SEQ ID NO: 507) | DAY |

TABLE 2-continued

VL CDR and FR amino acid sequences

| | | | | |
|---|---|---|---|---|
| RA015.11_L<br>C66.2 | QSVLTQPASVSGSPGQSI<br>TISCTGT<br>(SEQ ID NO: 510) | SSDVGNYN<br>L<br>(SEQ ID NO: 511) | VSWYQQHPGKA<br>PKLMIY<br>(SEQ ID NO: 512) | EDS |
| RA056.11_<br>KC9.2 | RSPKAPVTLSLSPGERA<br>TLSCRAS<br>(SEQ ID NO: 513) | QSVSSY<br>(SEQ ID NO: 509) | LAWYQQKPGQA<br>PRLLIY<br>(SEQ ID NO: 507) | DAS |
| RA056.11_<br>KC34.2 | MTPTAPVTLSASVGDR<br>VTITCRAS<br>(SEQ ID NO: 514) | QGISSY<br>(SEQ ID NO: 488) | LAWYQQKPGKA<br>PKLLIY<br>(SEQ ID NO: 515) | AAS |
| RA056.11_L<br>C38.2 | QSVLTQPASVSGPPGQSI<br>AISCTGT<br>(SEQ ID NO: 516) | NSDVGAY<br>NY<br>(SEQ ID NO: 517) | VSWYQQHPGKA<br>PKLMIY<br>(SEQ ID NO: 518) | EVS |
| RA056.11_L<br>C41.2 | QSVLTQPPSVSVAPGKT<br>ARITCGGN<br>(SEQ ID NO: 519) | NIGSKS<br>(SEQ ID NO: 520) | VHWYQQKPGQA<br>PVLVIY<br>(SEQ ID NO: 521) | YDS |
| RA056.11_<br>KC48.2 | YDPTAPVTLSASVGDRV<br>TITCRAS<br>(SEQ ID NO: 522) | QSISSY<br>(SEQ ID NO: 476) | LNWYQQKPGKA<br>PKLLIY<br>(SEQ ID NO: 523) | AAS |
| RA056.11_<br>KC81.2 | PPAPLTLSVSPGERATLS<br>CRAS<br>(SEQ ID NO: 524) | QSVSSN<br>(SEQ ID NO: 525) | LAWYQQKPGQA<br>PRLLIY<br>(SEQ ID NO: 507) | GAS |
| RA056.11_<br>KC29.1 | KIVMAQSPATLSLSPGE<br>RTTLSGRAS<br>(SEQ ID NO: 526) | QSVHNIY<br>(SEQ ID NO: 527) | LPWYQQKPGQA<br>ARLLIY<br>(SEQ ID NO: 528) | GTS |
| RA056.11_L<br>C33.1 | QSVLTQSPSASASLGAS<br>VKLTCTLT<br>(SEQ ID NO: 529) | SGHSNYA<br>(SEQ ID NO: 530) | IAWHQQQPERGP<br>RYLMK<br>(SEQ ID NO: 531) | VNSD<br>GSH<br>(SEQ ID NO: 532) |
| RA056.11_L<br>C35.1 | QSVLTQPPSASGSPGQS<br>VTISCTGT<br>(SEQ ID NO: 533) | SSDVGGYN<br>Y<br>(SEQ ID NO: 534) | VSWYQQHPGKA<br>PKLMIY<br>(SEQ ID NO: 535) | EVS |
| RA056.11_L<br>C45.1 | QSVLTQSPSASASLGAS<br>VKLTCTLT<br>(SEQ ID NO: 536) | SGHSNYA<br>(SEQ ID NO: 537) | IAWHQQQPERGP<br>RYLMK<br>(SEQ ID NO: 538) | VNSD<br>GSH<br>(SEQ ID NO: 532) |
| RA056.11_L<br>C56.1 | QSVLTQPASVSGSPGQSI<br>TISCTGT<br>(SEQ ID NO: 539) | SSDVGGYN<br>H<br>(SEQ ID NO: 540) | VSWYQQHPGKA<br>PKLMIY<br>(SEQ ID NO: 541) | DVN |
| RA056.11_L<br>C66.1 | QSVLTQPRSVSGSPGQS<br>VTISCTGT<br>(SEQ ID NO: 542) | SSDVGDYK<br>Y<br>(SEQ ID NO: 543) | VSWYQQYPGKA<br>PRLMIY<br>(SEQ ID NO: 544) | DVI |
| RA056.11_L<br>C68.1 | QSVLTQPASVSGSPGQSI<br>TISCTGT<br>(SEQ ID NO: 545) | SSDVGSYS<br>L<br>(SEQ ID NO: 546) | VSWFQQHPGRAP<br>KLIIY<br>(SEQ ID NO: 547) | EGS |
| RA056.11_<br>KC76.1 | LMTQAPVTLSVSPGERA<br>TLSCRAS<br>(SEQ ID NO: 548) | QSVSSN<br>(SEQ ID NO: 549) | LAWYQQKPGQA<br>PRLLIY<br>(SEQ ID NO: 550) | GAS |
| RA056.11_L<br>C80.1 | QSVLTQPASVSGSPGQSI<br>TISCTGT<br>(SEQ ID NO: 551) | SSDVGGYN<br>Y<br>(SEQ ID NO: 552) | VSWYQQHPGKA<br>PKLMIY<br>(SEQ ID NO: 553) | DVS |
| RA056.11_L<br>C12.2 | QSVLTQPPSVSAAPGQK<br>VTISCSGS<br>(SEQ ID NO: 554) | SSNIGNNY<br>(SEQ ID NO: 555) | VSWYQQLPGTAP<br>KLLIY<br>(SEQ ID NO: 556) | DNN |
| RA056.11_<br>KC20.2 | SPQAPVTLSLSPGERAT<br>LSCRAS<br>(SEQ ID NO: 557) | QSVSSY<br>(SEQ ID NO: 509) | LAWYQQKPGQA<br>PRLLIY<br>(SEQ ID NO: 558) | DAS |
| RA056.11_L<br>C23.2 | QFVLTQSLSVSVALGQT<br>ANITCGGH<br>(SEQ ID NO: 559) | NIVAKT<br>(SEQ ID NO: 560) | VHWYQQKSGQA<br>PVLVIY<br>(SEQ ID NO: 561) | RDT |

TABLE 2-continued

VL CDR and FR amino acid sequences

| ID | FR1 | CDR1 | FR2 | CDR2 |
|---|---|---|---|---|
| RA056.11_LC36.2 | QSVLTQPASVSGSPGQSITISCTGT (SEQ ID NO: 562) | SSDVGGYNY (SEQ ID NO: 563) | VSWYQQHPGKAPKLMIY (SEQ ID NO: 564) | DVS |
| RA056.11_LC39.2 | QSVLTQPPSASGTPGQRVTISCSGS (SEQ ID NO: 565) | SSNIGNNY (SEQ ID NO: 566) | VYWYQQLPGTAPKLLIY (SEQ ID NO: 567) | RNN |
| RA056.11_KC45.2 | PQAPVTLSASVGDRITITCRAS (SEQ ID NO: 568) | QSISRY (SEQ ID NO: 569) | LNWYQQKPGRAPNLLIY (SEQ ID NO: 570) | AAS |
| RA056.11_KC54.2 | DDPKAPATLSLSPGDRATLSCRAS (SEQ ID NO: 571) | QSVSSY (SEQ ID NO: 509) | LAWYQQKPGQPPRLLIF (SEQ ID NO: 572) | DAS |
| RA056.11_KC56.2 | LDDPQDPVSLSASVGDKVTITCRAS (SEQ ID NO: 573) | QSISSH (SEQ ID NO: 574) | LNWYQQPGKAPNLLIY (SEQ ID NO: 575) | AAS |
| RA056.11_KC75.2 | MIQSPVCLAVSLGERATINCKSS (SEQ ID NO: 576) | QSVSYSSNNKDH (SEQ ID NO: 577) | LAWYLQRSGQPPQLLIY (SEQ ID NO: 578) | WAS |
| RA056.11_KC94.2 | MTPQAPVTLSLSPGERATLSCRAS (SEQ ID NO: 579) | QSVNYY (SEQ ID NO: 580) | LAWYQQKPGRAPRLLIY (SEQ ID NO: 581) | DAS |
| RA056.11_LC95.2 | QSVLTQPASVSGSPGQSITISCAGT (SEQ ID NO: 582) | STDLGTYHL (SEQ ID NO: 583) | VSWYQQHPGKAPKLLIY (SEQ ID NO: 584) | EGS |
| RA056.11_LC95.1 | QSQLTQPESASGSRGQWITISITGT (SEQ ID NO: 585) | SSDSGGYSY (SEQ ID NO: 586) | VSGSQQQPGKAPKLIIF (SEQ ID NO: 587) | EVD |
| RA056.11_KC96.1 | PQAPATLSASVGDRVTITCRAS (SEQ ID NO: 588) | QVIRND (SEQ ID NO: 589) | LGWYQQKPGNAPKRLIY (SEQ ID NO: 590) | AAS |
| RA056.11_KC58.2 | YDPKAPLTLSLSPGERATLSCRAS (SEQ ID NO: 591) | QTVSSSS (SEQ ID NO: 592) | LAWYQQKPGQAPRLLIY (SEQ ID NO: 593) | SAS |
| RA056.11_KC93.2 | HDPQAPVTLSVSPGERVTLSCRAS (SEQ ID NO: 594) | QSVYSN (SEQ ID NO: 595) | LAWYQLKPGQGPRLLIY (SEQ ID NO: 596) | SAS |
| RA057.11_KC2.1 | LTPQDPVTLSASVGDRVTITCQAS (SEQ ID NO: 597) | QDISNY (SEQ ID NO: 598) | LNWYQQKPGKAPKLLIY (SEQ ID NO: 649) | DAS |
| RA057.11_KC17.1 | YDPTAPVTLSASVGDRVTITCRAS (SEQ ID NO: 600) | QSISSY (SEQ ID NO: 476) | LNWYQQKPGKAPKLLIY (SEQ ID NO: 601) | AAS |
| RA057.11_LC28.1 | QSVLTQPPSASGTPGQRVTISCSGS (SEQ ID NO: 602) | SSNIGSNT (SEQ ID NO: 603) | VNWYQQLPGTAPKLLIY (SEQ ID NO: 604) | SNN |
| RA057.11_KC35.1 | PALFFSPATLSLSSGERATLSCRAS (SEQ ID NO: 605) | QSVISSY (SEQ ID NO: 606) | LAWYQQKPGQAPRLLIY (SEQ ID NO: 607) | GAS |
| RA057.11_KC44.1 | PQAPATLSASVGDRVTITCRAS (SEQ ID NO: 608) | QSISSW (SEQ ID NO: 609) | LAWYQQKPGKAPKLLIY (SEQ ID NO: 610) | KAS |
| RA057.11_KC51.1 | CSMTSDSSHPASTGDRVTITCRAS (SEQ ID NO: 611) | QGISSY (SEQ ID NO: 488) | LAWYQQKPGKAPKLLIY (SEQ ID NO: 612) | AAS |
| RA057.11_LC56.1 | QSVLTQPPSVSVSPGQTARITCSGD (SEQ ID NO: 613) | ALPKQY (SEQ ID NO: 614) | AYWYQQKPGQAPVLVIY (SEQ ID NO: 615) | KDS |

TABLE 2-continued

VL CDR and FR amino acid sequences

| Ab identifier | FR1 | CDR1 | FR2 | CDR2 |
|---|---|---|---|---|
| RA057.11_LC61.1 | QSVLTQPPSASGTPGQRVTISCSGS (SEQ ID NO: 616) | SSNIGSNT (SEQ ID NO: 617) | VNWYQQLPGTAPKLLIY (SEQ ID NO: 618) | SNN |
| RA057.11_KC62.1 | TPQYPLTLSASVGDRVTITCQAS (SEQ ID NO: 619) | QDISNY (SEQ ID NO: 620) | LNWYQQKPGKAPKLLIY (SEQ ID NO: 621) | DAS |
| RA057.11_LC62.1 | QSVLTQPPSASGTPGQRVTISCSGS (SEQ ID NO: 622) | SSNIGSNT (SEQ ID NO: 623) | VNWYQQLPGTAPKLLIY (SEQ ID NO: 624) | SNN |
| RA057.11_LC67.1 | QSVLTQPASVSGSPGQSITISCTGT (SEQ ID NO: 625) | SSDVGSYNL (SEQ ID NO: 626) | VSWYQQHPGKAPKLMIY (SEQ ID NO: 627) | EGS |
| RA057.11_KC71.1 | YEPPIPVTLAVSLGERATINCKSS (SEQ ID NO: 628) | QSVLYSSNNKNY (SEQ ID NO: 629) | LAWYQQKPGQPPKLLIY (SEQ ID NO: 630) | WAS |
| RA057.11_KC82.1 | YDPPAPVTLSLSPGERATLSCRAS (SEQ ID NO: 631) | QSVSSSY (SEQ ID NO: 485) | LAWYQQKPGQAPRLLIY (SEQ ID NO: 632) | GAS |
| RA057.11_LC82.1 | QSVLTQPASVSGSPGQSITISCTGT (SEQ ID NO: 633) | SSDVGSYNL (SEQ ID NO: 634) | VSWYQQHPGKAPKLMIY (SEQ ID NO: 635) | EGS |
| RA057.11_KC89.1 | IEPTAPVTLSLSPGERATLSCRAS (SEQ ID NO: 636) | QSVSSSY (SEQ ID NO: 485) | LAWYQQKPGQAPRLLIY (SEQ ID NO: 637) | GAS |
| RA057.11_KC50.1 | HDPQAPFTLSLSPGERATMSCRAS (SEQ ID NO: 638) | LSVSSNY (SEQ ID NO: 639) | LAWYQQKPGQAPRLLIY (SEQ ID NO: 640) | GAS |
| RA057.11_LC72.1 | QSVLTQPPSASGTPGQRVTISCSGS (SEQ ID NO: 641) | RSNIGSNT (SEQ ID NO: 642) | VNWYRQLPGTAPKLLIY (SEQ ID NO: 643) | SND |
| RA057.11_LC78.1 | QSVLTQPHSVSGSPGKTVTISCTRS (SEQ ID NO: 644) | SGSIASSY (SEQ ID NO: 645) | VQWYQQRPGSSPTTVIY (SEQ ID NO: 646) | EDN |
| RA057.11_KC80.1 | SCSIFQTPATLSLSPGERDTLSCRAS (SEQ ID NO: 647) | QSVSSNY (SEQ ID NO: 648) | LSWYQQKPGQAPRLLIY (SEQ ID NO: 649) | GAS |
| RA057.11_LC93.1 | QSVLTQPASVSGSPGQSITISCTGS (SEQ ID NO: 650) | SSDVGGYDY (SEQ ID NO: 651) | VSWYQQHPGKAPKLMIF (SEQ ID NO: 652) | EVS |
| RA057.11_LC25.1 | QSVLTQPPSKSGTPGQRVTISCYGS (SEQ ID NO: 653) | RSNIGSTT (SEQ ID NO: 654) | VNWFQQLPESAPKLLIH (SEQ ID NO: 655) | SND |
| RA057.11_KC47.1 | PASPKSPVTLSLSPGERATLSCRAS (SEQ ID NO: 656) | QSVGNSF (SEQ ID NO: 657) | LAWYQQKPGQTPRLLIY (SEQ ID NO: 658) | GAS |
| RA057.11_LC47.1 | QSVLTQPASVSGSPGQSITISCTGT (SEQ ID NO: 659) | SGDVENYNV (SEQ ID NO: 660) | VSWYQQHPGKAPKLIIY (SEQ ID NO: 661) | EVT |

| Ab identifier | FR3 | CDR3 |
|---|---|---|
| RA015.11_KC88.1 | SLQSGVPSRFSGSGSGTDFTLTISSLQPEDFATYYC (SEQ ID NO: 662) | QQSYSTPYT (SEQ ID NO: 663) |
| RA015.11_KC94.1 | TLESGVPSRFSGSGSGTEFTLTISSLQPDDFATYYC (SEQ ID NO: 664) | QQYNSYSWT (SEQ ID NO: 665) |
| RA015.11_LC12.2 | ERPSGIPERFSGSNSGNTATLTISRVEAGDEADYHC (SEQ ID NO: 666) | QVWDSSSDHPGV (SEQ ID NO: 667) |
| RA015.11_KC19.2 | SRATGLPDRFSGSGSGTDFTLTISRLEPEDCAVYYC (SEQ ID NO: 668) | QQYGSSHT (SEQ ID NO: 669) |

TABLE 2-continued

VL CDR and FR amino acid sequences

| | | |
|---|---|---|
| RA015.11_KC 83.2 | TLQSGVPSRFSGSGSGTEFTLTISSLQPEDF ATYYC (SEQ ID NO: 670) | QQLNSYPLT (SEQ ID NO: 671) |
| RA015.11_KC 58.1 | TRTTGIPARFSGSGSGTEFTLTITSLQSEDF AVYYC (SEQ ID NO: 672) | QQYNNWPQST (SEQ ID NO: 673) |
| RA015.11_LC 68.1 | NRPSGVPDRFSGSKSGTSASLAITGLQAED EADYYC (SEQ ID NO: 674) | QSYDSSLSGSV (SEQ ID NO: 675) |
| RA015.11_LC 81.1 | DRPSGIPERFSGSNSGNTATLTISRVEAGD EADYFC (SEQ ID NO: 676) | QVWDSSFDRPD (SEQ ID NO: 677) |
| RA015.11_KC 91.1 | NLETGVPSRFSGSGSGTDFTFTISSLQPEDT ATYYC (SEQ ID NO: 678) | QQYANVFT (SEQ ID NO: 679) |
| RA015.11_KC 95.1 | TRESGVPDRFSGSGSGTDFTLTISSLQAED VAVYYC (SEQ ID NO: 680) | QQYYSNPYT (SEQ ID NO: 681) |
| RA015.11_KC 17.2 | SRATGIPDRISGSGSGTDFTLTISRLEPEDF VVYYC (SEQ ID NO: 682) | QQYGSSPWT (SEQ ID NO: 683) |
| RA015.11_KC 64.2 | NRATGIPARFSGSGSGTDFTLTISSLEPEDF AVYYC (SEQ ID NO: 684) | QQRSNWPGT (SEQ ID NO: 685) |
| RA015.11_LC 66.2 | KRPSGVSNRFSGSKSGNTASLTISGLQAED EADYYC (SEQ ID NO: 686) | CSYAGSSTLYV (SEQ ID NO: 687) |
| RA056.11_KC 9.2 | NRATGIPARFSGSGSGTDFTLTISSLEPEDF AVYYC (SEQ ID NO: 688) | QQRSNWPPT (SEQ ID NO: 689) |
| RA056.11_KC 34.2 | TLQSGVPSRFSGSGSGTDFTLTISSLQPEDF ATYYC (SEQ ID NO: 690) | QQLNSYPLT (SEQ ID NO: 691) |
| RA056.11_LC 38.2 | NRPSGVSDRFSGSKSGNTASLTISGLQAED EANYYC (SEQ ID NO: 692) | SSYTSSSTWV (SEQ ID NO: 693) |
| RA056.11_LC 41.2 | DRPSGIPERFSGSNSGNTATLTISRVEAGD EADYYC (SEQ ID NO: 694) | QVWDSSSDHYV (SEQ ID NO: 695) |
| RA056.11_KC 48.2 | SLQSGVPSRFSGSGSGTDFTLTISSLQPEDF ATYYC (SEQ ID NO: 696) | QQSYSTPYT (SEQ ID NO: 697) |
| RA056.11_KC 81.2 | TRATGIPARFSGSGSGTEFTLTISSLQSEDF AVYYC (SEQ ID NO: 698) | QQYNNWPLWT (SEQ ID NO: 699) |
| RA056.11_KC 29.1 | SRSTGVTDRFSGSGSGTDFTLTISRLESEDF AVYFC (SEQ ID NO: 700) | QHYESSPPVFT (SEQ ID NO: 701) |
| RA056.11_LC 33.1 | NKGDGIPDRFSGSSSGAERYLTISSLQSDD EADYYC (SEQ ID NO: 702) | QTWDTGIQV (SEQ ID NO: 703) |
| RA056.11_LC 35.1 | KRPSGVPDRFSGSKSGNTASLTVSGLQAE DEADYYC (SEQ ID NO: 704) | SSYAGSNNYV (SEQ ID NO: 705) |
| RA056.11_LC 45.1 | NKGDGIPDRFSGSSSGAERYLTISSLQSDD EADYYC (SEQ ID NO: 706) | QTWDTGIQV (SEQ ID NO: 707) |
| RA056.11_LC 56.1 | NRPSGVSHRFSGSKSGNRASLTISGLQAED EADYYC (SEQ ID NO: 708) | SSYTSSSSLLYV (SEQ ID NO: 709) |
| RA056.11_LC 66.1 | KRPSGVPDRFSGSKSDNTASLTISGLQAED EADYYC (SEQ ID NO: 710) | CSYVGSYTVA (SEQ ID NO: 711) |
| RA056.11_LC 68.1 | QRPSGVSNRFSGSKSGNTASLTISGLQTED EAHYYC (SEQ ID NO: 712) | CSYAAGNTRV (SEQ ID NO: 713) |
| RA056.11_KC 76.1 | TRATGIPARFSGSGSGTEFTLTISSLQSEDF AVYYC (SEQ ID NO: 714) | QQYNNLYT (SEQ ID NO: 715) |
| RA056.11_LC 80.1 | NRPSGVSNRFSGSKSGNTASLTISGLQAED EADYYC (SEQ ID NO: 716) | SSYTSSSTVV (SEQ ID NO: 717) |
| RA056.11_LC 12.2 | QRPSGIPDRFSGSKSGTSATLGITGLQTGD EADYYC (SEQ ID NO: 718) | GTWDSSLSAVV (SEQ ID NO: 719) |
| RA056.11_KC 20.2 | NRATGIPARFSGSGSGTDFTLTITNLEPEDF AVYYC (SEQ ID NO: 720) | QQRSNWPPT (SEQ ID NO: 721) |

TABLE 2-continued

VL CDR and FR amino acid sequences

| | | |
|---|---|---|
| RA056.11_LC 23.2 | NRPSRIPERFSGSTSGNTATLTIRTAQAGD EADYYC (SEQ ID NO: 722) | QVWDISSVV (SEQ ID NO: 723) |
| RA056.11_LC 36.2 | NRPSGVSNRFSGSKSGNTASLTISGLQAED EADYYC (SEQ ID NO: 724) | SSYTSSSTLV (SEQ ID NO: 725) |
| RA056.11_LC 39.2 | QRPSGIPDRFSGSKSGTSASLAISGLRSEDE ADYYC (SEQ ID NO: 726) | AAWDDSLSGWV (SEQ ID NO: 727) |
| RA056.11_KC 45.2 | ALQSGVPSRFSGSGSGTDFTLTISSLQPEDF ATYYC (SEQ ID NO: 728) | QQSSTTPLT (SEQ ID NO: 729) |
| RA056.11_KC 54.2 | TRATGIPARFSGSGSGTDFTLTISSLEPEDF AHYYC (SEQ ID NO: 730) | QLRSNWRT (SEQ ID NO: 731) |
| RA056.11_KC 56.2 | TLQYGVPSRFSGSGSGTDFILTISNLQPEDF ATYYC (SEQ ID NO: 732) | QQSFSMPFT (SEQ ID NO: 733) |
| RA056.11_KC 75.2 | TRKSGVPDRFSGSGSGTDFTLTISSLQAED VAVYYC (SEQ ID NO: 734) | QQYYITPPT (SEQ ID NO: 735) |
| RA056.11_KC 94.2 | NRATGVPARFSGRGSGTDFTLTISSLEPED FAVYYC (SEQ ID NO: 736) | QLRSNWLLT (SEQ ID NO: 737) |
| RA056.11_LC 95.2 | RRPSGISDRFSGSKSGDTAALTISGLQAED EADYYC (SEQ ID NO: 738) | CSYAGTWV (SEQ ID NO: 739) |
| RA056.11_LC 95.1 | IRPSGAWDCFCGSKSDYTASATMSRFQAQ DEAEYDC (SEQ ID NO: 740) | NSISSTSTNNV (SEQ ID NO: 741) |
| RA056.11_KC 96.1 | ILQSGVPSRFSGSGFGTEFTLTISSLQPEDF ATYYC (SEQ ID NO: 742) | LQHNSFPWT (SEQ ID NO: 743) |
| RA056.11_KC 58.2 | SRATGIPDRFSGSGSGTDFTLTISRLEPEDS AVYHC (SEQ ID NO: 744) | QQYGSSPGT (SEQ ID NO: 745) |
| RA056.11 KC 93.2 | TRATGIPVRFSGSGSGTEFTLSISSLQSEDF AVYLC (SEQ ID NO: 746) | QQYYNWPPIT (SEQ ID NO: 747) |
| RA057.11_KC 2.1 | NLETGVPSRFSGSGSGTDFTFTISSLQPEDI ATYYC (SEQ ID NO: 748) | QQYDNLPYT (SEQ ID NO: 749) |
| RA057.11_KC 17.1 | SLQSGVPSRFSGSGSGTDFTLTISSLQPEDF ATYYC (SEQ ID NO: 750) | QQSYSTPPLST (SEQ ID NO: 751) |
| RA057.11_LC 28.1 | QRPSGVPDRFSGSKSGTSASLAISGLQSED EADYYC (SEQ ID NO: 752) | AAWDDSLNGVV (SEQ ID NO: 753) |
| RA057.11_KC 35.1 | SRATGIPDRFSGSGSGTDFTLTISRLEPEDF AVYYC (SEQ ID NO: 754) | QQHGSSPYT (SEQ ID NO: 755) |
| RA057.11_KC 44.1 | SLESGVPSRFSGSGSGTEFTLTISSLQPDDF ATYYC (SEQ ID NO: 756) | QQYNSYPWT (SEQ ID NO: 757) |
| RA057.11_KC 51.1 | TLQSGVPSRFSGSGSGTDFTLTISCLQSEDF ATYYC (SEQ ID NO: 758) | QQYSYPT (SEQ ID NO: 759) |
| RA057.11_LC 56.1 | ERPSGLPERFSGSSSGTTVTLTISGVQAEDE ADYYC (SEQ ID NO: 760) | QSADSSGLV (SEQ ID NO: 761) |
| RA057.11_LC 61.1 | QRPSGVPDRFSGSKSGTSASLAISGLQSED EADYYC (SEQ ID NO: 762) | AAWDDSLNGWV (SEQ ID NO: 763) |
| RA057.11_KC 62.1 | NLETGVPSRFSGSGSGTDFTFTISSLQPEDI ATYYC (SEQ ID NO: 764) | QQYDNLPLT (SEQ ID NO: 765) |
| RA057.11_LC 62.1 | QRPSGVPDRFSGSKSGTSASLAISGLQSED EADYYC (SEQ ID NO: 766) | AAWDDSLNGPV (SEQ ID NO: 767) |
| RA057.11_LC 67.1 | KRPSGVSNRFSGSKSGNTASLTISGLQAED EADYYC (SEQ ID NO: 768) | CSYAGSSTL (SEQ ID NO: 769) |
| RA057.11_KC 71.1 | TRESGVPDRFSGSGSGTDFTLTISSLQAED VAVYYC (SEQ ID NO: 770) | QQYYSTPLT (SEQ ID NO: 771) |
| RA057.11_KC 82.1 | SRATGIPDRFSGSGSGTDFTLTISRLEPEDF AVYYC (SEQ ID NO: 772) | QQYGSSPPYT (SEQ ID NO: 773) |

TABLE 2-continued

VL CDR and FR amino acid sequences

| | | |
|---|---|---|
| RA057.11_LC 82.1 | KRPSGVSNRFSGSKSGNTASLTISGLQAED EADYYC (SEQ ID NO: 774) | CSYAGSPV (SEQ ID NO: 775) |
| RA057.11_KC 89.1 | SRATGIPDRFSGSGSGTDFTLTISRLEPEDF AVYYC (SEQ ID NO: 776) | QQYGSSPLT (SEQ ID NO: 777) |
| RA057.11_KC 50.1 | SRATGIPDRFSGGGSGTDYTLTISRLEPEDF AVYYC (SEQ ID NO: 778) | QQYGSSPVYS (SEQ ID NO: 779) |
| RA057.11_LC 72.1 | QRPSGVPDRFSASKSGTSASLAISGLQSED EADYYC (SEQ ID NO: 780) | SAWDNSLNGYF (SEQ ID NO: 781) |
| RA057.11_LC 78.1 | QRPSGVPDRFSGSIDSSSNSASLTITGLKTE DEADYYC (SEQ ID NO: 782) | WSYDNYQEI (SEQ ID NO: 783) |
| RA057.11_KC 80.1 | SRATGIPDRFSGSGSGTDFTLTISRLEPEDF AVYYC (SEQ ID NO: 784) | QQYGTSPWT (SEQ ID NO: 785) |
| RA057.11_LC 93.1 | NRPSGVSNRFIGSKSGNTASLTISGLQAED EADYYC (SEQ ID NO: 786) | SSYTTSSDLV (SEQ ID NO: 787) |
| RA057.11_LC 25.1 | QRPSGVPDRFSGSKSDTSASLAISGLQSED EADYYC (SEQ ID NO: 788) | AAWDASLKV (SEQ ID NO: 789) |
| RA057.11_KC 47.1 | SRATGIPDRFSGSGSGTDFTLTISRLEREDF AVYYC (SEQ ID NO: 790) | QQYGSSPGT (SEQ ID NO: 791) |
| RA057.11_LC 47.1 | KRPSGVSNRFSGSKSGNTASLTISGLQAED EADYYC (SEQ ID NO: 792) | CSSASFTISWV (SEQ ID NO: 793) |

TABLE 2A

VL CDR and FR amino acid sequences

| Ab identifier | FR1 | CDR1 | FR2 | CDR2 |
|---|---|---|---|---|
| RA061.11_K C29.1 | CCSMTQSPATLSASVGDR VTISCQAN (SEQ ID NO: 794) | QDIKKS (SEQ ID NO: 795) | FNWYHQKPGRA PKVLIY (SEQ ID NO: 796) | DSV |
| RA061.11_K C35.1 | SCSMTQSPVTLSASVGDR VTITCRAS (SEQ ID NO: 797) | QTIYSW (SEQ ID NO: 798) | LAWYQQKPGKA PKLLIY (SEQ ID NO: 799) | QAS |
| RA061.11_L C40.1 | SYELTQPLSVSVALGQTA RITCGGN (SEQ ID NO: 800) | NIGSKN (SEQ ID NO: 801) | VHWYQQKPGQA PVLVIY (SEQ ID NO: 802) | RDS |
| RA061.11_K C43.1 | CRAMTQSPVTLSVSPGER ATLSCRAS (SEQ ID NO: 803) | QRVSSN (SEQ ID NO: 804) | LAWYQQKPGQA PRLLIY (SEQ ID NO: 805) | GAS |
| RA061.11_K C44.1 | CCSMTQTPATLSASVGDR VTITCRAS (SEQ ID NO: 806) | QSISSW (SEQ ID NO: 807) | LAWYQQKPGKA PKLLIY (SEQ ID NO: 808) | KAS |
| RA061.11_K C47.1 | VWSMTQTPGTLSASVGD RVTITCRAS (SEQ ID NO: 809) | QGISNY (SEQ ID NO: 810) | LAWFQQKPGKA PKSLIY (SEQ ID NO: 811) | AAS |
| RA061.11_K C65.1 | AMTQSPVTLSASVGDRVT ITCRAS (SEQ ID NO: 812) | QFISSA (SEQ ID NO: 813) | LAWYQQKPGKA PKLLIY (SEQ ID NO: 814) | DAS |
| RA061.11_K C66.1 | VCSMTQSPATLSLSPGER ATLSCRAS (SEQ ID NO: 815) | QSVSTSY (SEQ ID NO: 816) | LAWYQQKPGQA PRLLMY (SEQ ID NO: 817) | GAS |
| RA061.11_K C67.1 | SWSMTQSPATLSLSAGER ATLSCRAS (SEQ ID NO: 818) | QSVTTF (SEQ ID NO: 819) | LAWYQQKPGQA PRLLIY (SEQ ID NO: 820) | DAT |

TABLE 2A-continued

VL CDR and FR amino acid sequences

| Ab identifier | FR1 | CDR1 | FR2 | CDR2 |
|---|---|---|---|---|
| RA061.11_KC71.1 | VCSMTQTPGTLSLSPGERATLSCRAS (SEQ ID NO: 821) | QSVSSSY (SEQ ID NO: 485) | LAWYQQKPGQAPRLLIY (SEQ ID NO: 822) | GAS |
| RA061.11_KC72.1 | VWFMDQSPGALCLSAGERATLSCRAS (SEQ ID NO: 823) | QSVSSSY (SEQ ID NO: 485) | LAWCQQKPFQAPRLLME (SEQ ID NO: 824) | WCI |
| RA061.11_KC80.1 | CCSMTQSPVTLPVTLGQPASISCRSS (SEQ ID NO: 825) | QSLVHSDGNTY (SEQ ID NO: 826) | LNWFQQRPGQSPRRLIY (SEQ ID NO: 827) | KVS |
| RA061.11_KC82.1 | CWSMTQTPVTLPVTLGQPASISCRSS (SEQ ID NO: 828) | QSLVYSDGNTY (SEQ ID NO: 829) | LNWFQQRPGQSPRRLIY (SEQ ID NO: 830) | KVS |
| RA061.11_LC89.1 | QSVLTQPPSVSGSPGQSVTISCTGT (SEQ ID NO: 831) | NSDVGTYDR (SEQ ID NO: 832) | VSWYQQPPGTAPKLIIY (SEQ ID NO: 833) | EVN |
| RA061.11_KC90.1 | CCSMTQTPGVLGLSPGERATLSCRVS (SEQ ID NO: 834) | QRKTSTS (SEQ ID NO: 835) | LVRYQQRPGQAPTLLMY (SEQ ID NO: 836) | GTS |
| RA061.11_KC95.1 | CCALTQSPATLPVTPGEPASISCKSS (SEQ ID NO: 837) | QSLLHSNGYNY (SEQ ID NO: 838) | LAWYLQKPGQSPQLLFY (SEQ ID NO: 839) | LGS |

| Ab identifier | FR3 | CDR3 |
|---|---|---|
| RA061.11_KC29.1 | ILETGVPSRFSGSGSGTHFTLTISSLQPEDIGTYYC (SEQ ID NO: 840) | QQYEHLPLT (SEQ ID NO: 841) |
| RA061.11_KC35.1 | NLEIGVPSRFSGSGSGTEFTLTISSLQPDDFATYYC (SEQ ID NO: 842) | QQYSTDSLYT (SEQ ID NO: 843) |
| RA061.11_LC40.1 | NRPSGIPERFSGSNSGNTATLTISRAQAGDEADYYC (SEQ ID NO: 844) | QVWDSSTVV (SEQ ID NO: 845) |
| RA061.11_KC43.1 | TRATGIPARFSGSGSGTDFTLTISDIQSEDFAYYYC (SEQ ID NO: 846) | QHYNNWPPWT (SEQ ID NO: 847) |
| RA061.11_KC44.1 | SLESGVPSRFSGSGSGTEFTLTISSLQPDDFATYYC (SEQ ID NO: 848) | QQYNSYSLA (SEQ ID NO: 849) |
| RA061.11_KC47.1 | SLQSGVPSKFSGSGSGTDFTLAISSLQPEDFATYYC (SEQ ID NO: 850) | QQYNSYPLT (SEQ ID NO: 581) |
| RA061.11_KC65.1 | SLESGVPSRFSGSGSGTDFTLTISSLQPEDFATYYC (SEQ ID NO: 852) | QQFNSYPST (SEQ ID NO: 853) |
| RA061.11_KC66.1 | RRAAGISDRFSGSGSGTDFALTISRLEPEDFAVYYC (SEQ ID NO: 854) | QEYGSSPGT (SEQ ID NO: 855) |
| RA061.11_KC67.1 | NRATGIPARFSGSGSGTDFTLTISSLEPEDFAVYYC (SEQ ID NO: 856) | QHRYGWPPG (SEQ ID NO: 857) |
| RA061.11_KC71.1 | SRATGIPDRFSGSGSGTDFTLTISRLEPEDFAVYYC (SEQ ID NO: 858) | QQYGSSPNT (SEQ ID NO: 859) |
| RA061.11_KC72.1 | QQGHWHPRQVQWQWVWDKTSLSPSADWSLKILHCIT (SEQ ID NO: 860) | VSSMVAHLS (SEQ ID NO: 861) |
| RA061.11_KC80.1 | NRDSGVPDRFSGSGSGTDFTLKISRVEAEDVGVYYC (SEQ ID NO: 862) | MQGTHWPPWT (SEQ ID NO: 863) |
| RA061.11_KC82.1 | NWDSGVPDRFSGSGSGTDFTLKISRVEAEDVGVYYC (SEQ ID NO: 864) | MQGTLHRF (SEQ ID NO: 865) |
| RA061.11_LC89.1 | NRPSGVPDRFSGSKSGNTASLTISGLQAEDEADYYC (SEQ ID NO: 866) | CSYRSGRTFV (SEQ ID NO: 867) |
| RA061.11_KC90.1 | NRATGIPDRFSGSGSGTDFTVTISRLEPEDFAMYYC (SEQ ID NO: 868) | QQFDSSPWT (SEQ ID NO: 869) |

TABLE 2A-continued

VL CDR and FR amino acid sequences

| | | | |
|---|---|---|---|
| RA061.11_KC 95.1 | DRASGVPDRFSGSGSGTDFTLKISRVEPED VGVYYC (SEQ ID NO: 870) | | MQGLHTPLT (SEQ ID NO: 871) |

TABLE 3

VH amino acid sequences (VDJ)

| Ab identifier | V-D-J-REGION |
|---|---|
| RA015-11_88.1 | EVQLEESGPGLVKPSETLSLTCTVSGGSISSYYWSWIRQPAGKGLEWIGRIYTSGS TNYNPSLKSRVTMSVDTSKNQFSLKLSSVTAADTAVYYCAREVPTPYFDLWGRG TLVTVSS (SEQ ID NO: 872) |
| RA015-11_94.1 | QVQLVESGAEVKKPGASVKVSCKASGYSFTSYAMHWVRQAPGQRLEWMGWIN DGNGNTKYSQKFQGRVTITRDTSASTAYMGLSSLRSEDTAVYYCARGGEDGYG DSYNAFDLWGQGTMVTVSQ (SEQ ID NO: 873) |
| RA015-11_12.2 | EVQLVESGGGLVKPGGSLRLSCAASGFTFSNAWMSWVRQAPGKGLEWVGRIKS KANGETIDYAAPVKGRFTISRDDSKNTLYLQMNSLKTEDTAVYYCATHFESCGG DCSNWWGQGTLVTVSS (SEQ ID NO: 874) |
| RA015-11_19.2 | QVQLVQSGAEVKKPGASVKVSCKASGYTFTGYYMHWVRQAPGQGLEWMGWI NPNSGDTNYAQKFQGRVIMTRDTSISAAYMELSSLRSDDTAVYYCGRVGGGRQL WLKDNYDYFYMDVWGKGTTVTVSS (SEQ ID NO: 875) |
| RA015-11_83.2 | EVQLVESGGGLVQPGGSLRLSCTASGFTFSSYEMNWVRQAPGKGLEWVSYISSS GTTIYYADSVKGRFTISRDNAKNSLYLQMHSLRAEDTAVYYCARDMPHFLYSSR WYPFDYWGQGTPVTVSS (SEQ ID NO: 876) |
| RA015-11_58.1 | QVQLVESGGGLVQSGGSLRLSCSASGFRFSGHAMHWVRQPAGKGLEYISAISGN GEATYYAGSVKGRFTISRDNFKNTLYLQMTSLRPEDTAVYYCVTEIVGANRWVP VGPWGQGTLVTVSS (SEQ ID NO: 877) |
| RA015-11_68.1 | EVQLEESGPGLVKPSQTLSLTCTVSGGSISSGDYYWSWIRQHPGKGLEWIGYIYY SGSTYYNPSLKSRVTISVDTSKNQFSLKLSSVTAADTAVYYCARAISWADGYYM DVWGKGTTVTVSS (SEQ ID NO: 878) |
| RA015-11_81.1 | EVQLVESGAEVKKPGASVKVSCKASGYTFSDYFIHWVRQAPGQGLEWMGWINP HSDDTNIAQKFQGRVTLPMDTSISTAYMEITRLESDDTAIYYCARGAYGDPLHIW GQGTVVTVSS (SEQ ID NO: 879) |
| RA015-11_91.1 | EVQLVESGGGLVKPGGSLRLSCAASGFTFSTYTMIWVRQAPGKGLEWVSSISGSG SYIFYADSVKGRFTISRDNPKNSLYLQMNSLRADDTAVYYCARWRAGVPSYFDY WGQGTLVTVSS (SEQ ID NO: 880) |
| RA015-11_95.1 | EVQLVQSGPEVKKPGTSVKVSCKASGFTSSRSAVQWLRQTRGQRLEWIGGIVVG SGNTNYAPNFQDRVTITWDMSTRTAYMELSSLRSEDTAVYYCARGGSYVDYWG QGTLVTISS (SEQ ID NO: 881) |
| RA015-11_17.2 | EVQLVESGGGFVQPGGSLRLSCAASGFSIGNYALTWVRQAPGKRLEWVSSITGS GGDTYNADFMKGRFTMSRDLYKNTLYLHMNSLRAEDTAIYYCAKSPTDFWDD YLYYFDSWGQGTLVTVSS (SEQ ID NO: 882) |
| RA015-11_64.2 | EVQLVESGGDLVQPGRSLRLSCAASGFTFDDYDMHWVRQAPGKGLEWVSGIRW NSDTIGYADSVKGRFTISRDNARNSLYLQMNSLRAEDTALYYCAKDISSYDDTSG YYYNWGQGTLVTVSS (SEQ ID NO: 883) |
| RA015-11_66.2 | EVQLQESGPGLVKPSGTLSLTCAVSGGSISITNWWTWVRQPPGKGLEWIGEIYHS GYTNYNPSLKTRVTISVDKSKNHLSLKLSFVTAADTAVYYCARKGTYSTDSYDG FDIWGQGTMVTVSS (SEQ ID NO: 884) |
| RA056-11_9.2 | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCANCETGERRWY YYGSGTIREAFDIWGQGTMVTVSQ (SEQ ID NO: 885) |
| RA056-11_34.2 | EVQLVESGGGLVKPGGSLRLSCAASGFTFSSYSMNWVRQAPGKGLEWVSSISSSS SYIYYADSVKGRFTISRDNAKNSLYLQMNSLRAEDTAVYYCARPRQLGSVWFDP WGQGTLVTVSS (SEQ ID NO: 886) |
| RA056-11_38.2 | EVQLEESGGGVVQPGRSLRLSCAASGFTFSRNGMHWVRQAPGKGLEWVAVIWY DGSNRYYTDSVKGRFTISRDNSRNTLYLQMDSLKPEDTALYYCAKDRSSSWYFD HWGQGALITISS (SEQ ID NO: 887) |

TABLE 3-continued

| VH amino acid sequences (VDJ) | |
|---|---|
| Ab identifier | V-D-J-REGION |
| RA056-11_41.2 | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCARGSGTFDYWG QGTLVTVSS (SEQ ID NO: 888) |
| RA056-11_48.2 | QVQLQESGPGLVKPSQTLSLTCTVSGGSISSGGYYWSWIRQHPGKGLEWIGYIYY SGSTYYNPSLKSRVTISVDTSKNQFSLKLSSVTAADTAVYYCARVSLNSSSSLIHY YYYMDVWGKGTTVTWRA (SEQ ID NO: 889) |
| RA056-11_81.2 | EVQLVESGGGLVQPGGSLRLSCSASGFTFSSYAMHWVRQAPGKGLEYVSAISSN GGSTYYADSVKGRFTISRDNSKNTLYLQMSSLRAEDTAVYYCVKEYDFWSGYY YRGATRTTPNFDYWGQGTLVTVSS (SEQ ID NO: 890) |
| RA056-11_29.1 | EVQLVESGAEVKKPGASVKVSCKASGYTFNTYEINWVRQATGQGLEWMGWMN PNSGDTVYAQKCQGRVSMTRHTSTSTASMELISLIFEDTAVYYCARAAGVGVAL DYWGQGTLLTVSS (SEQ ID NO: 891) |
| RA056-11_33.1 | EVQLVESGGGLVKPGGSLRLSCAASGFTFSNAWMSWVRQAPGKGLEWVGRIKS KANGETLDYAAPVKGRLTISRDDSKNTLYLQMNSLKTEDTAVYYCATHFESCGG DCSNWWGQGTLVTVSS (SEQ ID NO: 892) |
| RA056-11_35.1 | QVQLVESGGGLVQPGGSLRLSCAASGFTFSSYEMNWVRQAPGKGLEWVSYICSS GSTIYYADSVKGRFTISRDNAKNSLYLQMNSLRAEDTAVYYCAGVHMYYYDSS GYYYDDYWGQGTMVTVSS (SEQ ID NO: 893) |
| RA056-11_45.1 | EVQLVESGGGVVQPGRSLRLSCGATGFTFSSHAMHWVRQVAGKGLEWVAVISD DSSEKYYADSVRGRFIISRDNAKDTVYLQMNSLRPDDTAVYYCATPHRLLDSCSS TSCYVVAFDLWGHGTMVTVSL (SEQ ID NO: 894) |
| RA056-11_56.1 | QVQLVESGGGLVQPGESLRLSCAASGFTFGNYAMSWVRQAPGKGLAWVAATS GSGGSTYYAGSVK*CFTISRDNSKITLYLQVHSLRPEDTAVYYCAKGTLSGFATT FDYWGQGTLVTVSS (SEQ ID NO: 895) |
| RA056-11_66.1 | QVQLQESGPRLVKPSETLSLTCTVSGGSISSSDHYWAWIRQPPGKGLAYIGIIYYT GSTYYNPSLKSRVSISVDTSKNQFSLNVNSVTAADTGVYYCARRHIGRHYYFDY WGQGTLVTVSS (SEQ ID NO: 896) |
| RA056-11_68.1 | EVQLVESGPGLVRPSQTLSLTCTVAGGSVSSGSYHWSWIRQPPGKGLEWIGYIFY SGTTKYNPSLKSRVTISTDVSKNQFSLKLKSVTAADTAVYYCARDASIAARPPWG MDVWGQGTTVTVSS (SEQ ID NO: 897) |
| RA056-11_76.1 | QVQLVESGAEVKKPGSSVKVSCKASGGTFSSYAISWVRQAPGQGLEWMGGIIPIF GTANYAQKFQGRVTITADESTSTAYMELSSLRSEDTAVYYCARVRITIFGVVMV KSDNWFDPWGQGTLVTVSS (SEQ ID NO: 898) |
| RA056-11_80.1 | EVQLVESGGGLVQPGGSLRLSCAASGFTFSSYEMNWVRQAPGKGLEWVSYIICS DGVIYYADSVKGRFTISRDNAKNSLYLQMNSLRAEDTAVYYCAGVHLYYYDSS GYYYDDYWGQGTMVTVSS (SEQ ID NO: 899) |
| RA056-11_12.2 | EVQLVESGPGLVKPSETLSLTCTVSGGSISPYYWNWIRQPPGKRLEWIGYVYYNG NTNYNPSLKSRVTISVDTPKNQFSLRLSSVTAADTAVYYCSGYGVDYFDYWGQG TLVTVSS (SEQ ID NO: 900) |
| RA056-11_20.2 | QVQLVQSGAEVKKSGESLWISCKGSGYSFTRYWIGWVRQMPGKGLEWMGIISP GDSNTRYSPSFQGQVTISADKSISTAYLQLSSLKASDIATYYCARQGYYDRSPRPH YMDVWGKGTTVTVSS (SEQ ID NO: 901) |
| RA056-11_23.2 | EVQLVESGGGVVKPGRSLRLSCAASGFNLSSYGMHWVRQAPGKGLEWVAVVW YDGRNKFYTDSVKGRFTISRDNSINSVYLQMNSLRAEDTAIYYCARVTSRVVAA AGGYFDHWGQGTLVTVSS (SEQ ID NO: 902) |
| RA056-11_36.2 | EVQLQESGPRLVKPSETLSLTCTVSGGSISSSDHYWAWIRQPPGKGLAYIGIIYYT GSTYYNPSLKSRVSISVDTSKNQFSLNVNSVTAADTGVYYCARRHIGRHYYFDY WGQGTLVTVSS (SEQ ID NO: 903) |
| RA056-11_39.2 | QVQLVESGGDLVQPGRSLRLSCAASGFTFDDYDMHWVRQAPGKGLEWVSGIR WNSDTIGYADSVKGRFTISRDNARNSLYLQMNSLRAEDTALYYCAKDISSYDDT SGYYYNWGQGTLVTVSS (SEQ ID NO: 904) |
| RA056-11_45.2 | QVQLVESGGGVVQPGRSLRLSCAASGFTFSNYGIHWVRQAPGKGLEWMAFISHD GSKKNYADSVKGRFTISRDNSKNTLYLQMNRLRVEDTAIYHCAKDIVVVPAATS LLGGYYYYMDVWGKGTTTVTVSS (SEQ ID NO: 905) |
| RA056-11_54.2 | QVQLVESGAEVKTPGASVKVSCKTSGYTFTSYYIHWVRQAPGQGLEWMGIINPS AGSTTYPQKFQGRVTMTRDRSTSTVYMELSSLRSEDTAVYYCARDGLEARRTTS SHPHYYMDVWDKGTTVTVSS (SEQ ID NO: 906) |

TABLE 3-continued

VH amino acid sequences (VDJ)

Ab
identifier V-D-J-REGION

RA056-　　QVQLQQWGAGLLKPSETLSLTCVVYGGSFSGYYWSIRQSPGKGLEWIGEVNH
11_56.2　　SGSSYYNPSLKSRVTISVDTSKDQFSLKLTSVTAADTAVYYCAKKKGRVGIAYM
　　　　　　EVWDKGTTVTISS (SEQ ID NO: 907)

RA056-　　EVQLQQSGPGLVKPSETLSLTCTVSGGSISSYYWSWIRQPPGKGLEWIGYIHHSGS
11_75.2　　ADYNPSLKGRVTISLDTSKKQFSLKLRFVTTADTALYYCARTPYPPLDWYFDLW
　　　　　　GRGTLVTVSS (SEQ ID NO: 908)

RA056-　　QVQLVQSGGGVVQPGRSLRLSCAASGFTFSGYGMHWVRQAPGKGLEWVAFISF
11_94.2　　DGSDKYYAASVKGRFTLSRDNSKNTLYLKINSLRTEDTAVYYCAKEVREYTDY
　　　　　　WGQGTLVTVSS (SEQ ID NO: 909)

RA056-　　EVQLVESGGGLVQPGGSLRLSCAASGFTFTDNAMTWVRQAPGKGLEWVSTIRN
11_95.2　　NGQNTYYTDSVKGRFTISRDNFNNMVYLQMSSLRAEDTAVYYCAKLVGITHLS
　　　　　　AAPWTWGQGTMVTVSS (SEQ ID NO: 910)

RA056-　　EVQLVESGGGLVQPGGSLRLSCAVSGFTFRNYAMSWVRQAPGKGLEWVSSISDT
11_95.1　　GFSTYYADSVKGRFAISRDNSKNRLYLEMNSLRADDTAIYYCAKVPHQLVPIWF
　　　　　　DPWGQGTQVTVSS (SEQ ID NO: 911)

RA056-　　VQLVEMGGGRIVQPGRSLSLSCAASGFSFSSHAMHWVRQAPGKGLEWVAVISY
11_96.2　　DGGDKNYADSVRGRFTISRDNSEDTLYLQMNGLRTEDTAMYFCTRDARGVRNA
　　　　　　FDLWGQGTMLTVSS (SEQ ID NO: 912)

RA056-　　QVQLVQSGADVKKPGASVKISCKASGYTFTAYAIHWVRQAPGQRLEWMGWIN
11_58.2　　AGNGNTKYSQKFQGRVTITRDTSANTSYMDLSSLRSEDTAVYFCARSLYCSTHS
　　　　　　CSFLHLYWGQGALVTVSS (SEQ ID NO: 913)

RA056-　　EVQLQESGPGLVEPSGTLSLTCVVSGGSITSSNWWSWVRQPPGKGPEWIGEIYHI
11_93.2　　GDSNYNPSLKSRVTMSVDKSKNQFSLKLRSVTAADTAIYYCARTFWSGSYSRYF
　　　　　　DSWGQGTLVTVSS (SEQ ID NO: 914)

RA057.1　　QVQLVESGAEVKKPGASVKVSCKASGYTFTSYYMHWVRQAPGQGLEWMGIINP
1_2.1　　　SGGSTSYAQKFQGRVTMTRDTSTSTVYMELSSLRSEDTAVYYCARFGRHDYGG
　　　　　　KDDYWGQGTLVTVSS (SEQ ID NO: 915)

RA057.1　　QVQLVESGPGLVKPSQTLSLTCTVSGGSISSGGYYWSWIRQHPGKGLEWIGYIYY
1_17.1　　 SGSTYYNPSLKSRVTISVDTSKNQFSLKLSSVTAADTAVYYCARDQITMVRGGD
　　　　　　GQNYYYYMDVWGKGTTVTVSS (SEQ ID NO: 916)

RA057.1　　QVQLVESGGGLVKPGGSLRLSCAASGFTFSSYSMNWVRQAPGKGLEWVSSISSS
1_28.1　　 SSYIYYADSVKGRFTISRDNAKNSLYLQMNSLRAEDTAVYYCARDVGDIVVVTA
　　　　　　SLDYWGQGTLVTVSS (SEQ ID NO: 917)

RA057.1　　QVQLVEWGAGLLKPSETLSLTCAVYGGSFSGYYWSWIRQPPGKGLEWIGEINHS
1_35.1　　 GSTNYNPSLKSRVTISVDTSKNQFSLKLSSVTAADTAVYYCARGWAYSSSWYRR
　　　　　　MISFDYWGQGTLVTVSS (SEQ ID NO: 918)

RA057.1　　QVQLVQSGAEVKKPGASVKVSCKASGYTFTSYYMHWVRQAPGQGLEWMGIINP
1_44.1　　 SGGSTSYAQKFQGRVTMTRDTSTSTVYMELSSLRSEDTAVYYCARVGGGYYDSS
　　　　　　GGALDYWGQGTLVTVSS (SEQ ID NO: 919)

RA057.1　　EVQLEESGPGLVKPSETLSLTCTVSGGSISSYYWSWIRQPPGKGLEWIGYIYYSGS
1_51.1　　 TNYNPSLKSRVTISVDTSKNQFSLKLSSVTAADTAVYYCARRVGSPYCGGDCYP
　　　　　　AFDIWGQGTMVTVSQ (SEQ ID NO: 920)

RA057.1　　QVQLVESGAEVKKPGESLKISCKGSGYSFTSYWIGWVRQMPGKGLEWMGIIYPG
1_56.1　　 DSDTRYSPSFQGQVTISADKSISTAYLQWSSLKASDTAMYYCARILVDCSSTSCY
　　　　　　YYYYYMDVWGKGTTVTVS (SEQ ID NO: 921)

RA057.1　　QVQLVESGGGLVKPGGSLRLSCAASGFTFSSYSMNWVRQAPGKGLEWVSSISSS
1_61.1　　 SSYIYYADSVKGRFTISRDNAKNSLYLQMNSLRAEDTAVYYCARGGSSWYYFDY
　　　　　　WGQGTLVTVSS (SEQ ID NO: 922)

RA057.1　　QVQLVESGGGLVQPGGSLRLSCAASGFTFSSYWMSWVRQAPGKGLEWVANIKQ
1_62.1　　 DGSEKYYVDSVKGRFTISRDNAKNSLYLQMNSLRAEDTAVYYCARELFHILSYW
　　　　　　GQGTLVTVSS (SEQ ID NO: 923)

RA057.1　　EVQLQESGPGLVKPSETLSLTCTVSGGSISSYYWSWIRQPPGKGLEWIGYIYYSGS
1_67.1　　 TNYNPSLKSRVTISVDTSKNQFSLKLSSVTAADTAVYYCARRESSRLGNAFDIWG
　　　　　　QGTMVTVSQ (SEQ ID NO: 924)

TABLE 3-continued

VH amino acid sequences (VDJ)

| Ab identifier | V-D-J-REGION |
|---|---|
| RA057.1 1_71.1 | QVQLVQSGAEVKKPGASVKVSCKASGYTFTSYGISWVRQAPGQGLEWMGWISA YNGNTNYAQKLQGRVTMTTDTSTSTAYMELRSLRSDDTAVYYCARDLNSYYFD YWGQGTLVTVSS (SEQ ID NO: 925) |
| RA057.1 1_82.1 | QVQLVESGAEVKKPGASVKVSCKVSGYTLTELSMHWVRQAPGKGLEWMGGFD PEDGETIYAQKFQGRVTMTEDTSTDTAYMELSSLRSEDTAVYYCATPIVLGAFDI WGQGTMVTVSQ (SEQ ID NO: 926) |
| RA057.1 1_89.1 | QVQLVQSGAEVKKPGASVKVSCKASGYTFTSYGISWVRQAPGQGLEWMGWISA YNGNTNYAQKLQGRVTMTTDTSTSTAYMELRSLRSDDTAVYYCARRYCSSTSC YKGSYYYYYYMDVWGKGTTVTVSS (SEQ ID NO: 927) |
| RA057.1 1_50.1 | QVQLVESGGGLVQPGRSLRLSCAASGFTFEDYAMHWVRQVPGKGLEWVSSISW NSVTIDYADSVKGRFTISRDNARNSLYLQMNSLRPEDTALYYCAAGSYRYYYYC IDVWGKGTTVTVSS (SEQ ID NO: 928) |
| RA057.1 1_72.1 | QVQLVESGGGLVQPGGSLRLSCAASGFTFYDYDMSWVRQAPGKGLQWVSTITL SGVTAYYADSVKGRFTISRDNSKNMVYLQMNSLRAEDTAVYYCAKHWDSWGQ GTPVTVSS (SEQ ID NO: 929) |
| RA057.1 1_78.1 | QVQLVESGGGLVKPGGSLRLSCAASGFTFSSYSMNWVRQAPGKGLEWVSFISSS SSYMHYADSVKDRFIISRDNANNSLYLQMNSLTAEDTGVYYCARLGYDFWSGH RHWGQGTLVTVSS (SEQ ID NO: 930) |
| RA057.1 1_80.1 | QVQLVESGGGLVQPGGSLRLSCAASGFTFSSYEMNWVRQAPGKGLEWVSYICSS GSTIYYADSVKGRFTISRDNAKNSLYLQMNSLRAEDTAVYYCVGVHLYYYDSSG YYYDDYWGQGTLVTVSS (SEQ ID NO: 931) |
| RA057.1 1_93.1 | QVQLVESGGGLVQPGGSLRLSCAASGFTFSSYWMHWVRQAPGKGLVWVARIKT DGSITGHADSVKGRFSVSRDNAKNTLYLQMNSLRAEDTGVYFCARDGGEAYDF WSDNHRFYFYYYMDVWGKGTTVSVSS (SEQ ID NO: 932) |
| RA057.1 1_25.1 | EVQLVESGGGLVQPGGSLRLSCAAPGFSFSSHWMSWVRQAPGKGLEWVANIKA DGSEKYYIDSVKGRFSISRDNAKKSLYLQMNSLRAEDTAVYYCARDQVEQQLVL GYFYYYMDVWGKGTTVTVSS (SEQ ID NO: 933) |
| RA057.1 1_47.1 | QVQLVQSGGGLVQPGGSLRLSCAASGFTFSNYWMTWVRQAPGKGLEWVANIK QDGSQKYYVDSVKGRFTISRDNAENSLYLQMNGLRAEDTAVYYCARDPRAYDY WSGYYEGYFDYWGQGSLVTVSS (SEQ ID NO: 934) |

TABLE 3A

VH amino acid sequences (VDJ)

| Ab identifier | V-D-J-REGION |
|---|---|
| RA061.1 1_G29.1 | QVQLQESGSGLVRSSQNLSLTCSVSGGSVSRGGASWGWVRQPPGQGLEWIGYIT HSGTTFSNPSLKSRVMISKDKSQNHFSLSLTSVTVADTAVYFCARWSTAFDRWG QGTLVTVSS (SEQ ID NO: 935) |
| RA061.1 1_G35.1 | EVQLVESGGGSVQPGGSLRLSCAASGFTFSSHWIHWVRQAPGKGLVCVSRINSD GSSTSYADSVKGRFTISRDNAKNMVYLQMNSLRAEDTAVDLGTSDRRSQFRRSG RAPWDAFDIWGQGTMVTVSS (SEQ ID NO: 936) |
| RA061.1 1_G40.1 | QVQLVESGGGLVQPGGSLRLSCATSRFTFSNYAMNWVRQAPGKGLEWVSAISGS GGTTYYADSVKGRFTISRDNSRNSLYLQMNSLRGEDTAVYYCVKESVGALLWEI DDWQFFDYWGQGTLVTVSS (SEQ ID NO: 937) |
| RA061.1 1_M43.1 | EVQLQESGPGLVKPSETLSLTCTVSGGSITSDTFYWGWVRQPPGKGLEWIASISYS GSTFYNPSLKSRVTMSVDTSKNQFSLHLNSVTAADTAVFYCAKHGGGMATSFD YWGQGTLVTVSS (SEQ ID NO: 938) |
| RA061.1 1_M44.1 | EVQLVQSGAEVKKPGASVKVSCKASGYTFTSYGISWVRQAPGQGLEWMGWISA YNGNTNYAQKLQGRVTMTTDTSTSTAYMELRSLRSDDTAVYYCARDTDHYFD YWGQGTLVTVSS (SEQ ID NO: 939) |
| RA061.1 1_M47.1 | QVQLVQSGAEVKKPGASVKVSCKASGYTFTSYYMHWVRQAPGQGLEWMGIINP SGGSTSYAQKFQGRVTMTRDTSTSTVYMELSSLRSEDTAVYYCAREGAIAAAGF DYWGQGTLVTVSS (SEQ ID NO: 940) |

TABLE 3A-continued

VH amino acid sequences (VDJ)

| Ab identifier | V-D-J-REGION |
|---|---|
| RA061.1 1_G65.1 | QVQLVESGGVVVQPGGSLRLSCAASGFTFDDYAIHWVRQAPGKGLEWVSLISW DGGSTYYADSVKGRFTISRDNSKNSLYLQMNSLRTEDTALYYCAKDTAILFGGSS FDYWGQGTLVTVSS (SEQ ID NO: 941) |
| RA061.1 1_G66.1 | QVQLVESGGGLIQPGGSLRLSCAASGFTVSGNYMSWVRQAPGRGLEWVSVIYST GDTYYAESVKGRFTVSRDDNSKSSVKVVVEQTESRGHGRVLLCERKGQWLVQR YGRLGQGTTVTVSS (SEQ ID NO: 942) |
| RA061.1 1_G67.1 | QVQLVQSGAEVKKPGESLKISCHGSGYTFSNYWIGWVRQMPGKGLEWMGIIYT GDSYSRYSPSFQGLGDVAVDESLSTAYLEWSSLKASDTAMYYCVRQWENRGWS IAYWGQGTLVTVSS (SEQ ID NO: 943) |
| RA061.1 1_M71.1 | EVQLQESGPGLVKPSETLSLTCTVSGGSISSSSYYWGWIRQPPGKGLEWIGSIYYS GSTYYNPSLKSRVTISVDTSKNQFSLKLSSVTAADTAVYYCARHLRYNWFDPWG QGTLVTVSS (SEQ ID NO: 944) |
| RA061.1 1_M72.1 | EVQLVESGGGLVQPGGSLRLSCAASGFTFSSYAMSWVRQAPGKGLEWVSAISGS GGSTYYADSVKGRFTISRDNSKNTLYLQMNSLRAEDTAVYYCAKMLFTPWEVT WLRPYFDYWGQGTLVTVSS (SEQ ID NO: 945) |
| RA061.1 1_M80.1 | EVQLVESGGGLVQPGGSLRLSCAASGFTFSSYWMHWVRQAPGKGLVWVSRINS DGSSTSYADSVKGRFTISRDNAKNTLYLQMNSLRAEDTAVYYCASLVPAAGGD YWGQGTLVTVSS (SEQ ID NO: 946) |
| RA061.1 1_M82.1 | QVQLVESGGGLVQPGGSLRLSCAASGFTFSSYSMNWVRQAPGKGLEWVSYISSS SSTIYYADSVKGRFTISRDNAKNSLYLQMNSLRAEDTAVYYCARGSPYSSSSSVR GMDVWGQGTTVTVSS (SEQ ID NO: 947) |
| RA061.1 1_A89.1 | QVQLVQSGGGLVQPGGSLTLSCAVSGFTVRSSYVSWLRQTPGKGLEWVSVIFSG GSTSYADFVKGRFTMSRDNSKNTLYLQMDSLRSDDTAVYYCAKGGWELTNWF DPWGQGTLVTVSS (SEQ ID NO: 948) |
| RA061.1 1_A90.1 | EVQLVESGGGLVQPGGSLRLSCEASGFNFENYAMDWVRQAPGKGLEWVSGITW NSGKIHYADSVKGRFTISRDNAKNSLFLQMNNLRHEDTALYYCAKASGEDFPDY WGQGTLVTVSS (SEQ ID NO: 949) |
| RA061.1 1_A95.1 | QVQLVESGGCVVQPGRSLRLSCAASGFTFSTYAMYWVRQAPGEGLEWVAVISY HGSNKYYADSVKGRFTISRDNSKNTLYLLMNSLRAEDTAVYYCARDPGWSGSI MDYYYGMDVWGQGTTVIVSP (SEQ ID NO: 950) |

TABLE 4

VL amino acid sequence (VJ)

| Ab identifier | V-J-REGION |
|---|---|
| RA015.11_ KC88.1 | FVSQTPATLSASVGDRVTITCRASQSISSYLNWYQQKPGKVPKLLIYAASSLQS GVPSRFSGSGSGTDFTLTISSLQPEDFATYYCQQSYSTPYTFGQGTKLEIK (SEQ ID NO: 951) |
| RA015.11_ KC94.1 | MTPTIPVTLSASVGDRVTITCRASQSISNWLAWYQQKPGKAPKLLIYKASTLES GVPSRFSGSGSGTEFTLTISSLQPDDFATYYCQQYNSYSWTFGQGTKVEIK (SEQ ID NO: 952) |
| RA015.11_ LC12.2 | QSELTQPPSVSVAPGQTARITCGGNNIGSKSVHWYQQKPGQAPVLVVYDDSER PSGIPERFSGSNSGNTATLTISRVEAGDEADYHCQVWDSSSDHPGVFGGGTKLT V (SEQ ID NO: 953) |
| RA015.11_ KC19.2 | YHDPQAPLTLSLSPGERATLSCRASQSVSSSYLAWYQQKPGQAPRLLIYGASSR ATGIPDRFSGSGSGTDFTLTISRLEPEDCAVYYCQQYGSSHTFGQGTKLEIK (SEQ ID NO: 954) |
| RA015.11_ KC83.2 | HDPQAPATLSASVGDRVTITCRASQGISSYLAWYQQKPGKAPNLLIYAASTLQS GVPSRFSGSGSGTEFTLTISSLQPEDFATYYCQQLNSYPLTFGGGTKVEIK (SEQ ID NO: 955) |
| RA015.11_ KC58.1 | MTLIIPVTLSLSPGERATLSCRASQSIRSNLAWYQQKPGQAPRLLIHGASTRTTG IPARFSGSGSGTEFTLTITSLQSEDFAVYYCQQYNNWPQSTFGQGTKVEIR (SEQ ID NO: 956) |

TABLE 4-continued

| VL amino acid sequence (VJ) |
|---|

Ab identifier V-J-REGION

RA015.11_
LC68.1
QFVLTQPPSVSGAPGQRVTISCTGSSSNIGAGYDVHWYQQLPGTAPKLLIYGNS
NRPSGVPDRFSGSKSGTSASLAITGLQAEDEADYYCQSYDSSLSGSVFGGGTTL
TVL (SEQ ID NO: 957)

RA015.11_
LC81.1
QSVLTQTPSVSVAPGQTAIITCGGHSIGNRAVHWYQQKPGQAPVVVVYDDSD
RPSGIPERFSGSNSGNTATLTISRVEAGDEADYFCQVWDSSFDRPDFGTGTKVT
VL (SEQ ID NO: 958)

RA015.11_
KC91.1
LLSLHIPVTLSASVGDRVTITCQASQDITKYLNWYQQKPGKAPKLLIYDVSNLE
TGVPSRFSGSGSGTDFTFTISSLQPEDTATYYCQQYANVFTFGPGTKVDIK
(SEQ ID NO: 959)

RA015.11_
KC95.1
SSHIPVTLAVSLGERATINCKSSQSVLYYSNSKNYLTWYQQKPGQPPKLLIYWA
STRESGVPDRFSGSGSGTDFTLTISSLQAEDVAVYYCQQYYSNPYTFGQGTKVE
IK (SEQ ID NO: 960)

RA015.11_
KC17.2
YDPTAPATLSLSPGERATLSCRASQSVRSSYLAWYQQKPGQAPRLLIYGASSRA
TGIPDRISGSGSGTDFTLTISRLEPEDFVVYYCQQYGSSPWTFGQGTKVEIK
(SEQ ID NO: 961)

RA015.11_
KC64.2
LPQAPATLSLSPGERATLSCRASQSVSSYLAWYQQKPGQAPRLLIYDAYNRAT
GIPARFSGSGSGTDFTLTISSLEPEDFAVYYCQQRSNWPGTFGQGTKVEIK
(SEQ ID NO: 962)

RA015.11_
LC66.2
QSVLTQPASVSGSPGQSITISCTGTSSDVGNYNLVSWYQQHPGKAPKLMIYEDS
KRPSGVSNRFSGSKSGNTASLTISGLQAEDEADYYCCSYAGSSTLYVFGAGTK
VTVL (SEQ ID NO: 963)

RA056.11_
KC9.2
RSPKAPVTLSLSPGERATLSCRASQSVSSYLAWYQQKPGQAPRLLIYDASNRAT
GIPARFSGSGSGTDFTLTISSLEPEDFAVYYCQQRSNWPPTFGGGTKVEIK
(SEQ ID NO: 964)

RA056.11_
KC34.2
MTPTAPVTLSASVGDRVTITCRASQGISSYLAWYQQKPGKAPKLLIYAASTLQS
GVPSRFSGSGSGTDFTLTISSLQPEDFATYYCQQLNSYPLTFGGGTKVEIK
(SEQ ID NO: 965)

RA056.11_
LC38.2
QSVLTQPASVSGPPGQSIAISCTGTNSDVGAYNYVSWYQQHPGKAPKLMIYEV
SNRPSGVSDRFSGSKSGNTASLTISGLQAEDEANYYCSSYTSSSTWVFGGGTKL
TVL (SEQ ID NO: 966)

RA056.11_
LC41.2
QSVLTQPPSVSVAPGKTARITCGGNNIGSKSVHWYQQKPGQAPVLVIYYDSDR
PSGLPERFSGSNSGNTATLTISRVEAGDEADYYCQVWDSSSDHYVFGTGTKVT
VL (SEQ ID NO: 967)

RA056.11_
KC48.2
YDPTAPVTLSASVGDRVTITCRASQSISSYLNWYQQKPGKAPKLLIYAASSLQS
GVPSRFSGSGSGTDFTLTISSLQPEDFATYYCQQSYSTPYTFGQGTKLEIK
(SEQ ID NO: 968)

RA056.11_
KC81.2
PPAPLTLSVSPGERATLSCRASQSVSSNLAWYQQKPGQAPRLLIYGASTRATGI
PARFSGSGSGTEFTLTISSLQSEDFAVYYCQQYNNWPLWTFGQGTKLEIK
(SEQ ID NO: 969)

RA056.11_
KC29.1
KIVMAQSPATLSLSPGERTTLSGRASQSVHNIYLPWYQQKPGQAARLLIYGTSS
RSTGVTDRFSGSGSGTDFTLTISRLESEDFAVYFCQHYESSPPVFTFGPGTKVDI
K (SEQ ID NO: 970)

RA056.11_
LC33.1
QSVLTQSPSASASLGASVKLTCTLTSGHSNYAIAWHQQQPERGPRYLMKVNSD
GSHNKGDGIPDRFSGSSSGAERYLTISSLQSDDEADYYCQTWDTGIQVFGPGTK
VTVL (SEQ ID NO: 971)

RA056.11_
LC35.1
QSVLTQPPSASGSPGQSVTISCTGTSSDVGGYNYVSWYQQHPGKAPKLMIYEV
SKRPSGVPDRFSGSKSGNTASLTVSGLQAEDEADYYCSSYAGSNNYVFGTGTK
VTVL (SEQ ID NO: 972)

RA056.11_
LC45.1
QSVLTQSPSASASLGASVKLTCTLTSGHSNYAIAWHQQQPERGPRYLMKVNSD
GSHNKGDGIPDRFSGSSSGAERYLTISSLQSDDEADYYCQTWDTGIQVFGPGTK
VTVL (SEQ ID NO: 973)

RA056.11_
LC56.1
QSVLTQPASVSGSPGQSITISCTGTSSDVGGYNHVSWYQQHPGKAPKLMIYDV
NNRPSGVSHRFSGSKSGNRASLTISGLQAEDEADYYCSSYTSSSSLLYVFGSGT
KVTVL (SEQ ID NO: 974)

TABLE 4-continued

| VL amino acid sequence (VJ) |
|---|

Ab identifier V-J-REGION

RA056.11_
LC66.1
QSVLTQPRSVSGSPGQSVTISCTGTSSDVGDYKYVSWYQQYPGKAPRLMIYDV
IKRPSGVPDRFSGSKSDNTASLTISGLQAEDEADYYCCSYVGSYTVAFGGGTKL
TVL (SEQ ID NO: 975)

RA056.11_
LC68.1
QSVLTQPASVSGSPGQSITISCTGTSSDVGSYSLVSWFQQHPGRAPKLIIYEGSQ
RPSGVSNRFSGSKSGNTASLTISGLQTEDEAHYYCCSYAAGNTRVFGGGTKLT
VL (SEQ ID NO: 976)

RA056.11_
KC76.1
LMTQAPVTLSVSPGERATLSCRASQSVSSNLAWYQQKPGQAPRLLIYGASTRA
TGIPARFSGSGSGTEFTLTISSLQSEDFAVYYCQQYNNLYTFGQGTKLEIK
(SEQ ID NO: 977)

RA056.11_
LC80.1
QSVLTQPASVSGSPGQSITISCTGTSSDVGGYNYVSWYQQHPGKAPKLMIYDV
SNRPSGVSNRFSGSKSGNTASLTISGLQAEDEADYYCSSYTSSSTVVFGGGTKL
TVL (SEQ ID NO: 978)

RA056.11_
LC12.2
QSVLTQPPSVSAAPGQKVTISCSGSSSNIGNNYVSWYQQLPGTAPKLLIYDNNQ
RPSGIPDRFSGSKSGTSATLGITGLQTGDEADYYCGTWDSSLSAVVFGGGTKLT
VL (SEQ ID NO: 979)

RA056.11_
KC20.2
SPQAPVTLSLSPGERATLSCRASQSVSSYLAWYQQKPGQAPRLLIYDASNRAT
GIPARFSGSGSGTDFTLTITNLEPEDFAVYYCQQRSNWPPTFGQGTKVEIK
(SEQ ID NO: 980)

RA056.11_
LC23.2
QFVLTQSLSVSVALGQTANITCGGHNIVAKTVHWYQQKSGQAPVLVIYRDTN
RPSRLPERFSGSTSGNTATLTIRTAQAGDEADYYCQVWDISSVVFGGGTKLTVL
(SEQ ID NO: 981)

RA056.11_
LC36.2
QSVLTQPASVSGSPGQSITISCTGTSSDVGGYNYVSWYQQHPGKAPKLMIYDV
SNRPSGVSNRFSGSKSGNTASLTISGLQAEDEADYYCSSYTSSSTLVFGGGTKL
TVL (SEQ ID NO: 982)

RA056.11_
LC39.2
QSVLTQPPSASGTPGQRVTISCSGSSSNIGNNYVYWYQQLPGTAPKLLIYRNNQ
RPSGIPDRFSGSKSGTSASLAISGLRSEDEADYYCAAWDDSLSGWVFGGGTKL
TVL (SEQ ID NO: 983)

RA056.11_
KC45.2
PQAPVTLSASVGDRITITCRASQSISRYLNWYQQKPGRAPNLLIYAASALQSGV
PSRFSGSGSGTDFTLTISSLQPEDFATYYCQQSSTTPLTFGGGTKVEIN
(SEQ ID NO: 984)

RA056.11_
KC54.2
DDPKAPATLSLSPGDRATLSCRASQSVSSYLAWYQQKPGQPPRLLIFDASTRAT
GIPARFSGSGSGTDFTLTISSLEPEDFAHYYCQLRSNWRTFGGGTKVEIK
(SEQ ID NO: 985)

RA056.11_
KC56.2
LDDPQDPVSLSASVGDKVTITCRASQSISSHLNWYQQQPGKAPNLLIYAASTLQ
YGVPSRFSGSGSGTDFILTISNLQPEDFATYYCQQSFSMPFTFGPGTKVDVK
(SEQ ID NO: 986)

RA056.11_
KC75.2
MIQSPVCLAVSLGERATINCKSSQSVSYSSNNKDHLAWYLQRSGQPPQLLIYW
ASTRKSGVPDRFSGSGSGTDFTLTISSLQAEDVAVYYCQQYYITPPTFGQGTKV
EIK (SEQ ID NO: 987)

RA056.11_
KC94.2
MTPQAPVTLSLSPGERATLSCRASQSVNYYLAWYQQKPGRAPRLLIYDASNRA
TGVPARFSGRGSGTDFTLTISSLEPEDFAVYYCQLRSNWLLTFGGGTNVEIK
(SEQ ID NO: 988)

RA056.11_
LC95.2
QSVLTQPASVSGSPGQSITISCAGTSTDLGTYHLVSWYQQHPGKAPKLLIYEGS
RRPSGISDRFSGSKSGDTAALTISGLQAEDEADYYCCSYAGTWVFGGGTKVTV
L (SEQ ID NO: 989)

RA056.11_
LC95.1
QSQLTQPESASGSRGQWITISITGTSSDSGGYSYVSGSQQQPGKAPKLIIFEVDIR
PSGAWDCFCGSKSDYTASATMSRFQAQDEAEYDCNSISSTSTNNVFGRRTTGR
PSIRQLRRLGD (SEQ ID NO: 990)

RA056.11_
KC96.1
PQAPATLSASVGDRVTITCRASQVIRNDLGWYQQKPGNAPKRLIYAASILQSG
VPSRFSGSGFGTEFTLTISSLQPEDFATYYCLHNSFPWTFGQGTKVEIK
(SEQ ID NO: 991)

RA056.11_
KC58.2
YDPKAPLTLSLSPGERATLSCRASQTVSSSSLAWYQQKPGQAPRLLIYSASSRA
TGIPDRFSGSGSGTDFTLTISRLEPEDSAVYHCQQYGSSPGTFGQGTKLEIK
(SEQ ID NO: 992)

TABLE 4-continued

| VL amino acid sequence (VJ) |
|---|

Ab identifier V-J-REGION

RA056.11_  HDPQAPVTLSVSPGERVTLSCRASQSVYSNLAWYQLKPGQGPRLLIYSASTRA
KC93.2     TGIPVRFSGSGSGTEFTLSISSLQSEDFAVYLCQQYYNWPPITFGQGTRLESK
           (SEQ ID NO: 993)

RA057.11_  LTPQDPVTLSASVGDRVTITCQASQDISNYLNWYQQKPGKAPKLLIYDASNLE
KC2.1      TGVPSRFSGSGSGTDFTFTISSLQPEDIATYYCQQYDNLPYTFGQGTKLEIK
           (SEQ ID NO: 994)

RA057.11_  YDPTAPVTLSASVGDRVTITCRASQSISSYLNWYQQKPGKAPKLLIYAASSLQS
KC17.1     GVPSRFSGSGSGTDFTLTISSLQPEDFATYYCQQSYSTPPLSTFGPGTKVDIK
           (SEQ ID NO: 995)

RA057.11_  QSVLTQPPSASGTPGQRVTISCSGSSSNIGSNTVNWYQQLPGTAPKLLIYSNNQ
LC28.1     RPSGVPDRFSGSKSGTSASLAISGLQSEDEADYYCAAWDDSLNGVVFGGGTKL
           TVL (SEQ ID NO: 996)

RA057.11_  PALFFSPATLSLSSGERATLSCRASQSVISSYLAWYQQKPGQAPRLLIYGASSRA
KC35.1     TGIPDRFSGSGSGTDFTLTISRLEPEDFAVYYCQQHGSSPYTFGQGTKLEIK
           (SEQ ID NO: 997)

RA057.11_  PQAPATLSASVGDRVTITCRASQSISSWLAWYQQKPGKAPKLLIYKASSLESGV
KC44.1     PSRFSGSGSGTEFTLTISSLQPDDFATYYCQQYNSYPWTFGRRDQRW
           (SEQ ID NO: 998)

RA057.11_  CSMTSDSSHPASTGDRVTITCRASQGISSYLAWYQQKPGKAPKLLIYAASTLQS
KC51.1     GVPSRFSGSGSGTDFTLTISCLQSEDFATYYCQQYYSYPTFGPGTKVDIK
           (SEQ ID NO: 999)

RA057.11_  QSVLTQPPSVSVSPGQTARITCSGDALPKQYAYWYQQKPGQAPVLVIYKDSER
LC56.1     PSGIPERFSGSSSGTTVTLTISGVQAEDEADYYCQSADSSGLVFGGGTKLTVL
           (SEQ ID NO: 1000)

RA057.11_  QSVLTQPPSASGTPGQRVTISCSGSSSNIGSNTVNWYQQLPGTAPKLLIYSNNQ
LC61.1     RPSGVPDRFSGSKSGTSASLAISGLQSEDEADYYCAAWDDSLNGWVFGGRTKL
           TVL (SEQ ID NO: 1001)

RA057.11_  TPQYPLTLSASVGDRVTITCQASQDISNYLNWYQQKPGKAPKLLIYDASNLET
KC62.1     GVPSRFSGSGSGTDFTFTISSLQPEDIATYYCQQYDNLPLTFGQGTKLEIK
           (SEQ ID NO: 1002)

RA057.11_  QSVLTQPPSASGTPGQRVTISCSGSSSNIGSNTVNWYQQLPGTAPKLLIYSNNQ
LC62.1     RPSGVPDRFSGSKSGTSASLAISGLQSEDEADYYCAAWDDSLNGPVFGGGTKL
           TS (SEQ ID NO: 1003)

RA057.11_  QSVLTQPASVSGSPGQSITISCIGTSSDVGSYNLVSWYQQHPGKAPKLMIYEGS
LC67.1     KRPSGVSNRFSGSKSGNTASLTISGLQAEDEADYYCCSYAGSSTLFGGGTKLTV
           L (SEQ ID NO: 1004)

RA057.11_  YEPPIPVTLAVSLGERATINCKSSQSVLYSSNNKNYLAWYQQKPGQPPKLLIYW
KC71.1     ASTRESGVPDRFSGSGSGTDFTLTISSLQAEDVAVYYCQQYYSTPLTFGGGTKV
           EIK (SEQ ID NO: 1005)

RA057.11_  YDPPAPVTLSLSPGERATLSCRASQSVSSSYLAWYQQKPGQAPRLLIYGASSRA
KC82.1     TGIPDRFSGSGSGTDFTLTISRLEPEDFAVYYCQQYGSSPPYTFGQGTKLEIK
           (SEQ ID NO: 1006)

RA057.11_  QSVLTQPASVSGSPGQSITISCTGTSSDVGSYNLVSWYQQHPGKAPKLMIYEGS
LC82.1     KRPSGVSNRFSGSKSGNTASLTISGLQAEDEADYYCCSYAGSPVFGGGTKLTV
           L (SEQ ID NO: 1007)

RA057.11_  IEPTAPVTLSLSPGERATLSCRASQSVSSSYLAWYQQKPGQAPRLLIYGASSRAT
KC89.1     GIPDRFSGSGSGTDFTLTISRLEPEDFAVYYCQQYGSSPLTFGGGTKVEIK
           (SEQ ID NO: 1008)

RA057.11_  HDPQAPFTLSLSPGERATMSCRASLSVSSNYLAWYQQKPGQAPRLLIYGASSR
KC50.1     ATGIPDRFSGGGSGTDYTLTISRLEPEDFAVYYCQQYGSSPVYSFGQGTKLEIK
           (SEQ ID NO: 1009)

RA057.11_  QSVLTQPPSASGTPGQRVTISCSGSRSNIGSNTVNWYRQLPGTAPKLLIYSNDQ
LC72.1     RPSGVPDRFSASKSGTSASLAISGLQSEDEADYYCSAWDNSLNGYFFGPGTKV
           TVL (SEQ ID NO: 1010)

TABLE 4-continued

VL amino acid sequence (VJ)

Ab
identifier V-J-REGION

RA057.11_ QSVLTQPHSVSGSPGKTVTISCTRSSGSIASSYVQWYQQRPGSSPTTVIYEDNQR
LC78.1    PSGVPDRFSGSIDSSSNSASLTITGLKTEDEADYYCWSYDNYQEIFGSGTTVTVL
          (SEQ ID NO: 1011)

RA057.11_ SCSIFQTPATLSLSPGERDTLSCRASQSVSSNYLSWYQQKPGQAPRLLIYGASSR
KC80.1    ATGIPDRFSGSGSGTDFTLTISRLEPEDFAVYYCQQYGTSPWTFGQGTKVEIK
          (SEQ ID NO: 1012)

RA057.11_ QSVLTQPASVSGSPGQSITISCIGSSSDVGGYDYVSWYQQHPGKAPKLMIFEVS
LC93.1    NRPSGVSNRFIGSKSGNTASLTISGLQAEDEADYYCSSYTTSSDLVFGGGTKLT
          VL (SEQ ID NO: 1013)

RA057.11_ QSVLTQPPSKSGTPGQRVTISCYGSRSNIGSTTVNWFQQLPESAFKLLIHSNDQR
LC25.1    PSGVPDRFSGSKSDTSASLAISGLQSEDEADYYCAAWDASLKVFLLGTGTKVT
          VL (SEQ ID NO: 1014)

RA057.11_ PASPKSPVTLSLSPGERATLSCRASQSVGNSFLAWYQQKPGQTPRLLIYGASSR
KC47.1    ATGIPDRFSGSGSGTDFTLTISRLEREDFAVYYCQQYGSSPGTFGQGTKVEVK
          (SEQ ID NO: 1015)

RA057.11_ QSVLTQPASVSGSPGQSITISCTGTSGDVENYNVVSWYQQHPGKAPKLIIYEVT
LC47.1    KRPSGVSNRFSGSKSGNTASLTISGLQAEDEADYYCCSSASFTISWVFGGGTKL
          TVL (SEQ ID NO: 1016)

TABLE 4A

VL amino acid sequence (VJ)

Ab
identifier V-J-REGION

RA061.11_ CCSMTQSPATLSASVGDRVTISCQANQDIKKSFNWYHQKPGRAPKVLIYDSVIL
KC29.1    ETGVPSRFSGSGSGTHFTLTISSLQPEDIGTYYCQQYEHLPLTFGGGTKVELK
          (SEQ ID NO: 1017)

RA061.11_ SCSMTQSPVTLSASVGDRVTITCRASQTIYSWLAWYQQKPGKAPKLLIYQASN
KC35.1    LEIGVPSRFSGSGSGTEFTLTISSLQPDDFATYYCQQYSTDSLYTFGQGTKLEIK
          (SEQ ID NO: 1018)

RA061.11_ SYELTQPLSVSVALGQTARITCGGNNIGSKNVHWYQQKPGQAPVLVIYRDSNR
LC40.1    PSGIPERFSGSNSGNTATLTISRAQAGDEADYYCQVWDSSTVVFGGGTKLTVL
          (SEQ ID NO: 1019)

RA061.11_ CRAMTQSPVTLSVSPGERATLSCRASQRVSSNLAWYQQKPGQAPRLLIYGAST
KC43.1    RATGIPARFSGSGSGTDFTLTISDIQSEDFAYYYCQHYNNWPPWTFGQGTKVEI
          K (SEQ ID NO: 1020)

RA061.11_ CCSMTQTPATLSASVGDRVTITCRASQSISSWLAWYQQKPGKAPKLLIYKASSL
KC44.1    ESGVPSRFSGSGSGTEFTLTISSLQPDDFATYYCQQYNSYSLAFGQGTKVEIK
          (SEQ ID NO: 1021)

RA061.11_ VWSMTQTPGTLSASVGDRVTITCRASQGISNYLAWFQQKPGKAPKSLIYAASS
KC47.1    LQSGVPSKFSGSGSGTDFTLAISSLQPEDFATYYCQQYNSYPLTFGGGTKVEIK
          (SEQ ID NO: 1022)

RA061.11_ AMTQSPVTLSASVGDRVTITCRASQFISSALAWYQQKPGKAPKLLIYDASSLES
KC65.1    GVPSRFSGSGSGTDFTLTISSLQPEDFATYYCQQFNSYPSTFGPGTKVDIK
          (SEQ ID NO: 1023)

RA061.11_ VCSMTQSPATLSLSPGERATLSCRASQSVSTSYLAWYQQKPGQAPRLLMYGAS
KC66.1    RRAAGISDRFSGSGSGTDFALTISRLEPEDFAVYYCQEYGSSPGTFGQGTKLEIK
          (SEQ ID NO: 1024)

RA061.11_ SWSMTQSPATLSLSAGERATLSCRASQSVTTFLAWYQQKPGQAPRLLIYDATN
KC67.1    RATGIPARFSGSGSGTDFTLTISSLEPEDFAVYYCQHRYGWPPGFGGGTKVEIK
          (SEQ ID NO: 1025)

RA061.11_ VCSMTQTPGTLSLSPGERATLSCRASQSVSSSYLAWYQQKPGQAPRLLIYGASS
KC71.1    RATGIPDRFSGSGSGTDFTLTISRLEPEDFAVYYCQQYGSSPNTFGGGTKVEIK
          (SEQ ID NO: 1026)

TABLE 4A-continued

VL amino acid sequence (VJ)

| Ab identifier | V-J-REGION |
|---|---|
| RA061.11_KC72.1 | VWFMDQSPGALCLSAGERATLSCRASQSVSSSYLAWCQQKPFQAPRLLMEWC IQQGHWHPRQVQWQWVWDKTSLSPSADWSLKILHCITVSSMVAHLSLSAEGP RWRSN (SEQ ID NO: 1027) |
| RA061.11_KC80.1 | CCSMTQSPVTLPVTLGQPASISCRSSQSLVHSDGNTYLNWFQQRPGQSPRRLIY KVSNRDSGVPDRFSGSGSGTDFTLKISRVEAEDVGVYYCMQGTHWPPWTFGQ GTKVEIK (SEQ ID NO: 1028) |
| RA061.11_KC82.1 | CWSMTQTPVTLPVTLGQPASISCRSSQSLVYSDGNTYLNWFQQRPGQSPRRLIY KVSNWDSGVPDRFSGSGSGTDFTLKISRVEAEDVGVYYCMQGTLHRFFGGGT KVEIK (SEQ ID NO: 1029) |
| RA061.11_LC89.1 | QSVLTQPPSVSGSPGQSVTISCTGTNSDVGTYDRVSWYQQPPGTAPKLIIYEVN NRPSGVPDRFSGSKSGNTASLTISGLQAEDEADYYCCSYRSGRTFVFGTGTKVT VL (SEQ ID NO: 1030) |
| RA061.11_KC90.1 | CCSMTQTPGVLGLSPGERATLSCRVSQRKTSTSLVRYQQRPGQAPTLLMYGTS NRATGIPDRFSGSGSGTDFTVTISRLEPEDFAMYYCQQFDSSPWTFGQGTKVEF T (SEQ ID NO: 1031) |
| RA061.11_KC95.1 | CCALTQSPATLPVTPGEPASISCKSSQSLLHSNGYNYLAWYLQKPGQSPQLLFY LGSDRASGVPDRFSGSGSGTDFTLKISRVEPEDVGVYYCMQGLHTPLTFGGGT KVEIK (SEQ ID NO: 1032) |

The antibody according to the present invention comprises 3 or 6 of the CDR sequences as provided in Tables 1 and 2 or Tables 1A and 2A. For example the antibody may comprise three CDR sequences as provided in Tables 1 or 2, or Tables 1A or 2A, if it is a domain antibody (either all three VH or all three VL).

In particular, the antibody may comprise a CDR3 sequence as provided in Table 1 or Table 1A.

The antibody may comprise a VH and VL CDR3 pair as provided in Tables 1 and 2 or Tables 1A and 2A. The antibody may comprise the corresponding CDR1, CDR2 and CDR3 sequences from a VH/VL pair as provided in Tables 1 and 2 or Tables 1A and 2A. The term "corresponding" means that the CDR sequences are associated with the same antibody identifier. The term "pair" means that the VH and VL are associated with the same antibody identifier.

The CDR sequence may be identical to a sequence provided in Table 1 or 2, or Table 1A or 2A. The CDR sequence may comprise one, two, three, four or five amino acid substitutions compared to a CDR sequence provided in Table 1 or 2, or Table 1A or 2A. The CDR sequence may have 80, 90, 95, 97, 98 or 99% identity with a CDR sequence provided in Table 1 or 2, or Table 1A or 2A.

The antibody may comprise a VH and/or VL sequence as provided in Table 3 or 4, or Table 3A or 4A, respectively. Table 3 and Table 3A provide the VDJ sequence of VH chain and Table 4 and Table 4A provide the VJ sequence of VL chain. The antibody may comprise a VH/VL pair of sequences as provided in Tables 3 and 4 or Tables 3A and 4A.

The VH or VL sequence may have 70, 80, 90, 95, 97, 98 or 99% identity with a VH or VL sequence provided in Table 3 or 4, or Table 3A or 4A.

Identity comparisons can be conducted by eye, or more usually, with the aid of readily available sequence comparison programs. These commercially available computer programs can calculate % identity between two or more sequences. A suitable computer program for carrying out such an alignment is the GCG Wisconsin Bestfit package (University of Wisconsin, U.S.A.; Devereux et al., 1984, Nucleotide sequences Research 12:387). Examples of other software than can perform sequence comparisons include, but are not limited to, the BLAST package, in particular IgBlast (see Ausubel et al., 1999 ibid—Chapter 18), FASTA, in particular IMGT, (Atschul et al., 1990, J. Mol. Biol., 403-410) and the GENEWORKS suite of comparison tools. Both BLAST and FASTA are available for offline and online searching.

Once the software has produced an optimal alignment, it is possible to calculate % identity. The software typically does this as part of the sequence comparison and generates a numerical result.

The antibody of the present invention may be a chimeric antibody. Chimeric antibodies may be produced by transplanting antibody variable domains from one species (for example, a mouse) onto antibody constant domains from another species (for example a human).

The antibody of the present invention may be a full-length, classical antibody. For example the antibody may be an IgG, IgM or IgA molecule.

The antibody may be a functional antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody, (iv) the dAb fragment, which consists of a single variable domain, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains.

The present invention also provides heavy and light chain dimers of the antibodies of the invention, or any minimal fragment thereof such as Fvs or single chain antibodies.

Single chain antibodies are formed by linking the heavy and light chain fragments of the Fv region via an amino acid bridge, resulting in a single chain polypeptide.

The antibody described herein may be a multispecific antibody, and notably a bispecific antibody, also sometimes referred to as "diabodies". These are antibodies that bind to two (or more) different antigens. Diabodies can be manufactured in a variety of ways known in the art, e.g., prepared chemically or from hybrid hybridomas. The antibody may be a minibody. Minibodies are minimized antibody-like proteins comprising a scFv joined to a CH3 domain. In some cases, the scFv can be joined to the Fc region, and may include some or all of the hinge region.

The antibody may be a domain antibody (also referred to as a single-domain antibody or nanobody). This is an antibody fragment containing a single monomeric single variable antibody domain. Examples of single-domain antibodies include, but are not limited to, VHH fragments originally found in camelids and VNAR fragments originally found in cartilaginous fishes. Single-domain antibodies may also be generated by splitting the dimeric variable domains from common IgG molecules into monomers.

The antibody may be a synthetic antibody (also referred to as an antibody mimetic). Antibody mimetics include, but are not limited to, Affibodies, DARPins, Anticalins, Avimers, Versabodies and Duocalins.

Antibodies of the present invention may be produced by suitable methods which are well known in the art. Nucleotide sequences encoding immunoglobulins or immunoglobulin-like molecules can be expressed in a variety of heterologous expression systems. Large glycosylated proteins including immunoglobulins are efficiently secreted and assembled from eukaryotic cells, particularly mammalian cells. Small, non-glycosylated fragments such as Fab, Fv or scFv fragments can be produced in functional form in mammalian cells or bacterial cells.

Thus, one method of making an antibody of the present invention involves introducing a nucleotide sequence of the present invention into a replicable vector, introducing the vector into a compatible host cell, and growing the host cell under conditions which bring about replication of the vector. The vector may be recovered from the host cell.

Preferably, a nucleotide sequence of the present invention which is inserted into a vector is operably linked to a control sequence that is capable of providing for the expression of the coding sequence by the host cell, i.e. the vector is an expression vector. The polypeptide produced by a host recombinant cell may be secreted or may be contained intracellularly depending on the sequence and/or vector used. As will be understood by those of skill in the art, expression vectors containing the polypeptide coding sequences can be designed with signal sequences which direct secretion of the polypeptide coding sequences through a particular prokaryotic or eukaryotic cell membrane.

The vectors described herein may be transformed or transfected into a suitable host cell to provide for expression of a polypeptide comprising a peptide sequence as provided by the present invention. This process may comprise culturing a host cell transformed with an expression vector under conditions to provide for expression by the vector a coding sequence comprising a polypeptide sequence of the present invention and optionally recovery of the expressed polypeptide. The vectors, for example, may be a plasmid or virus vector providing an origin of replication, a promoter to the expression of the said polypeptide and optionally a regulator of the promoter. The vectors may contain one or more selectable marker genes, for example an ampicillin resistance gene in the case of a bacterial plasmid or a neomycin resistance gene for a mammalian vector. The expression of a polypeptide sequence of the invention may be constitutive such that it is continually produced, or inducible, such that a stimulus is required to initiate expression. In the case of an inducible promoter, polypeptide production can be initiated when require by, for example, addition of an inducer substance to the culture medium, for example dexamethasone or IPTG.

Purification of expressed antibodies may be performed using techniques which are well known in the art. For example antibodies may be purified by ion exchange chromatography or affinity chromatography using Protein A, Protein G or Protein L.

Also provided herein is an entity (i.e. a peptide) which binds to the antigen binding site of an antibody according to the present invention. Such entities may be identified using competitive binding assays which are well-known in the art, for example using radiolabeled competitive binding assays.

These competitive binding entities may be termed 'mimotopes'. A mimotope is a macromolecule, often a peptide, which mimics the structure of an epitope. Because of this property it causes an antibody response similar to the one elicited by the epitope. An antibody for a given epitope antigen will recognize a mimotope which mimics that epitope. Mimotopes to antibodies of the present invention may be identified using phage display techniques and are useful a therapeutic entities and vaccines.

Neutrophil Extracellular Traps

The antibodies of the present invention may bind Neutrophil extracellular traps (NETs).

NETs are networks of extracellular fibres, primarily composed of DNA, released from neutrophils, which bind pathogens.

Upon in vitro activation with the pharmacological agent Phorbol 12-myristate 13-acetate (PMA), interleukin 8 (IL-8) or lipopolysaccharide (LPS), neutrophils release granule proteins and chromatin to form an extracellular fibril matrix known as NETs through an active process.

Analysis by immunofluorescence corroborated that NETs contained proteins from azurophilic granules (neutrophil elastase, cathepsin G and myeloperoxidase) as well as proteins from specific granules (lactoferrin) and tertiary granules (gelatinase), yet CD63, actin, tubulin and various other cytoplasmatic proteins were not present. NETs provide for a high local concentration of antimicrobial components and bind microbes extracellularly independent of phagocytic uptake. In addition to their antimicrobial properties, NETs may serve as a physical barrier that prevents further spread of the pathogens. Furthermore, delivering the granule proteins into NETs may keep potentially injurious proteins like proteases from diffusing away and inducing damage in tissue adjacent to the site of inflammation.

High-resolution scanning electron microscopy has shown that NETs consist of stretches of DNA and globular protein domains with diameters of 15-17 nm and 25 nm, respectively. These aggregate into larger threads with a diameter of 50 nm. However, under flow conditions, NETs can form much larger structures, hundreds of nanometers in length and width.

The formation of NETs is regulated by the lipoxygenase pathway—during certain forms of activation (including contact with bacteria), oxidized products of 5-lipoxygenase in the neutrophils form 5-HETE-phospholipids that inhibit NET formation. Evidence from laboratory experiments suggests that NETs are removed by macrophages.

The contribution of NETs to autoimmunity in RA has been highlighted by evidence that RA unstimulated synovial neutrophils display enhanced NETosis. Is has also been shown that NETosis is correlated with autoantibodies to citrullinated antigens (ACPA) and with systemic inflammatory markers.

Citrullinated Histone 2A, Histone 2B and Histone H4

An antibody of the invention may specifically bind (i.e. target) a citrullinated protein derived from a neutrophil extracellular traps (NETs).

For example, the antibody may bind citrullinated histone 2 A (cit-H2A) and/or cit-H2B and/or cit-H4.

NETs are known to comprise a chromatin meshwork and citrullinated histones. Citrullination is a post-translational modification catalysed by the peptidyl arginine deiminases (PAD). In particular, type IV (PAD4), has been suggested to play an important role in the histones citrullination during NETosis.

Citrullination or deimination is the conversion of the amino acid arginine in a protein into the amino acid citrulline in which peptidylarginine deiminases (PADs) replace the primary ketimine group (=NH) by a ketone group (=O). Arginine is positively charged at a neutral pH, whereas citrulline is uncharged. This increases the hydrophobicity of the protein, leading to changes in protein folding. Therefore, citrullination can change the structure and function of proteins.

Histones proteins, H2A, H2B, H3 and H4 have been identified in NETs and it has been reported that an increase in histone citrullination is associated with chromatin decondensation during NETs formation.

Nucleotide Sequences

The present invention also provides nucleotide sequences encoding the VH and/or VL peptide sequences or the CDR peptide sequences described herein. The present invention also provides nucleotide sequences encoding antibodies comprising the VH and/or VL peptide sequences or the CDR peptide sequences described herein.

It will be understood that numerous different nucleotide sequences can encode the same $V_H$ and/or $V_L$ peptide sequences, or CDR peptide sequences as a result of the degeneracy of the genetic code. In addition, it is to be understood that the skilled persons may, using routine techniques, make nucleotide substitutions that do not affect the polypeptide encoded by the nucleotide sequence. This may be performed to reflect the codon usage of any particular host organism in which the polypeptide of the present invention is to be expressed.

Variants and homologues of the nucleotide sequences described herein may be obtained using degenerative PCR, which will use primers designed to target sequences within the variants and homologues encoding conserved amino acids sequences within the sequences of the present invention. Alternatively, such nucleotide sequences may be obtained by site directed mutagenesis of characterised sequences. This may be useful for example where silent nucleotide sequences are required to sequences to optimise codon preferences for a particular host cell in which the nucleotide sequences are being expressed. Other sequence changes may be desired in order to introduce restriction enzyme recognition sites, or alter the binding specificity of the polypeptide encoded by the nucleotide sequences.

Due to the inherent degeneracy of the genetic code, other DNA sequences which encode substantially the same or a functionally equivalent amino acid sequence, may be used to clone and express the polypeptide. As will be understood by those skilled in the art, it may be advantageous to produce the polypeptides of the present invention possessing non-naturally occurring codons. Codons preferred by a particular prokaryotic or eukaryotic host can be selected, for example, to increase the rate of the polypeptide expression or to produce recombinant RNA transcripts having desired properties, such as a longer half-life, than transcripts produced from naturally occurring sequence.

Uses

In one aspect, the present invention provides the use of an antibody according to the first aspect of the invention in a diagnostic test for RA. Specifically provided is the use of an antibody as a positive control in a diagnostic test for RA.

The term "positive control" is used herein according to its normal meaning to refer to an agent used to assess the validity of a test result (i.e. herein the test result is the result of a sample derived from a subject).

The diagnostic test involves determining the presence of antibodies against a specific antigen in a sample derived from a RA patient by contacting the sample to be tested with a candidate antigen. Binding of antibodies within the sample to the candidate antigen is determined using detection methods known in the art (i.e. radiolabelling, fluorescence etc.). The antibody according to the present invention which is used as positive control is therefore an antibody which has been determined to bind the specific candidate antigen and thus provides a reliable positive signal to demonstrate the validity of the assay.

The sample may be a synovial tissue or a synovial fluid sample. The sample may be derived from any synovial joint, for example the knee or hip joint of a subject. The sample may be a peripheral blood sample or a serum sample.

The diagnostic test may be an ELISA, immunofluorescence, western blot or a chip-based high throughput assay.

The present invention also provides the use of an antibody according to the first aspect of the invention for exacerbating or increasing the symptoms in an animal model of RA. Such a use comprises administering an antibody according to the present invention to the animal to either induce or exacerbate arthritis symptoms. Alternatively, the antibody could prevent/improve experimental arthritis in animal models of RA.

Animal models for RA are well known in the art. For example the present use may be performed with the collagen-induced arthritis (CIA) model, the collagen-antibody-induced arthritis model, Zymosan-induced arthritis model, Antigen-induced arthritis model, TNF-α transgenic mouse model of inflammatory arthritis, K/B×N model, SKG model, Human/SCID chimeric mice or Human DR4-CD4 mice.

In another aspect, an antibody according to the present invention may be used to provide a therapeutic agent for use in treating RA. For example, the present invention provides the use of an antibody according to the first aspect of the invention to identify mimotopes to the antibody.

Mimotopes of the epitopes bound by antibodies of the present invention may be for use in treating RA. For example the mimotopes may be provided in as a vaccine for use in the treatment of RA.

Method

The present invention also provides a method for determining the antibody repertoire of B cells obtained from a synovial tissue sample, said method comprising the steps of: i) disrupting the tissue sample and generating a single cell suspension, ii) isolating individual B cells; and iii) amplifying and determining the VH and VL sequences of the individual B cells.

The sample may be from a subject with RA. The synovial joint may display active inflammation at the time the sample is taken. The tissue sample may comprise germinal centres.

The term "isolating individual B cells" refers to the act of separating a B cell from the remainder of the cells within the population. Method for isolating individual B cells include fluorescence-activated cell sorting (FACS) using a B cell specific cell marker such as CD19 and/or CD20. The B cells should be isolated such that an individual B cell is separated from the remaining B cells present within the sample. This may involve, for example, separating individual B cells into individual tubes or individual wells of a PCR plate.

The nucleotide sequence encoding the VH and VL regions expressed by individual B cells isolated may be determined using a number of techniques which are well known in the art. Such techniques typically involve the isolation of mRNA from the cell, followed by generation of cDNA and determining the nucleotide sequence of regions of interest using specific primers and first-generation sequencing techniques. Amplification of the VH and/or VL sequences may be performed by nested PCR. Alternatively the sequence of the VH and VL regions of an individual B cell may be determined using second-generation sequencing techniques.

Determining the nucleotide sequence encoding the VH and VL domains expressed by an individual B cell may comprise identifying the nucleotide sequence encoding for the whole of the VH or VL domain. Alternatively, determining the nucleotide sequence encoding the VH and VL domains may comprise determining the sequence of the CDRs. Determining the sequence encoding the VH and VL domains may comprise determining the nucleotide sequence encoding the CDR3.

The method of may further comprise the step of determining the level of sequence identity shared between the VH and VL regions of different individual B cells isolated from the tissue sample. The level of sequence identity shared by VH and/or VL sequences isolated from B cells may further be used in order to identify sequences which have arisen through affinity maturation.

The sequences derived from antibodies identified according to the method of the present invention are thus sequences which are directly associated with the in vivo site of disease (i.e. a synovial joint in RA). In particular pairs of VH/VL sequences identified using the method of the present invention are VH/VL pairs which are shown to occur in the disease setting. Further, antibody sequences which have arisen via affinity maturation within local germinal centres are highly relevant to disease processes.

The "antibody repertoire" of a tissue sample therefore refers to the VH and/or VL encoding nucleotide sequences or the CDR encoding nucleotide sequences present within a population of B cells isolated from the tissue sample. As the VH and VL domains are the primary determinants antigen-recognition by an antibody, identifying the antibody repertoire of a tissue sample allows the range of antigens recognised within said tissue sample to be determined.

The present invention also provides an antibody which targets a citrullinated protein derived from a neutrophil extracellular traps (NETs).

The citrullinated protein may be citrullinated histone 2 A (cit-H2A) and/or cit-H2B.

The antibody may be identified using the method outlined above.

The invention will now be further described by way of Examples, which are meant to serve to assist one of ordinary skill in the art in carrying out the invention and are not intended in any way to limit the scope of the invention.

EXAMPLES

Example 1—Generation of Synovial B Cell Monoclonal Antibodies

Preparation of Mononuclear Cells from Synovial Tissue and Phenotypic Characterisation by Fluorescence Activated Cell Sorting (FACS)

Mononuclear cells were isolated from synovial tissue specimens obtained from hip or knee joint replacement surgery.

Figure 2:
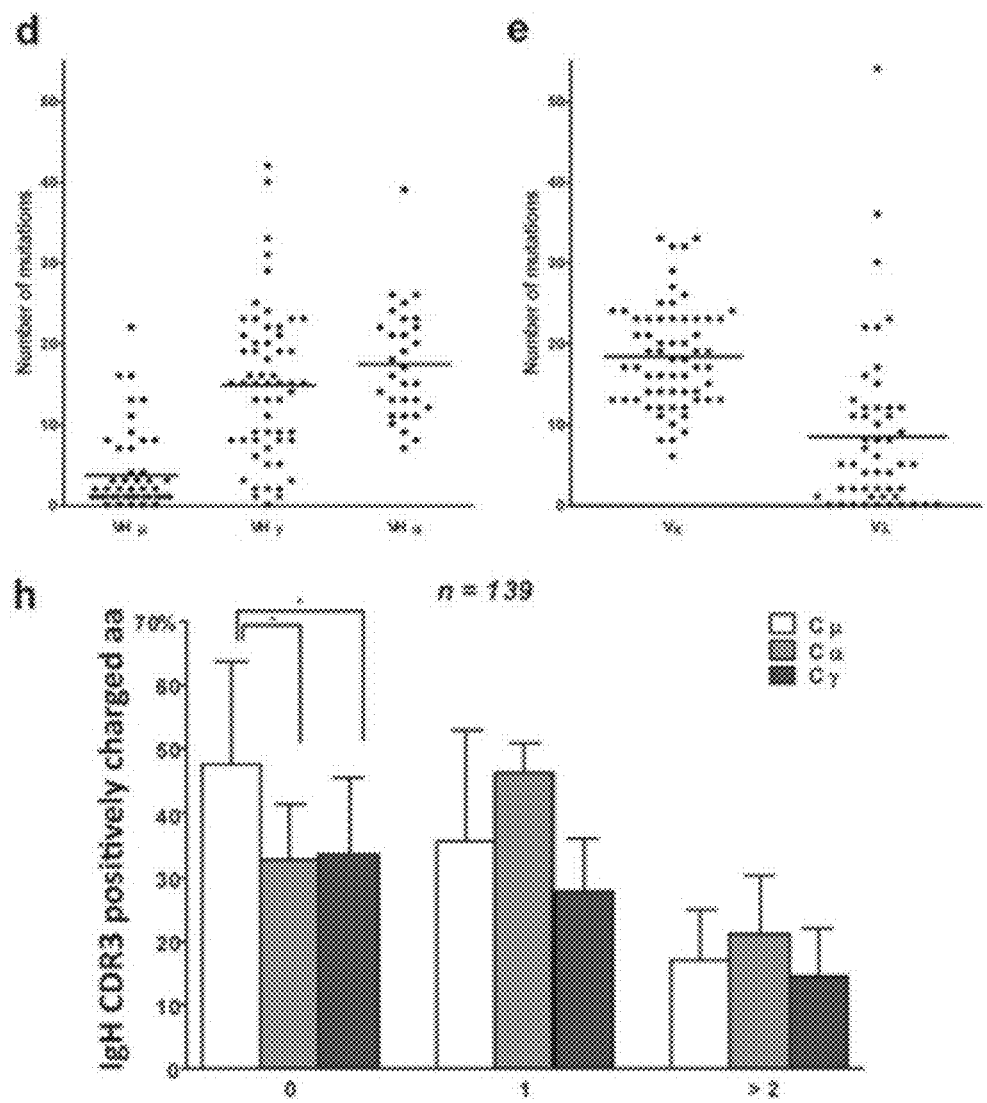
FIG. 2—Histological characterization of synovial ELS, single synovial CD19+ cell sorting and VH/VL Ig gene analysis demonstrating intra-synovial antigen-driven B cell affinity maturation and clonal diversification.
(a) Representative immunohistological characterization of synovial tissue samples from RA patients used in this study (RA015/11, RA056/11 and RA057/11). To assess the presence of ELS sequential paraffin tissue sections were stained for CD20 (B cells, left panel), CD3 (T cells, central panel) and CD138 (plasma cells, right panel), respectively. (b) Isolation strategy of single CD19+RA synovial B cells. Mononuclear cells were surface labelled with fluorochrome-coupled anti-CD19 and anti-CD3 antibodies; the sorting gate strategy for single CD19+CD3− B cell is shown. A total of 50,000 events is shown in the FACS plot. (c) The frequencies of µ, γ, and a heavy chain among all CD19+ B cells for which VH sequences were obtained are shown. (d-e) Ig gene sequences of CD19+ synovial B cells were analysed for the absolute numbers of somatic mutations in VH genes (FRs+CDRs) (shown separately for IgM, IgG and IgA clones in d) as well as VL genes (κ and λ shown separately in e). (f) Frequency of replacement (R) and silent (S) mutation ratio in FR (white) and CDR (black) regions for IgM, IgG and IgA is shown. Significant differences between the R/S ratio in FR vs CDR regions of IgG and IgA clones are shown: (g) IgH CDR3 aa length and (h) number of positively charged aa in the CDR3 is shown for each heavy chain isotype separately. (i) Genealogic trees generated by comparison of Ig VH sequences of synovial B cells. The synovial B cell clones are depicted as white circle, the putative common progenitor as grey circle and the germline sequences as black circle. The number inside the circle corresponds to the name of the clone and the number beside the line represents the additional mutation.

Single CD19+ lesional B cells from synovial cell suspension obtained from 3 joint replacements of ELS+/ACPA+ RA patients were sorted (FIG. 2a-b). Sequence analysis on a total of 139 different VH/JH regions and 175 VL regions (Vκ=94; Vλ=81) demonstrated that the VH/VL gene repertoire of the synovial B cells was not significantly different compared to peripheral blood (PB) CD5-IgM+ B cells of healthy. IgG and IgA synovial B cell clones showed significantly higher number of SHM in their VH region compared to IgM, ~50% of which displayed germline sequences (FIG. 2d); additionally the number of SHM in VL was higher in κ compared to λ chains (FIG. 1e). Switched B cell clones showed i) high ratios of replacement (R) to silent (S) mutations in CDR1-2 compared to the FR1-3 regions (FIG. 2f), ii) a shorter CDR3 length compared to unswitched un-mutated IgM+ clones (FIG. 2g) and iii) a higher frequency of positively charged aa frequently used by autoreactive B cells Example 2—Determination of the Immunoreactivity of the Isolated Synovial Antibodies Matching VH and VL Ig genes from 66 individual B cells were cloned into specific expression vectors and produced in vitro full recombinant monoclonal antibodies (rmAbs) as complete IgG1. Sufficient yield (>5 µg/ml) was obtained from 59 rmAbs (RA015/11=12; RA056/11=26; RA057/11=21) which were used for downstream analysis.

Figure 3:
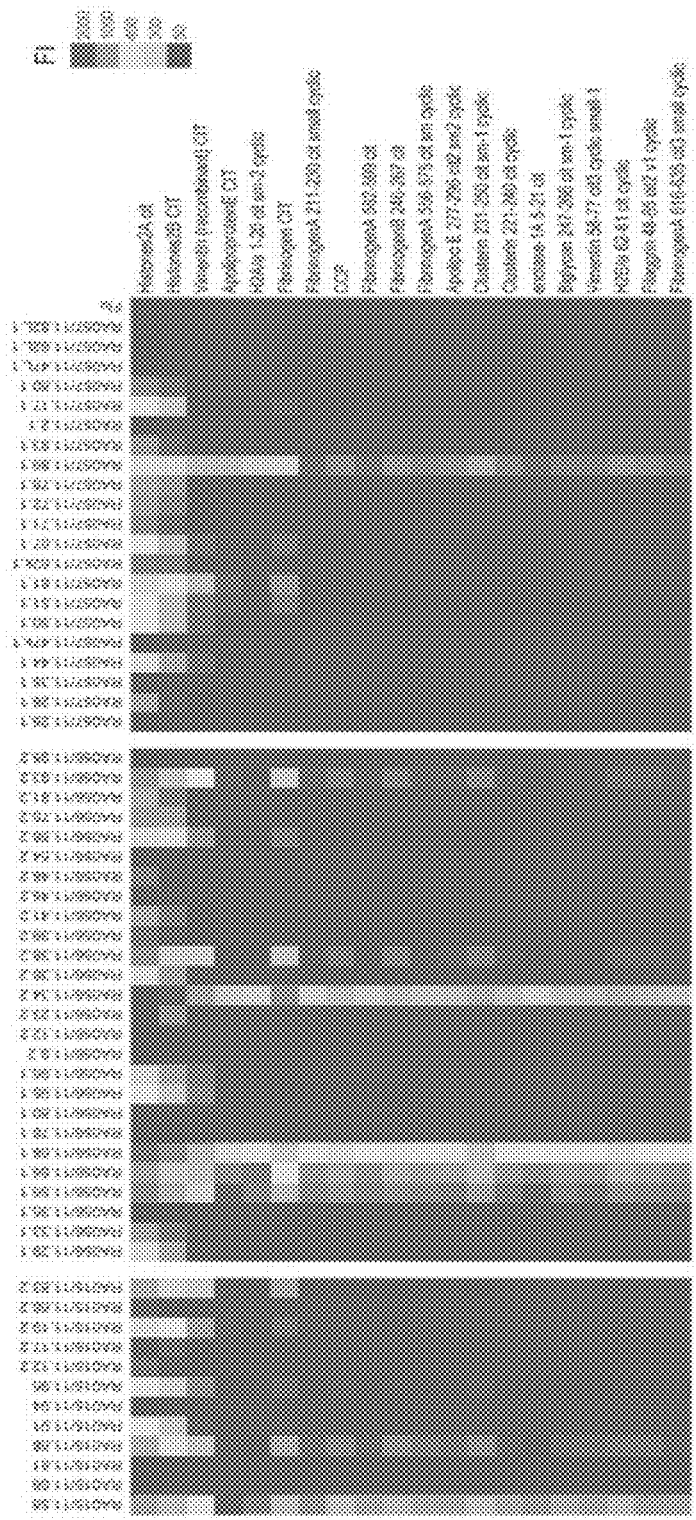
FIG. 3—Characterization of the binding of the RA synovial rmAbs towards citrullinated antigens demonstrates biased immunoreactivity towards citrullinated histones.
(a) Multiplex autoantibody assay (luminex) heatmap. Heatmap tiles reflect the amount of IgG autoantibody binding reactivity based on the fluorescence intensity scale as indicated on the top right. Recombinant rmAb IDs (individual columns, top labelling) and the location of each citrullinated antigen in the assay (individual rows, right side legend) are shown. (b) Column bar graph representation of the mean fluorescence intensity (FI+SEM) of the luminex heatmap for each citrullinated antigen. (c) Pie charts showing the general percentage of reactivity towards citH2A (top) and citH2B (bottom) histones of the RA rmAbs after correction for background signal and the breakdown of the prevalence in each individual synovial tissue. (d-e) Binding of the RA and control rmAbs (30 naïve and memory B cell clones from SS patients) to native and in vitro citrullinated histone H2A and H2B tested by ELISA. Results are grouped according to tissues' donors and shown as increase percentage of binding comparing native vs citrullinated histones. A flu control rmAb is shown in red. The dotted horizontal line represents the cut-off for positivity of the rmAbs which was determined as the mean+2SD of the reactivity of 30 SS control rmAbs (right panel). (f) Binding of the synovial rmAbs (black circles if non-reactive and coloured circles if reactive) and control rmAbs (open circles) to citrullinated histone H2A peptides tested by ELISA (H2A 1-21 Cit; H2A 27-47 Cit; H2A 69-90 Cit; H2A 79-98 Cit; H2A 94-113 Cit). Results are expressed as absorbance at 405 nm. Each coloured circle represents an individual RA rmAb.
Figure 3:
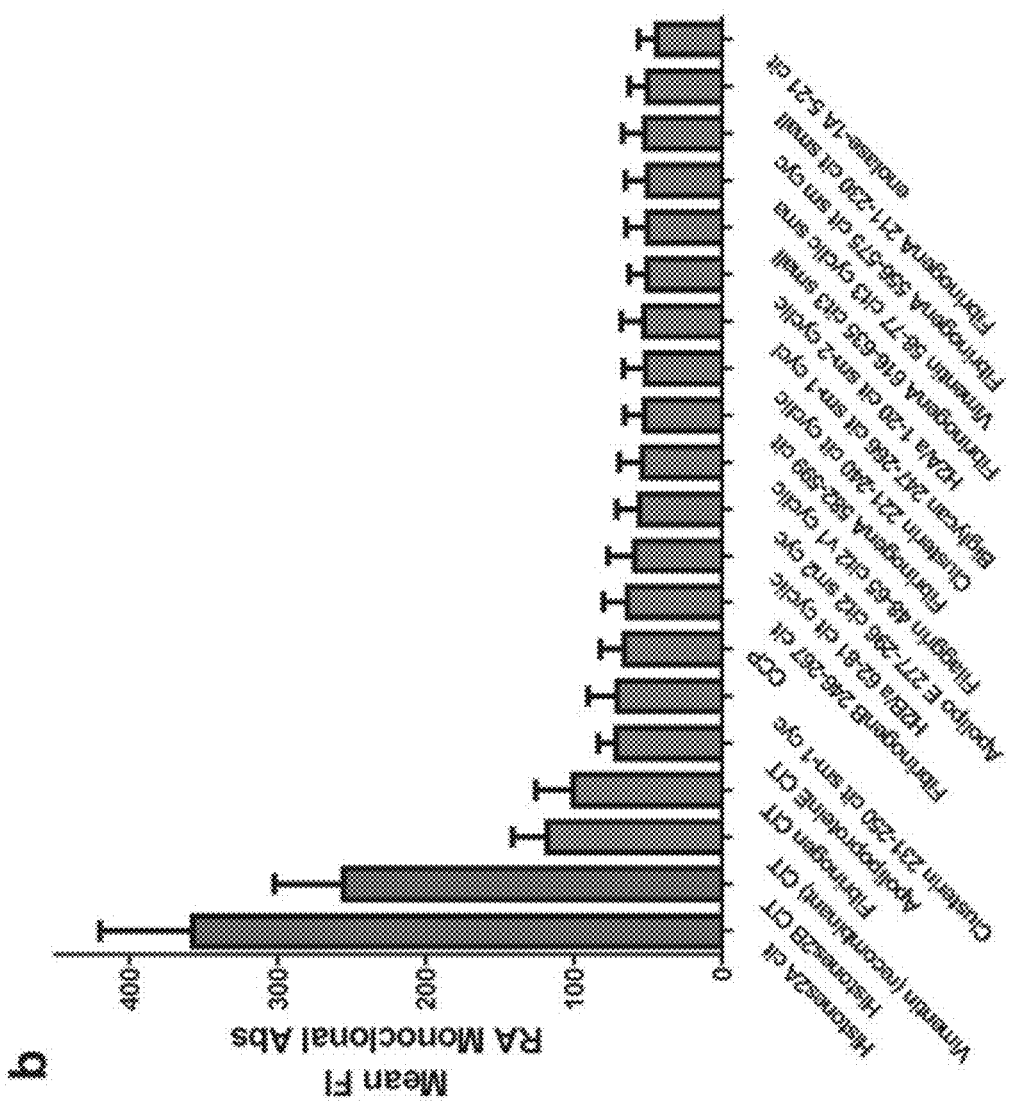
Figure 3:
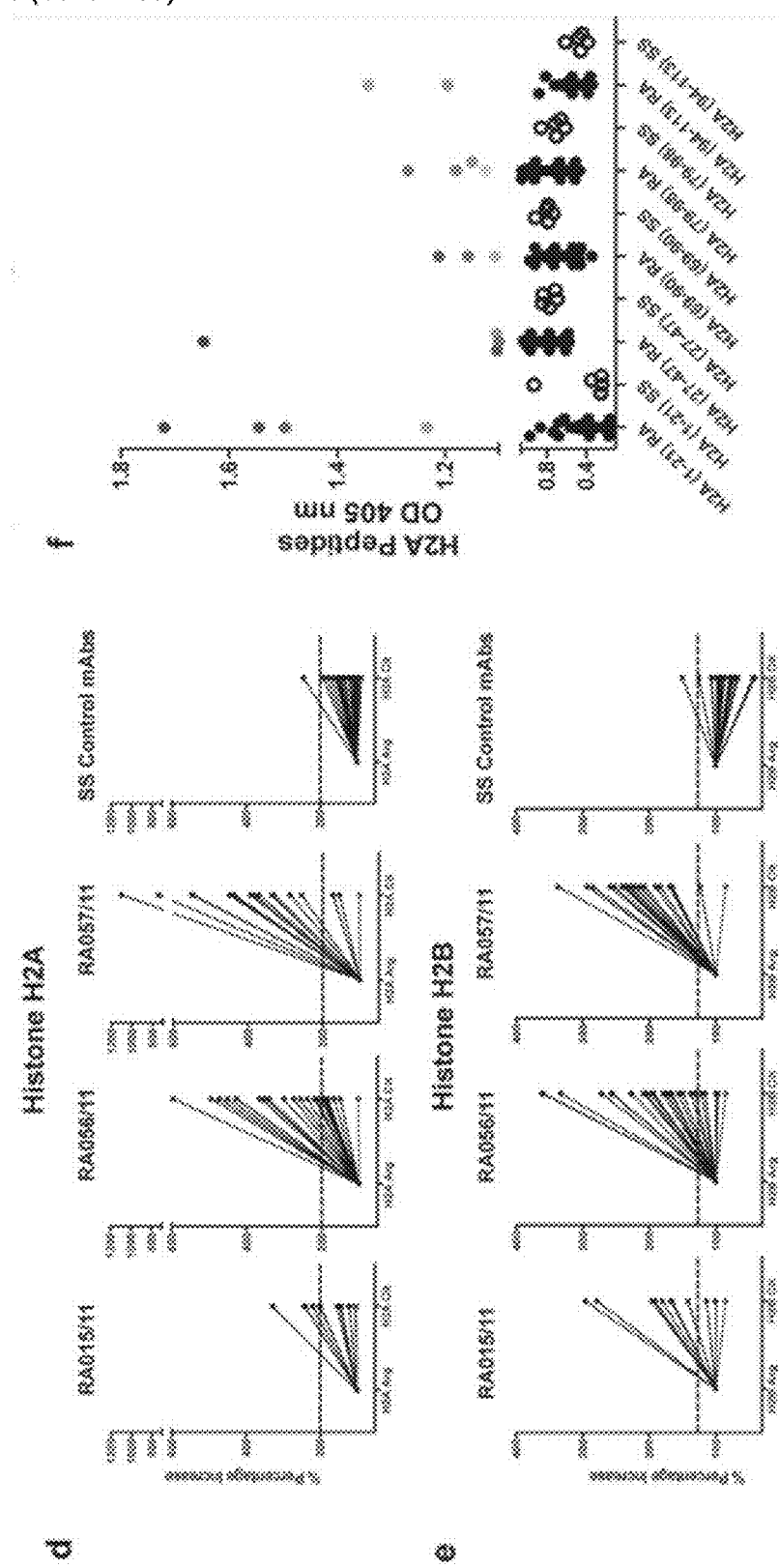

The rmAbs were screened in an autoantigen microarray platform which contains >300 peptides and proteins in their native and post-translationally modified form (Robinson et al.) and a multiplex antigen assay containing 20 RA-associated citrullinated antigens. Several RA rmAbs showed strong immunoreactivity towards citrullinated histones H2A (citH2A) and citH2B by multiplex assay (FIG. 3a) with reactivity to histones H2A and H2B also frequently observed in the protein array heatmap. Quantitative analysis confirmed that the strongest reactivity was directed against citH2A and citH2B followed by citrullinated vimentin and fibrinogen (FIG. 3b).

Additionally, 5 rmAbs displayed binding to different citrullinated antigens, highlighting the existence of clones with multiple citrullinated reactivity. Overall, 41% (24 out of 59) and 34% (20 out of 59) of the clones were considered as reactive against citH2A and citH2B, respectively (FIG. 3c). Such reactivity was confirmed to be disease-specific as it was not detectable in 30 control rmAbs from circulating naïve and memory B cells of 5 Sjögren's syndrome (SS) patients.

The immunoreactivity of the RA rmAbs towards the native vs citrullinated form of H2A and H2B histones was determined by ELISA. As shown in FIG. 3d-e, a significant increase was detected in the binding to citH2A/H2B compared to native H2A/H2B histones in a large proportion of rmAbs from ELS+ACPA+RA synovial B cells but not in either naïve or memory SS B cells or flu control rmAb. While no immunodominant reactivity was identified to synthetic citrullinated H2A peptides spanning the whole histone H2A length, different antibodies recognised different citrullinated H2A epitopes, suggesting the occurrence of in situ "epitope spreading" (FIG. 3f). It was also demonstrated that the immunoreactivity observed against citrullinated histones or multiple citrullinated antigens was not due to polyreactivity, a phenomenon frequently observed in rmAbs generated from naïve B cells. Accordingly, only 1/59 clones (RA057/11.35.1) displayed polyreactivity against multiple structurally unrelated antigens such as ss/dsDNA, LPS and insulin.

Figure 4:
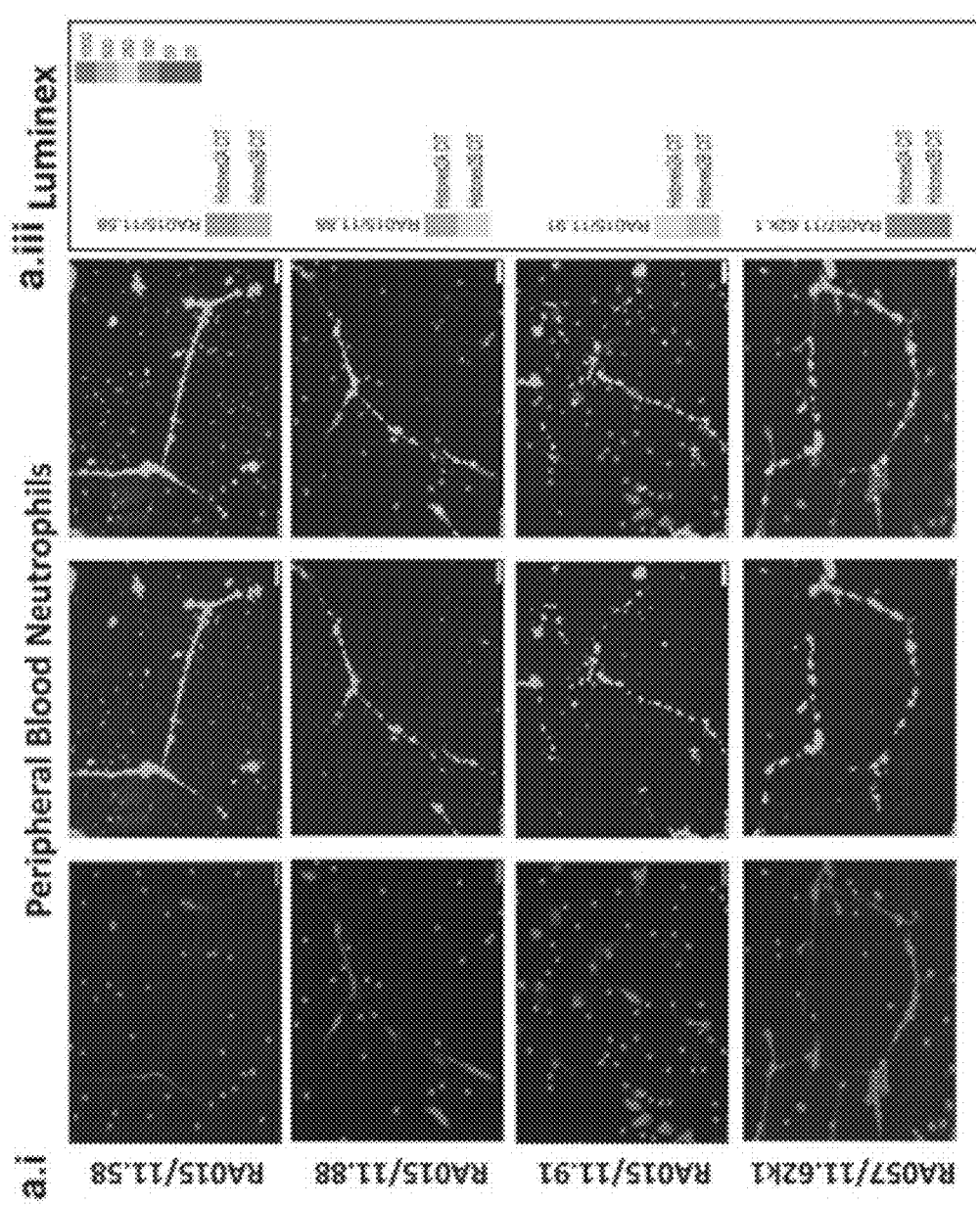
FIG. 4—RA synovial rmAbs display selective immunoreactivity towards neutrophil NETs which is dependent on somatic hypermutation.
(a) Representative pictures of PMA-stimulated neutrophils incubated with RA synovial (a.i) vs control SS rmAbs (a.ii) demonstrating selective immunoreactivity of RA rmAbs towards NETs. NETs are clearly evident as web-like structures rich in nuclear material stained by DAPI (blue, left columns) and are strongly bound by RA synovial (but not SS) rmAbs (green, middle columns, with overlap staining in the right columns) Corresponding multiplex tiles reporting the binding of the same rmAb towards citH2A and citH2B histones are reported beside each IF staining (a.iii) demonstrating good accordance with anti-NET staining (b) Binding of the RA synovial rmAbs to NETs is confirmed also in using PMA-stimulated synovial fluid neutrophils. (c) Pie chart displaying the percentage of synovial rmAbs reacting towards NETs within individual synovial tissue demonstrated that up to 42% of the intrasynovial humoral response is directed towards NETs. (d) Sub-analysis of the ELISA immunoreactivity towards citH2A and citH2B histones demonstrates significantly higher binding in anti-NET+vs anti-NET− clones. (e) Sub-analysis of the anti-citH2A (top) and citH2B (bottom) histone reactivity in ELISA according to the number of somatic mutations in the VH regions of IgM (left), IgG (central) and IgA (right) clones, demonstrates progressive increase immunoreactivity according to the mutational load in all isotypes. (f) Reversal to germline (GL) sequences by overlapping PCR in representative individual anti-NET+RA rmAb invariably abrogated the binding to NETs. The family usage, CDR3 sequence and the total number of somatic mutations in the FR and CDR regions of VH and VL Ig genes prior to reversal to GL sequences is shown beside each IF staining *p<0.05; **p<0.01
Figure 4:
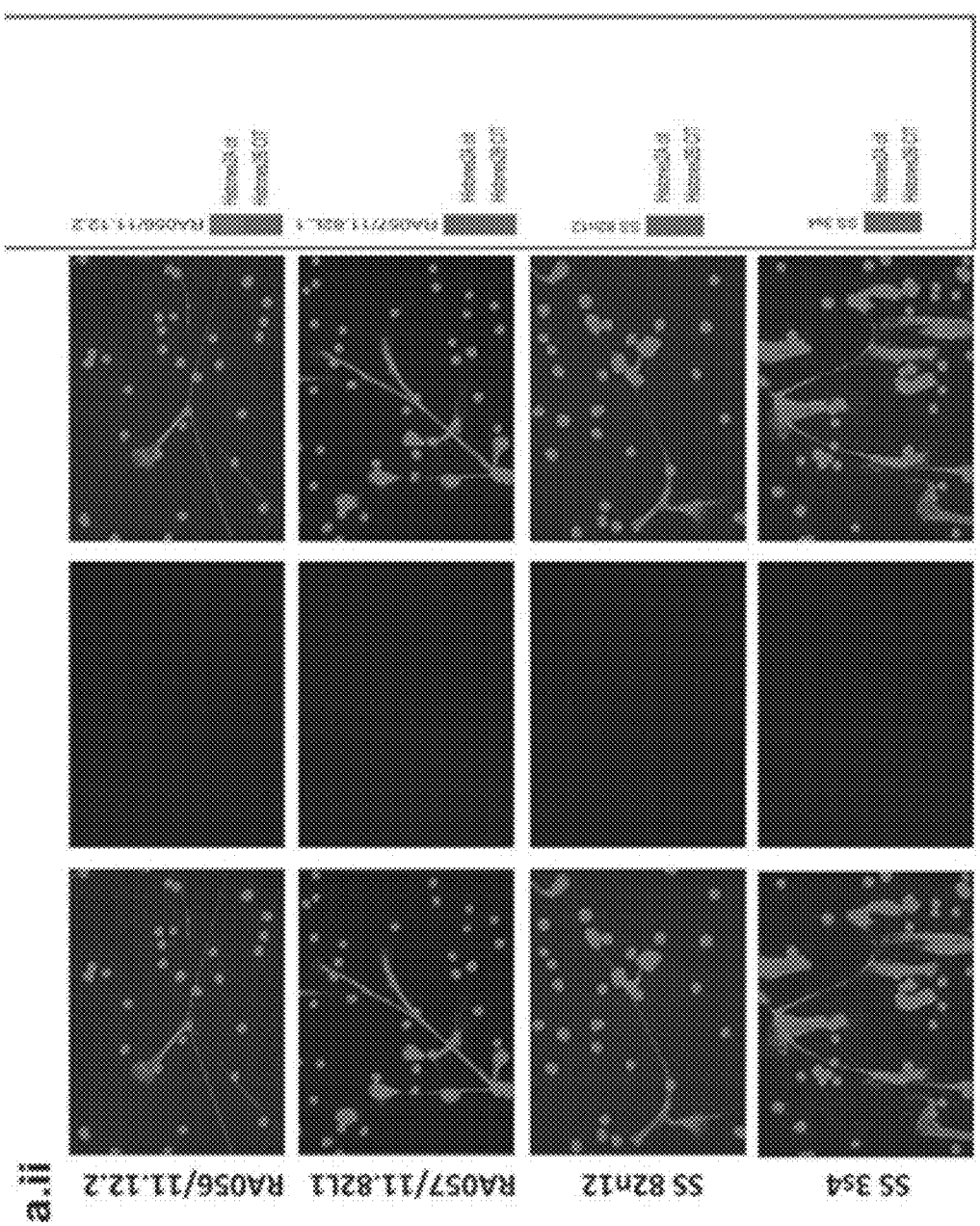

Synovial rmAbs displayed strong binding to NETs generated from either PB neutrophils of healthy donors (FIG. 4a.i) or from RA SF neutrophils (FIG. 4b) in large proportion: 33%, 42% and 19% of the total synovial antibody response of patients RA015/11, RA056/11 and RA057/11, respectively (FIG. 3c) Immunoreactivity of the RA rmAbs was restricted to NETs with negligible binding to the nucleus of neutrophils not undergoing NETosis. Conversely, none of the rmAbs generated from SS patients displayed NET reactivity (FIG. 4a.ii-3b). Reactivity towards NETs in the cell-based assay was strongly associated with higher immunobinding to citrullinated histones in the multiplex assay (see multiplex tiles in FIG. 4a.iii) and in ELISA (FIG. 4d).

Immunolabelling of NETs using RA rmAbs demonstrated exact colocalization with an anti-citH4 polyclonal antibody, confirming that anti-NET synovial mAbs specifically bind citrullinated histones externalized during NETosis. Several RA rmAbs also reacted with a band corresponding to citH4 in immunoblot using acid-extracted NET proteins from PB PMA-stimulated neutrophils as substrate. Another important question was whether affinity maturation via SHM was required for the binding of the RA rmAbs to NET antigens.

A progressive increase in the mutational load within the VH Ig genes was associated with higher reactivity to citrullinated histones in all isotypes tested, with the strongest difference observed in IgG-switched clones (FIG. 4e). Selected highly mutated rmAbs with strong NETs reactivity in immunofluorescence to the corresponding VH and VL Ig germline sequences by overlapping PCR were reverted. rmAbs reverted into their germline sequence invariably lost all the reactivity towards NETs at the identical concentration (FIG. 4f). Overall, these data strongly suggest that antigen-driven SHM is required for the immunoreactivity of RA synovial B cell clones to NET-associated autoantigens.

Example 3—rmAbs in In Vivo Disease

Figure 5:
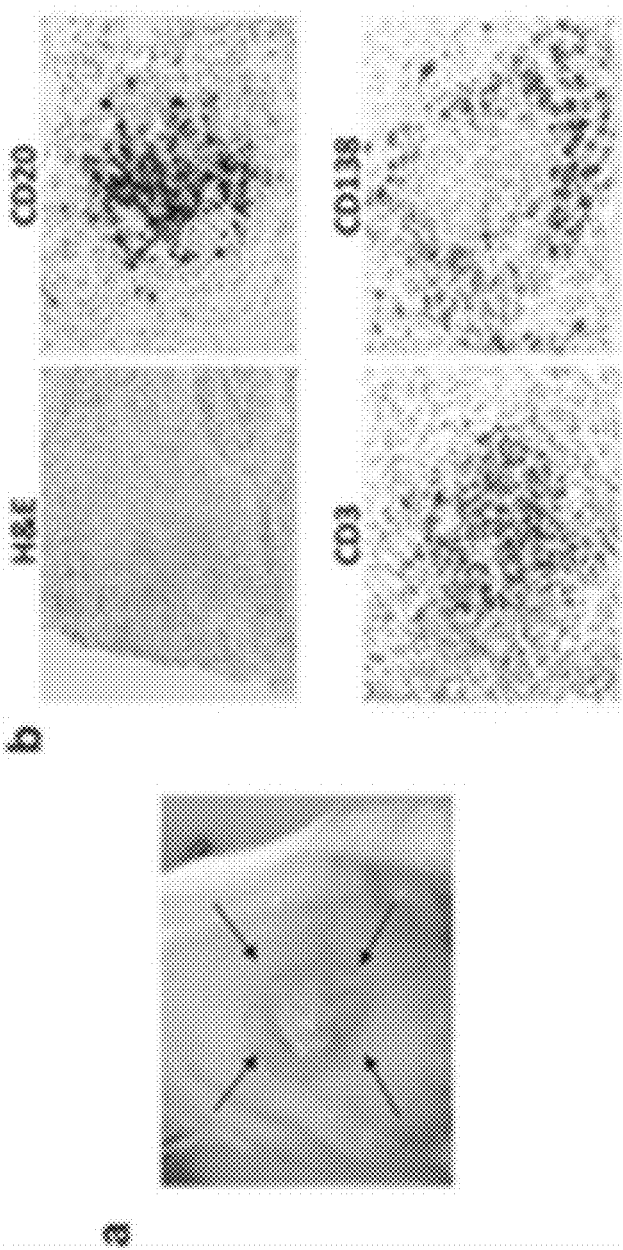
FIG. 5—ELS+RA synovia are self-maintained and release anti-NET and anti-citrullinated histone antibodies in vivo when engrafted in the Hu-RA/SCID chimeric model.
(a) RA ELS+ synovial tissues RA015/11 and RA056/11 transplanted into SCID mice (arrow depict site of transplant) displayed persistent ELS after 4 weeks post-engraftment as shown in representative pictures of sequential analysis of paraffin embedded sections stained for H&E and for CD20 (B cells), CD3 (T cells) and CD138 (plasma cells) (b). (c) Serum from Hu-RA SCID mice engrafted with RA015/11 and RA056/11 synovia reproduced the reactivity towards NETs in PMA-stimulated neutrophils. Representative pictures with NETs visualised by DAPI (blue) and the binding of human IgG in green are shown. (d) Binding of the human IgG in Hu-RA SCID mice to citrullinated vs unmodified H2A and H2B histones by ELISA confirmed the immunoreactivity observed with the rmAbs from the same patients. Results are shown as increase percentage in immunoreactivity in citrullinated vs native H2A and H2B histones. (e) Stratification of synovial RA grafts based on citH2A and citH2B immunoreactivity vs non-reactive demonstrated increased synovial expression of mRNA transcripts for CXCL13 and LTβ in anti-citH2A and citH2B reactive vs non-reactive samples. *p<0.05
Figure 5:
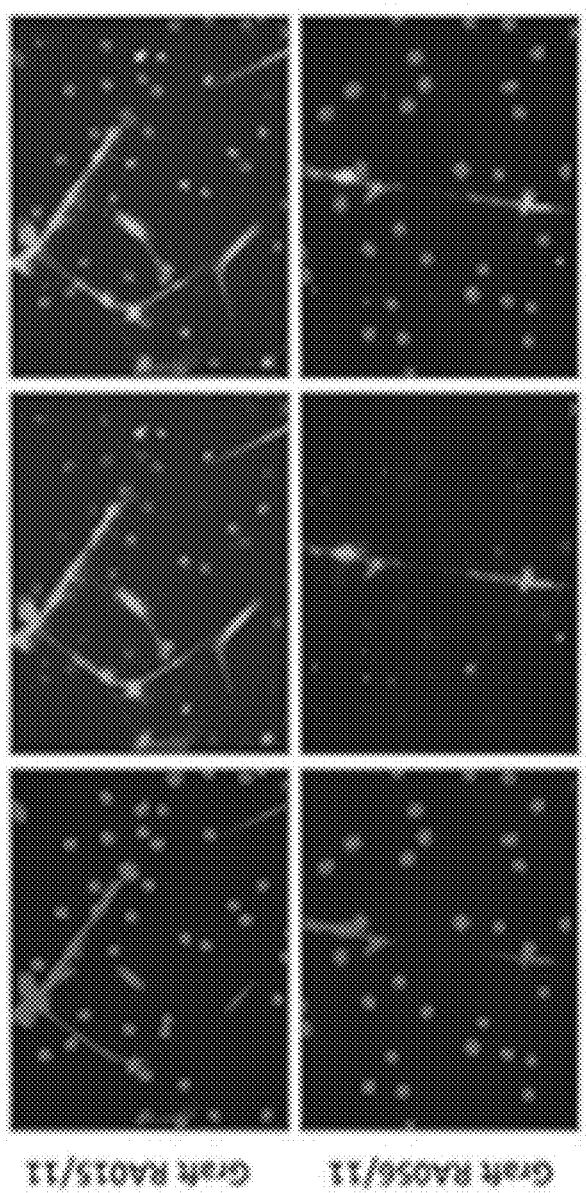
Figure 5:
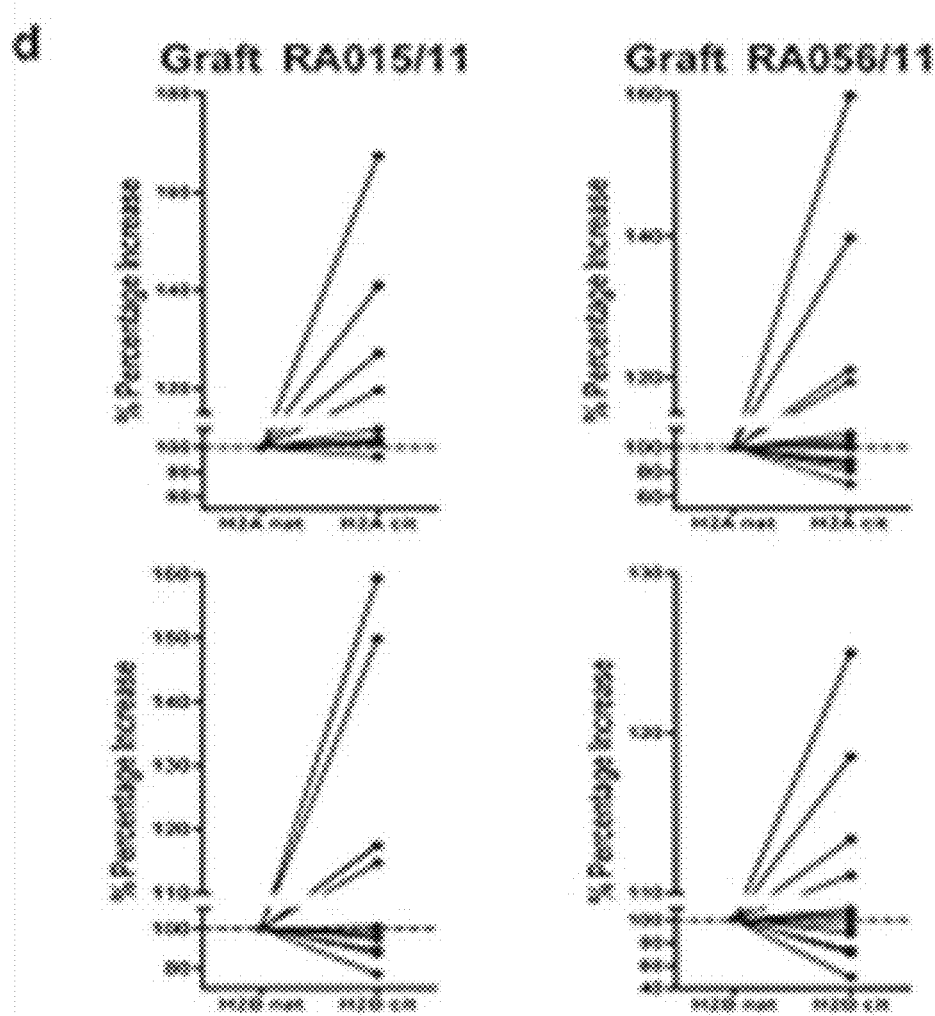
Figure 5:
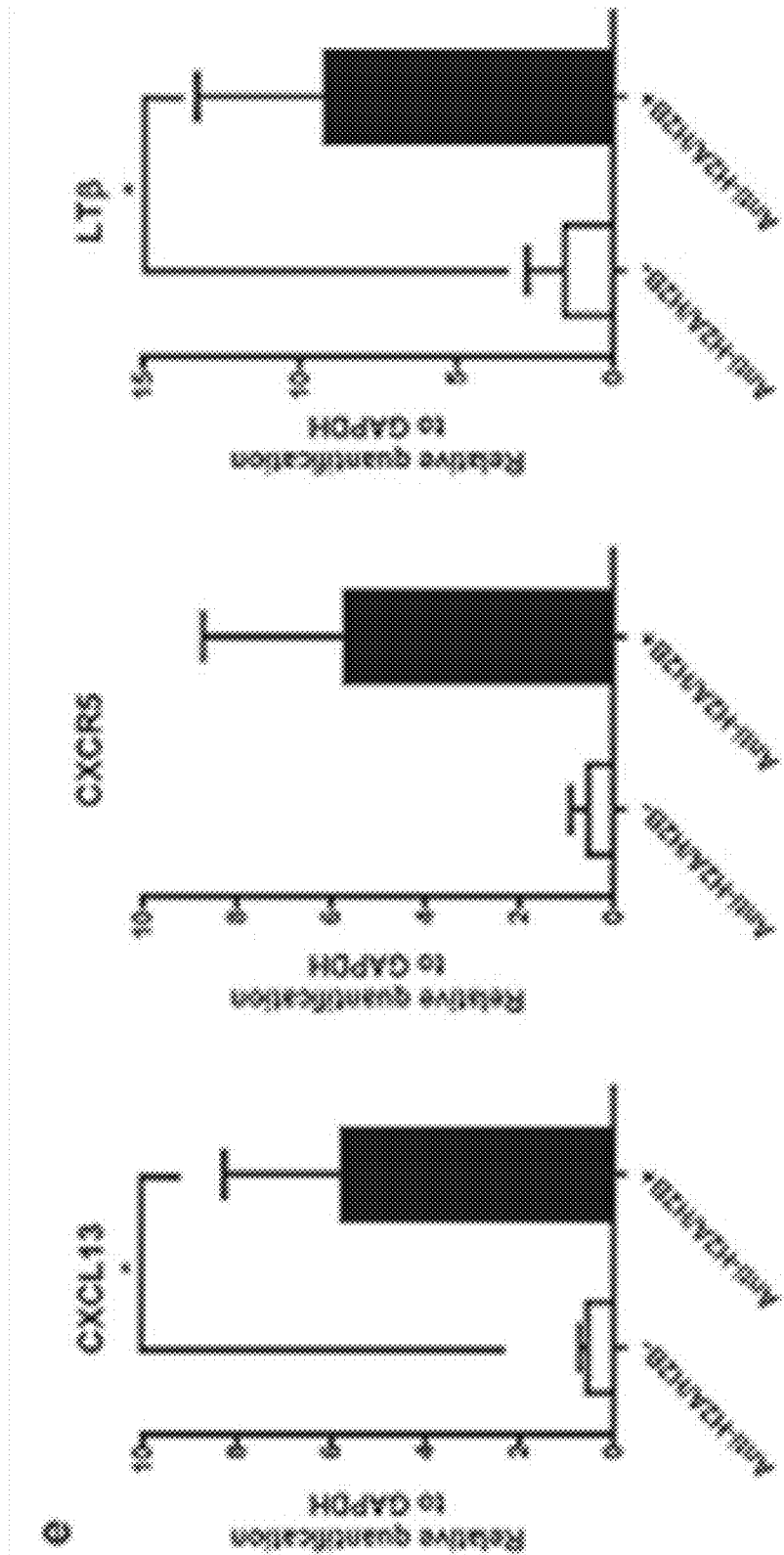
Figure 7:
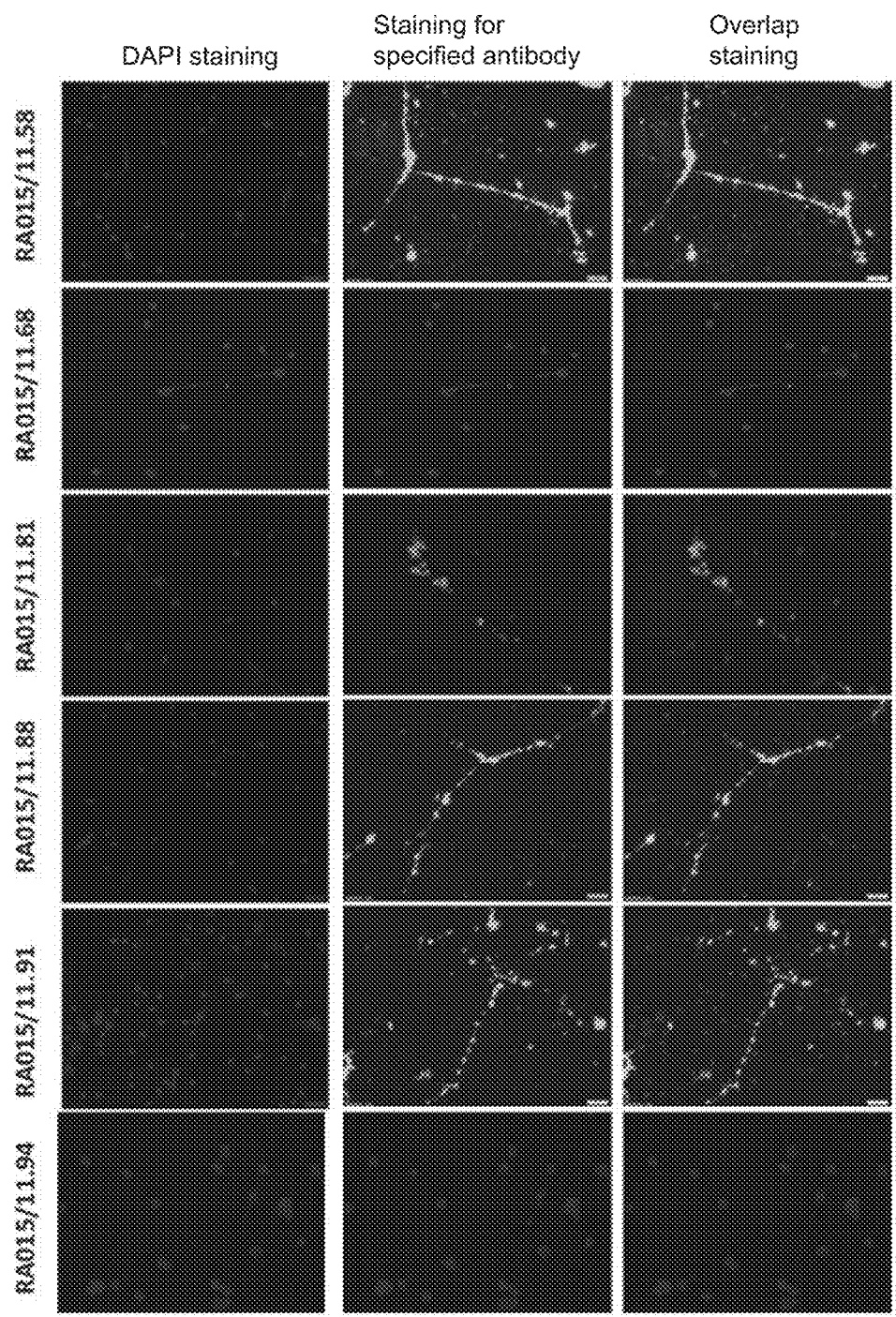
FIG. 7—Micrographs showing reactivity of each antibody against Neutrophil Extracellular Traps (NETs).

An in vivo chimeric human RA/SCID mouse transplantation model was utilised (FIG. 5a), whereby a total of 31 SCID mice were transplanted with synovial tissues from either patient. RA synovial ELS were self-maintained for several weeks in the absence of recirculating immune cells (FIG. 5b) and released IgG ACPA autoantibodies (measured as total anti-CCP IgG, not shown). Strikingly, mouse sera from mice transplanted with RA015/11 or RA056/11 grafts contained autoreactive human anti-NET IgG (FIG. 5c) and/ or anti-citH2A/citH2B histones antibodies (FIG. 5d). Additionally, mouse sera reactive against citrullinated histones/ NETs displayed higher tissue levels of CXCL13, CXCR5 and LTβ mRNA, which are master regulators of ectopic lymphoid neogenesis and are selectively unpregulated in ELS+RA synovium (FIG. 5e). These data provides direct demonstration that the presence of ELS is associated with functional activation of autoreactive B cells and the production of anti-NET autoantibodies.

Materials and Methods
Patients

Three synovial tissues from total joint replacement (2 knees and 1 hip) were obtained after informed consent (LREC 05/Q0703/198) from ACPA+RA patients (all females, main age 70.5 year, range 66-75, all on combination DMARD therapy including methotrexate) diagnosed according to the revised ACR criteria. Synovial tissue was dissected and processed as previously described (Humby, F., et al. *PLoS medicine* 6, e 1 (2009)).

Histological Characterization of Lymphocytic Aggregates within RA Synovial Tissue Sequential paraffin-embedded 3 µm sections of synovial tissue were stained for the markers CD3, CD20 and CD138 following routine H&E staining to classify the lymphocytic infiltration as aggregate or diffuse, as previously reported (Humby, F., et al).

Synovial Mononuclear Cell Isolation, FACS Labelling and CD19+ Cell Sorting Mononuclear cells were isolated from fresh synovial tissue specimens obtained as above. Briefly, the synovial tissue was cut into small pieces and enzymatically digested in 1.5 ml RPMI (supplemented with 2% FBS) with 37 µl collagenase D (100 mg/ml, Roche) and 2 µl DNase I (10 mg/ml) at 37° C. for 1 hour under shaking in a water-bath with tiny magnetic stirrers. After the first digestion, the sample was incubated in 1.5 ml RPMI (supplemented with 2% FBS) with 37 µl collagenase/dispase mix solution (100 mg/ml, Roche) and 2 µl DNase I (10 mg/ml) at 37° C. for 30 min under shaking in the water-bath. After the second incubation, 15 µl of 0.5 M EDTA were added to stop the reaction. The samples were then filtered through 40 µm cell strainer (Sigma) to remove undigested tissue and centrifuged at 1200 rpm for 10 min. The cells were resuspended in complete tissue culture media. Cells viability was determined by Trypan blue exclusion test Immunofluorescence labeling for flow cytometry was performed by staining the purified mononuclear cells on ice with PerCPCy5.5 anti-human CD19 (clone SJ25C1; BD Biosciences) and FITC anti-human CD3 (clone HIT3a, eBioscience) in order to differentiate CD3-CD19+ B cells from CD3+CD19− T cells. Incubation with antibodies was performed in the dark at 4° C. for 30 min in PBS+2% fetal calf serum (FCS). Flow cytometric analysis and sorting was performed with a FACSAria flow cytometer (Becton Dickinson). Single CD19+ cells were sorted directly into 96-well plates (Eppendorf) containing 4 µl/well of ice-cold 0.5×PBS, 100 mM DTT (Invitrogen), 40 U/µl RNasin Ribonuclease Inhibitor (Promega) as previously described 12. Plates were sealed with adhesive PCR foil (4titude) and immediately frozen on dry ice before storage at −80° C.

Single Cell RT-PCR and Immunoglobulin VH and VL Gene Amplification cDNA was synthesized in a total volume of 14.5 µl per well in the original 96-well sorting plate. In brief, total RNA from single cells was reverse transcribed in nuclease-free water (Qiagen) using 300 ng/µl random hexamer primers (Roche), 25 mM each nucleotide dNTP-mix (Invitrogen), 100 mM DTT (Invitrogen), 10% NP-40 (Sigma), 40 U/µl RNasin (Promega), and 50 U Superscript III reverse transcriptase (Invitrogen). Reverse transcription, single-cell RT-PCR reactions, and immunoglobulin V gene amplification were performed. Briefly, for each cell IgH and corresponding IgL chain (Igκ and Igλ) gene transcripts were amplified independently by nested PCR starting from 3 µl of cDNA as template. cDNA from CD3-CD19+ B cells isolated from synovial tissue was amplified using reverse primers that bind the Cμ, Cγ or Cα constant region in three independent nested PCR. All PCR reactions were performed in 96-well plates in a total volume of 40 μl per well containing 50 mM each primer 12, 25 mM each nucleotide dNTPmix (Invitrogen) and 1.2 U HotStar Taq DNA polymerase (Qiagen). All nested PCR reactions with family-specific primers were performed with 3 μl of unpurified first PCR product.

Ig Gene Sequence Analysis

Aliquots of VH, Vκ and Vλ chains second PCR products were sequenced with the respective reverse primer (Beckman Coulter Genomics) and the sequences were analyzed by IgBlast (http://www.ncbi.nlm.nih.gov/igblast/) to identify germline V(D)J gene segments with highest homology. IgH complementary determining region CDR3 length and the number of positively (Histidine (H), Arginine (R), Lysine (K)) and negatively charged (Aspartate (D), Glutamate (E)) amino acids were determined. CDR3 length was determined as indicated in IgBlast by counting the amino acid residues following framework region FR3 up to the conserved tryptophan-glycine motif in all JH segments or up to the conserved phenylalanine-glycine motif in JL segments. The V gene somatic mutations was performed using IMGT/V-QUEST search page (http://imgt.org/IMGT_vquest) in order to characterize the silent versus non-silent mutation in each FR region and CDR region to determine the R/S ratio.

Expression Vector Cloning and Monoclonal Antibody Production

The expression vector cloning strategy and antibody production were performed. Briefly, before cloning all PCR products were digested with the respective restriction enzymes AgeI, SalI, BsiWI and XhoI (all from NEB). Digested PCR products were ligated using the T4 DNA Ligase (NEB) into human IgG1, Igκ or Igλ expression vector. Competent E. coli DH10β bacteria (New England Biolabs) were transformed at 42° C. with 3 μl of the ligation product. Colonies were screened by PCR and PCR products of the expected size (650 bp for Igγ1, 700 bp for Igκ and 590 bp for Igλ) were sequenced to confirm identity with the original PCR products. To express the antibodies in vitro, cells of the Human Embryonic Kidney (HEK) 293T cell line were cultured in 6 well plates (Falcon, BD) and co-transfected with plasmids encoding the IgH and IgL chain originally amplified from the same B cell. Transient transfection of exponentially growing 293T cells was performed by Polyethylenimine (Sigma) at 60-70% cell confluency. Tissue culture supernatants with the secreted antibodies were stored at 4° C. with 0.05% sodium azide. Recombinant antibody concentrations were determined by IgG ELISA before and after purification with Protein G beads (GE Healthcare).

Synovial Antigen Microarray Profiling

The synovial antigen microarray production, probing and scanning protocol has been previously described (Hueber, W., et al. *Arthritis and rheumatism* 52, 2645-2655 (2005)). Briefly, each antigen was robotically spotted in ordered arrays onto poly-L-lysine microscope slides at 0.2 mg/ml concentration. Each array was blocked with PBS 1×, 3% FCS and 0.05% Tween 20 overnight on a rocking platform at 4° C. Arrays were probed with the rmAbs at a working concentration of 10 μg/ml for 1 hour on a rocking platform at 4° C. followed by washing and incubation with Cy3-conjugated goat anti-human secondary antibody. The arrays were scanned using a GenePix 4400A scanner and the net mean pixel intensities of each feature were determined using GenePix Pro 7.0 software. The net median pixel intensity of each feature above the background was used.

Multiplex Autoantibody Assay

The multiplex autoantibodies assay containing 20 citrullinated RA-associated antigens was performed as previously published (Robinson, W. H, *Nature medicine* 8, 295-301 (2002)). Briefly, the rmAbs were added at a final concentration of 10 μg/ml to custom Bio-Plex™ beads associated with RA putative autoantigens and incubated at room temperature for 1 hour. After washing, PE anti-human IgG antibody was added to the beads and incubated at room temperature. After another wash, the beads mix was passed through a laser detector using a Luminex 200 running Bio-Plex Software V.5.0 (Bio-Rad, Hercules, Calif., USA). The fluorescence of PE detected reflects the amount of antibodies that bind to the beads.

Arginine Deimination of Histone H2A and H2B

Histones H2A and H2B purified from bovine thymus tissue (ImmunoVision) were incubated at 1 mg/ml with rabbit skeletal muscle PAD (7 U/mg fibrinogen; Sigma) in 0.1 M Tris-HCl (pH 7.4), 10 mM CaCl2, and 5 mM DTT for 2 h at 50° C. After incubation each histone was stored at −80° C. in aliquots of 100 μl each.

ELISA Assay for Anti-Citrullinated H2A and H2B

ELISA plates (Thermo Scientific) were coated with 50 μl/well citrullinated or unmodified histones H2A or H2B at a final concentration of 10 μg/ml in 1×PBS. Plates were washed with 1×PBS and 0.1% Tween 20 before incubation for 1 hour with 200 μl/well 1% BSA in 1×PBS and washed again. Samples were transferred into the ELISA plate at a concentration of 10 μg/ml and incubated for 2 hours (SCID serum was diluted 1:10). Unbound antibodies were removed by washing before incubation for 1 hour with 50 μl/well of horseradish peroxidase (HRP) coupled goat anti-human IgG (Becton Dickinson). Assays were developed using TMB Substrate Reagent Set (BD OptEIA). Optical densities (OD) were measured at 450 nm. All steps were performed at room temperature.

ELISA for Anti-citH2A Peptides

ELISA plates (Costar™ 96-well half area plates) were coated with 25 μl/well citrullinated or peptides derived from H2A at a final concentration of 10 μg/ml in 1×PBS and incubated overnight at 4° C. Plates were then washed with 1×PBS before saturation for 1 hour with 75 μl/well 1% Porcine Gelatin in 1×PBS and washed again. Samples diluted in 1×PBS, 0.5% Porcine gelatin, 0.05% Tween-20 at a concentration of 10 μg/ml, were transferred into the ELISA plate and incubated for 2 hours at RT. Unbound antibodies were removed by 3 washings in 1×PBX, 0.05% Tween-20, before incubation for 2 hour RT with 25 μl/well of horseradish peroxidase (HRP) coupled goat anti-human IgG (Becton Dickinson) 1/3000 in dilution buffer. Assays were developed using Alkaline Phosphatase (Sigma). Optical densities (OD) were measured at 405 nm.

Characterization of Polyreactivity by ELISA

To test the reactivity against different allo- and auto-antigens, supernatants were tested for polyreactivity against double and single-stranded DNA (dsDNA and ssDNA), lipopolysaccharide (LPS) and insulin by ELISA. Antibodies that reacted against at least two structurally diverse self- and non-self-antigens were defined as polyreactive. Internal controls for polyreactivity were added on each plate consisting of the recombinant monoclonal antibodies mGO53 (negative), JB40 (low polyreactive), and ED38 (highly polyreactive).

Neutrophils Isolation, Stimulation of NETosis and Immunofluorescence Microscopy on NETs Neutrophils were isolated from peripheral blood of healthy blood donors or the synovial fluid of 2 RA patients using discontinuous gradient centrifugation. For immunofluorescence microscopy, purified neutrophils were seeded onto cell culture cover slides at $2\times10^5$ cells/well and activated with 100 nM PMA for 4 h at 37° C. After fixation in 4% (final concentration) paraformaldehyde and incubation with protein block solution (DAKO), NETs were stained with RA synovial rmAbs or SS control rmAbs diluted in PBS 1× for 1 hour at room temperature. As positive control, a polyclonal rabbit anti-histone H4 (citrulline 3; Millipore) was diluted in DAKO antibody diluent (DAKO) for 2 h at RT. After 3 washes with TBS 1×, Alexa 488 goat anti-human IgG (Invitrogen, 1:200) or Alexa 555 goat anti-rabbit IgG (Invitrogen, 1:200) diluted in antibody diluent (DAKO) was added for 30 min at room temperature. After further washes, DAPI (Invitrogen) was added to visualize the NETs. All sections were visualised using an Olympus BX60 microscope. All monoclonal antibodies have been tested at a final concentration of 10 µg/ml.

Neutrophils Preparation and NETs Protein Acid Extraction for Immunoblotting

In preparation for immunoblotting, neutrophils obtained from buffy coats of healthy donors were seeded in Petri dishes in RPMI at $2\times10^6$ cells/well and activated with 100 nM phorbol myristate acetate (PMA) for 4 h at 37° C. After removing the medium, the wells were washed 2×10 min with Dulbecco-modified phosphate buffer saline (D-PBS) and incubated for 20 min at 37° C. with 10 U/ml DNase I (Sigma) in RPMI. DNase activity was stopped by adding EDTA 5 mM (final concentration). The samples were then centrifuged at 3000 g to remove intact cells and intact nuclei; the supernatants containing NETs proteins were processed as described below. NETs were incubated overnight in $H_2SO_4$ 0.2 M at 4° C. with agitation. Acid extracted proteins were then precipitated with 33% trichloroacetic acid (TCA) for 2 h at 4° C., washed twice with acetone and suspended in $ddH_2O27$. Protein concentrations were determined using bicinchoninic acid (BCA) Protein Assay (Pierce, Rockford, Ill., USA).

SDS-PAGE and Immunoblotting

Acid extracted proteins from NETs were resolved in a 16.5% Tris-Tricine-sodium dodecyl sulfate polyacrylamide gel electrophoresis (SDS PAGE) (Bio-Rad, Hercules, Calif., USA) under non-reducing conditions and blotted onto polyvinylidenfluoride (PVDF) (Millipore, Billerica, Mass., USA). The membrane strips were saturated for 30 min at room temperature in tris buffer saline (TBS) containing 5% bovine serum albumine (BSA) and 0.05% Tween-20, and incubated overnight at 4° C. with the synovial rmAbs at 10 µg/ml, control rmAbs at 10 µg/ml, anti-Histone H4 (Upstate, Millipore), and anti-histone H4 (citrulline 3) (Upstate, Millipore) rabbit antisera diluted 1:500. HRP coupled goat antihuman IgG (1:30000) and goat anti-rabbit (1:5000) diluted in TBS containing 0.1% Tween-20 were used as detection antibodies for the rmAbs and histones, respectively, and incubated 30 min at room temperature. Peroxidase activity was visualised by means of enhanced chemiluminescence using Luminata Western HRP Substrate (Millipore). Control rmAbs derive from single sorted naïve and memory B cells of Sjögren's syndrome patients. Images were acquired and analysed using the VersaDoc Imaging System and QuantityOne analysis software (Bio-Rad).

Overlap PCR to Revert Mutated IgH and IgL Chain Genes to Germline Sequence

Mutated VH and VL regions were reverted into their germline (GL) counterpart sequence. This consisted of two (if J gene germline) or three (if J gene mutated) independent first PCR reactions followed by a nested overlapping PCR to join the amplicons generated with the first PCRs. As templates for the first reactions we used plasmids containing the rmAbs clone specific CDR3 regions and plasmids derived from naïve B cells, containing the corresponding unmutated VH and VL genes. All reverted IgH and IgL chain PCR products were sequenced before and after cloning to confirm the absence of mutations. GL antibodies were expressed and tested in fluorescence microscopy on NETs as described above.

RA Synovial Tissue Transplantation into SCID Mice

Human synovium from the same 2 RA patients (RA015/11 and RA056/11) undergoing arthroplasty from which the monoclonal antibodies were generated were transplanted subcutaneously into Beige SCID-17 mice. Four weeks post-transplantation animals were sacrificed and underwent terminal bleed. Serum was collected and stored at −20° C. for subsequent analysis of human APCA, anti-NETs and anti-citrullinated histone antibodies. Furthermore, at culling each synovial graft was harvested and divided into two parts; one part was paraffin embedded for later histological characterization and one part was stored in RNA-later at −80° C. for quantitative real-time RT PCR.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. An antibody which comprises a variable heavy (VH) chain comprising CDR1, CDR2 and CDR3, and a variable light (VL) chain comprising CDR1, CDR2 and CDR3, wherein the VH-CDR1 amino acid sequence is GGTFSSYA (SEQ ID NO: 106), wherein the VH-CDR2 amino acid sequence is IIPIFGTA (SEQ ID NO: 108), wherein the VH-CDR 3 amino acid sequence is VRITIFGVVMVKSDNWFDP (SEQ ID NO: 306), wherein the VL-CDR1 amino acid sequence is QSVSSN (SEQ ID NO: 549), wherein the VL-CDR2 amino acid sequence is GAS, and wherein the VL-CDR3 amino acid sequence is QQYNNLYT (SEQ ID NO: 715);
  wherein the antibody is selected from the group consisting of a recombinant full-length antibody comprising the VH and VL chains from one species and a constant domain from a different species; a recombinant functional antibody fragment, wherein the VH chain and VL chain are joined by a polypeptide linker; a chimeric antibody; a bispecific antibody; a minibody; and an antibody fusion, wherein the antibody is conjugated to a non-antibody molecule.

2. The antibody according to claim 1 which comprises a VH amino acid sequence QVQLVESGAEVKKPGSSVKVSCKASGGTFSSYAISWVRQAPGQGLEWMGGIIPIFGTAN YAQKFQGRVTITADESTSTAYMELSSLRSEDTAVYYCARVRITIFGVVMVKSDNWFDP WGQGTLVTVSS (SEQ ID NO: 898) and a VL amino acid sequence LMTQAPVTLSVSPGERATLSCRASQSVSSNLAWYQQKPGQAPRLLIYGASTRATGIPARF SGSGSGTEFTLTISSLQSEDFAVYYCQQYNNLYTFGQGTKLEIK (SEQ ID NO: 977), or a sequence which has at least 90% sequence identity thereto.

3. The antibody according to claim 1, wherein the antibody comprises the VH and VL chains and an exchanged constant region.

4. The antibody according to claim 3, wherein the exchanged constant region is from a different immunoglobulin isotype and/or a different species.

5. The antibody according to claim 1, wherein the antibody is a chimeric or human antibody.

6. The antibody according to claim 1, wherein the antibody is a bispecific antibody.

7. The antibody according to claim 1, wherein the antibody is a recombinant functional antibody fragment, wherein the VH chain and VL chain are joined by a polypeptide linker.

8. A method of detecting antibodies against a candidate antigen in a rheumatoid arthritis patient, the method comprising performing an assay comprising:
  (a) contacting a sample from the patient with the candidate antigen and contacting the antibody according to claim 1 with the candidate antigen, wherein the antibody according to claim 1 specifically binds to the candidate antigen; and
  (b) determining whether the sample from the patient contains an antibody that specifically binds to the candidate antigen;
  wherein the antibody according to claim 1 acts as a positive control.

9. The method according to claim 8 wherein the assay is an ELISA assay.

10. A method of exacerbating arthritis symptoms in an animal model of rheumatoid arthritis, the method comprising administering to the animal the antibody according to claim 1.

* * * * *

UNITED STATES PATENT AND TRADEMARK OFFICE
CERTIFICATE OF CORRECTION

| | | |
|---|---|---|
| PATENT NO. | : 10,590,188 B2 | Page 1 of 1 |
| APPLICATION NO. | : 15/317340 | |
| DATED | : March 17, 2020 | |
| INVENTOR(S) | : Michele Bombardieri, Costantino Pitzalis and Elisa Corsiero | |

It is certified that error appears in the above-identified patent and that said Letters Patent is hereby corrected as shown below:

On the Title Page

Item [72], Line 2:
Constantino Pitzalis, London (GB)
Should read:
--Costantino Pitzalis, London (GB)--.

Signed and Sealed this
Twenty-third Day of June, 2020

Andrei Iancu
*Director of the United States Patent and Trademark Office*

SEQUENCE LISTING

```
<160> NUMBER OF SEQ ID NOS: 1039

<210> SEQ ID NO 1
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 1

Glu Val Gln Leu Glu Glu Ser Gly Pro Gly Leu Val Lys Pro Ser Glu
```

```
1               5                   10                  15
Thr Leu Ser Leu Thr Cys Thr Val Ser
            20                  25

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 2

Gly Gly Ser Ile Ser Ser Tyr Tyr
1               5

<210> SEQ ID NO 3
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 3

Trp Ser Trp Ile Arg Gln Pro Ala Gly Lys Gly Leu Glu Trp Ile Gly
1               5                   10                  15
Arg

<210> SEQ ID NO 4
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 4

Ile Tyr Thr Ser Gly Ser Thr
1               5

<210> SEQ ID NO 5
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 5

Gln Val Gln Leu Val Glu Ser Gly Ala Glu Val Lys Lys Pro Gly Ala
1               5                   10                  15
Ser Val Lys Val Ser Cys Lys Ala Ser
            20                  25

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 6

Gly Tyr Ser Phe Thr Ser Tyr Ala
1               5
```

```
<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 7

Met His Trp Val Arg Gln Ala Pro Gly Gln Arg Leu Glu Trp Met Gly
1               5                   10                  15
Trp

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 8

Ile Asn Asp Gly Asn Gly Asn Thr
1               5

<210> SEQ ID NO 9
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 9

Glu Val Gln Leu Val Glu Ser Gly Gly Gly Leu Val Lys Pro Gly Gly
1               5                   10                  15
Ser Leu Arg Leu Ser Cys Ala Ala Ser
            20                  25

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 10

Gly Phe Thr Phe Ser Asn Ala Trp
1               5

<210> SEQ ID NO 11
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 11

Met Ser Trp Val Arg Gln Ala Pro Gly Lys Gly Leu Glu Trp Val Gly
1               5                   10                  15
Arg
```

```
<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 12

Ile Lys Ser Lys Ala Asn Gly Glu Thr Ile
1               5                   10

<210> SEQ ID NO 13
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 14

Gly Tyr Thr Phe Thr Gly Tyr Tyr
1               5

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 15

Met His Trp Val Arg Gln Ala Pro Gly Gln Gly Leu Glu Trp Met Gly
1               5                   10                  15

Trp

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 16

Ile Asn Pro Asn Ser Gly Asp Thr
1               5

<210> SEQ ID NO 17
<211> LENGTH: 25
<212> TYPE: PRT
<213> ORGANISM: Artificial Sequence
```

```
<220> FEATURE:
<221> NAME/KEY: source
<223> OTHER INFORMATION: /note="VH FR1 sequence"

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Thr Ala Ser
            20                  25

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 18

Gly Phe Thr Phe Ser Ser Tyr Glu
1               5

<210> SEQ ID NO 19
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 19

Met Asn Trp Val Arg Gln Ala Pro Gly Lys Gly Leu Glu Trp Val Ser
1               5                   10                  15

Tyr

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 20

Ile Ser Ser Ser Gly Thr Thr Ile
1               5

<210> SEQ ID NO 21
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 21

Gln Val Gln Leu Val Glu Ser Gly Gly Gly Leu Val Gln Ser Gly Gly
1               5                   10                  15

Ser Leu Arg Leu Ser Cys Ser Ala Ser
            20                  25

<210> SEQ ID NO 22
<211> LENGTH: 8
<212> TYPE: PRT
<213> ORGANISM: Artificial Sequence
<220> FEATURE:
```

```
<221> NAME/KEY: source
<223> OTHER INFORMATION: /note="VH CDR1 sequence"

<400> SEQUENCE: 22

Gly Phe Arg Phe Ser Gly His Ala
1               5

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 23

Met His Trp Val Arg Gln Pro Ala Gly Lys Gly Leu Glu Tyr Ile Ser
1               5                   10                  15

Ala

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 24

Ile Ser Gly Asn Gly Glu Ala Thr
1               5

<210> SEQ ID NO 25
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 25

Glu Val Gln Leu Glu Glu Ser Gly Pro Gly Leu Val Lys Pro Ser Gln
1               5                   10                  15

Thr Leu Ser Leu Thr Cys Thr Val Ser
            20                  25

<210> SEQ ID NO 26
<211> LENGTH: 10
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 26

Gly Gly Ser Ile Ser Ser Gly Asp Tyr Tyr
1               5                   10

<210> SEQ ID NO 27
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 27
```

Trp Ser Trp Ile Arg Gln His Pro Gly Lys Gly Leu Glu Trp Ile Gly
1               5                   10                  15

Tyr

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 28

Ile Tyr Tyr Ser Gly Ser Thr
1               5

<210> SEQ ID NO 29
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 29

Glu Val Gln Leu Val Glu Ser Gly Ala Glu Val Lys Lys Pro Gly Ala
1               5                   10                  15

Ser Val Lys Val Ser Cys Lys Ala Ser
            20                  25

<210> SEQ ID NO 30
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 30

Gly Tyr Thr Phe Ser Asp Tyr Phe
1               5

<210> SEQ ID NO 31
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 31

Ile His Trp Val Arg Gln Ala Pro Gly Gln Gly Leu Glu Trp Met Gly
1               5                   10                  15

Trp

<210> SEQ ID NO 32
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 32

Ile Asn Pro His Ser Asp Asp Thr

<210> SEQ ID NO 33
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 33

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 34
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 34

Gly Phe Thr Phe Ser Thr Tyr Thr
1               5

<210> SEQ ID NO 35
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 35

Met Ile Trp Val Arg Gln Ala Pro Gly Lys Gly Leu Glu Trp Val Ser
1               5                   10                  15

Ser

<210> SEQ ID NO 36
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 36

Ile Ser Gly Ser Gly Ser Tyr Ile
1               5

<210> SEQ ID NO 37
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 37

Glu Val Gln Leu Val Gln Ser Gly Pro Glu Val Lys Lys Pro Gly Thr
1               5                   10                  15

Ser Val Lys Val Ser Cys Lys Ala Ser
            20                  25

```
<210> SEQ ID NO 38
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 38

Gly Phe Thr Ser Ser Arg Ser Ala
1               5

<210> SEQ ID NO 39
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 39

Val Gln Trp Leu Arg Gln Thr Arg Gly Gln Arg Leu Glu Trp Ile Gly
1               5                   10                  15

Gly

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 40

Ile Val Val Gly Ser Gly Asn Thr
1               5

<210> SEQ ID NO 41
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 41

Glu Val Gln Leu Val Glu Ser Gly Gly Gly Phe Val Gln Pro Gly Gly
1               5                   10                  15

Ser Leu Arg Leu Ser Cys Ala Ala Ser
            20                  25

<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 42

Gly Phe Ser Ile Gly Asn Tyr Ala
1               5

<210> SEQ ID NO 43
<211> LENGTH: 17
```

```
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 43

Leu Thr Trp Val Arg Gln Ala Pro Gly Lys Arg Leu Glu Trp Val Ser
1               5                   10                  15

Ser

<210> SEQ ID NO 44
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 44

Ile Thr Gly Ser Gly Gly Asp Thr
1               5

<210> SEQ ID NO 45
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 45

Glu Val Gln Leu Val Glu Ser Gly Gly Asp Leu Val Gln Pro Gly Arg
1               5                   10                  15

Ser Leu Arg Leu Ser Cys Ala Ala Ser
            20                  25

<210> SEQ ID NO 46
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 46

Gly Phe Thr Phe Asp Asp Tyr Asp
1               5

<210> SEQ ID NO 47
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 47

Met His Trp Val Arg Gln Ala Pro Gly Lys Gly Leu Glu Trp Val Ser
1               5                   10                  15

Gly

<210> SEQ ID NO 48
<211> LENGTH: 8
<212> TYPE: PRT
<213> ORGANISM: Artificial Sequence
```

```
<220> FEATURE:
<221> NAME/KEY: source
<223> OTHER INFORMATION: /note="VH CDR2 sequence"

<400> SEQUENCE: 48

Ile Arg Trp Asn Ser Asp Thr Ile
1               5

<210> SEQ ID NO 49
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 49

Glu Val Gln Leu Gln Glu Ser Gly Pro Gly Leu Val Lys Pro Ser Gly
1               5                   10                  15

Thr Leu Ser Leu Thr Cys Ala Val Ser
            20                  25

<210> SEQ ID NO 50
<211> LENGTH: 9
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 50

Gly Gly Ser Ile Ser Ile Thr Asn Trp
1               5

<210> SEQ ID NO 51
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 51

Trp Thr Trp Val Arg Gln Pro Pro Gly Lys Gly Leu Glu Trp Ile Gly
1               5                   10                  15

Glu

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 52

Ile Tyr His Ser Gly Tyr Thr
1               5

<210> SEQ ID NO 53
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"
```

```
<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 54
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 54

Gly Phe Thr Phe Ser Ser Tyr Ala
1               5

<210> SEQ ID NO 55
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 55

Met Ser Trp Val Arg Gln Ala Pro Gly Lys Gly Leu Glu Trp Val Ser
1               5                   10                  15

Ala

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 56

Ile Ser Gly Ser Gly Gly Ser Thr
1               5

<210> SEQ ID NO 57
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 57

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 58
```

```
Gly Phe Thr Phe Ser Ser Tyr Ser
1               5

<210> SEQ ID NO 59
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 59

Met Asn Trp Val Arg Gln Ala Pro Gly Lys Gly Leu Glu Trp Val Ser
1               5                   10                  15

Ser

<210> SEQ ID NO 60
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 60

Ile Ser Ser Ser Ser Ser Tyr Ile
1               5

<210> SEQ ID NO 61
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 61

Glu Val Gln Leu Glu Glu Ser Gly Gly Gly Val Val Gln Pro Gly Arg
1               5                   10                  15

Ser Leu Arg Leu Ser Cys Ala Ala Ser
            20                  25

<210> SEQ ID NO 62
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 62

Gly Phe Thr Phe Ser Arg Asn Gly
1               5

<210> SEQ ID NO 63
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 63

Met His Trp Val Arg Gln Ala Pro Gly Lys Gly Leu Glu Trp Val Ala
1               5                   10                  15
```

Val

<210> SEQ ID NO 64
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 64

Ile Trp Tyr Asp Gly Ser Asn Arg
1               5

<210> SEQ ID NO 65
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 66
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 66

Gly Phe Thr Phe Ser Ser Tyr Ala
1               5

<210> SEQ ID NO 67
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 67

Met Ser Trp Val Arg Gln Ala Pro Gly Lys Gly Leu Glu Trp Val Ser
1               5                   10                  15

Ala

<210> SEQ ID NO 68
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 68

Ile Ser Gly Ser Gly Gly Ser Thr
1               5

<210> SEQ ID NO 69

<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 69

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 70

Gly Gly Ser Ile Ser Ser Gly Gly Tyr Tyr
1               5                   10

<210> SEQ ID NO 71
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 71

Trp Ser Trp Ile Arg Gln His Pro Gly Lys Gly Leu Glu Trp Ile Gly
1               5                   10                  15

Tyr

<210> SEQ ID NO 72
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 72

Ile Tyr Tyr Ser Gly Ser Thr
1               5

<210> SEQ ID NO 73
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 74
<211> LENGTH: 8

```
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 74

Gly Phe Thr Phe Ser Ser Tyr Ala
1               5

<210> SEQ ID NO 75
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 75

Met His Trp Val Arg Gln Ala Pro Gly Lys Gly Leu Glu Tyr Val Ser
1               5                   10                  15

Ala

<210> SEQ ID NO 76
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 76

Ile Ser Ser Asn Gly Gly Ser Thr
1               5

<210> SEQ ID NO 77
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 77

Glu Val Gln Leu Val Glu Ser Gly Ala Glu Val Lys Lys Pro Gly Ala
1               5                   10                  15

Ser Val Lys Val Ser Cys Lys Ala Ser
            20                  25

<210> SEQ ID NO 78
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 78

Gly Tyr Thr Phe Asn Thr Tyr Glu
1               5

<210> SEQ ID NO 79
<211> LENGTH: 17
<212> TYPE: PRT
<213> ORGANISM: Artificial Sequence
<220> FEATURE:
<221> NAME/KEY: source
```

```
<223> OTHER INFORMATION: /note="VH FR2 sequence"

<400> SEQUENCE: 79

Ile Asn Trp Val Arg Gln Ala Thr Gly Gln Gly Leu Glu Trp Met Gly
1               5                   10                  15

Trp

<210> SEQ ID NO 80
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 80

Met Asn Pro Asn Ser Gly Asp Thr
1               5

<210> SEQ ID NO 81
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 81

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 82
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 82

Gly Phe Thr Phe Ser Asn Ala Trp
1               5

<210> SEQ ID NO 83
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 83

Met Ser Trp Val Arg Gln Ala Pro Gly Lys Gly Leu Glu Trp Val Gly
1               5                   10                  15

Arg

<210> SEQ ID NO 84
<211> LENGTH: 10
<212> TYPE: PRT
<213> ORGANISM: Artificial Sequence
<220> FEATURE:
<221> NAME/KEY: source
<223> OTHER INFORMATION: /note="VH CDR2 sequence"
```

```
<400> SEQUENCE: 84

Ile Lys Ser Lys Ala Asn Gly Glu Thr Ile
1               5                   10

<210> SEQ ID NO 85
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 86
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 86

Gly Phe Thr Phe Ser Ser Tyr Glu
1               5

<210> SEQ ID NO 87
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 87

Met Asn Trp Val Arg Gln Ala Pro Gly Lys Gly Leu Glu Trp Val Ser
1               5                   10                  15

Tyr

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 88

Ile Cys Ser Ser Gly Ser Thr Ile
1               5

<210> SEQ ID NO 89
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 89

Glu Val Gln Leu Val Glu Ser Gly Gly Gly Val Val Gln Pro Gly Arg
1               5                   10                  15
```

Ser Leu Arg Leu Ser Cys Gly Ala Thr
            20                  25

<210> SEQ ID NO 90
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 90

Gly Phe Thr Phe Ser Ser His Ala
1               5

<210> SEQ ID NO 91
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 91

Met His Trp Val Arg Gln Val Ala Gly Lys Gly Leu Glu Trp Val Ala
1               5                   10                  15

Val

<210> SEQ ID NO 92
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 92

Ile Ser Asp Asp Ser Ser Glu Lys
1               5

<210> SEQ ID NO 93
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 93

Gln Val Gln Leu Val Glu Ser Gly Gly Gly Leu Val Gln Pro Gly Glu
1               5                   10                  15

Ser Leu Arg Leu Ser Cys Ala Ala Ser
            20                  25

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 94

Gly Phe Thr Phe Gly Asn Tyr Ala
1               5

<210> SEQ ID NO 95
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 95

Met Ser Trp Val Arg Gln Ala Pro Gly Lys Gly Leu Ala Trp Val Ala
1               5                   10                  15

Ala

<210> SEQ ID NO 96
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 96

Thr Ser Gly Ser Gly Gly Ser Thr
1               5

<210> SEQ ID NO 97
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 97

Glu Val Gln Leu Gln Glu Ser Gly Pro Arg Leu Val Lys Pro Ser Glu
1               5                   10                  15

Thr Leu Ser Leu Thr Cys Thr Val Ser
            20                  25

<210> SEQ ID NO 98
<211> LENGTH: 10
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 98

Gly Gly Ser Ile Ser Ser Ser Asp His Tyr
1               5                   10

<210> SEQ ID NO 99
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 99

Trp Ala Trp Ile Arg Gln Pro Pro Gly Lys Gly Leu Ala Tyr Ile Gly
1               5                   10                  15

Ile

<210> SEQ ID NO 100

```
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 100

Ile Tyr Tyr Thr Gly Ser Thr
1               5

<210> SEQ ID NO 101
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 101

Glu Val Gln Leu Val Glu Ser Gly Pro Gly Leu Val Arg Pro Ser Gln
1               5                   10                  15

Thr Leu Ser Leu Thr Cys Thr Val Ala
            20                  25

<210> SEQ ID NO 102
<211> LENGTH: 10
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 102

Gly Gly Ser Val Ser Ser Gly Ser Tyr His
1               5                   10

<210> SEQ ID NO 103
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 103

Trp Ser Trp Ile Arg Gln Pro Pro Gly Lys Gly Leu Glu Trp Ile Gly
1               5                   10                  15

Tyr

<210> SEQ ID NO 104
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 104

Ile Phe Tyr Ser Gly Thr Thr
1               5

<210> SEQ ID NO 105
<211> LENGTH: 25
<212> TYPE: PRT
<213> ORGANISM: Artificial Sequence
<220> FEATURE:
```

```
<221> NAME/KEY: source
<223> OTHER INFORMATION: /note="VH FR1 sequence"

<400> SEQUENCE: 105

Gln Val Gln Leu Val Glu Ser Gly Ala Glu Val Lys Pro Gly Ser
1               5                   10                  15

Ser Val Lys Val Ser Cys Lys Ala Ser
            20                  25

<210> SEQ ID NO 106
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 106

Gly Gly Thr Phe Ser Ser Tyr Ala
1               5

<210> SEQ ID NO 107
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 107

Ile Ser Trp Val Arg Gln Ala Pro Gly Gln Gly Leu Glu Trp Met Gly
1               5                   10                  15

Gly

<210> SEQ ID NO 108
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 108

Ile Ile Pro Ile Phe Gly Thr Ala
1               5

<210> SEQ ID NO 109
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 110
<211> LENGTH: 8
<212> TYPE: PRT
<213> ORGANISM: Artificial Sequence
<220> FEATURE:
<221> NAME/KEY: source
```

```
<223> OTHER INFORMATION: /note="VH CDR1 sequence"

<400> SEQUENCE: 110

Gly Phe Thr Phe Ser Ser Tyr Glu
1               5

<210> SEQ ID NO 111
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 111

Met Asn Trp Val Arg Gln Ala Pro Gly Lys Gly Leu Glu Trp Val Ser
1               5                   10                  15

Tyr

<210> SEQ ID NO 112
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 112

Ile Ile Cys Ser Asp Gly Val Ile
1               5

<210> SEQ ID NO 113
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 113

Glu Val Gln Leu Val Glu Ser Gly Pro Gly Leu Val Lys Pro Ser Glu
1               5                   10                  15

Thr Leu Ser Leu Thr Cys Thr Val Ser
            20                  25

<210> SEQ ID NO 114
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 114

Gly Gly Ser Ile Ser Pro Tyr Tyr
1               5

<210> SEQ ID NO 115
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 115
```

```
Trp Asn Trp Ile Arg Gln Pro Pro Gly Lys Arg Leu Glu Trp Ile Gly
1               5                   10                  15

Tyr
```

<210> SEQ ID NO 116
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 116

```
Val Tyr Tyr Asn Gly Asn Thr
1               5
```

<210> SEQ ID NO 117
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 117

```
Gln Val Gln Leu Val Gln Ser Gly Ala Glu Val Lys Lys Ser Gly Glu
1               5                   10                  15

Ser Leu Trp Ile Ser Cys Lys Gly Ser
            20                  25
```

<210> SEQ ID NO 118
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 118

```
Gly Tyr Ser Phe Thr Arg Tyr Trp
1               5
```

<210> SEQ ID NO 119
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 119

```
Ile Gly Trp Val Arg Gln Met Pro Gly Lys Gly Leu Glu Trp Met Gly
1               5                   10                  15

Ile
```

<210> SEQ ID NO 120
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 120

```
Ile Ser Pro Gly Asp Ser Asn Thr
1               5
```

<210> SEQ ID NO 121
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 121

Glu Val Gln Leu Val Glu Ser Gly Gly Gly Val Val Lys Pro Gly Arg
1               5                   10                  15

Ser Leu Arg Leu Ser Cys Ala Ala Ser
            20                  25

<210> SEQ ID NO 122
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 122

Gly Phe Asn Leu Ser Ser Tyr Gly
1               5

<210> SEQ ID NO 123
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 123

Met His Trp Val Arg Gln Ala Pro Gly Lys Gly Leu Glu Trp Val Ala
1               5                   10                  15

Val

<210> SEQ ID NO 124
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 124

Val Trp Tyr Asp Gly Arg Asn Lys
1               5

<210> SEQ ID NO 125
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 125

Glu Val Gln Leu Gln Glu Ser Gly Pro Arg Leu Val Lys Pro Ser Glu
1               5                   10                  15

Thr Leu Ser Leu Thr Cys Thr Val Ser
            20                  25

```
<210> SEQ ID NO 126
<211> LENGTH: 10
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 126

Gly Gly Ser Ile Ser Ser Ser Asp His Tyr
1               5                   10

<210> SEQ ID NO 127
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 127

Trp Ala Trp Ile Arg Gln Pro Pro Gly Lys Gly Leu Ala Tyr Ile Gly
1               5                   10                  15

Ile

<210> SEQ ID NO 128
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 128

Ile Tyr Tyr Thr Gly Ser Thr
1               5

<210> SEQ ID NO 129
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 129

Gln Val Gln Leu Val Glu Ser Gly Gly Asp Leu Val Gln Pro Gly Arg
1               5                   10                  15

Ser Leu Arg Leu Ser Cys Ala Ala Ser
            20                  25

<210> SEQ ID NO 130
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 130

Gly Phe Thr Phe Asp Asp Tyr Asp
1               5

<210> SEQ ID NO 131
<211> LENGTH: 17
<212> TYPE: PRT
```

<213> ORGANISM: Artificial Sequence
<220> FEATURE:
<221> NAME/KEY: source
<223> OTHER INFORMATION: /note="VH FR2 sequence"

<400> SEQUENCE: 131

Met His Trp Val Arg Gln Ala Pro Gly Lys Gly Leu Glu Trp Val Ser
1               5                   10                  15

Gly

<210> SEQ ID NO 132
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 132

Ile Arg Trp Asn Ser Asp Thr Ile
1               5

<210> SEQ ID NO 133
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 133

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 134
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 134

Gly Phe Thr Phe Ser Asn Tyr Gly
1               5

<210> SEQ ID NO 135
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 135

Ile His Trp Val Arg Gln Ala Pro Gly Lys Gly Leu Glu Trp Met Ala
1               5                   10                  15

Phe

<210> SEQ ID NO 136
<211> LENGTH: 8
<212> TYPE: PRT
<213> ORGANISM: Artificial Sequence
<220> FEATURE:

```
<221> NAME/KEY: source
<223> OTHER INFORMATION: /note="VH CDR2 sequence"

<400> SEQUENCE: 136

Ile Ser His Asp Gly Ser Lys Lys
1               5

<210> SEQ ID NO 137
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 137

Gln Val Gln Leu Val Glu Ser Gly Ala Glu Val Lys Thr Pro Gly Ala
1               5                   10                  15

Ser Val Lys Val Ser Cys Lys Thr Ser
            20                  25

<210> SEQ ID NO 138
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 138

Gly Tyr Thr Phe Thr Ser Tyr Tyr
1               5

<210> SEQ ID NO 139
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 139

Ile His Trp Val Arg Gln Ala Pro Gly Gln Gly Leu Glu Trp Met Gly
1               5                   10                  15

Ile

<210> SEQ ID NO 140
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 140

Ile Asn Pro Ser Ala Gly Ser Thr
1               5

<210> SEQ ID NO 141
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 141
```

```
Gln Val Gln Leu Gln Gln Trp Gly Ala Gly Leu Leu Lys Pro Ser Glu
1               5                   10                  15

Thr Leu Ser Leu Thr Cys Val Val Tyr
            20                  25

<210> SEQ ID NO 142
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 142

Gly Gly Ser Phe Ser Gly Tyr Tyr
1               5

<210> SEQ ID NO 143
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 143

Trp Ser Trp Ile Arg Gln Ser Pro Gly Lys Gly Leu Glu Trp Ile Gly
1               5                   10                  15

Glu

<210> SEQ ID NO 144
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 144

Val Asn His Ser Gly Ser Ser
1               5

<210> SEQ ID NO 145
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 145

Glu Val Gln Leu Gln Gln Ser Gly Pro Gly Leu Val Lys Pro Ser Glu
1               5                   10                  15

Thr Leu Ser Leu Thr Cys Thr Val Ser
            20                  25

<210> SEQ ID NO 146
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 146
```

Gly Gly Ser Ile Ser Ser Tyr Tyr
1               5

<210> SEQ ID NO 147
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 147

Trp Ser Trp Ile Arg Gln Pro Pro Gly Lys Gly Leu Glu Trp Ile Gly
1               5                   10                  15

Tyr

<210> SEQ ID NO 148
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 148

Ile His His Ser Gly Ser Ala
1               5

<210> SEQ ID NO 149
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 149

Gln Val Gln Leu Val Gln Ser Gly Gly Gly Val Val Gln Pro Gly Arg
1               5                   10                  15

Ser Leu Arg Leu Ser Cys Ala Ala Ser
            20                  25

<210> SEQ ID NO 150
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 150

Gly Phe Thr Phe Ser Gly Tyr Gly
1               5

<210> SEQ ID NO 151
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 151

Met His Trp Val Arg Gln Ala Pro Gly Lys Gly Leu Glu Trp Val Ala
1               5                   10                  15

Phe

```
<210> SEQ ID NO 152
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 152

Ile Ser Phe Asp Gly Ser Asp Lys
1               5

<210> SEQ ID NO 153
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 154
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 154

Gly Phe Thr Phe Thr Asp Asn Ala
1               5

<210> SEQ ID NO 155
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 155

Met Thr Trp Val Arg Gln Ala Pro Gly Lys Gly Leu Glu Trp Val Ser
1               5                   10                  15

Thr

<210> SEQ ID NO 156
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 156

Ile Arg Asn Asn Gly Gln Asn Thr
1               5

<210> SEQ ID NO 157
<211> LENGTH: 25
```

```
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 157

Glu Val Gln Leu Val Glu Ser Gly Gly Gly Leu Val Gln Pro Gly Gly
1               5                   10                  15
Ser Leu Arg Leu Ser Cys Ala Val Ser
            20                  25

<210> SEQ ID NO 158
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 158

Gly Phe Thr Phe Arg Asn Tyr Ala
1               5

<210> SEQ ID NO 159
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 159

Met Ser Trp Val Arg Gln Ala Pro Gly Lys Gly Leu Glu Trp Val Ser
1               5                   10                  15
Ser

<210> SEQ ID NO 160
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 160

Ile Ser Asp Thr Gly Phe Ser Thr
1               5

<210> SEQ ID NO 161
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 161

Val Gln Leu Val Glu Met Gly Gly Gly Arg Ile Val Gln Pro Gly Arg
1               5                   10                  15
Ser Leu Ser Leu Ser Cys Ala Ala Ser
            20                  25

<210> SEQ ID NO 162
<211> LENGTH: 8
<212> TYPE: PRT
```

```
<213> ORGANISM: Artificial Sequence
<220> FEATURE:
<221> NAME/KEY: source
<223> OTHER INFORMATION: /note="VH CDR1 sequence"

<400> SEQUENCE: 162

Gly Phe Ser Phe Ser Ser His Ala
1               5

<210> SEQ ID NO 163
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 163

Met His Trp Val Arg Gln Ala Pro Gly Lys Gly Leu Glu Trp Val Ala
1               5                   10                  15

Val

<210> SEQ ID NO 164
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 164

Ile Ser Tyr Asp Gly Gly Asp Lys
1               5

<210> SEQ ID NO 165
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 165

Gln Val Gln Leu Val Gln Ser Gly Ala Asp Val Lys Lys Pro Gly Ala
1               5                   10                  15

Ser Val Lys Ile Ser Cys Lys Ala Ser
            20                  25

<210> SEQ ID NO 166
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 166

Gly Tyr Thr Phe Thr Ala Tyr Ala
1               5

<210> SEQ ID NO 167
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"
```

```
<400> SEQUENCE: 167

Ile His Trp Val Arg Gln Ala Pro Gly Gln Arg Leu Glu Trp Met Gly
1               5                   10                  15

Trp

<210> SEQ ID NO 168
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 168

Ile Asn Ala Gly Asn Gly Asn Thr
1               5

<210> SEQ ID NO 169
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 169

Glu Val Gln Leu Gln Glu Ser Gly Pro Gly Leu Val Glu Pro Ser Gly
1               5                   10                  15

Thr Leu Ser Leu Thr Cys Val Val Ser
            20                  25

<210> SEQ ID NO 170
<211> LENGTH: 9
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 170

Gly Gly Ser Ile Thr Ser Ser Asn Trp
1               5

<210> SEQ ID NO 171
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 171

Trp Ser Trp Val Arg Gln Pro Pro Gly Lys Gly Pro Glu Trp Ile Gly
1               5                   10                  15

Glu

<210> SEQ ID NO 172
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 172
```

```
Ile Tyr His Ile Gly Asp Ser
1               5
```

<210> SEQ ID NO 173
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 173

```
Gln Val Gln Leu Val Glu Ser Gly Ala Glu Val Lys Lys Pro Gly Ala
1               5                   10                  15

Ser Val Lys Val Ser Cys Lys Ala Ser
            20                  25
```

<210> SEQ ID NO 174
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 174

```
Gly Tyr Thr Phe Thr Ser Tyr Tyr
1               5
```

<210> SEQ ID NO 175
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 175

```
Met His Trp Val Arg Gln Ala Pro Gly Gln Gly Leu Glu Trp Met Gly
1               5                   10                  15

Ile
```

<210> SEQ ID NO 176
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 176

```
Ile Asn Pro Ser Gly Gly Ser Thr
1               5
```

<210> SEQ ID NO 177
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 177

```
Gln Val Gln Leu Val Glu Ser Gly Pro Gly Leu Val Lys Pro Ser Gln
1               5                   10                  15
```

```
Thr Leu Ser Leu Thr Cys Thr Val Ser
            20                  25

<210> SEQ ID NO 178
<211> LENGTH: 10
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 178

Gly Gly Ser Ile Ser Ser Gly Gly Tyr Tyr
1               5                   10

<210> SEQ ID NO 179
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 179

Trp Ser Trp Ile Arg Gln His Pro Gly Lys Gly Leu Glu Trp Ile Gly
1               5                   10                  15

Tyr

<210> SEQ ID NO 180
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 180

Ile Tyr Tyr Ser Gly Ser Thr
1               5

<210> SEQ ID NO 181
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 181

Gln Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 182
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 182

Gly Phe Thr Phe Ser Ser Tyr Ser
1               5
```

-continued

```
<210> SEQ ID NO 183
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 183

Met Asn Trp Val Arg Gln Ala Pro Gly Lys Gly Leu Glu Trp Val Ser
1               5                   10                  15

Ser

<210> SEQ ID NO 184
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 184

Ile Ser Ser Ser Ser Ser Tyr Ile
1               5

<210> SEQ ID NO 185
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 185

Gln Val Gln Leu Val Glu Trp Gly Ala Gly Leu Leu Lys Pro Ser Glu
1               5                   10                  15

Thr Leu Ser Leu Thr Cys Ala Val Tyr
            20                  25

<210> SEQ ID NO 186
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 186

Gly Gly Ser Phe Ser Gly Tyr Tyr
1               5

<210> SEQ ID NO 187
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 187

Trp Ser Trp Ile Arg Gln Pro Pro Gly Lys Gly Leu Glu Trp Ile Gly
1               5                   10                  15

Glu

<210> SEQ ID NO 188
<211> LENGTH: 7
```

```
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 188

Ile Asn His Ser Gly Ser Thr
1               5

<210> SEQ ID NO 189
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 190
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 190

Gly Tyr Thr Phe Thr Ser Tyr Tyr
1               5

<210> SEQ ID NO 191
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 191

Met His Trp Val Arg Gln Ala Pro Gly Gln Gly Leu Glu Trp Met Gly
1               5                   10                  15

Ile

<210> SEQ ID NO 192
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 192

Ile Asn Pro Ser Gly Gly Ser Thr
1               5

<210> SEQ ID NO 193
<211> LENGTH: 25
<212> TYPE: PRT
<213> ORGANISM: Artificial Sequence
<220> FEATURE:
<221> NAME/KEY: source
```

<223> OTHER INFORMATION: /note="VH FR1 sequence"

<400> SEQUENCE: 193

Glu Val Gln Leu Glu Glu Ser Gly Pro Gly Leu Val Lys Pro Ser Glu
1               5                   10                  15

Thr Leu Ser Leu Thr Cys Thr Val Ser
            20                  25

<210> SEQ ID NO 194
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 194

Gly Gly Ser Ile Ser Ser Tyr Tyr
1               5

<210> SEQ ID NO 195
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 195

Trp Ser Trp Ile Arg Gln Pro Pro Gly Lys Gly Leu Glu Trp Ile Gly
1               5                   10                  15

Tyr

<210> SEQ ID NO 196
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 196

Ile Tyr Tyr Ser Gly Ser Thr
1               5

<210> SEQ ID NO 197
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 197

Gln Val Gln Leu Val Glu Ser Gly Ala Glu Val Lys Lys Pro Gly Glu
1               5                   10                  15

Ser Leu Lys Ile Ser Cys Lys Gly Ser
            20                  25

<210> SEQ ID NO 198
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

```
<400> SEQUENCE: 198

Gly Tyr Ser Phe Thr Ser Tyr Trp
1               5

<210> SEQ ID NO 199
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 199

Ile Gly Trp Val Arg Gln Met Pro Gly Lys Gly Leu Glu Trp Met Gly
1               5                   10                  15

Ile

<210> SEQ ID NO 200
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 200

Ile Tyr Pro Gly Asp Ser Asp Thr
1               5

<210> SEQ ID NO 201
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 201

Gln Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 202
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 202

Gly Phe Thr Phe Ser Ser Tyr Ser
1               5

<210> SEQ ID NO 203
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 203

Met Asn Trp Val Arg Gln Ala Pro Gly Lys Gly Leu Glu Trp Val Ser
```

```
1               5                   10                  15

Ser

<210> SEQ ID NO 204
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 204

Ile Ser Ser Ser Ser Ser Tyr Ile
1               5

<210> SEQ ID NO 205
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 205

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 206
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 206

Gly Phe Thr Phe Ser Ser Tyr Trp
1               5

<210> SEQ ID NO 207
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 207

Met Ser Trp Val Arg Gln Ala Pro Gly Lys Gly Leu Glu Trp Val Ala
1               5                   10                  15

Asn

<210> SEQ ID NO 208
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 208

Ile Lys Gln Asp Gly Ser Glu Lys
1               5
```

```
<210> SEQ ID NO 209
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 209

Glu Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 210
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 210

Gly Gly Ser Ile Ser Ser Tyr Tyr
1               5

<210> SEQ ID NO 211
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 211

Trp Ser Trp Ile Arg Gln Pro Pro Gly Lys Gly Leu Glu Trp Ile Gly
1               5                   10                  15

Tyr

<210> SEQ ID NO 212
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 212

Ile Tyr Tyr Ser Gly Ser Thr
1               5

<210> SEQ ID NO 213
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 213

Gln Val Gln Leu Val Gln Ser Gly Ala Glu Val Lys Lys Pro Gly Ala
1               5                   10                  15

Ser Val Lys Val Ser Cys Lys Ala Ser
            20                  25
```

```
<210> SEQ ID NO 214
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 214

Gly Tyr Thr Phe Thr Ser Tyr Gly
1               5

<210> SEQ ID NO 215
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 215

Ile Ser Trp Val Arg Gln Ala Pro Gly Gln Gly Leu Glu Trp Met Gly
1               5                   10                  15

Trp

<210> SEQ ID NO 216
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 216

Ile Ser Ala Tyr Asn Gly Asn Thr
1               5

<210> SEQ ID NO 217
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 217

Gln Val Gln Leu Val Glu Ser Gly Ala Glu Val Lys Lys Pro Gly Ala
1               5                   10                  15

Ser Val Lys Val Ser Cys Lys Val Ser
            20                  25

<210> SEQ ID NO 218
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 218

Gly Tyr Thr Leu Thr Glu Leu Ser
1               5

<210> SEQ ID NO 219
<211> LENGTH: 17
<212> TYPE: PRT
<213> ORGANISM: Artificial Sequence
```

```
<220> FEATURE:
<221> NAME/KEY: source
<223> OTHER INFORMATION: /note="VH FR2 sequence"

<400> SEQUENCE: 219

Met His Trp Val Arg Gln Ala Pro Gly Lys Gly Leu Glu Trp Met Gly
1               5                   10                  15

Gly

<210> SEQ ID NO 220
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 220

Phe Asp Pro Glu Asp Gly Glu Thr
1               5

<210> SEQ ID NO 221
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 221

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 222
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 222

Gly Tyr Thr Phe Thr Ser Tyr Gly
1               5

<210> SEQ ID NO 223
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 223

Ile Ser Trp Val Arg Gln Ala Pro Gly Gln Gly Leu Glu Trp Met Gly
1               5                   10                  15

Trp

<210> SEQ ID NO 224
<211> LENGTH: 8
<212> TYPE: PRT
<213> ORGANISM: Artificial Sequence
<220> FEATURE:
<221> NAME/KEY: source
```

```
<223> OTHER INFORMATION: /note="VH CDR2 sequence"

<400> SEQUENCE: 224

Ile Ser Ala Tyr Asn Gly Asn Thr
1               5

<210> SEQ ID NO 225
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 225

Gln Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 226
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 226

Gly Phe Thr Phe Glu Asp Tyr Ala
1               5

<210> SEQ ID NO 227
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 227

Met His Trp Val Arg Gln Val Pro Gly Lys Gly Leu Glu Trp Val Ser
1               5                   10                  15

Ser

<210> SEQ ID NO 228
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 228

Ile Ser Trp Asn Ser Val Thr Ile
1               5

<210> SEQ ID NO 229
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 229
```

```
Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 230
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 230

Gly Phe Thr Phe Tyr Asp Tyr Asp
1               5

<210> SEQ ID NO 231
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 231

Met Ser Trp Val Arg Gln Ala Pro Gly Lys Gly Leu Gln Trp Val Ser
1               5                   10                  15

Thr

<210> SEQ ID NO 232
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 232

Ile Thr Leu Ser Gly Val Thr Ala
1               5

<210> SEQ ID NO 233
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 233

Gln Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 234
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 234

Gly Phe Thr Phe Ser Ser Tyr Ser
```

```
1               5

<210> SEQ ID NO 235
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 235

Met Asn Trp Val Arg Gln Ala Pro Gly Lys Gly Leu Glu Trp Val Ser
1               5                   10                  15

Phe

<210> SEQ ID NO 236
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 236

Ile Ser Ser Ser Ser Ser Tyr Met
1               5

<210> SEQ ID NO 237
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 237

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 238
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 238

Gly Phe Thr Phe Ser Ser Tyr Glu
1               5

<210> SEQ ID NO 239
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 239

Met Asn Trp Val Arg Gln Ala Pro Gly Lys Gly Leu Glu Trp Val Ser
1               5                   10                  15

Tyr
```

```
<210> SEQ ID NO 240
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 240

Ile Cys Ser Ser Gly Ser Thr Ile
1               5

<210> SEQ ID NO 241
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 241

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 242
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 242

Gly Phe Thr Phe Ser Ser Tyr Trp
1               5

<210> SEQ ID NO 243
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 243

Met His Trp Val Arg Gln Ala Pro Gly Lys Gly Leu Val Trp Val Ala
1               5                   10                  15

Arg

<210> SEQ ID NO 244
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 244

Ile Lys Thr Asp Gly Ser Ile Thr
1               5

<210> SEQ ID NO 245
<211> LENGTH: 25
<212> TYPE: PRT
```

<213> ORGANISM: Artificial Sequence
<220> FEATURE:
<221> NAME/KEY: source
<223> OTHER INFORMATION: /note="VH FR1 sequence"

<400> SEQUENCE: 245

Glu Val Gln Leu Val Glu Ser Gly Gly Gly Leu Val Gln Pro Gly Gly
1               5                   10                  15

Ser Leu Arg Leu Ser Cys Ala Ala Pro
            20                  25

<210> SEQ ID NO 246
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 246

Gly Phe Ser Phe Ser Ser His Trp
1               5

<210> SEQ ID NO 247
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 247

Met Ser Trp Val Arg Gln Ala Pro Gly Lys Gly Leu Glu Trp Val Ala
1               5                   10                  15

Asn

<210> SEQ ID NO 248
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 248

Ile Lys Ala Asp Gly Ser Glu Lys
1               5

<210> SEQ ID NO 249
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 249

Gln Val Gln Leu Val Gln Ser Gly Gly Gly Leu Val Gln Pro Gly Gly
1               5                   10                  15

Ser Leu Arg Leu Ser Cys Ala Ala Ser
            20                  25

<210> SEQ ID NO 250
<211> LENGTH: 8
<212> TYPE: PRT
<213> ORGANISM: Artificial Sequence

```
<220> FEATURE:
<221> NAME/KEY: source
<223> OTHER INFORMATION: /note="VH CDR1 sequence"

<400> SEQUENCE: 250

Gly Phe Thr Phe Ser Asn Tyr Trp
1               5

<210> SEQ ID NO 251
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 251

Met Thr Trp Val Arg Gln Ala Pro Gly Lys Gly Leu Glu Trp Val Ala
1               5                   10                  15

Asn

<210> SEQ ID NO 252
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 252

Ile Lys Gln Asp Gly Ser Gln Lys
1               5

<210> SEQ ID NO 253
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 253

Asn Tyr Asn Pro Ser Leu Lys Ser Arg Val Thr Met Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 254
<211> LENGTH: 9
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 254

Glu Val Pro Thr Pro Tyr Phe Asp Leu
1               5

<210> SEQ ID NO 255
<211> LENGTH: 38
<212> TYPE: PRT
<213> ORGANISM: Artificial Sequence
<220> FEATURE:
```

<221> NAME/KEY: source
<223> OTHER INFORMATION: /note="VH FR3 sequence"

<400> SEQUENCE: 255

Lys Tyr Ser Gln Lys Phe Gln Gly Arg Val Thr Ile Thr Arg Asp Thr
1               5                   10                  15

Ser Ala Ser Thr Ala Tyr Met Gly Leu Ser Ser Leu Arg Ser Glu Asp
            20                  25                  30

Thr Ala Val Tyr Tyr Cys
            35

<210> SEQ ID NO 256
<211> LENGTH: 15
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 256

Gly Gly Glu Asp Gly Tyr Gly Asp Ser Tyr Asn Ala Phe Asp Leu
1               5                   10                  15

<210> SEQ ID NO 257
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 257

Asp Tyr Ala Ala Pro Val Lys Gly Arg Phe Thr Ile Ser Arg Asp Asp
1               5                   10                  15

Ser Lys Asn Thr Leu Tyr Leu Gln Met Asn Ser Leu Lys Thr Glu Asp
            20                  25                  30

Thr Ala Val Tyr Tyr Cys
            35

<210> SEQ ID NO 258
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 258

His Phe Glu Ser Cys Gly Gly Asp Cys Ser Asn Trp
1               5                   10

<210> SEQ ID NO 259
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 259

Asn Tyr Ala Gln Lys Phe Gln Gly Arg Val Ile Met Thr Arg Asp Thr
1               5                   10                  15

Ser Ile Ser Ala Ala Tyr Met Glu Leu Ser Ser Leu Arg Ser Asp Asp
            20                  25                  30

Thr Ala Val Tyr Tyr Cys
        35

<210> SEQ ID NO 260
<211> LENGTH: 20
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 260

Val Gly Gly Gly Arg Gln Leu Trp Leu Lys Asp Asn Tyr Asp Tyr Phe
1               5                   10                  15

Tyr Met Asp Val
        20

<210> SEQ ID NO 261
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 261

Tyr Tyr Ala Asp Ser Val Lys Gly Arg Phe Thr Ile Ser Arg Asp Asn
1               5                   10                  15

Ala Lys Asn Ser Leu Tyr Leu Gln Met His Ser Leu Arg Ala Glu Asp
            20                  25                  30

Thr Ala Val Tyr Tyr Cys
        35

<210> SEQ ID NO 262
<211> LENGTH: 16
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 262

Asp Met Pro His Phe Leu Tyr Ser Ser Arg Trp Tyr Pro Phe Asp Tyr
1               5                   10                  15

<210> SEQ ID NO 263
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 263

Tyr Tyr Ala Gly Ser Val Lys Gly Arg Phe Thr Ile Ser Arg Asp Asn
1               5                   10                  15

Phe Lys Asn Thr Leu Tyr Leu Gln Met Thr Ser Leu Arg Pro Glu Asp
            20                  25                  30

Thr Ala Val Tyr Tyr Cys
        35

<210> SEQ ID NO 264
<211> LENGTH: 13
<212> TYPE: PRT
<213> ORGANISM: Artificial Sequence

```
<220> FEATURE:
<221> NAME/KEY: source
<223> OTHER INFORMATION: /note="VH CDR3 sequence"

<400> SEQUENCE: 264

Glu Ile Val Gly Ala Asn Arg Trp Val Pro Val Gly Pro
1               5                   10

<210> SEQ ID NO 265
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 265

Tyr Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 266
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 266

Ala Ile Ser Trp Ala Asp Gly Tyr Tyr Met Asp Val
1               5                   10

<210> SEQ ID NO 267
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 267

Asn Ile Ala Gln Lys Phe Gln Gly Arg Val Thr Leu Pro Met Asp Thr
1               5                   10                  15

Ser Ile Ser Thr Ala Tyr Met Glu Ile Thr Arg Leu Glu Ser Asp Asp
            20                  25                  30

Thr Ala Ile Tyr Tyr Cys
        35

<210> SEQ ID NO 268
<211> LENGTH: 9
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 268

Gly Ala Tyr Gly Asp Pro Leu His Ile
1               5

<210> SEQ ID NO 269
```

```
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 269

Phe Tyr Ala Asp Ser Val Lys Gly Arg Phe Thr Ile Ser Arg Asp Asn
1               5                   10                  15
Pro Lys Asn Ser Leu Tyr Leu Gln Met Asn Ser Leu Arg Ala Asp Asp
            20                  25                  30
Thr Ala Val Tyr Tyr Cys
        35

<210> SEQ ID NO 270
<211> LENGTH: 11
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 270

Trp Arg Ala Gly Val Pro Ser Tyr Phe Asp Tyr
1               5                   10

<210> SEQ ID NO 271
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 271

Asn Tyr Ala Pro Asn Phe Gln Asp Arg Val Thr Ile Thr Trp Asp Met
1               5                   10                  15
Ser Thr Arg Thr Ala Tyr Met Glu Leu Ser Ser Leu Arg Ser Glu Asp
            20                  25                  30
Thr Ala Val Tyr Tyr Cys
        35

<210> SEQ ID NO 272
<211> LENGTH: 7
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 272

Gly Gly Ser Tyr Val Asp Tyr
1               5

<210> SEQ ID NO 273
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 273

Tyr Asn Ala Asp Phe Met Lys Gly Arg Phe Thr Met Ser Arg Asp Leu
1               5                   10                  15
```

```
Tyr Lys Asn Thr Leu Tyr Leu His Met Asn Ser Leu Arg Ala Glu Asp
            20                  25                  30

Thr Ala Ile Tyr Tyr Cys
        35

<210> SEQ ID NO 274
<211> LENGTH: 15
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 274

Ser Pro Thr Asp Phe Trp Asp Asp Tyr Leu Tyr Tyr Phe Asp Ser
1               5                   10                  15

<210> SEQ ID NO 275
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 275

Gly Tyr Ala Asp Ser Val Lys Gly Arg Phe Thr Ile Ser Arg Asp Asn
1               5                   10                  15

Ala Arg Asn Ser Leu Tyr Leu Gln Met Asn Ser Leu Arg Ala Glu Asp
            20                  25                  30

Thr Ala Leu Tyr Tyr Cys
        35

<210> SEQ ID NO 276
<211> LENGTH: 14
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 276

Asp Ile Ser Ser Tyr Asp Asp Thr Ser Gly Tyr Tyr Tyr Asn
1               5                   10

<210> SEQ ID NO 277
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 277

Asn Tyr Asn Pro Ser Leu Lys Thr Arg Val Thr Ile Ser Val Asp Lys
1               5                   10                  15

Ser Lys Asn His Leu Ser Leu Lys Leu Ser Phe Val Thr Ala Ala Asp
            20                  25                  30

Thr Ala Val Tyr Tyr Cys
        35

<210> SEQ ID NO 278
<211> LENGTH: 14
<212> TYPE: PRT
```

```
<213> ORGANISM: Artificial Sequence
<220> FEATURE:
<221> NAME/KEY: source
<223> OTHER INFORMATION: /note="VH CDR3 sequence"

<400> SEQUENCE: 278

Lys Gly Thr Tyr Ser Thr Asp Ser Tyr Asp Gly Phe Asp Ile
1               5                   10

<210> SEQ ID NO 279
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 279

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 280
<211> LENGTH: 22
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 280

Cys Glu Thr Gly Glu Arg Arg Trp Tyr Tyr Gly Ser Gly Thr Ile
1               5                   10                  15

Arg Glu Ala Phe Asp Ile
            20

<210> SEQ ID NO 281
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 281

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 282
<211> LENGTH: 11
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 282

Pro Arg Gln Leu Gly Ser Val Trp Phe Asp Pro
```

<210> SEQ ID NO 283
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 283

Tyr Tyr Thr Asp Ser Val Lys Gly Arg Phe Thr Ile Ser Arg Asp Asn
1               5                   10                  15
Ser Arg Asn Thr Leu Tyr Leu Gln Met Asp Ser Leu Lys Pro Glu Asp
            20                  25                  30
Thr Ala Leu Tyr Tyr Cys
        35

<210> SEQ ID NO 284
<211> LENGTH: 10
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 284

Asp Arg Ser Ser Ser Trp Tyr Phe Asp His
1               5                   10

<210> SEQ ID NO 285
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 285

Tyr Tyr Ala Asp Ser Val Lys Gly Arg Phe Thr Ile Ser Arg Asp Asn
1               5                   10                  15
Ser Lys Asn Thr Leu Tyr Leu Gln Met Asn Ser Leu Arg Ala Glu Asp
            20                  25                  30
Thr Ala Val Tyr Tyr Cys
        35

<210> SEQ ID NO 286
<211> LENGTH: 7
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 286

Gly Ser Gly Thr Phe Asp Tyr
1               5

<210> SEQ ID NO 287
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

```
<400> SEQUENCE: 287

Tyr Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 288
<211> LENGTH: 18
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 288

Val Ser Leu Asn Ser Ser Ser Leu Ile His Tyr Tyr Tyr Met
1               5                   10                  15

Asp Val

<210> SEQ ID NO 289
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 289

Tyr Tyr Ala Asp Ser Val Lys Gly Arg Phe Thr Ile Ser Arg Asp Asn
1               5                   10                  15

Ser Lys Asn Thr Leu Tyr Leu Gln Met Ser Ser Leu Arg Ala Glu Asp
            20                  25                  30

Thr Ala Val Tyr Tyr Cys
        35

<210> SEQ ID NO 290
<211> LENGTH: 24
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 290

Val Lys Glu Tyr Asp Phe Trp Ser Gly Tyr Tyr Tyr Arg Gly Ala Thr
1               5                   10                  15

Arg Thr Thr Pro Asn Phe Asp Tyr
            20

<210> SEQ ID NO 291
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 291

Val Tyr Ala Gln Lys Cys Gln Gly Arg Val Ser Met Thr Arg His Thr
1               5                   10                  15

Ser Thr Ser Thr Ala Ser Met Glu Leu Ile Ser Leu Ile Phe Glu Asp
```

-continued

```
                    20                  25                  30

Thr Ala Val Tyr Tyr Cys
        35

<210> SEQ ID NO 292
<211> LENGTH: 10
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 292

Ala Ala Gly Val Gly Val Ala Leu Asp Tyr
1               5                   10

<210> SEQ ID NO 293
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 293

Asp Tyr Ala Ala Pro Val Lys Gly Arg Leu Thr Ile Ser Arg Asp Asp
1               5                   10                  15

Ser Lys Asn Thr Leu Tyr Leu Gln Met Asn Ser Leu Lys Thr Glu Asp
                    20                  25                  30

Thr Ala Val Tyr Tyr Cys
        35

<210> SEQ ID NO 294
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 294

His Phe Glu Ser Cys Gly Gly Asp Cys Ser Asn Trp
1               5                   10

<210> SEQ ID NO 295
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 295

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
                    20                  25                  30

Thr Ala Val Tyr Tyr Cys
        35

<210> SEQ ID NO 296
<211> LENGTH: 16
<212> TYPE: PRT
<213> ORGANISM: Artificial Sequence
<220> FEATURE:
```

```
<221> NAME/KEY: source
<223> OTHER INFORMATION: /note="VH CDR3 sequence"

<400> SEQUENCE: 296

Val His Met Tyr Tyr Tyr Asp Ser Ser Gly Tyr Tyr Tyr Asp Asp Tyr
1               5                   10                  15

<210> SEQ ID NO 297
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 297

Tyr Tyr Ala Asp Ser Val Arg Gly Arg Phe Ile Ile Ser Arg Asp Asn
1               5                   10                  15

Ala Lys Asp Thr Val Tyr Leu Gln Met Asn Ser Leu Arg Pro Asp Asp
            20                  25                  30

Thr Ala Val Tyr Tyr Cys
        35

<210> SEQ ID NO 298
<211> LENGTH: 20
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 298

Pro His Arg Leu Leu Asp Ser Cys Ser Ser Thr Ser Cys Tyr Val Val
1               5                   10                  15

Ala Phe Asp Leu
            20

<210> SEQ ID NO 299
<211> LENGTH: 37
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 299

Tyr Tyr Ala Gly Ser Val Lys Cys Phe Thr Ile Ser Arg Asp Asn Ser
1               5                   10                  15

Lys Ile Thr Leu Tyr Leu Gln Val His Ser Leu Arg Pro Glu Asp Thr
            20                  25                  30

Ala Val Tyr Tyr Cys
        35

<210> SEQ ID NO 300
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 300

Gly Thr Leu Ser Gly Phe Ala Thr Thr Phe Asp Tyr
1               5                   10
```

<210> SEQ ID NO 301
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 301

Tyr Tyr Asn Pro Ser Leu Lys Ser Arg Val Ser Ile Ser Val Asp Thr
1               5                   10                  15

Ser Lys Asn Gln Phe Ser Leu Asn Val Asn Ser Val Thr Ala Ala Asp
            20                  25                  30

Thr Gly Val Tyr Tyr Cys
        35

<210> SEQ ID NO 302
<211> LENGTH: 11
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 302

Arg His Ile Gly Arg His Tyr Tyr Phe Asp Tyr
1               5                   10

<210> SEQ ID NO 303
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 303

Lys Tyr Asn Pro Ser Leu Lys Ser Arg Val Thr Ile Ser Thr Asp Val
1               5                   10                  15

Ser Lys Asn Gln Phe Ser Leu Lys Leu Lys Ser Val Thr Ala Ala Asp
            20                  25                  30

Thr Ala Val Tyr Tyr Cys
        35

<210> SEQ ID NO 304
<211> LENGTH: 14
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 304

Asp Ala Ser Ile Ala Ala Arg Pro Pro Trp Gly Met Asp Val
1               5                   10

<210> SEQ ID NO 305
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 305

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 306
<211> LENGTH: 19
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 306

Val Arg Ile Thr Ile Phe Gly Val Val Met Val Lys Ser Asp Asn Trp
1               5                   10                  15

Phe Asp Pro

<210> SEQ ID NO 307
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 307

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 308
<211> LENGTH: 16
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 308

Val His Leu Tyr Tyr Tyr Asp Ser Ser Gly Tyr Tyr Tyr Asp Tyr
1               5                   10                  15

<210> SEQ ID NO 309
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 309

Asn Tyr Asn Pro Ser Leu Lys Ser Arg Val Thr Ile Ser Val Asp Thr
1               5                   10                  15

Pro Lys Asn Gln Phe Ser Leu Arg Leu Ser Ser Val Thr Ala Ala Asp
            20                  25                  30

Thr Ala Val Tyr Tyr Cys
        35

<210> SEQ ID NO 310
<211> LENGTH: 8
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 310

Tyr Gly Val Asp Tyr Phe Asp Tyr
1               5

<210> SEQ ID NO 311
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 311

Arg Tyr Ser Pro Ser Phe Gln Gly Gln Val Thr Ile Ser Ala Asp Lys
1               5                   10                  15

Ser Ile Ser Thr Ala Tyr Leu Gln Leu Ser Ser Leu Lys Ala Ser Asp
            20                  25                  30

Ile Ala Thr Tyr Tyr Cys
        35

<210> SEQ ID NO 312
<211> LENGTH: 15
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 312

Gln Gly Tyr Tyr Asp Arg Ser Pro Arg Pro His Tyr Met Asp Val
1               5                   10                  15

<210> SEQ ID NO 313
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 313

Phe Tyr Thr Asp Ser Val Lys Gly Arg Phe Thr Ile Ser Arg Asp Asn
1               5                   10                  15

Ser Ile Asn Ser Val Tyr Leu Gln Met Asn Ser Leu Arg Ala Glu Asp
            20                  25                  30

Thr Ala Ile Tyr Tyr Cys
        35

<210> SEQ ID NO 314
<211> LENGTH: 15
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 314

```
Val Thr Ser Arg Val Val Ala Ala Ala Gly Gly Tyr Phe Asp His
1               5                   10                  15
```

<210> SEQ ID NO 315
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 315

```
Tyr Tyr Asn Pro Ser Leu Lys Ser Arg Val Ser Ile Ser Val Asp Thr
1               5                   10                  15

Ser Lys Asn Gln Phe Ser Leu Asn Val Asn Ser Val Thr Ala Ala Asp
                20                  25                  30

Thr Gly Val Tyr Tyr Cys
            35
```

<210> SEQ ID NO 316
<211> LENGTH: 11
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 316

```
Arg His Ile Gly Arg His Tyr Tyr Phe Asp Tyr
1               5                   10
```

<210> SEQ ID NO 317
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 317

```
Gly Tyr Ala Asp Ser Val Lys Gly Arg Phe Thr Ile Ser Arg Asp Asn
1               5                   10                  15

Ala Arg Asn Ser Leu Tyr Leu Gln Met Asn Ser Leu Arg Ala Glu Asp
                20                  25                  30

Thr Ala Leu Tyr Tyr Cys
            35
```

<210> SEQ ID NO 318
<211> LENGTH: 14
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 318

```
Asp Ile Ser Ser Tyr Asp Asp Thr Ser Gly Tyr Tyr Tyr Asn
1               5                   10
```

<210> SEQ ID NO 319
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

```
<400> SEQUENCE: 319

Asn Tyr Ala Asp Ser Val Lys Gly Arg Phe Thr Ile Ser Arg Asp Asn
1               5                   10                  15

Ser Lys Asn Thr Leu Tyr Leu Gln Met Asn Arg Leu Arg Val Glu Asp
            20                  25                  30

Thr Ala Ile Tyr His Cys
        35

<210> SEQ ID NO 320
<211> LENGTH: 22
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 320

Asp Ile Val Val Pro Ala Ala Thr Ser Leu Leu Gly Gly Tyr Tyr
1               5                   10                  15

Tyr Tyr Tyr Met Asp Val
            20

<210> SEQ ID NO 321
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 321

Thr Tyr Pro Gln Lys Phe Gln Gly Arg Val Thr Met Thr Arg Asp Arg
1               5                   10                  15

Ser Thr Ser Thr Val Tyr Met Glu Leu Ser Ser Leu Arg Ser Glu Asp
            20                  25                  30

Thr Ala Val Tyr Tyr Cys
        35

<210> SEQ ID NO 322
<211> LENGTH: 19
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 322

Asp Gly Leu Glu Ala Arg Arg Thr Thr Ser Ser His Pro His Tyr Tyr
1               5                   10                  15

Met Asp Val

<210> SEQ ID NO 323
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 323

Tyr Tyr Asn Pro Ser Leu Lys Ser Arg Val Thr Ile Ser Val Asp Thr
1               5                   10                  15
```

Ser Lys Asp Gln Phe Ser Leu Lys Leu Thr Ser Val Thr Ala Ala Asp
            20                  25                  30

Thr Ala Val Tyr Tyr Cys
        35

<210> SEQ ID NO 324
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 324

Lys Lys Gly Arg Val Gly Ile Ala Tyr Met Glu Val
1               5                   10

<210> SEQ ID NO 325
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 325

Asp Tyr Asn Pro Ser Leu Lys Gly Arg Val Thr Ile Ser Leu Asp Thr
1               5                   10                  15

Ser Lys Lys Gln Phe Ser Leu Lys Leu Arg Phe Val Thr Thr Ala Asp
            20                  25                  30

Thr Ala Leu Tyr Tyr Cys
        35

<210> SEQ ID NO 326
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 326

Thr Pro Tyr Pro Pro Leu Asp Trp Tyr Phe Asp Leu
1               5                   10

<210> SEQ ID NO 327
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 327

Tyr Tyr Ala Ala Ser Val Lys Gly Arg Phe Thr Leu Ser Arg Asp Asn
1               5                   10                  15

Ser Lys Asn Thr Leu Tyr Leu Lys Ile Asn Ser Leu Arg Thr Glu Asp
            20                  25                  30

Thr Ala Val Tyr Tyr Cys
        35

<210> SEQ ID NO 328
<211> LENGTH: 8
<212> TYPE: PRT
<213> ORGANISM: Artificial Sequence

```
<220> FEATURE:
<221> NAME/KEY: source
<223> OTHER INFORMATION: /note="VH CDR3 sequence"

<400> SEQUENCE: 328

Glu Val Arg Glu Tyr Thr Asp Tyr
1               5

<210> SEQ ID NO 329
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 329

Tyr Tyr Thr Asp Ser Val Lys Gly Arg Phe Thr Ile Ser Arg Asp Asn
1               5                   10                  15

Phe Asn Asn Met Val Tyr Leu Gln Met Ser Ser Leu Arg Ala Glu Asp
            20                  25                  30

Thr Ala Val Tyr Tyr Cys
        35

<210> SEQ ID NO 330
<211> LENGTH: 13
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 330

Leu Val Gly Ile Thr His Leu Ser Ala Ala Pro Trp Thr
1               5                   10

<210> SEQ ID NO 331
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 331

Tyr Tyr Ala Asp Ser Val Lys Gly Arg Phe Ala Ile Ser Arg Asp Asn
1               5                   10                  15

Ser Lys Asn Arg Leu Tyr Leu Glu Met Asn Ser Leu Arg Ala Asp Asp
            20                  25                  30

Thr Ala Ile Tyr Tyr Cys
        35

<210> SEQ ID NO 332
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 332

Val Pro His Gln Leu Val Pro Ile Trp Phe Asp Pro
1               5                   10

<210> SEQ ID NO 333
```

```
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 333
```

Asn Tyr Ala Asp Ser Val Arg Gly Arg Phe Thr Ile Ser Arg Asp Asn
1               5                   10                  15

Ser Glu Asp Thr Leu Tyr Leu Gln Met Asn Gly Leu Arg Thr Glu Asp
            20                  25                  30

Thr Ala Met Tyr Phe Cys
        35

```
<210> SEQ ID NO 334
<211> LENGTH: 11
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 334
```

Asp Ala Arg Gly Val Arg Asn Ala Phe Asp Leu
1               5                   10

```
<210> SEQ ID NO 335
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 335
```

Lys Tyr Ser Gln Lys Phe Gln Gly Arg Val Thr Ile Thr Arg Asp Thr
1               5                   10                  15

Ser Ala Asn Thr Ser Tyr Met Asp Leu Ser Ser Leu Arg Ser Glu Asp
            20                  25                  30

Thr Ala Val Tyr Phe Cys
        35

```
<210> SEQ ID NO 336
<211> LENGTH: 15
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 336
```

Ser Leu Tyr Cys Ser Thr His Ser Cys Ser Phe Leu His Leu Tyr
1               5                   10                  15

```
<210> SEQ ID NO 337
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 337
```

Asn Tyr Asn Pro Ser Leu Lys Ser Arg Val Thr Met Ser Val Asp Lys
1               5                   10                  15

```
Ser Lys Asn Gln Phe Ser Leu Lys Leu Arg Ser Val Thr Ala Ala Asp
            20                  25                  30

Thr Ala Ile Tyr Tyr Cys
        35

<210> SEQ ID NO 338
<211> LENGTH: 13
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 338

Thr Phe Trp Ser Gly Ser Tyr Ser Arg Tyr Phe Asp Ser
1               5                   10

<210> SEQ ID NO 339
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 339

Ser Tyr Ala Gln Lys Phe Gln Gly Arg Val Thr Met Thr Arg Asp Thr
1               5                   10                  15

Ser Thr Ser Thr Val Tyr Met Glu Leu Ser Ser Leu Arg Ser Glu Asp
            20                  25                  30

Thr Ala Val Tyr Tyr Cys
        35

<210> SEQ ID NO 340
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 340

Phe Gly Arg His Asp Tyr Gly Gly Lys Asp Asp Tyr
1               5                   10

<210> SEQ ID NO 341
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 341

Tyr Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 342
<211> LENGTH: 21
<212> TYPE: PRT
```

```
<213> ORGANISM: Artificial Sequence
<220> FEATURE:
<221> NAME/KEY: source
<223> OTHER INFORMATION: /note="VH CDR3 sequence"

<400> SEQUENCE: 342

Asp Gln Ile Thr Met Val Arg Gly Gly Asp Gly Gln Asn Tyr Tyr Tyr
1               5                   10                  15

Tyr Tyr Met Asp Val
            20

<210> SEQ ID NO 343
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 343

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 344
<211> LENGTH: 14
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 344

Asp Val Gly Asp Ile Val Val Val Thr Ala Ser Leu Asp Tyr
1               5                   10

<210> SEQ ID NO 345
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 345

Asn Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 346
<211> LENGTH: 17
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 346

Gly Trp Ala Tyr Ser Ser Ser Trp Tyr Arg Arg Met Ile Ser Phe Asp
```

Tyr

<210> SEQ ID NO 347
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 347

Ser Tyr Ala Gln Lys Phe Gln Gly Arg Val Thr Met Thr Arg Asp Thr
1               5                   10                  15

Ser Thr Ser Thr Val Tyr Met Glu Leu Ser Ser Leu Arg Ser Glu Asp
            20                  25                  30

Thr Ala Val Tyr Tyr Cys
        35

<210> SEQ ID NO 348
<211> LENGTH: 15
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 348

Val Gly Gly Gly Tyr Tyr Asp Ser Ser Gly Gly Ala Leu Asp Tyr
1               5                   10                  15

<210> SEQ ID NO 349
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 349

Asn Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 350
<211> LENGTH: 17
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 350

Arg Val Gly Ser Pro Tyr Cys Gly Gly Asp Cys Tyr Pro Ala Phe Asp
1               5                   10                  15

Ile

<210> SEQ ID NO 351
<211> LENGTH: 38
<212> TYPE: PRT
<213> ORGANISM: Artificial Sequence

```
<220> FEATURE:
<221> NAME/KEY: source
<223> OTHER INFORMATION: /note="VH FR3 sequence"

<400> SEQUENCE: 351

Arg Tyr Ser Pro Ser Phe Gln Gly Gln Val Thr Ile Ser Ala Asp Lys
1               5                   10                  15

Ser Ile Ser Thr Ala Tyr Leu Gln Trp Ser Ser Leu Lys Ala Ser Asp
                20                  25                  30

Thr Ala Met Tyr Tyr Cys
        35

<210> SEQ ID NO 352
<211> LENGTH: 19
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 352

Ile Leu Val Asp Cys Ser Ser Thr Ser Cys Tyr Tyr Tyr Tyr Tyr
1               5                   10                  15

Met Asp Val

<210> SEQ ID NO 353
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 353

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
                20                  25                  30

Thr Ala Val Tyr Tyr Cys
        35

<210> SEQ ID NO 354
<211> LENGTH: 10
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 354

Gly Gly Ser Ser Trp Tyr Tyr Phe Asp Tyr
1               5                   10

<210> SEQ ID NO 355
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 355

Tyr Tyr Val Asp Ser Val Lys Gly Arg Phe Thr Ile Ser Arg Asp Asn
1               5                   10                  15
```

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 356
<211> LENGTH: 8
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 356

Glu Leu Phe His Ile Leu Ser Tyr
1               5

<210> SEQ ID NO 357
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 357

Asn Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 358
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 358

Arg Glu Ser Ser Arg Leu Gly Asn Ala Phe Asp Ile
1               5                   10

<210> SEQ ID NO 359
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 359

Asn Tyr Ala Gln Lys Leu Gln Gly Arg Val Thr Met Thr Thr Asp Thr
1               5                   10                  15

Ser Thr Ser Thr Ala Tyr Met Glu Leu Arg Ser Leu Arg Ser Asp Asp
            20                  25                  30

Thr Ala Val Tyr Tyr Cys
        35

<210> SEQ ID NO 360
<211> LENGTH: 9
<212> TYPE: PRT
<213> ORGANISM: Artificial Sequence -continued

```
<220> FEATURE:
<221> NAME/KEY: source
<223> OTHER INFORMATION: /note="VH CDR3 sequence"

<400> SEQUENCE: 360

Asp Leu Asn Ser Tyr Tyr Phe Asp Tyr
1               5

<210> SEQ ID NO 361
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 361

Ile Tyr Ala Gln Lys Phe Gln Gly Arg Val Thr Met Thr Glu Asp Thr
1               5                   10                  15

Ser Thr Asp Thr Ala Tyr Met Glu Leu Ser Ser Leu Arg Ser Glu Asp
            20                  25                  30

Thr Ala Val Tyr Tyr Cys
        35

<210> SEQ ID NO 362
<211> LENGTH: 9
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 362

Pro Ile Val Leu Gly Ala Phe Asp Ile
1               5

<210> SEQ ID NO 363
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 363

Asn Tyr Ala Gln Lys Leu Gln Gly Arg Val Thr Met Thr Thr Asp Thr
1               5                   10                  15

Ser Thr Ser Thr Ala Tyr Met Glu Leu Arg Ser Leu Arg Ser Asp Asp
            20                  25                  30

Thr Ala Val Tyr Tyr Cys
        35

<210> SEQ ID NO 364
<211> LENGTH: 22
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 364

Arg Tyr Cys Ser Ser Thr Ser Cys Tyr Lys Gly Ser Tyr Tyr Tyr Tyr
1               5                   10                  15

Tyr Tyr Tyr Met Asp Val
            20
```

```
<210> SEQ ID NO 365
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 365

Asp Tyr Ala Asp Ser Val Lys Gly Arg Phe Thr Ile Ser Arg Asp Asn
1               5                   10                  15

Ala Arg Asn Ser Leu Tyr Leu Gln Met Asn Ser Leu Arg Pro Glu Asp
            20                  25                  30

Thr Ala Leu Tyr Tyr Cys
        35

<210> SEQ ID NO 366
<211> LENGTH: 12
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 366

Gly Ser Tyr Arg Tyr Tyr Tyr Tyr Cys Ile Asp Val
1               5                   10

<210> SEQ ID NO 367
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 367

Tyr Tyr Ala Asp Ser Val Lys Gly Arg Phe Thr Ile Ser Arg Asp Asn
1               5                   10                  15

Ser Lys Asn Met Val Tyr Leu Gln Met Asn Ser Leu Arg Ala Glu Asp
            20                  25                  30

Thr Ala Val Tyr Tyr Cys
        35

<210> SEQ ID NO 368
<211> LENGTH: 4
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 368

His Trp Asp Ser
1

<210> SEQ ID NO 369
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 369
```

```
His Tyr Ala Asp Ser Val Lys Asp Arg Phe Ile Ile Ser Arg Asp Asn
1               5                   10                  15

Ala Asn Asn Ser Leu Tyr Leu Gln Met Asn Ser Leu Thr Ala Glu Asp
                20                  25                  30

Thr Gly Val Tyr Tyr Cys
        35

<210> SEQ ID NO 370
<211> LENGTH: 11
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 370

Leu Gly Tyr Asp Phe Trp Ser Gly His Arg His
1               5                   10

<210> SEQ ID NO 371
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 371

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
                20                  25                  30

Thr Ala Val Tyr Tyr Cys
        35

<210> SEQ ID NO 372
<211> LENGTH: 16
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 372

Val His Leu Tyr Tyr Tyr Asp Ser Ser Gly Tyr Tyr Tyr Asp Tyr
1               5                   10                  15

<210> SEQ ID NO 373
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 373

Gly His Ala Asp Ser Val Lys Gly Arg Phe Ser Val Ser Arg Asp Asn
1               5                   10                  15

Ala Lys Asn Thr Leu Tyr Leu Gln Met Asn Ser Leu Arg Ala Glu Asp
                20                  25                  30

Thr Gly Val Tyr Phe Cys
        35
```

```
<210> SEQ ID NO 374
<211> LENGTH: 23
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 374

Asp Gly Gly Glu Ala Tyr Asp Phe Trp Ser Asp Asn His Arg Phe Tyr
1               5                   10                  15

Phe Tyr Tyr Tyr Met Asp Val
            20

<210> SEQ ID NO 375
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 375

Tyr Tyr Ile Asp Ser Val Lys Gly Arg Phe Ser Ile Ser Arg Asp Asn
1               5                   10                  15

Ala Lys Lys Ser Leu Tyr Leu Gln Met Asn Ser Leu Arg Ala Glu Asp
            20                  25                  30

Thr Ala Val Tyr Tyr Cys
        35

<210> SEQ ID NO 376
<211> LENGTH: 19
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 376

Asp Gln Val Glu Gln Gln Leu Val Leu Gly Tyr Phe Tyr Tyr Tyr Tyr
1               5                   10                  15

Met Asp Val

<210> SEQ ID NO 377
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 377

Tyr Tyr Val Asp Ser Val Lys Gly Arg Phe Thr Ile Ser Arg Asp Asn
1               5                   10                  15

Ala Glu Asn Ser Leu Tyr Leu Gln Met Asn Gly Leu Arg Ala Glu Asp
            20                  25                  30

Thr Ala Val Tyr Tyr Cys
        35

<210> SEQ ID NO 378
<211> LENGTH: 18
<212> TYPE: PRT
<213> ORGANISM: Artificial Sequence
<220> FEATURE:
<221> NAME/KEY: source
```

<223> OTHER INFORMATION: /note="VH CDR3 sequence"

<400> SEQUENCE: 378

Asp Pro Arg Ala Tyr Asp Tyr Trp Ser Gly Tyr Tyr Glu Gly Tyr Phe
1               5                   10                  15

Asp Tyr

<210> SEQ ID NO 379
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 379

Gln Val Gln Leu Gln Glu Ser Gly Ser Gly Leu Val Arg Ser Ser Gln
1               5                   10                  15

Asn Leu Ser Leu Thr Cys Ser Val Ser
            20                  25

<210> SEQ ID NO 380
<211> LENGTH: 10
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 380

Gly Gly Ser Val Ser Arg Gly Gly Ala Ser
1               5                   10

<210> SEQ ID NO 381
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 381

Trp Gly Trp Val Arg Gln Pro Pro Gly Gln Gly Leu Glu Trp Ile Gly
1               5                   10                  15

Tyr

<210> SEQ ID NO 382
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 382

Ile Thr His Ser Gly Thr Thr
1               5

<210> SEQ ID NO 383
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

```
<400> SEQUENCE: 383

Glu Val Gln Leu Val Glu Ser Gly Gly Gly Ser Val Gln Pro Gly Gly
1               5                   10                  15

Ser Leu Arg Leu Ser Cys Ala Ala Ser
            20                  25

<210> SEQ ID NO 384
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 384

Gly Phe Thr Phe Ser Ser His Trp
1               5

<210> SEQ ID NO 385
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 385

Ile His Trp Val Arg Gln Ala Pro Gly Lys Gly Leu Val Cys Val Ser
1               5                   10                  15

Arg

<210> SEQ ID NO 386
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 386

Ile Asn Ser Asp Gly Ser Ser Thr
1               5

<210> SEQ ID NO 387
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 387

Gln Val Gln Leu Val Glu Ser Gly Gly Gly Leu Val Gln Pro Gly Gly
1               5                   10                  15

Ser Leu Arg Leu Ser Cys Ala Thr Ser
            20                  25

<210> SEQ ID NO 388
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 388
```

Arg Phe Thr Phe Ser Asn Tyr Ala
1               5

<210> SEQ ID NO 389
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 389

Met Asn Trp Val Arg Gln Ala Pro Gly Lys Gly Leu Glu Trp Val Ser
1               5                   10                  15

Ala

<210> SEQ ID NO 390
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 390

Ile Ser Gly Ser Gly Gly Thr Thr
1               5

<210> SEQ ID NO 391
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 391

Glu Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 392
<211> LENGTH: 10
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 392

Gly Gly Ser Ile Thr Ser Asp Thr Phe Tyr
1               5                   10

<210> SEQ ID NO 393
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 393

Trp Gly Trp Val Arg Gln Pro Pro Gly Lys Gly Leu Glu Trp Ile Ala
1               5                   10                  15

Ser

<210> SEQ ID NO 394
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 394

Ile Ser Tyr Ser Gly Ser Thr
1               5

<210> SEQ ID NO 395
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 395

Glu Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 396
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 396

Gly Tyr Thr Phe Thr Ser Tyr Gly
1               5

<210> SEQ ID NO 397
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 397

Ile Ser Trp Val Arg Gln Ala Pro Gly Gln Gly Leu Glu Trp Met Gly
1               5                   10                  15

Trp

<210> SEQ ID NO 398
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 398

Ile Ser Ala Tyr Asn Gly Asn Thr
1               5

<210> SEQ ID NO 399

```
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 399

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 400
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 400

Gly Tyr Thr Phe Thr Ser Tyr Tyr
1               5

<210> SEQ ID NO 401
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 401

Met His Trp Val Arg Gln Ala Pro Gly Gln Gly Leu Glu Trp Met Gly
1               5                   10                  15

Ile

<210> SEQ ID NO 402
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 402

Ile Asn Pro Ser Gly Gly Ser Thr
1               5

<210> SEQ ID NO 403
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 403

Gln Val Gln Leu Val Glu Ser Gly Gly Val Val Val Gln Pro Gly Gly
1               5                   10                  15

Ser Leu Arg Leu Ser Cys Ala Ala Ser
            20                  25

<210> SEQ ID NO 404
<211> LENGTH: 8
```

```
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 404

Gly Phe Thr Phe Asp Asp Tyr Ala
1               5

<210> SEQ ID NO 405
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 405

Ile His Trp Val Arg Gln Ala Pro Gly Lys Gly Leu Glu Trp Val Ser
1               5                   10                  15

Leu

<210> SEQ ID NO 406
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 406

Ile Ser Trp Asp Gly Gly Ser Thr
1               5

<210> SEQ ID NO 407
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 407

Gln Val Gln Leu Val Glu Ser Gly Gly Gly Leu Ile Gln Pro Gly Gly
1               5                   10                  15

Ser Leu Arg Leu Ser Cys Ala Ala Ser
            20                  25

<210> SEQ ID NO 408
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 408

Gly Phe Thr Val Ser Gly Asn Tyr
1               5

<210> SEQ ID NO 409
<211> LENGTH: 17
<212> TYPE: PRT
<213> ORGANISM: Artificial Sequence
<220> FEATURE:
<221> NAME/KEY: source
```

<223> OTHER INFORMATION: /note="VH FR2 sequence"

<400> SEQUENCE: 409

Met Ser Trp Val Arg Gln Ala Pro Gly Arg Gly Leu Glu Trp Val Ser
1               5                   10                  15
Val

<210> SEQ ID NO 410
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 410

Ile Tyr Ser Thr Gly Asp Thr
1               5

<210> SEQ ID NO 411
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 411

Gln Val Gln Leu Val Gln Ser Gly Ala Glu Val Lys Lys Pro Gly Glu
1               5                   10                  15
Ser Leu Lys Ile Ser Cys His Gly Ser
            20                  25

<210> SEQ ID NO 412
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 412

Gly Tyr Thr Phe Ser Asn Tyr Trp
1               5

<210> SEQ ID NO 413
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 413

Ile Gly Trp Val Arg Gln Met Pro Gly Lys Gly Leu Glu Trp Met Gly
1               5                   10                  15
Ile

<210> SEQ ID NO 414
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

```
<400> SEQUENCE: 414

Ile Tyr Thr Gly Asp Ser Tyr Ser
1               5

<210> SEQ ID NO 415
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 415

Glu Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 416
<211> LENGTH: 10
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 416

Gly Gly Ser Ile Ser Ser Ser Ser Tyr Tyr
1               5                   10

<210> SEQ ID NO 417
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 417

Trp Gly Trp Ile Arg Gln Pro Pro Gly Lys Gly Leu Glu Trp Ile Gly
1               5                   10                  15

Ser

<210> SEQ ID NO 418
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 418

Ile Tyr Tyr Ser Gly Ser Thr
1               5

<210> SEQ ID NO 419
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 419

Glu Val Gln Leu Val Glu Ser Gly Gly Gly Leu Val Gln Pro Gly Gly
1               5                   10                  15
```

Ser Leu Arg Leu Ser Cys Ala Ala Ser
            20                  25

<210> SEQ ID NO 420
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 420

Gly Phe Thr Phe Ser Ser Tyr Ala
1               5

<210> SEQ ID NO 421
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 421

Met Ser Trp Val Arg Gln Ala Pro Gly Lys Gly Leu Glu Trp Val Ser
1               5                   10                  15

Ala

<210> SEQ ID NO 422
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 422

Ile Ser Gly Ser Gly Gly Ser Thr
1               5

<210> SEQ ID NO 423
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 423

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 424
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 424

Gly Phe Thr Phe Ser Ser Tyr Trp
1               5

```
<210> SEQ ID NO 425
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 425

Met His Trp Val Arg Gln Ala Pro Gly Lys Gly Leu Val Trp Val Ser
1               5                   10                  15

Arg

<210> SEQ ID NO 426
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 426

Ile Asn Ser Asp Gly Ser Ser Thr
1               5

<210> SEQ ID NO 427
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 427

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 428
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 428

Gly Phe Thr Phe Ser Ser Tyr Ser
1               5

<210> SEQ ID NO 429
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 429

Met Asn Trp Val Arg Gln Ala Pro Gly Lys Gly Leu Glu Trp Val Ser
1               5                   10                  15

Tyr

<210> SEQ ID NO 430
```

```
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 430

Ile Ser Ser Ser Ser Ser Thr Ile
1               5

<210> SEQ ID NO 431
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 431

Gln Val Gln Leu Val Gln Ser Gly Gly Gly Leu Val Gln Pro Gly Gly
1               5                   10                  15

Ser Leu Thr Leu Ser Cys Ala Val Ser
            20                  25

<210> SEQ ID NO 432
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 432

Gly Phe Thr Val Arg Ser Ser Tyr
1               5

<210> SEQ ID NO 433
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 433

Val Ser Trp Leu Arg Gln Thr Pro Gly Lys Gly Leu Glu Trp Val Ser
1               5                   10                  15

Val

<210> SEQ ID NO 434
<211> LENGTH: 7
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 434

Ile Phe Ser Gly Gly Ser Thr
1               5

<210> SEQ ID NO 435
<211> LENGTH: 25
<212> TYPE: PRT
<213> ORGANISM: Artificial Sequence
<220> FEATURE:
```

```
<221> NAME/KEY: source
<223> OTHER INFORMATION: /note="VH FR1 sequence"

<400> SEQUENCE: 435

Glu Val Gln Leu Val Glu Ser Gly Gly Gly Leu Val Gln Pro Gly Gly
1               5                   10                  15

Ser Leu Arg Leu Ser Cys Glu Ala Ser
            20                  25

<210> SEQ ID NO 436
<211> LENGTH: 8
<212> TYPE: PRT
<213> ORGANISM: Artificial Sequence
<220> FEATURE:
<221> NAME/KEY: source
<223> OTHER INFORMATION: /note="VH CDR1 sequence"

<400> SEQUENCE: 436

Gly Phe Asn Phe Glu Asn Tyr Ala
1               5

<210> SEQ ID NO 437
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 437

Met Asp Trp Val Arg Gln Ala Pro Gly Lys Gly Leu Glu Trp Val Ser
1               5                   10                  15

Gly

<210> SEQ ID NO 438
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 438

Ile Thr Trp Asn Ser Gly Lys Ile
1               5

<210> SEQ ID NO 439
<211> LENGTH: 25
<212> TYPE: PRT
<213> ORGANISM: Artificial Sequence
<220> FEATURE:
<221> NAME/KEY: source
<223> OTHER INFORMATION: /note="VH FR1 sequence"

<400> SEQUENCE: 439

Gln Val Gln Leu Val Glu Ser Gly Gly Cys Val Val Gln Pro Gly Arg
1               5                   10                  15

Ser Leu Arg Leu Ser Cys Ala Ala Ser
            20                  25

<210> SEQ ID NO 440
<211> LENGTH: 8
<212> TYPE: PRT
<213> ORGANISM: Artificial Sequence
<220> FEATURE:
<221> NAME/KEY: source
```

-continued

<223> OTHER INFORMATION: /note="VH CDR1 sequence"

<400> SEQUENCE: 440

Gly Phe Thr Phe Ser Thr Tyr Ala
1               5

<210> SEQ ID NO 441
<211> LENGTH: 17
<212> TYPE: PRT
<213> ORGANISM: Artificial Sequence
<220> FEATURE:
<221> NAME/KEY: source
<223> OTHER INFORMATION: /note="VH FR2 sequence"

<400> SEQUENCE: 441

Met Tyr Trp Val Arg Gln Ala Pro Gly Glu Gly Leu Glu Trp Val Ala
1               5                   10                  15

Val

<210> SEQ ID NO 442
<211> LENGTH: 8
<212> TYPE: PRT
<213> ORGANISM: Artificial Sequence
<220> FEATURE:
<221> NAME/KEY: source
<223> OTHER INFORMATION: /note="VH CDR2 sequence"

<400> SEQUENCE: 442

Ile Ser Tyr His Gly Ser Asn Lys
1               5

<210> SEQ ID NO 443
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 443

Phe Ser Asn Pro Ser Leu Lys Ser Arg Val Met Ile Ser Lys Asp Lys
1               5                   10                  15

Ser Gln Asn His Phe Ser Leu Ser Leu Thr Ser Val Thr Val Ala Asp
                20                  25                  30

Thr Ala Val Tyr Phe Cys
            35

<210> SEQ ID NO 444
<211> LENGTH: 9
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 444

Ala Arg Trp Ser Thr Ala Phe Asp Arg
1               5

<210> SEQ ID NO 445
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 445

Ser Tyr Ala Asp Ser Val Lys Gly Arg Phe Thr Ile Ser Arg Asp Asn
1               5                   10                  15

Ala Lys Asn Met Val Tyr Leu Gln Met Asn Ser Leu Arg Ala Glu Asp
            20                  25                  30

Thr Ala Val Asp Leu Gly
        35

<210> SEQ ID NO 446
<211> LENGTH: 21
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 446

Thr Ser Asp Arg Arg Ser Gln Phe Arg Arg Ser Gly Arg Ala Pro Trp
1               5                   10                  15

Asp Ala Phe Asp Ile
            20

<210> SEQ ID NO 447
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 447

Tyr Tyr Ala Asp Ser Val Lys Gly Arg Phe Thr Ile Ser Arg Asp Asn
1               5                   10                  15

Ser Arg Asn Ser Leu Tyr Leu Gln Met Asn Ser Leu Arg Gly Glu Asp
            20                  25                  30

Thr Ala Val Tyr Tyr Cys
        35

<210> SEQ ID NO 448
<211> LENGTH: 20
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 448

Val Lys Glu Ser Val Gly Ala Leu Leu Trp Glu Ile Asp Asp Trp Gln
1               5                   10                  15

Phe Phe Asp Tyr
            20

<210> SEQ ID NO 449
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 449

Phe Tyr Asn Pro Ser Leu Lys Ser Arg Val Thr Met Ser Val Asp Thr
1               5                   10                  15

```
Ser Lys Asn Gln Phe Ser Leu His Leu Asn Ser Val Thr Ala Ala Asp
            20                  25                  30

Thr Ala Val Phe Tyr Cys
        35

<210> SEQ ID NO 450
<211> LENGTH: 13
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 450

Ala Lys His Gly Gly Gly Met Ala Thr Ser Phe Asp Tyr
1               5                   10

<210> SEQ ID NO 451
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 451

Asn Tyr Ala Gln Lys Leu Gln Gly Arg Val Thr Met Thr Thr Asp Thr
1               5                   10                  15

Ser Thr Ser Thr Ala Tyr Met Glu Leu Arg Ser Leu Arg Ser Asp Asp
            20                  25                  30

Thr Ala Val Tyr Tyr Cys
        35

<210> SEQ ID NO 452
<211> LENGTH: 10
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 452

Ala Arg Asp Thr Asp His Tyr Phe Asp Tyr
1               5                   10

<210> SEQ ID NO 453
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 453

Ser Tyr Ala Gln Lys Phe Gln Gly Arg Val Thr Met Thr Arg Asp Thr
1               5                   10                  15

Ser Thr Ser Thr Val Tyr Met Glu Leu Ser Ser Leu Arg Ser Glu Asp
            20                  25                  30

Thr Ala Val Tyr Tyr Cys
        35

<210> SEQ ID NO 454
<211> LENGTH: 13
<212> TYPE: PRT
```

```
<213> ORGANISM: Artificial Sequence
<220> FEATURE:
<221> NAME/KEY: source
<223> OTHER INFORMATION: /note="VH CDR3 sequence"

<400> SEQUENCE: 454

Ala Arg Glu Gly Ala Ile Ala Ala Ala Gly Phe Asp Tyr
1               5                   10

<210> SEQ ID NO 455
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 455

Tyr Tyr Ala Asp Ser Val Lys Gly Arg Phe Thr Ile Ser Arg Asp Asn
1               5                   10                  15

Ser Lys Asn Ser Leu Tyr Leu Gln Met Asn Ser Leu Arg Thr Glu Asp
            20                  25                  30

Thr Ala Leu Tyr Tyr Cys
        35

<210> SEQ ID NO 456
<211> LENGTH: 15
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 456

Ala Lys Asp Thr Ala Ile Leu Phe Gly Gly Ser Ser Phe Asp Tyr
1               5                   10                  15

<210> SEQ ID NO 457
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 457

Tyr Tyr Ala Glu Ser Val Lys Gly Arg Phe Thr Val Ser Arg Asp Asp
1               5                   10                  15

Asn Ser Lys Ser Ser Val Lys Val Val Val Glu Gln Thr Glu Ser Arg
            20                  25                  30

Gly His Gly Arg Val Leu
        35

<210> SEQ ID NO 458
<211> LENGTH: 15
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 458

Leu Cys Glu Arg Lys Gly Gln Trp Leu Val Gln Arg Tyr Gly Arg
1               5                   10                  15
```

-continued

```
<210> SEQ ID NO 459
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 459

Arg Tyr Ser Pro Ser Phe Gln Gly Leu Gly Asp Val Ala Val Asp Glu
1               5                   10                  15

Ser Leu Ser Thr Ala Tyr Leu Glu Trp Ser Ser Leu Lys Ala Ser Asp
                20                  25                  30

Thr Ala Met Tyr Tyr Cys
            35

<210> SEQ ID NO 460
<211> LENGTH: 13
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 460

Val Arg Gln Trp Glu Asn Arg Gly Trp Ser Ile Ala Tyr
1               5                   10

<210> SEQ ID NO 461
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 461

Tyr Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
                20                  25                  30

Thr Ala Val Tyr Tyr Cys
            35

<210> SEQ ID NO 462
<211> LENGTH: 11
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 462

Ala Arg His Leu Arg Tyr Asn Trp Phe Asp Pro
1               5                   10

<210> SEQ ID NO 463
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 463

Tyr Tyr Ala Asp Ser Val Lys Gly Arg Phe Thr Ile Ser Arg Asp Asn
```

-continued

```
                1               5                  10                  15
Ser Lys Asn Thr Leu Tyr Leu Gln Met Asn Ser Leu Arg Ala Glu Asp
                        20                  25                  30

Thr Ala Val Tyr Tyr Cys
                35

<210> SEQ ID NO 464
<211> LENGTH: 19
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 464

Ala Lys Met Leu Phe Thr Pro Trp Glu Val Thr Trp Leu Arg Pro Tyr
1               5                  10                  15

Phe Asp Tyr

<210> SEQ ID NO 465
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 465

Ser Tyr Ala Asp Ser Val Lys Gly Arg Phe Thr Ile Ser Arg Asp Asn
1               5                  10                  15

Ala Lys Asn Thr Leu Tyr Leu Gln Met Asn Ser Leu Arg Ala Glu Asp
                        20                  25                  30

Thr Ala Val Tyr Tyr Cys
                35

<210> SEQ ID NO 466
<211> LENGTH: 11
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 466

Ala Ser Leu Val Pro Ala Ala Gly Gly Asp Tyr
1               5                  10

<210> SEQ ID NO 467
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 467

Tyr Tyr Ala Asp Ser Val Lys Gly Arg Phe Thr Ile Ser Arg Asp Asn
1               5                  10                  15

Ala Lys Asn Ser Leu Tyr Leu Gln Met Asn Ser Leu Arg Ala Glu Asp
                        20                  25                  30

Thr Ala Val Tyr Tyr Cys
                35
```

-continued

```
<210> SEQ ID NO 468
<211> LENGTH: 17
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 468

Ala Arg Gly Ser Pro Tyr Ser Ser Ser Ser Val Arg Gly Met Asp
1               5                   10                  15

Val

<210> SEQ ID NO 469
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 469

Ser Tyr Ala Asp Phe Val Lys Gly Arg Phe Thr Met Ser Arg Asp Asn
1               5                   10                  15

Ser Lys Asn Thr Leu Tyr Leu Gln Met Asp Ser Leu Arg Ser Asp Asp
            20                  25                  30

Thr Ala Val Tyr Tyr Cys
        35

<210> SEQ ID NO 470
<211> LENGTH: 13
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 470

Ala Lys Gly Gly Trp Glu Leu Thr Asn Trp Phe Asp Pro
1               5                   10

<210> SEQ ID NO 471
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 471

His Tyr Ala Asp Ser Val Lys Gly Arg Phe Thr Ile Ser Arg Asp Asn
1               5                   10                  15

Ala Lys Asn Ser Leu Phe Leu Gln Met Asn Asn Leu Arg His Glu Asp
            20                  25                  30

Thr Ala Leu Tyr Tyr Cys
        35

<210> SEQ ID NO 472
<211> LENGTH: 11
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 472
```

Ala Lys Ala Ser Gly Glu Asp Phe Pro Asp Tyr
1               5                   10

<210> SEQ ID NO 473
<211> LENGTH: 38
<212> TYPE: PRT
<213> ORGANISM: Artificial Sequence
<220> FEATURE:
<221> NAME/KEY: source
<223> OTHER INFORMATION: /note="VH FR3 sequence"

<400> SEQUENCE: 473

Tyr Tyr Ala Asp Ser Val Lys Gly Arg Phe Thr Ile Ser Arg Asp Asn
1               5                   10                  15

Ser Lys Asn Thr Leu Tyr Leu Leu Met Asn Ser Leu Arg Ala Glu Asp
                20                  25                  30

Thr Ala Val Tyr Tyr Cys
            35

<210> SEQ ID NO 474
<211> LENGTH: 19
<212> TYPE: PRT
<213> ORGANISM: Artificial Sequence
<220> FEATURE:
<221> NAME/KEY: source
<223> OTHER INFORMATION: /note="VH CDR3 sequence"

<400> SEQUENCE: 474

Ala Arg Asp Pro Gly Trp Ser Gly Ser Ile Met Asp Tyr Tyr Tyr Gly
1               5                   10                  15

Met Asp Val

<210> SEQ ID NO 475
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 475

Phe Val Ser Gln Thr Pro Ala Thr Leu Ser Ala Ser Val Gly Asp Arg
1               5                   10                  15

Val Thr Ile Thr Cys Arg Ala Ser
                20

<210> SEQ ID NO 476
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 476

Gln Ser Ile Ser Ser Tyr
1               5

<210> SEQ ID NO 477
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 477

Leu Asn Trp Tyr Gln Gln Lys Pro Gly Lys Val Pro Lys Leu Leu Ile
1               5                   10                  15

Tyr

<210> SEQ ID NO 478
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 478

Met Thr Pro Thr Ile Pro Val Thr Leu Ser Ala Ser Val Gly Asp Arg
1               5                   10                  15

Val Thr Ile Thr Cys Arg Ala Ser
            20

<210> SEQ ID NO 479
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 479

Gln Ser Ile Ser Asn Trp
1               5

<210> SEQ ID NO 480
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 480

Leu Ala Trp Tyr Gln Gln Lys Pro Gly Lys Ala Pro Lys Leu Leu Ile
1               5                   10                  15

Tyr

<210> SEQ ID NO 481
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 481

Gln Ser Glu Leu Thr Gln Pro Pro Ser Val Ser Val Ala Pro Gly Gln
1               5                   10                  15

Thr Ala Arg Ile Thr Cys Gly Gly Asn
            20                  25

<210> SEQ ID NO 482
<211> LENGTH: 6
<212> TYPE: PRT
<213> ORGANISM: Artificial Sequence
<220> FEATURE:
<221> NAME/KEY: source

```
<223> OTHER INFORMATION: /note="VL CDR1 sequence"

<400> SEQUENCE: 482

Asn Ile Gly Ser Lys Ser
1               5

<210> SEQ ID NO 483
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 483

Val His Trp Tyr Gln Gln Lys Pro Gly Gln Ala Pro Val Leu Val Val
1               5                   10                  15

Tyr

<210> SEQ ID NO 484
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 484

Tyr His Asp Pro Gln Ala Pro Leu Thr Leu Ser Leu Ser Pro Gly Glu
1               5                   10                  15

Arg Ala Thr Leu Ser Cys Arg Ala Ser
            20                  25

<210> SEQ ID NO 485
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 485

Gln Ser Val Ser Ser Ser Tyr
1               5

<210> SEQ ID NO 486
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 486

Leu Ala Trp Tyr Gln Gln Lys Pro Gly Gln Ala Pro Arg Leu Leu Ile
1               5                   10                  15

Tyr

<210> SEQ ID NO 487
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"
```

-continued

<400> SEQUENCE: 487

His Asp Pro Gln Ala Pro Ala Thr Leu Ser Ala Ser Val Gly Asp Arg
1               5                   10                  15

Val Thr Ile Thr Cys Arg Ala Ser
            20

<210> SEQ ID NO 488
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 488

Gln Gly Ile Ser Ser Tyr
1               5

<210> SEQ ID NO 489
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 489

Leu Ala Trp Tyr Gln Gln Lys Pro Gly Lys Ala Pro Asn Leu Leu Ile
1               5                   10                  15

Tyr

<210> SEQ ID NO 490
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 490

Met Thr Leu Ile Ile Pro Val Thr Leu Ser Leu Ser Pro Gly Glu Arg
1               5                   10                  15

Ala Thr Leu Ser Cys Arg Ala Ser
            20

<210> SEQ ID NO 491
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 491

Gln Ser Ile Arg Ser Asn
1               5

<210> SEQ ID NO 492
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 492

Leu Ala Trp Tyr Gln Gln Lys Pro Gly Gln Ala Pro Arg Leu Leu Ile
1               5                   10                  15

His

<210> SEQ ID NO 493
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 493

Gln Phe Val Leu Thr Gln Pro Pro Ser Val Ser Gly Ala Pro Gly Gln
1               5                   10                  15

Arg Val Thr Ile Ser Cys Thr Gly Ser
            20                  25

<210> SEQ ID NO 494
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 494

Ser Ser Asn Ile Gly Ala Gly Tyr Asp
1               5

<210> SEQ ID NO 495
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 495

Val His Trp Tyr Gln Gln Leu Pro Gly Thr Ala Pro Lys Leu Leu Ile
1               5                   10                  15

Tyr

<210> SEQ ID NO 496
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 496

Gln Ser Val Leu Thr Gln Thr Pro Ser Val Ser Val Ala Pro Gly Gln
1               5                   10                  15

Thr Ala Ile Ile Thr Cys Gly Gly His
            20                  25

<210> SEQ ID NO 497
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

```
<400> SEQUENCE: 497

Ser Ile Gly Asn Arg Ala
1               5

<210> SEQ ID NO 498
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 498

Val His Trp Tyr Gln Gln Lys Pro Gly Gln Ala Pro Val Val Val Val
1               5                   10                  15

Tyr

<210> SEQ ID NO 499
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 499

Leu Leu Ser Leu His Ile Pro Val Thr Leu Ser Ala Ser Val Gly Asp
1               5                   10                  15

Arg Val Thr Ile Thr Cys Gln Ala Ser
            20                  25

<210> SEQ ID NO 500
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 500

Gln Asp Ile Thr Lys Tyr
1               5

<210> SEQ ID NO 501
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 501

Leu Asn Trp Tyr Gln Gln Lys Pro Gly Lys Ala Pro Lys Leu Leu Ile
1               5                   10                  15

Tyr

<210> SEQ ID NO 502
<211> LENGTH: 23
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 502
```

Ser Ser His Ile Pro Val Thr Leu Ala Val Ser Leu Gly Glu Arg Ala
1               5                   10                  15

Thr Ile Asn Cys Lys Ser Ser
            20

<210> SEQ ID NO 503
<211> LENGTH: 12
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 503

Gln Ser Val Leu Tyr Tyr Ser Asn Ser Lys Asn Tyr
1               5                   10

<210> SEQ ID NO 504
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 504

Leu Thr Trp Tyr Gln Gln Lys Pro Gly Gln Pro Pro Lys Leu Leu Ile
1               5                   10                  15

Tyr

<210> SEQ ID NO 505
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 505

Tyr Asp Pro Thr Ala Pro Ala Thr Leu Ser Leu Ser Pro Gly Glu Arg
1               5                   10                  15

Ala Thr Leu Ser Cys Arg Ala Ser
            20

<210> SEQ ID NO 506
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 506

Gln Ser Val Arg Ser Ser Tyr
1               5

<210> SEQ ID NO 507
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 507

Leu Ala Trp Tyr Gln Gln Lys Pro Gly Gln Ala Pro Arg Leu Leu Ile

```
1               5                  10                  15
Tyr

<210> SEQ ID NO 508
<211> LENGTH: 23
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 508

Leu Pro Gln Ala Pro Ala Thr Leu Ser Leu Ser Pro Gly Glu Arg Ala
1               5                  10                  15

Thr Leu Ser Cys Arg Ala Ser
            20

<210> SEQ ID NO 509
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 509

Gln Ser Val Ser Ser Tyr
1               5

<210> SEQ ID NO 510
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 510

Gln Ser Val Leu Thr Gln Pro Ala Ser Val Ser Gly Ser Pro Gly Gln
1               5                  10                  15

Ser Ile Thr Ile Ser Cys Thr Gly Thr
            20                  25

<210> SEQ ID NO 511
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 511

Ser Ser Asp Val Gly Asn Tyr Asn Leu
1               5

<210> SEQ ID NO 512
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 512

Val Ser Trp Tyr Gln Gln His Pro Gly Lys Ala Pro Lys Leu Met Ile
1               5                  10                  15
```

Tyr

<210> SEQ ID NO 513
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 513

Arg Ser Pro Lys Ala Pro Val Thr Leu Ser Leu Ser Pro Gly Glu Arg
1               5                   10                  15

Ala Thr Leu Ser Cys Arg Ala Ser
            20

<210> SEQ ID NO 514
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 514

Met Thr Pro Thr Ala Pro Val Thr Leu Ser Ala Ser Val Gly Asp Arg
1               5                   10                  15

Val Thr Ile Thr Cys Arg Ala Ser
            20

<210> SEQ ID NO 515
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 515

Leu Ala Trp Tyr Gln Gln Lys Pro Gly Lys Ala Pro Lys Leu Leu Ile
1               5                   10                  15

Tyr

<210> SEQ ID NO 516
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 516

Gln Ser Val Leu Thr Gln Pro Ala Ser Val Ser Gly Pro Pro Gly Gln
1               5                   10                  15

Ser Ile Ala Ile Ser Cys Thr Gly Thr
            20                  25

<210> SEQ ID NO 517
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

```
<400> SEQUENCE: 517

Asn Ser Asp Val Gly Ala Tyr Asn Tyr
1               5

<210> SEQ ID NO 518
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 518

Val Ser Trp Tyr Gln Gln His Pro Gly Lys Ala Pro Lys Leu Met Ile
1               5                   10                  15

Tyr

<210> SEQ ID NO 519
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 519

Gln Ser Val Leu Thr Gln Pro Pro Ser Val Ser Val Ala Pro Gly Lys
1               5                   10                  15

Thr Ala Arg Ile Thr Cys Gly Gly Asn
            20                  25

<210> SEQ ID NO 520
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 520

Asn Ile Gly Ser Lys Ser
1               5

<210> SEQ ID NO 521
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 521

Val His Trp Tyr Gln Gln Lys Pro Gly Gln Ala Pro Val Leu Val Ile
1               5                   10                  15

Tyr

<210> SEQ ID NO 522
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 522
```

```
Tyr Asp Pro Thr Ala Pro Val Thr Leu Ser Ala Ser Val Gly Asp Arg
1               5                   10                  15

Val Thr Ile Thr Cys Arg Ala Ser
            20
```

```
<210> SEQ ID NO 523
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 523

Leu Asn Trp Tyr Gln Gln Lys Pro Gly Lys Ala Pro Lys Leu Leu Ile
1               5                   10                  15

Tyr
```

```
<210> SEQ ID NO 524
<211> LENGTH: 22
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 524

Pro Pro Ala Pro Leu Thr Leu Ser Val Ser Pro Gly Glu Arg Ala Thr
1               5                   10                  15

Leu Ser Cys Arg Ala Ser
            20
```

```
<210> SEQ ID NO 525
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 525

Gln Ser Val Ser Ser Asn
1               5
```

```
<210> SEQ ID NO 526
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 526

Lys Ile Val Met Ala Gln Ser Pro Ala Thr Leu Ser Leu Ser Pro Gly
1               5                   10                  15

Glu Arg Thr Thr Leu Ser Gly Arg Ala Ser
            20                  25
```

```
<210> SEQ ID NO 527
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"
```

<400> SEQUENCE: 527

Gln Ser Val His Asn Ile Tyr
1               5

<210> SEQ ID NO 528
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 528

Leu Pro Trp Tyr Gln Gln Lys Pro Gly Gln Ala Ala Arg Leu Leu Ile
1               5                   10                  15

Tyr

<210> SEQ ID NO 529
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 529

Gln Ser Val Leu Thr Gln Ser Pro Ser Ala Ser Ala Ser Leu Gly Ala
1               5                   10                  15

Ser Val Lys Leu Thr Cys Thr Leu Thr
            20                  25

<210> SEQ ID NO 530
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 530

Ser Gly His Ser Asn Tyr Ala
1               5

<210> SEQ ID NO 531
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 531

Ile Ala Trp His Gln Gln Gln Pro Glu Arg Gly Pro Arg Tyr Leu Met
1               5                   10                  15

Lys

<210> SEQ ID NO 532
<211> LENGTH: 7
<212> TYPE: PRT
<213> ORGANISM: Artificial Sequence
<220> FEATURE:
<221> NAME/KEY: source
<223> OTHER INFORMATION: /note="VL CDR2 sequence"

<400> SEQUENCE: 532

```
Val Asn Ser Asp Gly Ser His
1               5
```

<210> SEQ ID NO 533
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 533

```
Gln Ser Val Leu Thr Gln Pro Pro Ser Ala Ser Gly Ser Pro Gly Gln
1               5                   10                  15
Ser Val Thr Ile Ser Cys Thr Gly Thr
            20                  25
```

<210> SEQ ID NO 534
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 534

```
Ser Ser Asp Val Gly Gly Tyr Asn Tyr
1               5
```

<210> SEQ ID NO 535
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 535

```
Val Ser Trp Tyr Gln Gln His Pro Gly Lys Ala Pro Lys Leu Met Ile
1               5                   10                  15
Tyr
```

<210> SEQ ID NO 536
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 536

```
Gln Ser Val Leu Thr Gln Ser Pro Ser Ala Ser Ala Ser Leu Gly Ala
1               5                   10                  15
Ser Val Lys Leu Thr Cys Thr Leu Thr
            20                  25
```

<210> SEQ ID NO 537
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 537

```
Ser Gly His Ser Asn Tyr Ala
```

```
<210> SEQ ID NO 538
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 538

Ile Ala Trp His Gln Gln Pro Glu Arg Gly Pro Arg Tyr Leu Met
1               5                   10                  15

Lys

<210> SEQ ID NO 539
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 539

Gln Ser Val Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 540
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 540

Ser Ser Asp Val Gly Gly Tyr Asn His
1               5

<210> SEQ ID NO 541
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 541

Val Ser Trp Tyr Gln Gln His Pro Gly Lys Ala Pro Lys Leu Met Ile
1               5                   10                  15

Tyr

<210> SEQ ID NO 542
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 542

Gln Ser Val Leu Thr Gln Pro Arg Ser Val Ser Gly Ser Pro Gly Gln
1               5                   10                  15
```

Ser Val Thr Ile Ser Cys Thr Gly Thr
            20                  25

<210> SEQ ID NO 543
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 543

Ser Ser Asp Val Gly Asp Tyr Lys Tyr
1               5

<210> SEQ ID NO 544
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 544

Val Ser Trp Tyr Gln Gln Tyr Pro Gly Lys Ala Pro Arg Leu Met Ile
1               5                   10                  15

Tyr

<210> SEQ ID NO 545
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 545

Gln Ser Val Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 546
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 546

Ser Ser Asp Val Gly Ser Tyr Ser Leu
1               5

<210> SEQ ID NO 547
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 547

Val Ser Trp Phe Gln Gln His Pro Gly Arg Ala Pro Lys Leu Ile Ile
1               5                   10                  15

Tyr

```
<210> SEQ ID NO 548
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 548

Leu Met Thr Gln Ala Pro Val Thr Leu Ser Val Ser Pro Gly Glu Arg
1               5                   10                  15

Ala Thr Leu Ser Cys Arg Ala Ser
            20

<210> SEQ ID NO 549
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 549

Gln Ser Val Ser Ser Asn
1               5

<210> SEQ ID NO 550
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 550

Leu Ala Trp Tyr Gln Gln Lys Pro Gly Gln Ala Pro Arg Leu Leu Ile
1               5                   10                  15

Tyr

<210> SEQ ID NO 551
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 551

Gln Ser Val Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 552
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 552

Ser Ser Asp Val Gly Gly Tyr Asn Tyr
1               5
```

<210> SEQ ID NO 553
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 553

Val Ser Trp Tyr Gln Gln His Pro Gly Lys Ala Pro Lys Leu Met Ile
1               5                   10                  15

Tyr

<210> SEQ ID NO 554
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 554

Gln Ser Val Leu Thr Gln Pro Pro Ser Val Ser Ala Ala Pro Gly Gln
1               5                   10                  15

Lys Val Thr Ile Ser Cys Ser Gly Ser
            20                  25

<210> SEQ ID NO 555
<211> LENGTH: 8
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 555

Ser Ser Asn Ile Gly Asn Asn Tyr
1               5

<210> SEQ ID NO 556
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 556

Val Ser Trp Tyr Gln Gln Leu Pro Gly Thr Ala Pro Lys Leu Leu Ile
1               5                   10                  15

Tyr

<210> SEQ ID NO 557
<211> LENGTH: 23
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 557

Ser Pro Gln Ala Pro Val Thr Leu Ser Leu Ser Pro Gly Glu Arg Ala
1               5                   10                  15

Thr Leu Ser Cys Arg Ala Ser
            20

```
<210> SEQ ID NO 558
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 558

Leu Ala Trp Tyr Gln Gln Lys Pro Gly Gln Ala Pro Arg Leu Leu Ile
1               5                   10                  15

Tyr

<210> SEQ ID NO 559
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 559

Gln Phe Val Leu Thr Gln Ser Leu Ser Val Ser Val Ala Leu Gly Gln
1               5                   10                  15

Thr Ala Asn Ile Thr Cys Gly Gly His
            20                  25

<210> SEQ ID NO 560
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 560

Asn Ile Val Ala Lys Thr
1               5

<210> SEQ ID NO 561
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 561

Val His Trp Tyr Gln Gln Lys Ser Gly Gln Ala Pro Val Leu Val Ile
1               5                   10                  15

Tyr

<210> SEQ ID NO 562
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 562

Gln Ser Val Leu Thr Gln Pro Ala Ser Val Ser Gly Ser Pro Gly Gln
1               5                   10                  15

Ser Ile Thr Ile Ser Cys Thr Gly Thr
```

20                  25

<210> SEQ ID NO 563
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 563

Ser Ser Asp Val Gly Gly Tyr Asn Tyr
1               5

<210> SEQ ID NO 564
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 564

Val Ser Trp Tyr Gln Gln His Pro Gly Lys Ala Pro Lys Leu Met Ile
1               5                   10                  15

Tyr

<210> SEQ ID NO 565
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 565

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25

<210> SEQ ID NO 566
<211> LENGTH: 8
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 566

Ser Ser Asn Ile Gly Asn Asn Tyr
1               5

<210> SEQ ID NO 567
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 567

Val Tyr Trp Tyr Gln Gln Leu Pro Gly Thr Ala Pro Lys Leu Leu Ile
1               5                   10                  15

Tyr

```
<210> SEQ ID NO 568
<211> LENGTH: 22
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 568

Pro Gln Ala Pro Val Thr Leu Ser Ala Ser Val Gly Asp Arg Ile Thr
1               5                   10                  15

Ile Thr Cys Arg Ala Ser
            20

<210> SEQ ID NO 569
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 569

Gln Ser Ile Ser Arg Tyr
1               5

<210> SEQ ID NO 570
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 570

Leu Asn Trp Tyr Gln Gln Lys Pro Gly Arg Ala Pro Asn Leu Leu Ile
1               5                   10                  15

Tyr

<210> SEQ ID NO 571
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 571

Asp Asp Pro Lys Ala Pro Ala Thr Leu Ser Leu Ser Pro Gly Asp Arg
1               5                   10                  15

Ala Thr Leu Ser Cys Arg Ala Ser
            20

<210> SEQ ID NO 572
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 572

Leu Ala Trp Tyr Gln Gln Lys Pro Gly Gln Pro Pro Arg Leu Leu Ile
1               5                   10                  15

Phe
```

-continued

<210> SEQ ID NO 573
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 573

Leu Asp Asp Pro Gln Asp Pro Val Ser Leu Ser Ala Ser Val Gly Asp
1               5                   10                  15

Lys Val Thr Ile Thr Cys Arg Ala Ser
            20                  25

<210> SEQ ID NO 574
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 574

Gln Ser Ile Ser Ser His
1               5

<210> SEQ ID NO 575
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 575

Leu Asn Trp Tyr Gln Gln Gln Pro Gly Lys Ala Pro Asn Leu Leu Ile
1               5                   10                  15

Tyr

<210> SEQ ID NO 576
<211> LENGTH: 23
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 576

Met Ile Gln Ser Pro Val Cys Leu Ala Val Ser Leu Gly Glu Arg Ala
1               5                   10                  15

Thr Ile Asn Cys Lys Ser Ser
            20

<210> SEQ ID NO 577
<211> LENGTH: 12
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 577

Gln Ser Val Ser Tyr Ser Ser Asn Asn Lys Asp His
1               5                   10

```
<210> SEQ ID NO 578
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 578

Leu Ala Trp Tyr Leu Gln Arg Ser Gly Gln Pro Pro Gln Leu Leu Ile
1               5                   10                  15

Tyr

<210> SEQ ID NO 579
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 579

Met Thr Pro Gln Ala Pro Val Thr Leu Ser Leu Ser Pro Gly Glu Arg
1               5                   10                  15

Ala Thr Leu Ser Cys Arg Ala Ser
            20

<210> SEQ ID NO 580
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 580

Gln Ser Val Asn Tyr Tyr
1               5

<210> SEQ ID NO 581
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 581

Leu Ala Trp Tyr Gln Gln Lys Pro Gly Arg Ala Pro Arg Leu Leu Ile
1               5                   10                  15

Tyr

<210> SEQ ID NO 582
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 582

Gln Ser Val Leu Thr Gln Pro Ala Ser Val Ser Gly Ser Pro Gly Gln
1               5                   10                  15

Ser Ile Thr Ile Ser Cys Ala Gly Thr
            20                  25
```

```
<210> SEQ ID NO 583
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 583

Ser Thr Asp Leu Gly Thr Tyr His Leu
1               5

<210> SEQ ID NO 584
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 584

Val Ser Trp Tyr Gln Gln His Pro Gly Lys Ala Pro Lys Leu Leu Ile
1               5                   10                  15

Tyr

<210> SEQ ID NO 585
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 585

Gln Ser Gln Leu Thr Gln Pro Glu Ser Ala Ser Gly Ser Arg Gly Gln
1               5                   10                  15

Trp Ile Thr Ile Ser Ile Thr Gly Thr
            20                  25

<210> SEQ ID NO 586
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 586

Ser Ser Asp Ser Gly Gly Tyr Ser Tyr
1               5

<210> SEQ ID NO 587
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 587

Val Ser Gly Ser Gln Gln Gln Pro Gly Lys Ala Pro Lys Leu Ile Ile
1               5                   10                  15

Phe
```

```
<210> SEQ ID NO 588
<211> LENGTH: 22
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 588

Pro Gln Ala Pro Ala Thr Leu Ser Ala Ser Val Gly Asp Arg Val Thr
1               5                   10                  15

Ile Thr Cys Arg Ala Ser
            20

<210> SEQ ID NO 589
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 589

Gln Val Ile Arg Asn Asp
1               5

<210> SEQ ID NO 590
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 590

Leu Gly Trp Tyr Gln Gln Lys Pro Gly Asn Ala Pro Lys Arg Leu Ile
1               5                   10                  15

Tyr

<210> SEQ ID NO 591
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 591

Tyr Asp Pro Lys Ala Pro Leu Thr Leu Ser Leu Ser Pro Gly Glu Arg
1               5                   10                  15

Ala Thr Leu Ser Cys Arg Ala Ser
            20

<210> SEQ ID NO 592
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 592

Gln Thr Val Ser Ser Ser Ser
1               5

<210> SEQ ID NO 593
```

```
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 593

Leu Ala Trp Tyr Gln Gln Lys Pro Gly Gln Ala Pro Arg Leu Leu Ile
1               5                   10                  15

Tyr

<210> SEQ ID NO 594
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 594

His Asp Pro Gln Ala Pro Val Thr Leu Ser Val Ser Pro Gly Glu Arg
1               5                   10                  15

Val Thr Leu Ser Cys Arg Ala Ser
            20

<210> SEQ ID NO 595
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 595

Gln Ser Val Tyr Ser Asn
1               5

<210> SEQ ID NO 596
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 596

Leu Ala Trp Tyr Gln Leu Lys Pro Gly Gln Gly Pro Arg Leu Leu Ile
1               5                   10                  15

Tyr

<210> SEQ ID NO 597
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 597

Leu Thr Pro Gln Asp Pro Val Thr Leu Ser Ala Ser Val Gly Asp Arg
1               5                   10                  15

Val Thr Ile Thr Cys Gln Ala Ser
            20
```

-continued

```
<210> SEQ ID NO 598
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 598

Gln Asp Ile Ser Asn Tyr
1               5

<210> SEQ ID NO 599
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 599

Leu Asn Trp Tyr Gln Gln Lys Pro Gly Lys Ala Pro Lys Leu Leu Ile
1               5                   10                  15

Tyr

<210> SEQ ID NO 600
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 600

Tyr Asp Pro Thr Ala Pro Val Thr Leu Ser Ala Ser Val Gly Asp Arg
1               5                   10                  15

Val Thr Ile Thr Cys Arg Ala Ser
            20

<210> SEQ ID NO 601
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 601

Leu Asn Trp Tyr Gln Gln Lys Pro Gly Lys Ala Pro Lys Leu Leu Ile
1               5                   10                  15

Tyr

<210> SEQ ID NO 602
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 602

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25
```

```
<210> SEQ ID NO 603
<211> LENGTH: 8
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 603

Ser Ser Asn Ile Gly Ser Asn Thr
1               5

<210> SEQ ID NO 604
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 604

Val Asn Trp Tyr Gln Gln Leu Pro Gly Thr Ala Pro Lys Leu Leu Ile
1               5                   10                  15

Tyr

<210> SEQ ID NO 605
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 605

Pro Ala Leu Phe Phe Ser Pro Ala Thr Leu Ser Leu Ser Ser Gly Glu
1               5                   10                  15

Arg Ala Thr Leu Ser Cys Arg Ala Ser
            20                  25

<210> SEQ ID NO 606
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 606

Gln Ser Val Ile Ser Ser Tyr
1               5

<210> SEQ ID NO 607
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 607

Leu Ala Trp Tyr Gln Gln Lys Pro Gly Gln Ala Pro Arg Leu Leu Ile
1               5                   10                  15

Tyr

<210> SEQ ID NO 608
```

```
<211> LENGTH: 22
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 608

Pro Gln Ala Pro Ala Thr Leu Ser Ala Ser Val Gly Asp Arg Val Thr
1               5                   10                  15

Ile Thr Cys Arg Ala Ser
            20

<210> SEQ ID NO 609
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 609

Gln Ser Ile Ser Ser Trp
1               5

<210> SEQ ID NO 610
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 610

Leu Ala Trp Tyr Gln Gln Lys Pro Gly Lys Ala Pro Lys Leu Leu Ile
1               5                   10                  15

Tyr

<210> SEQ ID NO 611
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 611

Cys Ser Met Thr Ser Asp Ser Ser His Pro Ala Ser Thr Gly Asp Arg
1               5                   10                  15

Val Thr Ile Thr Cys Arg Ala Ser
            20

<210> SEQ ID NO 612
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 612

Leu Ala Trp Tyr Gln Gln Lys Pro Gly Lys Ala Pro Lys Leu Leu Ile
1               5                   10                  15

Tyr
```

```
<210> SEQ ID NO 613
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 613

Gln Ser Val Leu Thr Gln Pro Pro Ser Val Ser Val Ser Pro Gly Gln
1               5                   10                  15

Thr Ala Arg Ile Thr Cys Ser Gly Asp
            20                  25

<210> SEQ ID NO 614
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 614

Ala Leu Pro Lys Gln Tyr
1               5

<210> SEQ ID NO 615
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 615

Ala Tyr Trp Tyr Gln Gln Lys Pro Gly Gln Ala Pro Val Leu Val Ile
1               5                   10                  15

Tyr

<210> SEQ ID NO 616
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 616

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25

<210> SEQ ID NO 617
<211> LENGTH: 8
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 617

Ser Ser Asn Ile Gly Ser Asn Thr
1               5

<210> SEQ ID NO 618
```

```
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 618

Val Asn Trp Tyr Gln Gln Leu Pro Gly Thr Ala Pro Lys Leu Leu Ile
1               5                   10                  15

Tyr

<210> SEQ ID NO 619
<211> LENGTH: 23
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 619

Thr Pro Gln Tyr Pro Leu Thr Leu Ser Ala Ser Val Gly Asp Arg Val
1               5                   10                  15

Thr Ile Thr Cys Gln Ala Ser
            20

<210> SEQ ID NO 620
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 620

Gln Asp Ile Ser Asn Tyr
1               5

<210> SEQ ID NO 621
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 621

Leu Asn Trp Tyr Gln Gln Lys Pro Gly Lys Ala Pro Lys Leu Leu Ile
1               5                   10                  15

Tyr

<210> SEQ ID NO 622
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 622

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25
```

<210> SEQ ID NO 623
<211> LENGTH: 8
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 623

Ser Ser Asn Ile Gly Ser Asn Thr
1               5

<210> SEQ ID NO 624
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 624

Val Asn Trp Tyr Gln Gln Leu Pro Gly Thr Ala Pro Lys Leu Leu Ile
1               5                   10                  15

Tyr

<210> SEQ ID NO 625
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 625

Gln Ser Val Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 626
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 626

Ser Ser Asp Val Gly Ser Tyr Asn Leu
1               5

<210> SEQ ID NO 627
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 627

Val Ser Trp Tyr Gln Gln His Pro Gly Lys Ala Pro Lys Leu Met Ile
1               5                   10                  15

Tyr

<210> SEQ ID NO 628
<211> LENGTH: 24

-continued

```
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 628

Tyr Glu Pro Pro Ile Pro Val Thr Leu Ala Val Ser Leu Gly Glu Arg
1               5                   10                  15

Ala Thr Ile Asn Cys Lys Ser Ser
            20

<210> SEQ ID NO 629
<211> LENGTH: 12
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 629

Gln Ser Val Leu Tyr Ser Ser Asn Asn Lys Asn Tyr
1               5                   10

<210> SEQ ID NO 630
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 630

Leu Ala Trp Tyr Gln Gln Lys Pro Gly Gln Pro Pro Lys Leu Leu Ile
1               5                   10                  15

Tyr

<210> SEQ ID NO 631
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 631

Tyr Asp Pro Pro Ala Pro Val Thr Leu Ser Leu Ser Pro Gly Glu Arg
1               5                   10                  15

Ala Thr Leu Ser Cys Arg Ala Ser
            20

<210> SEQ ID NO 632
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 632

Leu Ala Trp Tyr Gln Gln Lys Pro Gly Gln Ala Pro Arg Leu Leu Ile
1               5                   10                  15

Tyr

<210> SEQ ID NO 633
```

```
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 633

Gln Ser Val Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 634
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 634

Ser Ser Asp Val Gly Ser Tyr Asn Leu
1               5

<210> SEQ ID NO 635
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 635

Val Ser Trp Tyr Gln Gln His Pro Gly Lys Ala Pro Lys Leu Met Ile
1               5                   10                  15

Tyr

<210> SEQ ID NO 636
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 636

Ile Glu Pro Thr Ala Pro Val Thr Leu Ser Leu Ser Pro Gly Glu Arg
1               5                   10                  15

Ala Thr Leu Ser Cys Arg Ala Ser
            20

<210> SEQ ID NO 637
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 637

Leu Ala Trp Tyr Gln Gln Lys Pro Gly Gln Ala Pro Arg Leu Leu Ile
1               5                   10                  15

Tyr
```

```
<210> SEQ ID NO 638
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 638

His Asp Pro Gln Ala Pro Phe Thr Leu Ser Leu Ser Pro Gly Glu Arg
1               5                   10                  15

Ala Thr Met Ser Cys Arg Ala Ser
            20

<210> SEQ ID NO 639
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 639

Leu Ser Val Ser Ser Asn Tyr
1               5

<210> SEQ ID NO 640
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 640

Leu Ala Trp Tyr Gln Gln Lys Pro Gly Gln Ala Pro Arg Leu Leu Ile
1               5                   10                  15

Tyr

<210> SEQ ID NO 641
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 641

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25

<210> SEQ ID NO 642
<211> LENGTH: 8
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 642

Arg Ser Asn Ile Gly Ser Asn Thr
1               5

<210> SEQ ID NO 643
```

```
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 643

Val Asn Trp Tyr Arg Gln Leu Pro Gly Thr Ala Pro Lys Leu Leu Ile
1               5                   10                  15
Tyr

<210> SEQ ID NO 644
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 644

Gln Ser Val Leu Thr Gln Pro His Ser Val Ser Gly Ser Pro Gly Lys
1               5                   10                  15
Thr Val Thr Ile Ser Cys Thr Arg Ser
            20                  25

<210> SEQ ID NO 645
<211> LENGTH: 8
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 645

Ser Gly Ser Ile Ala Ser Ser Tyr
1               5

<210> SEQ ID NO 646
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 646

Val Gln Trp Tyr Gln Gln Arg Pro Gly Ser Ser Pro Thr Thr Val Ile
1               5                   10                  15
Tyr

<210> SEQ ID NO 647
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 647

Ser Cys Ser Ile Phe Gln Thr Pro Ala Thr Leu Ser Leu Ser Pro Gly
1               5                   10                  15
Glu Arg Asp Thr Leu Ser Cys Arg Ala Ser
            20                  25
```

```
<210> SEQ ID NO 648
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 648

Gln Ser Val Ser Ser Asn Tyr
1               5

<210> SEQ ID NO 649
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 649

Leu Ser Trp Tyr Gln Gln Lys Pro Gly Gln Ala Pro Arg Leu Leu Ile
1               5                   10                  15

Tyr

<210> SEQ ID NO 650
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 650

Gln Ser Val Leu Thr Gln Pro Ala Ser Val Ser Gly Ser Pro Gly Gln
1               5                   10                  15

Ser Ile Thr Ile Ser Cys Thr Gly Ser
            20                  25

<210> SEQ ID NO 651
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 651

Ser Ser Asp Val Gly Gly Tyr Asp Tyr
1               5

<210> SEQ ID NO 652
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 652

Val Ser Trp Tyr Gln Gln His Pro Gly Lys Ala Pro Lys Leu Met Ile
1               5                   10                  15

Phe

<210> SEQ ID NO 653
<211> LENGTH: 25
```

```
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 653

Gln Ser Val Leu Thr Gln Pro Pro Ser Lys Ser Gly Thr Pro Gly Gln
1               5                   10                  15

Arg Val Thr Ile Ser Cys Tyr Gly Ser
            20                  25

<210> SEQ ID NO 654
<211> LENGTH: 8
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 654

Arg Ser Asn Ile Gly Ser Thr Thr
1               5

<210> SEQ ID NO 655
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 655

Val Asn Trp Phe Gln Gln Leu Pro Glu Ser Ala Pro Lys Leu Leu Ile
1               5                   10                  15

His

<210> SEQ ID NO 656
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 656

Pro Ala Ser Pro Lys Ser Pro Val Thr Leu Ser Leu Ser Pro Gly Glu
1               5                   10                  15

Arg Ala Thr Leu Ser Cys Arg Ala Ser
            20                  25

<210> SEQ ID NO 657
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 657

Gln Ser Val Gly Asn Ser Phe
1               5

<210> SEQ ID NO 658
<211> LENGTH: 17
<212> TYPE: PRT
```

```
<213> ORGANISM: Artificial Sequence
<220> FEATURE:
<221> NAME/KEY: source
<223> OTHER INFORMATION: /note="VL FR2 sequence"

<400> SEQUENCE: 658

Leu Ala Trp Tyr Gln Gln Lys Pro Gly Gln Thr Pro Arg Leu Leu Ile
1               5                   10                  15

Tyr

<210> SEQ ID NO 659
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 659

Gln Ser Val Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 660
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 660

Ser Gly Asp Val Glu Asn Tyr Asn Val
1               5

<210> SEQ ID NO 661
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 661

Val Ser Trp Tyr Gln Gln His Pro Gly Lys Ala Pro Lys Leu Ile Ile
1               5                   10                  15

Tyr

<210> SEQ ID NO 662
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 662

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35
```

```
<210> SEQ ID NO 663
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 663

Gln Gln Ser Tyr Ser Thr Pro Tyr Thr
1               5

<210> SEQ ID NO 664
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 664

Thr Leu Glu Ser Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Thr Tyr Tyr Cys
        35

<210> SEQ ID NO 665
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 665

Gln Gln Tyr Asn Ser Tyr Ser Trp Thr
1               5

<210> SEQ ID NO 666
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 666

Glu Arg Pro Ser Gly Ile Pro Glu Arg Phe Ser Gly Ser Asn Ser Gly
1               5                   10                  15

Asn Thr Ala Thr Leu Thr Ile Ser Arg Val Glu Ala Gly Asp Glu Ala
            20                  25                  30

Asp Tyr His Cys
        35

<210> SEQ ID NO 667
<211> LENGTH: 12
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 667
```

Gln Val Trp Asp Ser Ser Ser Asp His Pro Gly Val
1               5                   10

<210> SEQ ID NO 668
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 668

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Cys Ala
                20                  25                  30

Val Tyr Tyr Cys
            35

<210> SEQ ID NO 669
<211> LENGTH: 8
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 669

Gln Gln Tyr Gly Ser Ser His Thr
1               5

<210> SEQ ID NO 670
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 670

Thr Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
                20                  25                  30

Thr Tyr Tyr Cys
            35

<210> SEQ ID NO 671
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 671

Gln Gln Leu Asn Ser Tyr Pro Leu Thr
1               5

<210> SEQ ID NO 672
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

```
<400> SEQUENCE: 672

Thr Arg Thr Thr Gly Ile Pro Ala Arg Phe Ser Gly Ser Gly Ser Gly
1               5                   10                  15

Thr Glu Phe Thr Leu Thr Ile Thr Ser Leu Gln Ser Glu Asp Phe Ala
            20                  25                  30

Val Tyr Tyr Cys
        35

<210> SEQ ID NO 673
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 673

Gln Gln Tyr Asn Asn Trp Pro Gln Ser Thr
1               5                   10

<210> SEQ ID NO 674
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 674

Asn Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 675
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 675

Gln Ser Tyr Asp Ser Ser Leu Ser Gly Ser Val
1               5                   10

<210> SEQ ID NO 676
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 676

Asp Arg Pro Ser Gly Ile Pro Glu Arg Phe Ser Gly Ser Asn Ser Gly
1               5                   10                  15

Asn Thr Ala Thr Leu Thr Ile Ser Arg Val Glu Ala Gly Asp Glu Ala
            20                  25                  30

Asp Tyr Phe Cys
        35
```

```
<210> SEQ ID NO 677
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 677

Gln Val Trp Asp Ser Ser Phe Asp Arg Pro Asp
1               5                   10

<210> SEQ ID NO 678
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 678

Asn Leu Glu Thr Gly Val Pro Ser Arg Phe Ser Gly Ser Gly Ser Gly
1               5                   10                  15

Thr Asp Phe Thr Phe Thr Ile Ser Ser Leu Gln Pro Glu Asp Thr Ala
            20                  25                  30

Thr Tyr Tyr Cys
        35

<210> SEQ ID NO 679
<211> LENGTH: 8
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 679

Gln Gln Tyr Ala Asn Val Phe Thr
1               5

<210> SEQ ID NO 680
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 680

Thr Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35

<210> SEQ ID NO 681
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 681
```

Gln Gln Tyr Tyr Ser Asn Pro Tyr Thr
1               5

<210> SEQ ID NO 682
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 682

Ser Arg Ala Thr Gly Ile Pro Asp Arg Ile Ser Gly Ser Gly Ser Gly
1               5                   10                  15

Thr Asp Phe Thr Leu Thr Ile Ser Arg Leu Glu Pro Glu Asp Phe Val
            20                  25                  30

Val Tyr Tyr Cys
        35

<210> SEQ ID NO 683
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 683

Gln Gln Tyr Gly Ser Ser Pro Trp Thr
1               5

<210> SEQ ID NO 684
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 684

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Val Tyr Tyr Cys
        35

<210> SEQ ID NO 685
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 685

Gln Gln Arg Ser Asn Trp Pro Gly Thr
1               5

<210> SEQ ID NO 686
<211> LENGTH: 36
<212> TYPE: PRT
<213> ORGANISM: Artificial Sequence
<220> FEATURE:
<221> NAME/KEY: source -continued
<223> OTHER INFORMATION: /note="VL FR3 sequence"

<400> SEQUENCE: 686

Lys Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 687
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 687

Cys Ser Tyr Ala Gly Ser Ser Thr Leu Tyr Val
1               5                   10

<210> SEQ ID NO 688
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 688

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Val Tyr Tyr Cys
        35

<210> SEQ ID NO 689
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 689

Gln Gln Arg Ser Asn Trp Pro Pro Thr
1               5

<210> SEQ ID NO 690
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 690

Thr Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys

<210> SEQ ID NO 691
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 691

Gln Gln Leu Asn Ser Tyr Pro Leu Thr
1               5

<210> SEQ ID NO 692
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 692

Asn Arg Pro Ser Gly Val Ser Asp Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asn Tyr Tyr Cys
        35

<210> SEQ ID NO 693
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 693

Ser Ser Tyr Thr Ser Ser Ser Thr Trp Val
1               5                   10

<210> SEQ ID NO 694
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 694

Asp Arg Pro Ser Gly Ile Pro Glu Arg Phe Ser Gly Ser Asn Ser Gly
1               5                   10                  15

Asn Thr Ala Thr Leu Thr Ile Ser Arg Val Glu Ala Gly Asp Glu Ala
            20                  25                  30

Asp Tyr Tyr Cys
        35

<210> SEQ ID NO 695
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

```
<400> SEQUENCE: 695

Gln Val Trp Asp Ser Ser Asp His Tyr Val
1               5                   10

<210> SEQ ID NO 696
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 696

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
            35

<210> SEQ ID NO 697
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 697

Gln Gln Ser Tyr Ser Thr Pro Tyr Thr
1               5

<210> SEQ ID NO 698
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 698

Thr Arg Ala Thr Gly Ile Pro Ala Arg Phe Ser Gly Ser Gly Ser Gly
1               5                   10                  15

Thr Glu Phe Thr Leu Thr Ile Ser Ser Leu Gln Ser Glu Asp Phe Ala
            20                  25                  30

Val Tyr Tyr Cys
            35

<210> SEQ ID NO 699
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 699

Gln Gln Tyr Asn Asn Trp Pro Leu Trp Thr
1               5                   10

<210> SEQ ID NO 700
<211> LENGTH: 36
<212> TYPE: PRT
<213> ORGANISM: Artificial Sequence
<220> FEATURE:
```

```
<221> NAME/KEY: source
<223> OTHER INFORMATION: /note="VL FR3 sequence"

<400> SEQUENCE: 700

Ser Arg Ser Thr Gly Val Thr Asp Arg Phe Ser Gly Ser Gly Ser Gly
1               5                   10                  15

Thr Asp Phe Thr Leu Thr Ile Ser Arg Leu Glu Ser Glu Asp Phe Ala
            20                  25                  30

Val Tyr Phe Cys
        35

<210> SEQ ID NO 701
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 701

Gln His Tyr Glu Ser Ser Pro Pro Val Phe Thr
1               5                   10

<210> SEQ ID NO 702
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 702

Asn Lys Gly Asp Gly Ile Pro Asp Arg Phe Ser Gly Ser Ser Ser Gly
1               5                   10                  15

Ala Glu Arg Tyr Leu Thr Ile Ser Ser Leu Gln Ser Asp Asp Glu Ala
            20                  25                  30

Asp Tyr Tyr Cys
        35

<210> SEQ ID NO 703
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 703

Gln Thr Trp Asp Thr Gly Ile Gln Val
1               5

<210> SEQ ID NO 704
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 704

Lys Arg Pro Ser Gly Val Pro Asp Arg Phe Ser Gly Ser Lys Ser Gly
1               5                   10                  15

Asn Thr Ala Ser Leu Thr Val Ser Gly Leu Gln Ala Glu Asp Glu Ala
            20                  25                  30
```

```
Asp Tyr Tyr Cys
        35

<210> SEQ ID NO 705
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 705

Ser Ser Tyr Ala Gly Ser Asn Asn Tyr Val
1               5                   10

<210> SEQ ID NO 706
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 706

Asn Lys Gly Asp Gly Ile Pro Asp Arg Phe Ser Gly Ser Ser Ser Gly
1               5                   10                  15

Ala Glu Arg Tyr Leu Thr Ile Ser Ser Leu Gln Ser Asp Asp Glu Ala
            20                  25                  30

Asp Tyr Tyr Cys
        35

<210> SEQ ID NO 707
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 707

Gln Thr Trp Asp Thr Gly Ile Gln Val
1               5

<210> SEQ ID NO 708
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 708

Asn Arg Pro Ser Gly Val Ser His Arg Phe Ser Gly Ser Lys Ser Gly
1               5                   10                  15

Asn Arg Ala Ser Leu Thr Ile Ser Gly Leu Gln Ala Glu Asp Glu Ala
            20                  25                  30

Asp Tyr Tyr Cys
        35

<210> SEQ ID NO 709
<211> LENGTH: 12
<212> TYPE: PRT
<213> ORGANISM: Artificial Sequence
<220> FEATURE:
<221> NAME/KEY: source
<223> OTHER INFORMATION: /note="VL CDR3 sequence"
```

```
<400> SEQUENCE: 709

Ser Ser Tyr Thr Ser Ser Ser Leu Leu Tyr Val
1               5                   10

<210> SEQ ID NO 710
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 710

Lys Arg Pro Ser Gly Val Pro Asp Arg Phe Ser Gly Ser Lys Ser Asp
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 711
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 711

Cys Ser Tyr Val Gly Ser Tyr Thr Val Ala
1               5                   10

<210> SEQ ID NO 712
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 712

Gln Arg Pro Ser Gly Val Ser Asn Arg Phe Ser Gly Ser Lys Ser Gly
1               5                   10                  15

Asn Thr Ala Ser Leu Thr Ile Ser Gly Leu Gln Thr Glu Asp Glu Ala
            20                  25                  30

His Tyr Tyr Cys
        35

<210> SEQ ID NO 713
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 713

Cys Ser Tyr Ala Ala Gly Asn Thr Arg Val
1               5                   10

<210> SEQ ID NO 714
<211> LENGTH: 36
<212> TYPE: PRT
<213> ORGANISM: Artificial Sequence
```

```
<220> FEATURE:
<221> NAME/KEY: source
<223> OTHER INFORMATION: /note="VL FR3 sequence"

<400> SEQUENCE: 714

Thr Arg Ala Thr Gly Ile Pro Ala Arg Phe Ser Gly Ser Gly Ser Gly
1               5                   10                  15

Thr Glu Phe Thr Leu Thr Ile Ser Ser Leu Gln Ser Glu Asp Phe Ala
                20                  25                  30

Val Tyr Tyr Cys
            35

<210> SEQ ID NO 715
<211> LENGTH: 8
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 715

Gln Gln Tyr Asn Asn Leu Tyr Thr
1               5

<210> SEQ ID NO 716
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 716

Asn Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
                20                  25                  30

Asp Tyr Tyr Cys
            35

<210> SEQ ID NO 717
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 717

Ser Ser Tyr Thr Ser Ser Ser Thr Val Val
1               5                   10

<210> SEQ ID NO 718
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 718

Gln Arg Pro Ser Gly Ile Pro Asp Arg Phe Ser Gly Ser Lys Ser Gly
1               5                   10                  15

Thr Ser Ala Thr Leu Gly Ile Thr Gly Leu Gln Thr Gly Asp Glu Ala
                20                  25                  30
```

Asp Tyr Tyr Cys
        35

<210> SEQ ID NO 719
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 719

Gly Thr Trp Asp Ser Ser Leu Ser Ala Val Val
1               5                   10

<210> SEQ ID NO 720
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 720

Asn Arg Ala Thr Gly Ile Pro Ala Arg Phe Ser Gly Ser Gly Ser Gly
1               5                   10                  15

Thr Asp Phe Thr Leu Thr Ile Thr Asn Leu Glu Pro Glu Asp Phe Ala
            20                  25                  30

Val Tyr Tyr Cys
        35

<210> SEQ ID NO 721
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 721

Gln Gln Arg Ser Asn Trp Pro Pro Thr
1               5

<210> SEQ ID NO 722
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 722

Asn Arg Pro Ser Arg Ile Pro Glu Arg Phe Ser Gly Ser Thr Ser Gly
1               5                   10                  15

Asn Thr Ala Thr Leu Thr Ile Arg Thr Ala Gln Ala Gly Asp Glu Ala
            20                  25                  30

Asp Tyr Tyr Cys
        35

<210> SEQ ID NO 723
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 723

Gln Val Trp Asp Ile Ser Ser Val Val
1               5

<210> SEQ ID NO 724
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 724

Asn Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 725
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 725

Ser Ser Tyr Thr Ser Ser Ser Thr Leu Val
1               5                   10

<210> SEQ ID NO 726
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 726

Gln Arg Pro Ser Gly Ile Pro Asp Arg Phe Ser Gly Ser Lys Ser Gly
1               5                   10                  15

Thr Ser Ala Ser Leu Ala Ile Ser Gly Leu Arg Ser Glu Asp Glu Ala
            20                  25                  30

Asp Tyr Tyr Cys
        35

<210> SEQ ID NO 727
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 727

Ala Ala Trp Asp Asp Ser Leu Ser Gly Trp Val
1               5                   10

<210> SEQ ID NO 728
<211> LENGTH: 36
<212> TYPE: PRT

```
<213> ORGANISM: Artificial Sequence
<220> FEATURE:
<221> NAME/KEY: source
<223> OTHER INFORMATION: /note="VL FR3 sequence"

<400> SEQUENCE: 728

Ala Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 729
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 729

Gln Gln Ser Ser Thr Thr Pro Leu Thr
1               5

<210> SEQ ID NO 730
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 730

Thr Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

His Tyr Tyr Cys
        35

<210> SEQ ID NO 731
<211> LENGTH: 8
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 731

Gln Leu Arg Ser Asn Trp Arg Thr
1               5

<210> SEQ ID NO 732
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 732

Thr Leu Gln Tyr Gly Val Pro Ser Arg Phe Ser Gly Ser Gly Ser Gly
1               5                   10                  15

Thr Asp Phe Ile Leu Thr Ile Ser Asn Leu Gln Pro Glu Asp Phe Ala
```

```
                    20                  25                  30

Thr Tyr Tyr Cys
        35

<210> SEQ ID NO 733
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 733

Gln Gln Ser Phe Ser Met Pro Phe Thr
1               5

<210> SEQ ID NO 734
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 734

Thr Arg Lys Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
                20                  25                  30

Val Tyr Tyr Cys
        35

<210> SEQ ID NO 735
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 735

Gln Gln Tyr Tyr Ile Thr Pro Pro Thr
1               5

<210> SEQ ID NO 736
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 736

Asn Arg Ala Thr Gly Val Pro Ala Arg Phe Ser Gly Arg Gly Ser Gly
1               5                   10                  15

Thr Asp Phe Thr Leu Thr Ile Ser Ser Leu Glu Pro Glu Asp Phe Ala
                20                  25                  30

Val Tyr Tyr Cys
        35

<210> SEQ ID NO 737
<211> LENGTH: 9
<212> TYPE: PRT
<213> ORGANISM: Artificial Sequence
<220> FEATURE:
```

```
<221> NAME/KEY: source
<223> OTHER INFORMATION: /note="VL CDR3 sequence"

<400> SEQUENCE: 737

Gln Leu Arg Ser Asn Trp Leu Leu Thr
1               5

<210> SEQ ID NO 738
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 738

Arg Arg Pro Ser Gly Ile Ser Asp Arg Phe Ser Gly Ser Lys Ser Gly
1               5                   10                  15

Asp Thr Ala Ala Leu Thr Ile Ser Gly Leu Gln Ala Glu Asp Glu Ala
            20                  25                  30

Asp Tyr Tyr Cys
        35

<210> SEQ ID NO 739
<211> LENGTH: 8
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 739

Cys Ser Tyr Ala Gly Thr Trp Val
1               5

<210> SEQ ID NO 740
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 740

Ile Arg Pro Ser Gly Ala Trp Asp Cys Phe Cys Gly Ser Lys Ser Asp
1               5                   10                  15

Tyr Thr Ala Ser Ala Thr Met Ser Arg Phe Gln Ala Gln Asp Glu Ala
            20                  25                  30

Glu Tyr Asp Cys
        35

<210> SEQ ID NO 741
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 741

Asn Ser Ile Ser Ser Thr Ser Thr Asn Asn Val
1               5                   10

<210> SEQ ID NO 742
<211> LENGTH: 36
```

```
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 742

Ile Leu Gln Ser Gly Val Pro Ser Arg Phe Ser Gly Ser Gly Phe Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 743
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 743

Leu Gln His Asn Ser Phe Pro Trp Thr
1               5

<210> SEQ ID NO 744
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 744

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Ser Ala
            20                  25                  30

Val Tyr His Cys
        35

<210> SEQ ID NO 745
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 745

Gln Gln Tyr Gly Ser Ser Pro Gly Thr
1               5

<210> SEQ ID NO 746
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 746

Thr Arg Ala Thr Gly Ile Pro Val Arg Phe Ser Gly Ser Gly Ser Gly
1               5                   10                  15
```

Thr Glu Phe Thr Leu Ser Ile Ser Ser Leu Gln Ser Glu Asp Phe Ala
            20                  25                  30

Val Tyr Leu Cys
        35

<210> SEQ ID NO 747
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 747

Gln Gln Tyr Tyr Asn Trp Pro Pro Ile Thr
1               5                   10

<210> SEQ ID NO 748
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 748

Asn Leu Glu Thr Gly Val Pro Ser Arg Phe Ser Gly Ser Gly Ser Gly
1               5                   10                  15

Thr Asp Phe Thr Phe Thr Ile Ser Ser Leu Gln Pro Glu Asp Ile Ala
            20                  25                  30

Thr Tyr Tyr Cys
        35

<210> SEQ ID NO 749
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 749

Gln Gln Tyr Asp Asn Leu Pro Tyr Thr
1               5

<210> SEQ ID NO 750
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 750

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 751
<211> LENGTH: 11
<212> TYPE: PRT
<213> ORGANISM: Artificial Sequence

```
<220> FEATURE:
<221> NAME/KEY: source
<223> OTHER INFORMATION: /note="VL CDR3 sequence"

<400> SEQUENCE: 751

Gln Gln Ser Tyr Ser Thr Pro Pro Leu Ser Thr
1               5                   10

<210> SEQ ID NO 752
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 752

Gln Arg Pro Ser Gly Val Pro Asp Arg Phe Ser Gly Ser Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 753
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 753

Ala Ala Trp Asp Asp Ser Leu Asn Gly Val Val
1               5                   10

<210> SEQ ID NO 754
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 754

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr Cys
        35

<210> SEQ ID NO 755
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 755

Gln Gln His Gly Ser Ser Pro Tyr Thr
1               5

<210> SEQ ID NO 756
```

```
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 756

Ser Leu Glu Ser Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Thr Tyr Tyr Cys
            35

<210> SEQ ID NO 757
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 757

Gln Gln Tyr Asn Ser Tyr Pro Trp Thr
1               5

<210> SEQ ID NO 758
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 758

Thr Leu Gln Ser Gly Val Pro Ser Arg Phe Ser Gly Ser Gly Ser Gly
1               5                   10                  15

Thr Asp Phe Thr Leu Thr Ile Ser Cys Leu Gln Ser Glu Asp Phe Ala
            20                  25                  30

Thr Tyr Tyr Cys
            35

<210> SEQ ID NO 759
<211> LENGTH: 8
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 759

Gln Gln Tyr Tyr Ser Tyr Pro Thr
1               5

<210> SEQ ID NO 760
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 760

Glu Arg Pro Ser Gly Ile Pro Glu Arg Phe Ser Gly Ser Ser Ser Gly
1               5                   10                  15
```

```
Thr Thr Val Thr Leu Thr Ile Ser Gly Val Gln Ala Glu Asp Glu Ala
            20                  25                  30

Asp Tyr Tyr Cys
        35

<210> SEQ ID NO 761
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 761

Gln Ser Ala Asp Ser Ser Gly Leu Val
1               5

<210> SEQ ID NO 762
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 762

Gln Arg Pro Ser Gly Val Pro Asp Arg Phe Ser Gly Ser Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 763
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 763

Ala Ala Trp Asp Asp Ser Leu Asn Gly Trp Val
1               5                   10

<210> SEQ ID NO 764
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 764

Asn Leu Glu Thr Gly Val Pro Ser Arg Phe Ser Gly Ser Gly Ser Gly
1               5                   10                  15

Thr Asp Phe Thr Phe Thr Ile Ser Ser Leu Gln Pro Glu Asp Ile Ala
            20                  25                  30

Thr Tyr Tyr Cys
        35

<210> SEQ ID NO 765
<211> LENGTH: 9
<212> TYPE: PRT
```

```
<213> ORGANISM: Artificial Sequence
<220> FEATURE:
<221> NAME/KEY: source
<223> OTHER INFORMATION: /note="VL CDR3 sequence"

<400> SEQUENCE: 765

Gln Gln Tyr Asp Asn Leu Pro Leu Thr
1               5

<210> SEQ ID NO 766
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 766

Gln Arg Pro Ser Gly Val Pro Asp Arg Phe Ser Gly Ser Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 767
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 767

Ala Ala Trp Asp Asp Ser Leu Asn Gly Pro Val
1               5                   10

<210> SEQ ID NO 768
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 768

Lys Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 769
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 769

Cys Ser Tyr Ala Gly Ser Ser Thr Leu
1               5
```

```
<210> SEQ ID NO 770
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 770

Thr Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35

<210> SEQ ID NO 771
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 771

Gln Gln Tyr Tyr Ser Thr Pro Leu Thr
1               5

<210> SEQ ID NO 772
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 772

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr Cys
        35

<210> SEQ ID NO 773
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 773

Gln Gln Tyr Gly Ser Ser Pro Pro Tyr Thr
1               5                   10

<210> SEQ ID NO 774
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 774

Lys Arg Pro Ser Gly Val Ser Asn Arg Phe Ser Gly Ser Lys Ser Gly
```

```
              1               5                  10                  15
Asn Thr Ala Ser Leu Thr Ile Ser Gly Leu Gln Ala Glu Asp Glu Ala
              20                  25                  30

Asp Tyr Tyr Cys
        35

<210> SEQ ID NO 775
<211> LENGTH: 8
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 775

Cys Ser Tyr Ala Gly Ser Pro Val
1               5

<210> SEQ ID NO 776
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 776

Ser Arg Ala Thr Gly Ile Pro Asp Arg Phe Ser Gly Ser Gly Ser Gly
1               5                  10                  15

Thr Asp Phe Thr Leu Thr Ile Ser Arg Leu Glu Pro Glu Asp Phe Ala
              20                  25                  30

Val Tyr Tyr Cys
        35

<210> SEQ ID NO 777
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 777

Gln Gln Tyr Gly Ser Ser Pro Leu Thr
1               5

<210> SEQ ID NO 778
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 778

Ser Arg Ala Thr Gly Ile Pro Asp Arg Phe Ser Gly Gly Gly Ser Gly
1               5                  10                  15

Thr Asp Tyr Thr Leu Thr Ile Ser Arg Leu Glu Pro Glu Asp Phe Ala
              20                  25                  30

Val Tyr Tyr Cys
        35

<210> SEQ ID NO 779
<211> LENGTH: 10
```

```
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 779

Gln Gln Tyr Gly Ser Ser Pro Val Tyr Ser
1               5                   10

<210> SEQ ID NO 780
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 780

Gln Arg Pro Ser Gly Val Pro Asp Arg Phe Ser Ala Ser Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 781
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 781

Ser Ala Trp Asp Asn Ser Leu Asn Gly Tyr Phe
1               5                   10

<210> SEQ ID NO 782
<211> LENGTH: 38
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 782

Gln Arg Pro Ser Gly Val Pro Asp Arg Phe Ser Gly Ser Ile Asp Ser
1               5                   10                  15

Ser Ser Asn Ser Ala Ser Leu Thr Ile Thr Gly Leu Lys Thr Glu Asp
            20                  25                  30

Glu Ala Asp Tyr Tyr Cys
        35

<210> SEQ ID NO 783
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 783

Trp Ser Tyr Asp Asn Tyr Gln Glu Ile
1               5
```

<210> SEQ ID NO 784
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 784

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr Cys
        35

<210> SEQ ID NO 785
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 785

Gln Gln Tyr Gly Thr Ser Pro Trp Thr
1               5

<210> SEQ ID NO 786
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 786

Asn Arg Pro Ser Gly Val Ser Asn Arg Phe Ile Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 787
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 787

Ser Ser Tyr Thr Thr Ser Ser Asp Leu Val
1               5                   10

<210> SEQ ID NO 788
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 788

Gln Arg Pro Ser Gly Val Pro Asp Arg Phe Ser Gly Ser Lys Ser Asp
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 789
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 789

Ala Ala Trp Asp Ala Ser Leu Lys Val
1               5

<210> SEQ ID NO 790
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 790

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Arg Glu Asp Phe Ala
            20                  25                  30

Val Tyr Tyr Cys
        35

<210> SEQ ID NO 791
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 791

Gln Gln Tyr Gly Ser Ser Pro Gly Thr
1               5

<210> SEQ ID NO 792
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 792

Lys Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 793

```
<211> LENGTH: 11
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 793

Cys Ser Ser Ala Ser Phe Thr Ile Ser Trp Val
1               5                   10

<210> SEQ ID NO 794
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 794

Cys Cys Ser Met Thr Gln Ser Pro Ala Thr Leu Ser Ala Ser Val Gly
1               5                   10                  15

Asp Arg Val Thr Ile Ser Cys Gln Ala Asn
            20                  25

<210> SEQ ID NO 795
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 795

Gln Asp Ile Lys Lys Ser
1               5

<210> SEQ ID NO 796
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 796

Phe Asn Trp Tyr His Gln Lys Pro Gly Arg Ala Pro Lys Val Leu Ile
1               5                   10                  15

Tyr

<210> SEQ ID NO 797
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 797

Ser Cys Ser Met Thr Gln Ser Pro Val Thr Leu Ser Ala Ser Val Gly
1               5                   10                  15

Asp Arg Val Thr Ile Thr Cys Arg Ala Ser
            20                  25

<210> SEQ ID NO 798
<211> LENGTH: 6
```

```
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 798

Gln Thr Ile Tyr Ser Trp
1               5

<210> SEQ ID NO 799
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 799

Leu Ala Trp Tyr Gln Gln Lys Pro Gly Lys Ala Pro Lys Leu Leu Ile
1               5                   10                  15

Tyr

<210> SEQ ID NO 800
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 800

Ser Tyr Glu Leu Thr Gln Pro Leu Ser Val Ser Val Ala Leu Gly Gln
1               5                   10                  15

Thr Ala Arg Ile Thr Cys Gly Gly Asn
            20                  25

<210> SEQ ID NO 801
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 801

Asn Ile Gly Ser Lys Asn
1               5

<210> SEQ ID NO 802
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 802

Val His Trp Tyr Gln Gln Lys Pro Gly Gln Ala Pro Val Leu Val Ile
1               5                   10                  15

Tyr

<210> SEQ ID NO 803
<211> LENGTH: 26
<212> TYPE: PRT
<213> ORGANISM: Artificial Sequence
```

```
<220> FEATURE:
<221> NAME/KEY: source
<223> OTHER INFORMATION: /note="VL FR1 sequence"

<400> SEQUENCE: 803

Cys Arg Ala Met Thr Gln Ser Pro Val Thr Leu Ser Val Ser Pro Gly
1               5                   10                  15

Glu Arg Ala Thr Leu Ser Cys Arg Ala Ser
            20                  25

<210> SEQ ID NO 804
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 804

Gln Arg Val Ser Ser Asn
1               5

<210> SEQ ID NO 805
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 805

Leu Ala Trp Tyr Gln Gln Lys Pro Gly Gln Ala Pro Arg Leu Leu Ile
1               5                   10                  15

Tyr

<210> SEQ ID NO 806
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 806

Cys Cys Ser Met Thr Gln Thr Pro Ala Thr Leu Ser Ala Ser Val Gly
1               5                   10                  15

Asp Arg Val Thr Ile Thr Cys Arg Ala Ser
            20                  25

<210> SEQ ID NO 807
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 807

Gln Ser Ile Ser Ser Trp
1               5

<210> SEQ ID NO 808
<211> LENGTH: 17
<212> TYPE: PRT
<213> ORGANISM: Artificial Sequence
<220> FEATURE:
```

```
<221> NAME/KEY: source
<223> OTHER INFORMATION: /note="VL FR2 sequence"

<400> SEQUENCE: 808

Leu Ala Trp Tyr Gln Gln Lys Pro Gly Lys Ala Pro Lys Leu Leu Ile
1               5                   10                  15
Tyr

<210> SEQ ID NO 809
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 809

Val Trp Ser Met Thr Gln Thr Pro Gly Thr Leu Ser Ala Ser Val Gly
1               5                   10                  15
Asp Arg Val Thr Ile Thr Cys Arg Ala Ser
            20                  25

<210> SEQ ID NO 810
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 810

Gln Gly Ile Ser Asn Tyr
1               5

<210> SEQ ID NO 811
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 811

Leu Ala Trp Phe Gln Gln Lys Pro Gly Lys Ala Pro Lys Ser Leu Ile
1               5                   10                  15
Tyr

<210> SEQ ID NO 812
<211> LENGTH: 24
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 812

Ala Met Thr Gln Ser Pro Val Thr Leu Ser Ala Ser Val Gly Asp Arg
1               5                   10                  15
Val Thr Ile Thr Cys Arg Ala Ser
            20

<210> SEQ ID NO 813
<211> LENGTH: 6
<212> TYPE: PRT
<213> ORGANISM: Artificial Sequence
```

```
<220> FEATURE:
<221> NAME/KEY: source
<223> OTHER INFORMATION: /note="VL CDR1 sequence"

<400> SEQUENCE: 813

Gln Phe Ile Ser Ser Ala
1               5

<210> SEQ ID NO 814
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 814

Leu Ala Trp Tyr Gln Gln Lys Pro Gly Lys Ala Pro Lys Leu Leu Ile
1               5                   10                  15

Tyr

<210> SEQ ID NO 815
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 815

Val Cys Ser Met Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 816
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 816

Gln Ser Val Ser Thr Ser Tyr
1               5

<210> SEQ ID NO 817
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 817

Leu Ala Trp Tyr Gln Gln Lys Pro Gly Gln Ala Pro Arg Leu Leu Met
1               5                   10                  15

Tyr

<210> SEQ ID NO 818
<211> LENGTH: 26
<212> TYPE: PRT
<213> ORGANISM: Artificial Sequence
<220> FEATURE:
<221> NAME/KEY: source
```

<223> OTHER INFORMATION: /note="VL FR1 sequence"

<400> SEQUENCE: 818

Ser Trp Ser Met Thr Gln Ser Pro Ala Thr Leu Ser Leu Ser Ala Gly
1               5                   10                  15

Glu Arg Ala Thr Leu Ser Cys Arg Ala Ser
            20                  25

<210> SEQ ID NO 819
<211> LENGTH: 6
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 819

Gln Ser Val Thr Thr Phe
1               5

<210> SEQ ID NO 820
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 820

Leu Ala Trp Tyr Gln Gln Lys Pro Gly Gln Ala Pro Arg Leu Leu Ile
1               5                   10                  15

Tyr

<210> SEQ ID NO 821
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 821

Val Cys Ser Met Thr Gln Thr Pro Gly Thr Leu Ser Leu Ser Pro Gly
1               5                   10                  15

Glu Arg Ala Thr Leu Ser Cys Arg Ala Ser
            20                  25

<210> SEQ ID NO 822
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 822

Leu Ala Trp Tyr Gln Gln Lys Pro Gly Gln Ala Pro Arg Leu Leu Ile
1               5                   10                  15

Tyr

<210> SEQ ID NO 823
<211> LENGTH: 26
<212> TYPE: PRT
<213> ORGANISM: Artificial Sequence
<220> FEATURE:

<221> NAME/KEY: source
<223> OTHER INFORMATION: /note="VL FR1 sequence"

<400> SEQUENCE: 823

Val Trp Phe Met Asp Gln Ser Pro Gly Ala Leu Cys Leu Ser Ala Gly
1               5                   10                  15
Glu Arg Ala Thr Leu Ser Cys Arg Ala Ser
            20                  25

<210> SEQ ID NO 824
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 824

Leu Ala Trp Cys Gln Gln Lys Pro Phe Gln Ala Pro Arg Leu Leu Met
1               5                   10                  15
Glu

<210> SEQ ID NO 825
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 825

Cys Cys Ser Met Thr Gln Ser Pro Val Thr Leu Pro Val Thr Leu Gly
1               5                   10                  15
Gln Pro Ala Ser Ile Ser Cys Arg Ser Ser
            20                  25

<210> SEQ ID NO 826
<211> LENGTH: 11
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 826

Gln Ser Leu Val His Ser Asp Gly Asn Thr Tyr
1               5                   10

<210> SEQ ID NO 827
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 827

Leu Asn Trp Phe Gln Gln Arg Pro Gly Gln Ser Pro Arg Arg Leu Ile
1               5                   10                  15
Tyr

<210> SEQ ID NO 828
<211> LENGTH: 26
<212> TYPE: PRT
<213> ORGANISM: Artificial Sequence

```
<220> FEATURE:
<221> NAME/KEY: source
<223> OTHER INFORMATION: /note="VL FR1 sequence"

<400> SEQUENCE: 828

Cys Trp Ser Met Thr Gln Thr Pro Val Thr Leu Pro Val Thr Leu Gly
1               5                   10                  15

Gln Pro Ala Ser Ile Ser Cys Arg Ser Ser
            20                  25

<210> SEQ ID NO 829
<211> LENGTH: 11
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 829

Gln Ser Leu Val Tyr Ser Asp Gly Asn Thr Tyr
1               5                   10

<210> SEQ ID NO 830
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 830

Leu Asn Trp Phe Gln Gln Arg Pro Gly Gln Ser Pro Arg Arg Leu Ile
1               5                   10                  15

Tyr

<210> SEQ ID NO 831
<211> LENGTH: 25
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 831

Gln Ser Val Leu Thr Gln Pro Pro Ser Val Ser Gly Ser Pro Gly Gln
1               5                   10                  15

Ser Val Thr Ile Ser Cys Thr Gly Thr
            20                  25

<210> SEQ ID NO 832
<211> LENGTH: 9
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 832

Asn Ser Asp Val Gly Thr Tyr Asp Arg
1               5

<210> SEQ ID NO 833
<211> LENGTH: 17
<212> TYPE: PRT
<213> ORGANISM: Artificial Sequence
<220> FEATURE:
```

<221> NAME/KEY: source
<223> OTHER INFORMATION: /note="VL FR2 sequence"

<400> SEQUENCE: 833

Val Ser Trp Tyr Gln Gln Pro Pro Gly Thr Ala Pro Lys Leu Ile Ile
1               5                   10                  15
Tyr

<210> SEQ ID NO 834
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 834

Cys Cys Ser Met Thr Gln Thr Pro Gly Val Leu Gly Leu Ser Pro Gly
1               5                   10                  15
Glu Arg Ala Thr Leu Ser Cys Arg Val Ser
            20                  25

<210> SEQ ID NO 835
<211> LENGTH: 7
<212> TYPE: PRT
<213> ORGANISM: Artificial Sequence
<220> FEATURE:
<221> NAME/KEY: source
<223> OTHER INFORMATION: /note="VL CDR1 sequence"

<400> SEQUENCE: 835

Gln Arg Lys Thr Ser Thr Ser
1               5

<210> SEQ ID NO 836
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 836

Leu Val Arg Tyr Gln Gln Arg Pro Gly Gln Ala Pro Thr Leu Leu Met
1               5                   10                  15
Tyr

<210> SEQ ID NO 837
<211> LENGTH: 26
<212> TYPE: PRT
<213> ORGANISM: Artificial Sequence
<220> FEATURE:
<221> NAME/KEY: source
<223> OTHER INFORMATION: /note="VL FR1 sequence"

<400> SEQUENCE: 837

Cys Cys Ala Leu Thr Gln Ser Pro Ala Thr Leu Pro Val Thr Pro Gly
1               5                   10                  15
Glu Pro Ala Ser Ile Ser Cys Lys Ser Ser
            20                  25

<210> SEQ ID NO 838
<211> LENGTH: 11
<212> TYPE: PRT
<213> ORGANISM: Artificial Sequence

```
<220> FEATURE:
<221> NAME/KEY: source
<223> OTHER INFORMATION: /note="VL CDR1 sequence"

<400> SEQUENCE: 838

Gln Ser Leu Leu His Ser Asn Gly Tyr Asn Tyr
1               5                   10

<210> SEQ ID NO 839
<211> LENGTH: 17
<212> TYPE: PRT
<213> ORGANISM: Artificial Sequence
<220> FEATURE:
<221> NAME/KEY: source
<223> OTHER INFORMATION: /note="VL FR2 sequence"

<400> SEQUENCE: 839

Leu Ala Trp Tyr Leu Gln Lys Pro Gly Gln Ser Pro Gln Leu Leu Phe
1               5                   10                  15

Tyr

<210> SEQ ID NO 840
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 840

Ile Leu Glu Thr Gly Val Pro Ser Arg Phe Ser Gly Ser Gly Ser Gly
1               5                   10                  15

Thr His Phe Thr Leu Thr Ile Ser Ser Leu Gln Pro Glu Asp Ile Gly
                20                  25                  30

Thr Tyr Tyr Cys
            35

<210> SEQ ID NO 841
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 841

Gln Gln Tyr Glu His Leu Pro Leu Thr
1               5

<210> SEQ ID NO 842
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 842

Asn Leu Glu Ile Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
                20                  25                  30

Thr Tyr Tyr Cys
            35
```

<210> SEQ ID NO 843
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 843

Gln Gln Tyr Ser Thr Asp Ser Leu Tyr Thr
1               5                   10

<210> SEQ ID NO 844
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 844

Asn Arg Pro Ser Gly Ile Pro Glu Arg Phe Ser Gly Ser Asn Ser Gly
1               5                   10                  15

Asn Thr Ala Thr Leu Thr Ile Ser Arg Ala Gln Ala Gly Asp Glu Ala
            20                  25                  30

Asp Tyr Tyr Cys
        35

<210> SEQ ID NO 845
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 845

Gln Val Trp Asp Ser Ser Thr Val Val
1               5

<210> SEQ ID NO 846
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 846

Thr Arg Ala Thr Gly Ile Pro Ala Arg Phe Ser Gly Ser Gly Ser Gly
1               5                   10                  15

Thr Asp Phe Thr Leu Thr Ile Ser Asp Ile Gln Ser Glu Asp Phe Ala
            20                  25                  30

Tyr Tyr Tyr Cys
        35

<210> SEQ ID NO 847
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 847

Gln His Tyr Asn Asn Trp Pro Pro Trp Thr
1               5                   10

<210> SEQ ID NO 848
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 848

Ser Leu Glu Ser Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Thr Tyr Tyr Cys
        35

<210> SEQ ID NO 849
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 849

Gln Gln Tyr Asn Ser Tyr Ser Leu Ala
1               5

<210> SEQ ID NO 850
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 850

Ser Leu Gln Ser Gly Val Pro Ser Lys Phe Ser Gly Ser Gly Ser Gly
1               5                   10                  15

Thr Asp Phe Thr Leu Ala Ile Ser Ser Leu Gln Pro Glu Asp Phe Ala
            20                  25                  30

Thr Tyr Tyr Cys
        35

<210> SEQ ID NO 851
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 851

Gln Gln Tyr Asn Ser Tyr Pro Leu Thr
1               5

<210> SEQ ID NO 852
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 852

Ser Leu Glu Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 853
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 853

Gln Gln Phe Asn Ser Tyr Pro Ser Thr
1               5

<210> SEQ ID NO 854
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 854

Arg Arg Ala Ala Gly Ile Ser Asp Arg Phe Ser Gly Ser Gly Ser Gly
1               5                   10                  15

Thr Asp Phe Ala Leu Thr Ile Ser Arg Leu Glu Pro Glu Asp Phe Ala
            20                  25                  30

Val Tyr Tyr Cys
        35

<210> SEQ ID NO 855
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 855

Gln Glu Tyr Gly Ser Ser Pro Gly Thr
1               5

<210> SEQ ID NO 856
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 856

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Val Tyr Tyr Cys
        35

<210> SEQ ID NO 857
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 857

Gln His Arg Tyr Gly Trp Pro Pro Gly
1               5

<210> SEQ ID NO 858
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 858

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr Cys
        35

<210> SEQ ID NO 859
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 859

Gln Gln Tyr Gly Ser Ser Pro Asn Thr
1               5

<210> SEQ ID NO 860
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 860

Gln Gln Gly His Trp His Pro Arg Gln Val Gln Trp Gln Trp Val Trp
1               5                   10                  15

Asp Lys Thr Ser Leu Ser Pro Ser Ala Asp Trp Ser Leu Lys Ile Leu
            20                  25                  30

His Cys Ile Thr
        35

<210> SEQ ID NO 861
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 861

Val Ser Ser Met Val Ala His Leu Ser
1               5

<210> SEQ ID NO 862
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 862

Asn Arg Asp Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 863
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 863

Met Gln Gly Thr His Trp Pro Pro Trp Thr
1               5                   10

<210> SEQ ID NO 864
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 864

Asn Trp Asp Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 865
<211> LENGTH: 8
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 865

Met Gln Gly Thr Leu His Arg Phe
1               5

<210> SEQ ID NO 866
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 866

Asn Arg Pro Ser Gly Val Pro Asp Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 867
<211> LENGTH: 10
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 867

Cys Ser Tyr Arg Ser Gly Arg Thr Phe Val
1               5                   10

<210> SEQ ID NO 868
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 868

Asn Arg Ala Thr Gly Ile Pro Asp Arg Phe Ser Gly Ser Gly Ser Gly
1               5                   10                  15

Thr Asp Phe Thr Val Thr Ile Ser Arg Leu Glu Pro Glu Asp Phe Ala
            20                  25                  30

Met Tyr Tyr Cys
        35

<210> SEQ ID NO 869
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 869

Gln Gln Phe Asp Ser Ser Pro Trp Thr
1               5

<210> SEQ ID NO 870
<211> LENGTH: 36
<212> TYPE: PRT
<213> ORGANISM: Artificial Sequence
<220> FEATURE:
<221> NAME/KEY: source
<223> OTHER INFORMATION: /note="VL FR3 sequence"

<400> SEQUENCE: 870

Asp Arg Ala Ser Gly Val Pro Asp Arg Phe Ser Gly Ser Gly Ser Gly
1               5                   10                  15

Thr Asp Phe Thr Leu Lys Ile Ser Arg Val Glu Pro Glu Asp Val Gly
            20                  25                  30

Val Tyr Tyr Cys

<210> SEQ ID NO 871
<211> LENGTH: 9
<212> TYPE: PRT
<213> ORGANISM: Artificial Sequence
<220> FEATURE:
<221> NAME/KEY: source
<223> OTHER INFORMATION: /note="VL CDR3 sequence"

<400> SEQUENCE: 871

Met Gln Gly Leu His Thr Pro Leu Thr
1               5

<210> SEQ ID NO 872
<211> LENGTH: 117
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 872

Glu Val Gln Leu Glu Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Val Pro Thr Pro Tyr Phe Asp Leu Trp Gly Arg Gly Thr Leu
            100                 105                 110

Val Thr Val Ser Ser
        115

<210> SEQ ID NO 873
<211> LENGTH: 124
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 873

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Ala Met His Trp Val Arg Gln Ala Pro Gly Gln Arg Leu Glu Trp Met
        35                  40                  45

Gly Trp Ile Asn Asp Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Gly Leu Ser Ser Leu Arg Ser Glu Asp Thr Ala Val Tyr Tyr Cys
                85                  90                  95

```
Ala Arg Gly Gly Glu Asp Gly Tyr Gly Asp Ser Tyr Asn Ala Phe Asp
            100                 105                 110

Leu Trp Gly Gln Gly Thr Met Val Thr Val Ser Gln
        115                 120
```

<210> SEQ ID NO 874
<211> LENGTH: 123
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 874

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Ala Asn Gly Glu Thr Ile Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Thr His Phe Glu Ser Cys Gly Asp Cys Ser Asn Trp
            100                 105                 110

Trp Gly Gln Gly Thr Leu Val Thr Val Ser Ser
        115                 120
```

<210> SEQ ID NO 875
<211> LENGTH: 129
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 875

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asp Thr Asn Tyr Ala Gln Lys Phe
    50                  55                  60

Gln Gly Arg Val Ile Met Thr Arg Asp Thr Ser Ile Ser Ala Ala Tyr
65                  70                  75                  80

Met Glu Leu Ser Ser Leu Arg Ser Asp Asp Thr Ala Val Tyr Tyr Cys
                85                  90                  95

Gly Arg Val Gly Gly Arg Gln Leu Trp Leu Lys Asp Asn Tyr Asp
            100                 105                 110

Tyr Phe Tyr Met Asp Val Trp Gly Lys Gly Thr Thr Val Thr Val Ser
        115                 120                 125

Ser
```

<210> SEQ ID NO 876
<211> LENGTH: 125
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 876

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Thr Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Val Tyr Tyr Cys
                85                  90                  95

Ala Arg Asp Met Pro His Phe Leu Tyr Ser Ser Arg Trp Tyr Pro Phe
            100                 105                 110

Asp Tyr Trp Gly Gln Gly Thr Pro Val Thr Val Ser Ser
        115                 120                 125

<210> SEQ ID NO 877
<211> LENGTH: 122
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 877

Gln Val Gln Leu Val Glu Ser Gly Gly Gly Leu Val Gln Ser Gly Gly
1               5                   10                  15

Ser Leu Arg Leu Ser Cys Ser Ala Ser Gly Phe Arg Phe Ser Gly His
            20                  25                  30

Ala Met His Trp Val Arg Gln Pro Ala Gly Lys Gly Leu Glu Tyr Ile
        35                  40                  45

Ser Ala Ile Ser Gly Asn Gly Glu Ala Thr Tyr Tyr Ala Gly Ser Val
    50                  55                  60

Lys Gly Arg Phe Thr Ile Ser Arg Asp Asn Phe Lys Asn Thr Leu Tyr
65                  70                  75                  80

Leu Gln Met Thr Ser Leu Arg Pro Glu Asp Thr Ala Val Tyr Tyr Cys
                85                  90                  95

Val Thr Glu Ile Val Gly Ala Asn Arg Trp Val Pro Val Gly Pro Trp
            100                 105                 110

Gly Gln Gly Thr Leu Val Thr Val Ser Ser
        115                 120

<210> SEQ ID NO 878
<211> LENGTH: 122
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 878

Glu Val Gln Leu Glu Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Ile Ser Trp Ala Asp Gly Tyr Tyr Met Asp Val Trp
            100                 105                 110

Gly Lys Gly Thr Thr Val Thr Val Ser Ser
            115                 120

<210> SEQ ID NO 879
<211> LENGTH: 118
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 879

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Phe Ile His Trp Val Arg Gln Ala Pro Gly Gln Gly Leu Glu Trp Met
        35                  40                  45

Gly Trp Ile Asn Pro His Ser Asp Asp Thr Asn Ile Ala Gln Lys Phe
    50                  55                  60

Gln Gly Arg Val Thr Leu Pro Met Asp Thr Ser Ile Ser Thr Ala Tyr
65                  70                  75                  80

Met Glu Ile Thr Arg Leu Glu Ser Asp Asp Thr Ala Ile Tyr Tyr Cys
                85                  90                  95

Ala Arg Gly Ala Tyr Gly Asp Pro Leu His Ile Trp Gly Gln Gly Thr
            100                 105                 110

Val Val Thr Val Ser Ser
        115

<210> SEQ ID NO 880
<211> LENGTH: 120
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 880

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Thr Met Ile Trp Val Arg Gln Ala Pro Gly Lys Gly Leu Glu Trp Val

```
                    35                  40                  45
Ser Ser Ile Ser Gly Ser Gly Ser Tyr Ile Phe Tyr Ala Asp Ser Val
        50                  55                  60
Lys Gly Arg Phe Thr Ile Ser Arg Asp Asn Pro Lys Asn Ser Leu Tyr
65                  70                  75                  80
Leu Gln Met Asn Ser Leu Arg Ala Asp Asp Thr Ala Val Tyr Tyr Cys
                85                  90                  95
Ala Arg Trp Arg Ala Gly Val Pro Ser Tyr Phe Asp Tyr Trp Gly Gln
            100                 105                 110
Gly Thr Leu Val Thr Val Ser Ser
            115                 120

<210> SEQ ID NO 881
<211> LENGTH: 116
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 881

Glu Val Gln Leu Val Gln Ser Gly Pro Glu Val Lys Lys Pro Gly Thr
1               5                   10                  15
Ser Val Lys Val Ser Cys Lys Ala Ser Gly Phe Thr Ser Ser Arg Ser
                20                  25                  30
Ala Val Gln Trp Leu Arg Gln Thr Arg Gly Gln Arg Leu Glu Trp Ile
            35                  40                  45
Gly Gly Ile Val Val Gly Ser Gly Asn Thr Asn Tyr Ala Pro Asn Phe
        50                  55                  60
Gln Asp Arg Val Thr Ile Thr Trp Asp Met Ser Thr Arg Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Gly Ser Tyr Val Asp Tyr Trp Gly Gln Gly Thr Leu Val
            100                 105                 110
Thr Ile Ser Ser
            115

<210> SEQ ID NO 882
<211> LENGTH: 124
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 882

Glu Val Gln Leu Val Glu Ser Gly Gly Gly Phe Val Gln Pro Gly Gly
1               5                   10                  15
Ser Leu Arg Leu Ser Cys Ala Ala Ser Gly Phe Ser Ile Gly Asn Tyr
                20                  25                  30
Ala Leu Thr Trp Val Arg Gln Ala Pro Gly Lys Arg Leu Glu Trp Val
            35                  40                  45
Ser Ser Ile Thr Gly Ser Gly Asp Thr Tyr Asn Ala Asp Phe Met
        50                  55                  60
Lys Gly Arg Phe Thr Met Ser Arg Asp Leu Tyr Lys Asn Thr Leu Tyr
65                  70                  75                  80
Leu His Met Asn Ser Leu Arg Ala Glu Asp Thr Ala Ile Tyr Tyr Cys
```

```
                    85                  90                  95
Ala Lys Ser Pro Thr Asp Phe Trp Asp Asp Tyr Leu Tyr Tyr Phe Asp
                100                 105                 110

Ser Trp Gly Gln Gly Thr Leu Val Thr Val Ser Ser
        115                 120

<210> SEQ ID NO 883
<211> LENGTH: 123
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 883

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Asp Asp Tyr
                20                  25                  30

Asp Met His Trp Val Arg Gln Ala Pro Gly Lys Gly Leu Glu Trp Val
            35                  40                  45

Ser Gly Ile Arg Trp Asn Ser Asp Thr Ile Gly Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ser Ser Tyr Asp Thr Ser Gly Tyr Tyr Tyr Asn
                100                 105                 110

Trp Gly Gln Gly Thr Leu Val Thr Val Ser Ser
        115                 120

<210> SEQ ID NO 884
<211> LENGTH: 123
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 884

Glu Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ile Thr
                20                  25                  30

Asn Trp Trp Thr Trp Val Arg Gln Pro Pro Gly Lys Gly Leu Glu Trp
            35                  40                  45

Ile Gly Glu Ile Tyr His Ser Gly Tyr Thr Asn Tyr Asn Pro Ser Leu
    50                  55                  60

Lys Thr Arg Val Thr Ile Ser Val Asp Lys Ser Lys Asn His Leu Ser
65                  70                  75                  80

Leu Lys Leu Ser Phe Val Thr Ala Ala Asp Thr Ala Val Tyr Tyr Cys
                85                  90                  95

Ala Arg Lys Gly Thr Tyr Ser Thr Asp Ser Tyr Asp Gly Phe Asp Ile
                100                 105                 110

Trp Gly Gln Gly Thr Met Val Thr Val Ser Ser
        115                 120
```

-continued

```
<210> SEQ ID NO 885
<211> LENGTH: 131
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 885

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Cys Glu Thr Gly Glu Arg Trp Tyr Tyr Tyr Gly Ser Gly
            100                 105                 110

Thr Ile Arg Glu Ala Phe Asp Ile Trp Gly Gln Gly Thr Met Val Thr
        115                 120                 125

Val Ser Gln
    130

<210> SEQ ID NO 886
<211> LENGTH: 120
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 886

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Gln Leu Gly Ser Val Trp Phe Asp Pro Trp Gly Gln
            100                 105                 110

Gly Thr Leu Val Thr Val Ser Ser
        115                 120

<210> SEQ ID NO 887
<211> LENGTH: 119
<212> TYPE: PRT
<213> ORGANISM: Artificial Sequence
<220> FEATURE:
<221> NAME/KEY: source
```

<223> OTHER INFORMATION: /note="VH V-D-J-Region sequence"

<400> SEQUENCE: 887

Glu Val Gln Leu Glu Glu Ser Gly Gly Gly Val Val Gln Pro Gly Arg
1               5                   10                  15

Ser Leu Arg Leu Ser Cys Ala Ala Ser Gly Phe Thr Phe Ser Arg Asn
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Arg Tyr Tyr Thr Asp Ser Val
    50                  55                  60

Lys Gly Arg Phe Thr Ile Ser Arg Asp Asn Ser Arg Asn Thr Leu Tyr
65                  70                  75                  80

Leu Gln Met Asp Ser Leu Lys Pro Glu Asp Thr Ala Leu Tyr Tyr Cys
                85                  90                  95

Ala Lys Asp Arg Ser Ser Ser Trp Tyr Phe Asp His Trp Gly Gln Gly
            100                 105                 110

Ala Leu Ile Thr Ile Ser Ser
        115

<210> SEQ ID NO 888
<211> LENGTH: 116
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 888

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Thr Phe Asp Tyr Trp Gly Gln Gly Thr Leu Val
            100                 105                 110

Thr Val Ser Ser
        115

<210> SEQ ID NO 889
<211> LENGTH: 128
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 889

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
              35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
65                   70                  75                  80

Ser Leu Lys Leu Ser Ser Val Thr Ala Ala Asp Thr Ala Val Tyr Tyr
                 85                  90                  95

Cys Ala Arg Val Ser Leu Asn Ser Ser Ser Leu Ile His Tyr Tyr
                100                 105                 110

Tyr Tyr Met Asp Val Trp Gly Lys Gly Thr Thr Val Thr Trp Arg Ala
            115                 120                 125

<210> SEQ ID NO 890
<211> LENGTH: 131
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 890

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Glu Tyr Asp Phe Trp Ser Gly Tyr Tyr Arg Gly Ala Thr
            100                 105                 110

Arg Thr Thr Pro Asn Phe Asp Tyr Trp Gly Gln Gly Thr Leu Val Thr
        115                 120                 125

Val Ser Ser
    130

<210> SEQ ID NO 891
<211> LENGTH: 119
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 891

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Asn Thr Tyr
            20                  25                  30

Glu Ile Asn Trp Val Arg Gln Ala Thr Gly Gln Gly Leu Glu Trp Met
        35                  40                  45

Gly Trp Met Asn Pro Asn Ser Gly Asp Thr Val Tyr Ala Gln Lys Cys
    50                  55                  60

```
Gln Gly Arg Val Ser Met Thr Arg His Thr Ser Thr Ser Thr Ala Ser
 65                  70                  75                  80

Met Glu Leu Ile Ser Leu Ile Phe Glu Asp Thr Ala Val Tyr Tyr Cys
                 85                  90                  95

Ala Arg Ala Ala Gly Val Gly Val Ala Leu Asp Tyr Trp Gly Gln Gly
            100                 105                 110

Thr Leu Leu Thr Val Ser Ser
        115

<210> SEQ ID NO 892
<211> LENGTH: 123
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 892

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Ala Asn Gly Glu Thr Ile Asp Tyr Ala Ala
        50                  55                  60

Pro Val Lys Gly Arg Leu Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Thr His Phe Glu Ser Cys Gly Gly Asp Cys Ser Asn Trp
            100                 105                 110

Trp Gly Gln Gly Thr Leu Val Thr Val Ser Ser
        115                 120

<210> SEQ ID NO 893
<211> LENGTH: 125
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 893

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Cys Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Gly Val His Met Tyr Tyr Tyr Asp Ser Ser Gly Tyr Tyr Tyr Asp
            100                 105                 110
```

```
Asp Tyr Trp Gly Gln Gly Thr Met Val Thr Val Ser Ser
        115                 120                 125
```

<210> SEQ ID NO 894
<211> LENGTH: 129
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 894

```
Glu Val Gln Leu Val Glu Ser Gly Gly Val Val Gln Pro Gly Arg
1               5                   10                  15

Ser Leu Arg Leu Ser Cys Gly Ala Thr Gly Phe Thr Phe Ser Ser His
                20                  25                  30

Ala Met His Trp Val Arg Gln Val Ala Gly Lys Gly Leu Glu Trp Val
            35                  40                  45

Ala Val Ile Ser Asp Asp Ser Glu Lys Tyr Tyr Ala Asp Ser Val
        50                  55                  60

Arg Gly Arg Phe Ile Ile Ser Arg Asp Asn Ala Lys Asp Thr Val Tyr
65                  70                  75                  80

Leu Gln Met Asn Ser Leu Arg Pro Asp Thr Ala Val Tyr Tyr Cys
                85                  90                  95

Ala Thr Pro His Arg Leu Leu Asp Ser Cys Ser Ser Thr Ser Cys Tyr
            100                 105                 110

Val Val Ala Phe Asp Leu Trp Gly His Gly Thr Met Val Thr Val Ser
        115                 120                 125

Leu
```

<210> SEQ ID NO 895
<211> LENGTH: 120
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 895

```
Gln Val Gln Leu Val Glu Ser Gly Gly Gly Leu Val Gln Pro Gly Glu
1               5                   10                  15

Ser Leu Arg Leu Ser Cys Ala Ala Ser Gly Phe Thr Phe Gly Asn Tyr
                20                  25                  30

Ala Met Ser Trp Val Arg Gln Ala Pro Gly Lys Gly Leu Ala Trp Val
            35                  40                  45

Ala Ala Thr Ser Gly Ser Gly Ser Thr Tyr Tyr Ala Gly Ser Val
        50                  55                  60

Lys Cys Phe Thr Ile Ser Arg Asp Asn Ser Lys Ile Thr Leu Tyr Leu
65                  70                  75                  80

Gln Val His Ser Leu Arg Pro Glu Asp Thr Ala Val Tyr Tyr Cys Ala
                85                  90                  95

Lys Gly Thr Leu Ser Gly Phe Ala Thr Thr Phe Asp Tyr Trp Gly Gln
            100                 105                 110

Gly Thr Leu Val Thr Val Ser Ser
        115                 120
```

<210> SEQ ID NO 896
<211> LENGTH: 121

```
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 896
```

Glu Val Gln Leu Gln Glu Ser Gly Pro Arg Leu Val Lys Pro Ser Glu
1               5                   10                  15

Thr Leu Ser Leu Thr Cys Thr Val Ser Gly Gly Ser Ile Ser Ser Ser
            20                  25                  30

Asp His Tyr Trp Ala Trp Ile Arg Gln Pro Pro Gly Lys Gly Leu Ala
        35                  40                  45

Tyr Ile Gly Ile Ile Tyr Tyr Thr Gly Ser Thr Tyr Tyr Asn Pro Ser
    50                  55                  60

Leu Lys Ser Arg Val Ser Ile Ser Val Asp Thr Ser Lys Asn Gln Phe
65                  70                  75                  80

Ser Leu Asn Val Asn Ser Val Thr Ala Ala Asp Thr Gly Val Tyr Tyr
                85                  90                  95

Cys Ala Arg Arg His Ile Gly Arg His Tyr Tyr Phe Asp Tyr Trp Gly
            100                 105                 110

Gln Gly Thr Leu Val Thr Val Ser Ser
        115                 120

```
<210> SEQ ID NO 897
<211> LENGTH: 124
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 897
```

Glu Val Gln Leu Val Glu Ser Gly Pro Gly Leu Val Arg Pro Ser Gln
1               5                   10                  15

Thr Leu Ser Leu Thr Cys Val Ala Gly Gly Ser Val Ser Ser Gly
            20                  25                  30

Ser Tyr His Trp Ser Trp Ile Arg Gln Pro Pro Gly Lys Gly Leu Glu
        35                  40                  45

Trp Ile Gly Tyr Ile Phe Tyr Ser Gly Thr Thr Lys Tyr Asn Pro Ser
    50                  55                  60

Leu Lys Ser Arg Val Thr Ile Ser Thr Asp Val Ser Lys Asn Gln Phe
65                  70                  75                  80

Ser Leu Lys Leu Lys Ser Val Thr Ala Ala Asp Thr Ala Val Tyr Tyr
                85                  90                  95

Cys Ala Arg Asp Ala Ser Ile Ala Ala Arg Pro Pro Trp Gly Met Asp
            100                 105                 110

Val Trp Gly Gln Gly Thr Thr Val Thr Val Ser Ser
        115                 120

```
<210> SEQ ID NO 898
<211> LENGTH: 128
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 898
```

Gln Val Gln Leu Val Glu Ser Gly Ala Glu Val Lys Lys Pro Gly Ser

```
1               5                   10                  15
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
65                      70                  75                  80

Met Glu Leu Ser Ser Leu Arg Ser Glu Asp Thr Ala Val Tyr Tyr Cys
            85                  90                  95

Ala Arg Val Arg Ile Thr Ile Phe Gly Val Val Met Val Lys Ser Asp
            100                 105                 110

Asn Trp Phe Asp Pro Trp Gly Gln Gly Thr Leu Val Thr Val Ser Ser
            115                 120                 125

<210> SEQ ID NO 899
<211> LENGTH: 125
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 899

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ser Tyr Ile Ile Cys Ser Asp Gly Val Ile Tyr Tyr Ala Asp Ser Val
            50                  55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
            85                  90                  95

Ala Gly Val His Leu Tyr Tyr Tyr Asp Ser Ser Gly Tyr Tyr Tyr Asp
            100                 105                 110

Asp Tyr Trp Gly Gln Gly Thr Leu Val Thr Val Ser Ser
            115                 120                 125

<210> SEQ ID NO 900
<211> LENGTH: 116
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 900

Glu Val Gln Leu Val Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Asn Trp Ile Arg Gln Pro Pro Gly Lys Arg Leu Glu Trp Ile
            35                  40                  45

Gly Tyr Val Tyr Tyr Asn Gly Asn Thr Asn Tyr Asn Pro Ser Leu Lys
```

```
                    50                  55                  60

Ser Arg Val Thr Ile Ser Val Asp Thr Pro Lys Asn Gln Phe Ser Leu
 65                  70                  75                  80

Arg Leu Ser Ser Val Thr Ala Ala Asp Thr Ala Val Tyr Tyr Cys Ser
                     85                  90                  95

Gly Tyr Gly Val Asp Tyr Phe Asp Tyr Trp Gly Gln Gly Thr Leu Val
                    100                 105                 110

Thr Val Ser Ser
            115

<210> SEQ ID NO 901
<211> LENGTH: 124
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 901

Gln Val Gln Leu Val Gln Ser Gly Ala Glu Val Lys Lys Ser Gly Glu
 1               5                  10                  15

Ser Leu Trp Ile Ser Cys Lys Gly Ser Gly Tyr Ser Phe Thr Arg Tyr
                20                  25                  30

Trp Ile Gly Trp Val Arg Gln Met Pro Gly Lys Gly Leu Glu Trp Met
            35                  40                  45

Gly Ile Ile Ser Pro Gly Asp Ser Asn Thr Arg Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Leu Ser Ser Leu Lys Ala Ser Asp Ile Ala Thr Tyr Tyr Cys
                 85                  90                  95

Ala Arg Gln Gly Tyr Tyr Asp Arg Ser Pro Arg Pro His Tyr Met Asp
                100                 105                 110

Val Trp Gly Lys Gly Thr Thr Val Thr Val Ser Ser
            115                 120

<210> SEQ ID NO 902
<211> LENGTH: 124
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 902

Glu Val Gln Leu Val Glu Ser Gly Gly Gly Val Val Lys Pro Gly Arg
 1               5                  10                  15

Ser Leu Arg Leu Ser Cys Ala Ala Ser Gly Phe Asn Leu Ser Ser Tyr
                20                  25                  30

Gly Met His Trp Val Arg Gln Ala Pro Gly Lys Gly Leu Glu Trp Val
            35                  40                  45

Ala Val Val Trp Tyr Asp Gly Arg Asn Lys Phe Tyr Thr Asp Ser Val
        50                  55                  60

Lys Gly Arg Phe Thr Ile Ser Arg Asp Asn Ser Ile Asn Ser Val Tyr
 65                  70                  75                  80

Leu Gln Met Asn Ser Leu Arg Ala Glu Asp Thr Ala Ile Tyr Tyr Cys
                 85                  90                  95

Ala Arg Val Thr Ser Arg Val Val Ala Ala Gly Gly Tyr Phe Asp
```

```
                    100                 105                 110
His Trp Gly Gln Gly Thr Leu Val Thr Val Ser Ser
            115                 120

<210> SEQ ID NO 903
<211> LENGTH: 121
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 903

Glu Val Gln Leu Gln Glu Ser Gly Pro Arg Leu Val Lys Pro Ser Glu
1               5                   10                  15

Thr Leu Ser Leu Thr Cys Thr Val Ser Gly Gly Ser Ile Ser Ser Ser
            20                  25                  30

Asp His Tyr Trp Ala Trp Ile Arg Gln Pro Pro Gly Lys Gly Leu Ala
        35                  40                  45

Tyr Ile Gly Ile Ile Tyr Tyr Thr Gly Ser Thr Tyr Tyr Asn Pro Ser
    50                  55                  60

Leu Lys Ser Arg Val Ser Ile Ser Val Asp Thr Ser Lys Asn Gln Phe
65                  70                  75                  80

Ser Leu Asn Val Asn Ser Val Thr Ala Ala Asp Thr Gly Val Tyr Tyr
                85                  90                  95

Cys Ala Arg Arg His Ile Gly Arg His Tyr Tyr Phe Asp Tyr Trp Gly
            100                 105                 110

Gln Gly Thr Leu Val Thr Val Ser Ser
            115                 120

<210> SEQ ID NO 904
<211> LENGTH: 123
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 904

Gln Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Asp Asp Tyr
            20                  25                  30

Asp Met His Trp Val Arg Gln Ala Pro Gly Lys Gly Leu Glu Trp Val
        35                  40                  45

Ser Gly Ile Arg Trp Asn Ser Asp Thr Ile Gly Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ser Ser Tyr Asp Asp Thr Ser Gly Tyr Tyr Tyr Asn
            100                 105                 110

Trp Gly Gln Gly Thr Leu Val Thr Val Ser Ser
            115                 120

<210> SEQ ID NO 905
<211> LENGTH: 131
<212> TYPE: PRT
```

<213> ORGANISM: Artificial Sequence
<220> FEATURE:
<221> NAME/KEY: source
<223> OTHER INFORMATION: /note="VH V-D-J-Region sequence"

<400> SEQUENCE: 905

```
Gln Val Gln Leu Val Glu Ser Gly Gly Val Val Gln Pro Gly Arg
1               5                   10                  15
Ser Leu Arg Leu Ser Cys Ala Ala Ser Gly Phe Thr Phe Ser Asn Tyr
                20                  25                  30
Gly Ile His Trp Val Arg Gln Ala Pro Gly Lys Gly Leu Glu Trp Met
            35                  40                  45
Ala Phe Ile Ser His Asp Gly Ser Lys Lys Asn Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Arg Leu Arg Val Glu Asp Thr Ala Ile Tyr His Cys
                85                  90                  95
Ala Lys Asp Ile Val Val Pro Ala Ala Thr Ser Leu Leu Gly Gly
                100                 105                 110
Tyr Tyr Tyr Tyr Tyr Met Asp Val Trp Gly Lys Gly Thr Thr Val Thr
            115                 120                 125
Val Ser Ser
    130
```

<210> SEQ ID NO 906
<211> LENGTH: 128
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 906

```
Gln Val Gln Leu Val Glu Ser Gly Ala Glu Val Lys Thr Pro Gly Ala
1               5                   10                  15
Ser Val Lys Val Ser Cys Lys Thr Ser Gly Tyr Thr Phe Thr Ser Tyr
                20                  25                  30
Tyr Ile His Trp Val Arg Gln Ala Pro Gly Gln Gly Leu Glu Trp Met
            35                  40                  45
Gly Ile Ile Asn Pro Ser Ala Gly Ser Thr Thr Tyr Pro Gln Lys Phe
        50                  55                  60
Gln Gly Arg Val Thr Met Thr Arg Asp Arg Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Gly Leu Glu Ala Arg Thr Thr Ser Ser His Pro His
                100                 105                 110
Tyr Tyr Met Asp Val Trp Asp Lys Gly Thr Thr Val Thr Val Ser Ser
            115                 120                 125
```

<210> SEQ ID NO 907
<211> LENGTH: 120
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 907

Gln Val Gln Leu Gln Gln Trp Gly Ala Gly Leu Leu Lys Pro Ser Glu
1               5                   10                  15

Thr Leu Ser Leu Thr Cys Val Val Tyr Gly Gly Ser Phe Ser Gly Tyr
            20                  25                  30

Tyr Trp Ser Trp Ile Arg Gln Ser Pro Gly Lys Gly Leu Glu Trp Ile
        35                  40                  45

Gly Glu Val Asn His Ser Gly Ser Ser Tyr Tyr Asn Pro Ser Leu Lys
    50                  55                  60

Ser Arg Val Thr Ile Ser Val Asp Thr Ser Lys Asp Gln Phe Ser Leu
65                  70                  75                  80

Lys Leu Thr Ser Val Thr Ala Ala Asp Thr Ala Val Tyr Tyr Cys Ala
                85                  90                  95

Lys Lys Lys Gly Arg Val Gly Ile Ala Tyr Met Glu Val Trp Asp Lys
            100                 105                 110

Gly Thr Thr Val Thr Ile Ser Ser
        115                 120

<210> SEQ ID NO 908
<211> LENGTH: 120
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 908

Glu Val Gln Leu Gln Gln Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile His His Ser Gly Ser Ala Asp Tyr Asn Pro Ser Leu Lys
    50                  55                  60

Gly Arg Val Thr Ile Ser Leu Asp Thr Ser Lys Lys Gln Phe Ser Leu
65                  70                  75                  80

Lys Leu Arg Phe Val Thr Thr Ala Asp Thr Ala Leu Tyr Tyr Cys Ala
                85                  90                  95

Arg Thr Pro Tyr Pro Pro Leu Asp Trp Tyr Phe Asp Leu Trp Gly Arg
            100                 105                 110

Gly Thr Leu Val Thr Val Ser Ser
        115                 120

<210> SEQ ID NO 909
<211> LENGTH: 117
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 909

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

```
Ala Phe Ile Ser Phe Asp Gly Ser Asp Lys Tyr Tyr Ala Ala Ser Val
            50                  55                  60

Lys Gly Arg Phe Thr Leu Ser Arg Asp Asn Ser Lys Asn Thr Leu Tyr
 65                  70                  75                  80

Leu Lys Ile Asn Ser Leu Arg Thr Glu Asp Thr Ala Val Tyr Tyr Cys
                 85                  90                  95

Ala Lys Glu Val Arg Glu Tyr Thr Asp Tyr Trp Gly Gln Gly Thr Leu
            100                 105                 110

Val Thr Val Ser Ser
            115

<210> SEQ ID NO 910
<211> LENGTH: 122
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 910

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Thr Asp Asn
            20                  25                  30

Ala Met Thr Trp Val Arg Gln Ala Pro Gly Lys Gly Leu Glu Trp Val
        35                  40                  45

Ser Thr Ile Arg Asn Asn Gly Gln Asn Thr Tyr Tyr Thr Asp Ser Val
    50                  55                  60

Lys Gly Arg Phe Thr Ile Ser Arg Asp Asn Phe Asn Asn Met Val Tyr
 65                  70                  75                  80

Leu Gln Met Ser Ser Leu Arg Ala Glu Asp Thr Ala Val Tyr Tyr Cys
                 85                  90                  95

Ala Lys Leu Val Gly Ile Thr His Leu Ser Ala Ala Pro Trp Thr Trp
            100                 105                 110

Gly Gln Gly Thr Met Val Thr Val Ser Ser
        115                 120

<210> SEQ ID NO 911
<211> LENGTH: 121
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 911

Glu Val Gln Leu Val Glu Ser Gly Gly Gly Leu Val Gln Pro Gly Gly
 1               5                   10                  15

Ser Leu Arg Leu Ser Cys Ala Val Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ser Ile Ser Asp Thr Gly Phe Ser Thr Tyr Tyr Ala Asp Ser Val
    50                  55                  60

Lys Gly Arg Phe Ala Ile Ser Arg Asp Asn Ser Lys Asn Arg Leu Tyr
 65                  70                  75                  80

Leu Glu Met Asn Ser Leu Arg Ala Asp Asp Thr Ala Ile Tyr Tyr Cys
                 85                  90                  95
```

Ala Lys Val Pro His Gln Leu Val Pro Ile Trp Phe Asp Pro Trp Gly
            100                 105                 110

Gln Gly Thr Gln Val Thr Val Ser Ser
        115                 120

<210> SEQ ID NO 912
<211> LENGTH: 120
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 912

Val Gln Leu Val Glu Met Gly Gly Gly Arg Ile Val Gln Pro Gly Arg
1               5                   10                  15

Ser Leu Ser Leu Ser Cys Ala Ala Ser Gly Phe Ser Phe Ser Ser His
            20                  25                  30

Ala Met His Trp Val Arg Gln Ala Pro Gly Lys Gly Leu Glu Trp Val
        35                  40                  45

Ala Val Ile Ser Tyr Asp Gly Asp Lys Asn Tyr Ala Asp Ser Val
    50                  55                  60

Arg Gly Arg Phe Thr Ile Ser Arg Asp Asn Ser Glu Asp Thr Leu Tyr
65                  70                  75                  80

Leu Gln Met Asn Gly Leu Arg Thr Glu Asp Thr Ala Met Tyr Phe Cys
                85                  90                  95

Thr Arg Asp Ala Arg Gly Val Arg Asn Ala Phe Asp Leu Trp Gly Gln
            100                 105                 110

Gly Thr Met Leu Thr Val Ser Ser
        115                 120

<210> SEQ ID NO 913
<211> LENGTH: 124
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 913

Gln Val Gln Leu Val Gln Ser Gly Ala Asp Val Lys Lys Pro Gly Ala
1               5                   10                  15

Ser Val Lys Ile Ser Cys Lys Ala Ser Gly Tyr Thr Phe Thr Ala Tyr
            20                  25                  30

Ala Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Asn Thr Ser Tyr
65                  70                  75                  80

Met Asp Leu Ser Ser Leu Arg Ser Glu Asp Thr Ala Val Tyr Phe Cys
                85                  90                  95

Ala Arg Ser Leu Tyr Cys Ser Thr His Ser Cys Ser Phe Leu His Leu
            100                 105                 110

Tyr Trp Gly Gln Gly Ala Leu Val Thr Val Ser Ser
        115                 120

<210> SEQ ID NO 914

<211> LENGTH: 122
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 914

Glu Val Gln Leu Gln Glu Ser Gly Pro Gly Leu Val Glu Pro Ser Gly
1               5                   10                  15

Thr Leu Ser Leu Thr Cys Val Val Ser Gly Ser Ile Thr Ser Ser
            20                  25                  30

Asn Trp Trp Ser Trp Val Arg Gln Pro Pro Gly Lys Gly Pro Glu Trp
        35                  40                  45

Ile Gly Glu Ile Tyr His Ile Gly Asp Ser Asn Tyr Asn Pro Ser Leu
    50                  55                  60

Lys Ser Arg Val Thr Met Ser Val Asp Lys Ser Lys Asn Gln Phe Ser
65                  70                  75                  80

Leu Lys Leu Arg Ser Val Thr Ala Ala Asp Thr Ala Ile Tyr Tyr Cys
                85                  90                  95

Ala Arg Thr Phe Trp Ser Gly Ser Tyr Ser Arg Tyr Phe Asp Ser Trp
            100                 105                 110

Gly Gln Gly Thr Leu Val Thr Val Ser Ser
        115                 120

<210> SEQ ID NO 915
<211> LENGTH: 121
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 915

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Phe Gly Arg His Asp Tyr Gly Gly Lys Asp Asp Tyr Trp Gly
            100                 105                 110

Gln Gly Thr Leu Val Thr Val Ser Ser
        115                 120

<210> SEQ ID NO 916
<211> LENGTH: 131
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 916

```
Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Gln Ile Thr Met Val Arg Gly Gly Asp Gly Gln Asn
            100                 105                 110

Tyr Tyr Tyr Tyr Tyr Met Asp Val Trp Gly Lys Gly Thr Thr Val Thr
            115                 120                 125

Val Ser Ser
    130
```

<210> SEQ ID NO 917
<211> LENGTH: 123
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 917

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Val Gly Asp Ile Val Val Val Thr Ala Ser Leu Asp Tyr
            100                 105                 110

Trp Gly Gln Gly Thr Leu Val Thr Val Ser Ser
        115                 120
```

<210> SEQ ID NO 918
<211> LENGTH: 125
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 918

```
Gln Val Gln Leu Val Glu Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30
```

```
Tyr Trp Ser Trp Ile Arg Gln Pro Gly Lys Gly Leu Glu Trp Ile
        35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Trp Ala Tyr Ser Ser Trp Tyr Arg Arg Met Ile Ser Phe
            100                 105                 110

Asp Tyr Trp Gly Gln Gly Thr Leu Val Thr Val Ser Ser
        115                 120                 125

<210> SEQ ID NO 919
<211> LENGTH: 124
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 919

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Val Gly Gly Gly Tyr Tyr Asp Ser Ser Gly Gly Ala Leu Asp
            100                 105                 110

Tyr Trp Gly Gln Gly Thr Leu Val Thr Val Ser Ser
        115                 120

<210> SEQ ID NO 920
<211> LENGTH: 125
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 920

Glu Val Gln Leu Glu Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80
```

Lys Leu Ser Ser Val Thr Ala Ala Asp Thr Ala Val Tyr Tyr Cys Ala
            85                  90                  95

Arg Arg Val Gly Ser Pro Tyr Cys Gly Gly Asp Cys Tyr Pro Ala Phe
            100                 105                 110

Asp Ile Trp Gly Gln Gly Thr Met Val Thr Val Ser Gln
            115                 120                 125

<210> SEQ ID NO 921
<211> LENGTH: 128
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 921

Gln Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Leu Val Asp Cys Ser Ser Thr Ser Cys Tyr Tyr Tyr Tyr
            100                 105                 110

Tyr Tyr Met Asp Val Trp Gly Lys Gly Thr Thr Val Thr Val Ser Ser
        115                 120                 125

<210> SEQ ID NO 922
<211> LENGTH: 119
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 922

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Tyr Phe Asp Tyr Trp Gly Gln Gly
            100                 105                 110

Thr Leu Val Thr Val Ser Ser
        115

<210> SEQ ID NO 923
<211> LENGTH: 117
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 923

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Phe His Ile Leu Ser Tyr Trp Gly Gln Gly Thr Leu
            100                 105                 110

Val Thr Val Ser Ser
        115

<210> SEQ ID NO 924
<211> LENGTH: 120
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 924

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Glu Ser Ser Arg Leu Gly Asn Ala Phe Asp Ile Trp Gly Gln
            100                 105                 110

Gly Thr Met Val Thr Val Ser Gln
        115                 120

<210> SEQ ID NO 925
<211> LENGTH: 118
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 925

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Asn Ser Tyr Tyr Phe Asp Tyr Trp Gly Gln Gly Thr
            100                 105                 110

Leu Val Thr Val Ser Ser
        115

<210> SEQ ID NO 926
<211> LENGTH: 118
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 926

Gln Val Gln Leu Val Glu Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Ile Val Leu Gly Ala Phe Asp Ile Trp Gly Gln Gly Thr
            100                 105                 110

Met Val Thr Val Ser Gln
        115

<210> SEQ ID NO 927
<211> LENGTH: 131
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 927

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met

-continued

```
                35                  40                  45
Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Arg Tyr Cys Ser Ser Thr Ser Cys Tyr Lys Gly Ser Tyr Tyr
            100                 105                 110

Tyr Tyr Tyr Tyr Tyr Met Asp Val Trp Gly Lys Gly Thr Thr Val Thr
        115                 120                 125

Val Ser Ser
    130

<210> SEQ ID NO 928
<211> LENGTH: 121
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 928

Gln Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Glu Asp Tyr
                 20                  25                  30

Ala Met His Trp Val Arg Gln Val Pro Gly Lys Gly Leu Glu Trp Val
            35                  40                  45

Ser Ser Ile Ser Trp Asn Ser Val Thr Ile Asp Tyr Ala Asp Ser Val
     50                  55                  60

Lys Gly Arg Phe Thr Ile Ser Arg Asp Asn Ala Arg Asn Ser Leu Tyr
 65                  70                  75                  80

Leu Gln Met Asn Ser Leu Arg Pro Glu Asp Thr Ala Leu Tyr Tyr Cys
                 85                  90                  95

Ala Ala Gly Ser Tyr Arg Tyr Tyr Tyr Tyr Cys Ile Asp Val Trp Gly
            100                 105                 110

Lys Gly Thr Thr Val Thr Val Ser Ser
        115                 120

<210> SEQ ID NO 929
<211> LENGTH: 113
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 929

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Tyr Asp Tyr
                 20                  25                  30

Asp Met Ser Trp Val Arg Gln Ala Pro Gly Lys Gly Leu Gln Trp Val
            35                  40                  45

Ser Thr Ile Thr Leu Ser Gly Val Thr Ala Tyr Tyr Ala Asp Ser Val
     50                  55                  60

Lys Gly Arg Phe Thr Ile Ser Arg Asp Asn Ser Lys Asn Met Val Tyr
```

```
                    65                  70                  75                  80
Leu Gln Met Asn Ser Leu Arg Ala Glu Asp Thr Ala Val Tyr Tyr Cys
                        85                  90                  95

Ala Lys His Trp Asp Ser Trp Gly Gln Gly Thr Pro Val Thr Val Ser
                        100                 105                 110

Ser

<210> SEQ ID NO 930
<211> LENGTH: 120
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 930

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Phe Ile Ser Ser Ser Ser Tyr Met His Tyr Ala Asp Ser Val
        50                  55                  60

Lys Asp Arg Phe Ile Ile Ser Arg Asp Asn Ala Asn Ser Leu Tyr
65                  70                  75                  80

Leu Gln Met Asn Ser Leu Thr Ala Glu Asp Thr Gly Val Tyr Tyr Cys
                        85                  90                  95

Ala Arg Leu Gly Tyr Asp Phe Trp Ser Gly His Arg His Trp Gly Gln
                        100                 105                 110

Gly Thr Leu Val Thr Val Ser Ser
            115                 120

<210> SEQ ID NO 931
<211> LENGTH: 125
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 931

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Cys Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                        85                  90                  95

Val Gly Val His Leu Tyr Tyr Tyr Asp Ser Ser Gly Tyr Tyr Tyr Asp
                        100                 105                 110

Asp Tyr Trp Gly Gln Gly Thr Leu Val Thr Val Ser Ser
            115                 120                 125
```

<210> SEQ ID NO 932
<211> LENGTH: 132
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 932

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ala Arg Ile Lys Thr Asp Gly Ser Ile Thr Gly His Ala Asp Ser Val
    50                  55                  60

Lys Gly Arg Phe Ser Val Ser Arg Asp Asn Ala Lys Asn Thr Leu Tyr
65                  70                  75                  80

Leu Gln Met Asn Ser Leu Arg Ala Glu Asp Thr Gly Val Tyr Phe Cys
                85                  90                  95

Ala Arg Asp Gly Gly Glu Ala Tyr Asp Phe Trp Ser Asp Asn His Arg
            100                 105                 110

Phe Tyr Phe Tyr Tyr Tyr Met Asp Val Trp Gly Lys Gly Thr Thr Val
        115                 120                 125

Ser Val Ser Ser
    130

<210> SEQ ID NO 933
<211> LENGTH: 128
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 933

Glu Val Gln Leu Val Glu Ser Gly Gly Gly Leu Val Gln Pro Gly Gly
1               5                   10                  15

Ser Leu Arg Leu Ser Cys Ala Ala Pro Gly Phe Ser Phe Ser Ser His
            20                  25                  30

Trp Met Ser Trp Val Arg Gln Ala Pro Gly Lys Gly Leu Glu Trp Val
        35                  40                  45

Ala Asn Ile Lys Ala Asp Gly Ser Glu Lys Tyr Tyr Ile Asp Ser Val
    50                  55                  60

Lys Gly Arg Phe Ser Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Val Glu Gln Gln Leu Val Leu Gly Tyr Phe Tyr Tyr
            100                 105                 110

Tyr Tyr Met Asp Val Trp Gly Lys Gly Thr Thr Val Thr Val Ser Ser
        115                 120                 125

<210> SEQ ID NO 934
<211> LENGTH: 127
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 934

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Gln Lys Tyr Tyr Val Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Gly Leu Arg Ala Glu Asp Thr Ala Val Tyr Tyr Cys
                85                  90                  95

Ala Arg Asp Pro Arg Ala Tyr Asp Tyr Trp Ser Gly Tyr Tyr Glu Gly
            100                 105                 110

Tyr Phe Asp Tyr Trp Gly Gln Gly Ser Leu Val Thr Val Ser Ser
        115                 120                 125
```

<210> SEQ ID NO 935
<211> LENGTH: 117
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 935

```
Gln Val Gln Leu Gln Glu Ser Gly Ser Gly Leu Val Arg Ser Ser Gln
1               5                   10                  15

Asn Leu Ser Leu Thr Cys Ser Val Ser Gly Gly Ser Val Ser Arg Gly
            20                  25                  30

Gly Ala Ser Trp Gly Trp Val Arg Gln Pro Pro Gly Gln Gly Leu Glu
        35                  40                  45

Trp Ile Gly Tyr Ile Thr His Ser Gly Thr Thr Phe Ser Asn Pro Ser
    50                  55                  60

Leu Lys Ser Arg Val Met Ile Ser Lys Asp Lys Ser Gln Asn His Phe
65                  70                  75                  80

Ser Leu Ser Leu Thr Ser Val Thr Val Ala Asp Thr Ala Val Tyr Phe
                85                  90                  95

Cys Ala Arg Trp Ser Thr Ala Phe Asp Arg Trp Gly Gln Gly Thr Leu
            100                 105                 110

Val Thr Val Ser Ser
        115
```

<210> SEQ ID NO 936
<211> LENGTH: 128
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 936

```
Glu Val Gln Leu Val Glu Ser Gly Gly Gly Ser Val Gln Pro Gly Gly
1               5                   10                  15
```

```
Ser Leu Arg Leu Ser Cys Ala Ala Ser Gly Phe Thr Phe Ser Ser His
        20                  25                  30

Trp Ile His Trp Val Arg Gln Ala Pro Gly Lys Gly Leu Val Cys Val
            35                  40                  45

Ser Arg Ile Asn Ser Asp Gly Ser Ser Thr Ser Tyr Ala Asp Ser Val
 50                  55                  60

Lys Gly Arg Phe Thr Ile Ser Arg Asp Asn Ala Lys Asn Met Val Tyr
 65                  70                  75                  80

Leu Gln Met Asn Ser Leu Arg Ala Glu Asp Thr Ala Val Asp Leu Gly
                85                  90                  95

Thr Ser Asp Arg Arg Ser Gln Phe Arg Arg Ser Gly Arg Ala Pro Trp
                100                 105                 110

Asp Ala Phe Asp Ile Trp Gly Gln Gly Thr Met Val Thr Val Ser Ser
            115                 120                 125
```

<210> SEQ ID NO 937
<211> LENGTH: 127
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 937

```
Gln Val Gln Leu Val Glu Ser Gly Gly Gly Leu Val Gln Pro Gly Gly
1               5                   10                  15

Ser Leu Arg Leu Ser Cys Ala Thr Ser Arg Phe Thr Phe Ser Asn Tyr
            20                  25                  30

Ala Met Asn Trp Val Arg Gln Ala Pro Gly Lys Gly Leu Glu Trp Val
            35                  40                  45

Ser Ala Ile Ser Gly Ser Gly Thr Thr Tyr Tyr Ala Asp Ser Val
 50                  55                  60

Lys Gly Arg Phe Thr Ile Ser Arg Asp Asn Ser Arg Asn Ser Leu Tyr
 65                  70                  75                  80

Leu Gln Met Asn Ser Leu Arg Gly Glu Asp Thr Ala Val Tyr Tyr Cys
                85                  90                  95

Val Lys Glu Ser Val Gly Ala Leu Leu Trp Glu Ile Asp Asp Trp Gln
                100                 105                 110

Phe Phe Asp Tyr Trp Gly Gln Gly Thr Leu Val Thr Val Ser Ser
            115                 120                 125
```

<210> SEQ ID NO 938
<211> LENGTH: 121
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 938

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Asp
            20                  25                  30

Thr Phe Tyr Trp Gly Trp Val Arg Gln Pro Pro Gly Lys Gly Leu Glu
            35                  40                  45

Trp Ile Ala Ser Ile Ser Tyr Ser Gly Ser Thr Phe Tyr Asn Pro Ser
 50                  55                  60
```

```
Leu Lys Ser Arg Val Thr Met Ser Val Asp Thr Ser Lys Asn Gln Phe
 65                  70                  75                  80

Ser Leu His Leu Asn Ser Val Thr Ala Ala Asp Thr Ala Val Phe Tyr
                 85                  90                  95

Cys Ala Lys His Gly Gly Gly Met Ala Thr Ser Phe Asp Tyr Trp Gly
            100                 105                 110

Gln Gly Thr Leu Val Thr Val Ser Ser
            115                 120

<210> SEQ ID NO 939
<211> LENGTH: 117
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 939

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Asp Thr Asp His Tyr Phe Asp Tyr Trp Gly Gln Gly Thr Leu
            100                 105                 110

Val Thr Val Ser Ser
        115

<210> SEQ ID NO 940
<211> LENGTH: 120
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 940

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Gly Ala Ile Ala Ala Ala Gly Phe Asp Tyr Trp Gly Gln
            100                 105                 110
```

```
Gly Thr Leu Val Thr Val Ser Ser
        115                 120

<210> SEQ ID NO 941
<211> LENGTH: 122
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 941

Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile His Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Thr Ala Ile Leu Phe Gly Gly Ser Ser Phe Asp Tyr Trp
            100                 105                 110

Gly Gln Gly Thr Leu Val Thr Val Ser Ser
        115                 120

<210> SEQ ID NO 942
<211> LENGTH: 121
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 942

Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Gly Asn
            20                  25                  30

Tyr Met Ser Trp Val Arg Gln Ala Pro Gly Arg Gly Leu Glu Trp Val
        35                  40                  45

Ser Val Ile Tyr Ser Thr Gly Asp Thr Tyr Tyr Ala Glu Ser Val Lys
50                  55                  60

Gly Arg Phe Thr Val Ser Arg Asp Asp Asn Ser Lys Ser Ser Val Lys
65                  70                  75                  80

Val Val Val Glu Gln Thr Glu Ser Arg Gly His Gly Arg Val Leu Leu
                85                  90                  95

Cys Glu Arg Lys Gly Gln Trp Leu Val Gln Arg Tyr Gly Arg Leu Gly
            100                 105                 110

Gln Gly Thr Thr Val Thr Val Ser Ser
        115                 120

<210> SEQ ID NO 943
<211> LENGTH: 120
<212> TYPE: PRT
<213> ORGANISM: Artificial Sequence
<220> FEATURE:
```

<221> NAME/KEY: source
<223> OTHER INFORMATION: /note="VH V-D-J-Region sequence"

<400> SEQUENCE: 943

Gln Val Gln Leu Val Gln Ser Gly Ala Glu Val Lys Pro Gly Glu
1               5                   10                  15

Ser Leu Lys Ile Ser Cys His Gly Ser Gly Tyr Thr Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Thr Gly Asp Ser Tyr Ser Arg Tyr Ser Pro Ser Phe
    50                  55                  60

Gln Gly Leu Gly Asp Val Ala Val Asp Glu Ser Leu Ser Thr Ala Tyr
65                  70                  75                  80

Leu Glu Trp Ser Ser Leu Lys Ala Ser Asp Thr Ala Met Tyr Tyr Cys
                85                  90                  95

Val Arg Gln Trp Glu Asn Arg Gly Trp Ser Ile Ala Tyr Trp Gly Gln
            100                 105                 110

Gly Thr Leu Val Thr Val Ser Ser
        115                 120

<210> SEQ ID NO 944
<211> LENGTH: 119
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 944

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Leu Arg Tyr Asn Trp Phe Asp Pro Trp Gly Gln Gly
            100                 105                 110

Thr Leu Val Thr Val Ser Ser
        115

<210> SEQ ID NO 945
<211> LENGTH: 126
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 945

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
                  20                  25                  30
Ala Met Ser Trp Val Arg Gln Ala Pro Gly Lys Gly Leu Glu Trp Val
              35                  40                  45
Ser Ala Ile Ser Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
              85                  90                  95
Ala Lys Met Leu Phe Thr Pro Trp Glu Val Thr Trp Leu Arg Pro Tyr
                 100                 105                 110
Phe Asp Tyr Trp Gly Gln Gly Thr Leu Val Thr Val Ser Ser
             115                 120                 125

<210> SEQ ID NO 946
<211> LENGTH: 118
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 946

Glu Val Gln Leu Val Glu Ser Gly Gly Gly Leu Val Gln Pro Gly Gly
 1                   5                  10                  15
Ser Leu Arg Leu Ser Cys Ala Ala Ser Gly Phe Thr Phe Ser Ser Tyr
                 20                  25                  30
Trp Met His Trp Val Arg Gln Ala Pro Gly Lys Gly Leu Val Trp Val
             35                  40                  45
Ser Arg Ile Asn Ser Asp Gly Ser Ser Thr Ser Tyr Ala Asp Ser Val
 50                  55                  60
Lys Gly Arg Phe Thr Ile Ser Arg Asp Asn Ala Lys Asn Thr Leu Tyr
 65                  70                  75                  80
Leu Gln Met Asn Ser Leu Arg Ala Glu Asp Thr Ala Val Tyr Tyr Cys
             85                  90                  95
Ala Ser Leu Val Pro Ala Ala Gly Gly Asp Tyr Trp Gly Gln Gly Thr
                 100                 105                 110
Leu Val Thr Val Ser Ser
         115

<210> SEQ ID NO 947
<211> LENGTH: 124
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 947

Gln Val Gln Leu Val Glu Ser Gly Gly Gly Leu Val Gln Pro Gly Gly
 1                   5                  10                  15
Ser Leu Arg Leu Ser Cys Ala Ala Ser Gly Phe Thr Phe Ser Ser Tyr
                 20                  25                  30
Ser Met Asn Trp Val Arg Gln Ala Pro Gly Lys Gly Leu Glu Trp Val
             35                  40                  45
Ser Tyr Ile Ser Ser Ser Ser Ser Thr Ile Tyr Tyr Ala Asp Ser Val
 50                  55                  60
Lys Gly Arg Phe Thr Ile Ser Arg Asp Asn Ala Lys Asn Ser Leu Tyr
```

```
            65                  70                  75                  80
Leu Gln Met Asn Ser Leu Arg Ala Glu Asp Thr Ala Val Tyr Tyr Cys
                    85                  90                  95

Ala Arg Gly Ser Pro Tyr Ser Ser Ser Ser Val Arg Gly Met Asp
                100                 105                 110

Val Trp Gly Gln Gly Thr Thr Val Thr Val Ser Ser
            115                 120
```

```
<210> SEQ ID NO 948
<211> LENGTH: 119
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 948

Gln Val Gln Leu Val Gln Ser Gly Gly Gly Leu Val Gln Pro Gly Gly
1               5                   10                  15

Ser Leu Thr Leu Ser Cys Ala Val Ser Gly Phe Thr Val Arg Ser Ser
                20                  25                  30

Tyr Val Ser Trp Leu Arg Gln Thr Pro Gly Lys Gly Leu Glu Trp Val
            35                  40                  45

Ser Val Ile Phe Ser Gly Gly Ser Thr Ser Tyr Ala Asp Phe Val Lys
        50                  55                  60

Gly Arg Phe Thr Met Ser Arg Asp Asn Ser Lys Asn Thr Leu Tyr Leu
65                  70                  75                  80

Gln Met Asp Ser Leu Arg Ser Asp Thr Ala Val Tyr Tyr Cys Ala
                85                  90                  95

Lys Gly Gly Trp Glu Leu Thr Asn Trp Phe Asp Pro Trp Gly Gln Gly
                100                 105                 110

Thr Leu Val Thr Val Ser Ser
            115
```

```
<210> SEQ ID NO 949
<211> LENGTH: 118
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 949

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Asn Phe Glu Asn Tyr
                20                  25                  30

Ala Met Asp Trp Val Arg Gln Ala Pro Gly Lys Gly Leu Glu Trp Val
            35                  40                  45

Ser Gly Ile Thr Trp Asn Ser Gly Lys Ile His Tyr Ala Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Asn Leu Arg His Glu Asp Thr Ala Leu Tyr Tyr Cys
                85                  90                  95

Ala Lys Ala Ser Gly Glu Asp Phe Pro Asp Tyr Trp Gly Gln Gly Thr
                100                 105                 110

Leu Val Thr Val Ser Ser
```

115

<210> SEQ ID NO 950
<211> LENGTH: 126
<212> TYPE: PRT
<213> ORGANISM: Artificial Sequence
<220> FEATURE:
<221> NAME/KEY: source
<223> OTHER INFORMATION: /note="VH V-D-J-Region sequence"

<400> SEQUENCE: 950

Gln Val Gln Leu Val Glu Ser Gly Gly Cys Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Tyr Trp Val Arg Gln Ala Pro Gly Glu Gly Leu Glu Trp Val
        35                  40                  45

Ala Val Ile Ser Tyr His Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Leu Met Asn Ser Leu Arg Ala Glu Asp Thr Ala Val Tyr Tyr Cys
                85                  90                  95

Ala Arg Asp Pro Gly Trp Ser Gly Ser Ile Met Asp Tyr Tyr Tyr Gly
            100                 105                 110

Met Asp Val Trp Gly Gln Gly Thr Thr Val Ile Val Ser Pro
        115                 120                 125

<210> SEQ ID NO 951
<211> LENGTH: 105
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 951

Phe Val Ser Gln Thr Pro Ala Thr Leu Ser Ala Ser Val Gly Asp Arg
1               5                   10                  15

Val Thr Ile Thr Cys Arg Ala Ser Gln Ser Ile Ser Ser Tyr Leu Asn
            20                  25                  30

Trp Tyr Gln Gln Lys Pro Gly Lys Val Pro Lys Leu Leu Ile Tyr Ala
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Ser Thr Pro Tyr Thr Phe
                85                  90                  95

Gly Gln Gly Thr Lys Leu Glu Ile Lys
            100                 105

<210> SEQ ID NO 952
<211> LENGTH: 105
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 952

```
Met Thr Pro Thr Ile Pro Val Thr Leu Ser Ala Ser Val Gly Asp Arg
1               5                   10                  15

Val Thr Ile Thr Cys Arg Ala Ser Gln Ser Ile Ser Asn Trp Leu Ala
            20                  25                  30

Trp Tyr Gln Gln Lys Pro Gly Lys Ala Pro Lys Leu Leu Ile Tyr Lys
        35                  40                  45

Ala Ser Thr Leu Glu Ser Gly Val Pro Ser Arg Phe Ser Gly Ser Gly
    50                  55                  60

Ser Gly Thr Glu Phe Thr Leu Thr Ile Ser Ser Leu Gln Pro Asp Asp
65                  70                  75                  80

Phe Ala Thr Tyr Tyr Cys Gln Gln Tyr Asn Ser Tyr Ser Trp Thr Phe
                85                  90                  95

Gly Gln Gly Thr Lys Val Glu Ile Lys
            100                 105
```

<210> SEQ ID NO 953
<211> LENGTH: 108
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 953

```
Gln Ser Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Glu Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr His Cys Gln Val Trp Asp Ser Ser Ser Asp His
                85                  90                  95

Pro Gly Val Phe Gly Gly Gly Thr Lys Leu Thr Val
            100                 105
```

<210> SEQ ID NO 954
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 954

```
Tyr His Asp Pro Gln Ala Pro Leu Thr Leu Ser Leu Ser Pro Gly Glu
1               5                   10                  15

Arg Ala Thr Leu Ser Cys Arg Ala Ser Gln Ser Val Ser Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80
```

```
Glu Asp Cys Ala Val Tyr Tyr Cys Gln Gln Tyr Gly Ser Ser His Thr
                85                  90                  95

Phe Gly Gln Gly Thr Lys Leu Glu Ile Lys
            100                 105
```

<210> SEQ ID NO 955
<211> LENGTH: 105
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 955

```
His Asp Pro Gln Ala Pro Ala Thr Leu Ser Ala Ser Val Gly Asp Arg
1               5                   10                  15

Val Thr Ile Thr Cys Arg Ala Ser Gln Gly Ile Ser Ser Tyr Leu Ala
                20                  25                  30

Trp Tyr Gln Gln Lys Pro Gly Lys Ala Pro Asn Leu Leu Ile Tyr Ala
            35                  40                  45

Ala Ser Thr Leu Gln Ser Gly Val Pro Ser Arg Phe Ser Gly Ser Gly
        50                  55                  60

Ser Gly Thr Glu Phe Thr Leu Thr Ile Ser Ser Leu Gln Pro Glu Asp
65                  70                  75                  80

Phe Ala Thr Tyr Tyr Cys Gln Gln Leu Asn Ser Tyr Pro Leu Thr Phe
                85                  90                  95

Gly Gly Gly Thr Lys Val Glu Ile Lys
            100                 105
```

<210> SEQ ID NO 956
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 956

```
Met Thr Leu Ile Ile Pro Val Thr Leu Ser Leu Ser Pro Gly Glu Arg
1               5                   10                  15

Ala Thr Leu Ser Cys Arg Ala Ser Gln Ser Ile Arg Ser Asn Leu Ala
                20                  25                  30

Trp Tyr Gln Gln Lys Pro Gly Gln Ala Pro Arg Leu Leu Ile His Gly
            35                  40                  45

Ala Ser Thr Arg Thr Thr Gly Ile Pro Ala Arg Phe Ser Gly Ser Gly
        50                  55                  60

Ser Gly Thr Glu Phe Thr Leu Thr Ile Thr Ser Leu Gln Ser Glu Asp
65                  70                  75                  80

Phe Ala Val Tyr Tyr Cys Gln Gln Tyr Asn Asn Trp Pro Gln Ser Thr
                85                  90                  95

Phe Gly Gln Gly Thr Lys Val Glu Ile Arg
            100                 105
```

<210> SEQ ID NO 957
<211> LENGTH: 111
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 957

Gln Phe Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Thr Leu Thr Val Leu
            100                 105                 110

<210> SEQ ID NO 958
<211> LENGTH: 108
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 958

Gln Ser Val Leu Thr Gln Thr Pro Ser Val Ser Val Ala Pro Gly Gln
1               5                   10                  15

Thr Ala Ile Ile Thr Cys Gly Gly His Ser Ile Gly Asn Arg Ala Val
            20                  25                  30

His Trp Tyr Gln Gln Lys Pro Gly Gln Ala Pro Val Val Val Val Tyr
            35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Phe Cys Gln Val Trp Asp Ser Ser Phe Asp Arg
                85                  90                  95

Pro Asp Phe Gly Thr Gly Thr Lys Val Thr Val Leu
            100                 105

<210> SEQ ID NO 959
<211> LENGTH: 105
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 959

Leu Leu Ser Leu His Ile Pro Val Thr Leu Ser Ala Ser Val Gly Asp
1               5                   10                  15

Arg Val Thr Ile Thr Cys Gln Ala Ser Gln Asp Ile Thr Lys Tyr Leu
            20                  25                  30

Asn Trp Tyr Gln Gln Lys Pro Gly Lys Ala Pro Lys Leu Leu Ile Tyr
            35                  40                  45

Asp Val Ser Asn Leu Glu Thr Gly Val Pro Ser Arg Phe Ser Gly Ser
50                  55                  60

```
Gly Ser Gly Thr Asp Phe Thr Phe Thr Ile Ser Ser Leu Gln Pro Glu
 65                  70                  75                  80

Asp Thr Ala Thr Tyr Tyr Cys Gln Gln Tyr Ala Asn Val Phe Thr Phe
                 85                  90                  95

Gly Pro Gly Thr Lys Val Asp Ile Lys
            100                 105

<210> SEQ ID NO 960
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 960

Ser Ser His Ile Pro Val Thr Leu Ala Val Ser Leu Gly Glu Arg Ala
  1               5                  10                  15

Thr Ile Asn Cys Lys Ser Ser Gln Ser Val Leu Tyr Tyr Ser Asn Ser
                 20                  25                  30

Lys Asn Tyr Leu Thr Trp Tyr Gln Gln Lys Pro Gly Gln Pro Pro Lys
             35                  40                  45

Leu Leu Ile Tyr Trp Ala Ser Thr Arg Glu Ser Gly Val Pro Asp Arg
 50                  55                  60

Phe Ser Gly Ser Gly Ser Gly Thr Asp Phe Thr Leu Thr Ile Ser Ser
 65                  70                  75                  80

Leu Gln Ala Glu Asp Val Ala Val Tyr Tyr Cys Gln Gln Tyr Tyr Ser
                 85                  90                  95

Asn Pro Tyr Thr Phe Gly Gln Gly Thr Lys Val Glu Ile Lys
            100                 105                 110

<210> SEQ ID NO 961
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 961

Tyr Asp Pro Thr Ala Pro Ala Thr Leu Ser Leu Ser Pro Gly Glu Arg
  1               5                  10                  15

Ala Thr Leu Ser Cys Arg Ala Ser Gln Ser Val Arg Ser Ser Tyr Leu
                 20                  25                  30

Ala Trp Tyr Gln Gln Lys Pro Gly Gln Ala Pro Arg Leu Leu Ile Tyr
             35                  40                  45

Gly Ala Ser Ser Arg Ala Thr Gly Ile Pro Asp Arg Ile Ser Gly Ser
 50                  55                  60

Gly Ser Gly Thr Asp Phe Thr Leu Thr Ile Ser Arg Leu Glu Pro Glu
 65                  70                  75                  80

Asp Phe Val Val Tyr Tyr Cys Gln Gln Tyr Gly Ser Ser Pro Trp Thr
                 85                  90                  95

Phe Gly Gln Gly Thr Lys Val Glu Ile Lys
            100                 105

<210> SEQ ID NO 962
<211> LENGTH: 104
<212> TYPE: PRT
<213> ORGANISM: Artificial Sequence
<220> FEATURE:
```

<221> NAME/KEY: source
<223> OTHER INFORMATION: /note="VL V-J-Region sequence"

<400> SEQUENCE: 962

Leu Pro Gln Ala Pro Ala Thr Leu Ser Leu Ser Pro Gly Glu Arg Ala
1               5                   10                  15

Thr Leu Ser Cys Arg Ala Ser Gln Ser Val Ser Ser Tyr Leu Ala Trp
            20                  25                  30

Tyr Gln Gln Lys Pro Gly Gln Ala Pro Arg Leu Leu Ile Tyr Asp Ala
        35                  40                  45

Tyr Asn Arg Ala Thr Gly Ile Pro Ala Arg Phe Ser Gly Ser Gly Ser
    50                  55                  60

Gly Thr Asp Phe Thr Leu Thr Ile Ser Ser Leu Glu Pro Glu Asp Phe
65                  70                  75                  80

Ala Val Tyr Tyr Cys Gln Gln Arg Ser Asn Trp Pro Gly Thr Phe Gly
                85                  90                  95

Gln Gly Thr Lys Val Glu Ile Lys
            100

<210> SEQ ID NO 963
<211> LENGTH: 111
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 963

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asn Tyr
            20                  25                  30

Asn Leu Val Ser Trp Tyr Gln Gln His Pro Gly Lys Ala Pro Lys Leu
        35                  40                  45

Met Ile Tyr Glu Asp Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu Tyr Val Phe Gly Ala Gly Thr Lys Val Thr Val Leu
            100                 105                 110

<210> SEQ ID NO 964
<211> LENGTH: 105
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 964

Arg Ser Pro Lys Ala Pro Val Thr Leu Ser Leu Ser Pro Gly Glu Arg
1               5                   10                  15

Ala Thr Leu Ser Cys Arg Ala Ser Gln Ser Val Ser Ser Tyr Leu Ala
            20                  25                  30

Trp Tyr Gln Gln Lys Pro Gly Gln Ala Pro Arg Leu Leu Ile Tyr Asp
        35                  40                  45

Ala Ser Asn Arg Ala Thr Gly Ile Pro Ala Arg Phe Ser Gly Ser Gly

```
                    50                  55                  60
Ser Gly Thr Asp Phe Thr Leu Thr Ile Ser Ser Leu Glu Pro Glu Asp
 65                  70                  75                  80

Phe Ala Val Tyr Tyr Cys Gln Gln Arg Ser Asn Trp Pro Pro Thr Phe
                     85                  90                  95

Gly Gly Gly Thr Lys Val Glu Ile Lys
                100                 105

<210> SEQ ID NO 965
<211> LENGTH: 105
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 965

Met Thr Pro Thr Ala Pro Val Thr Leu Ser Ala Ser Val Gly Asp Arg
  1               5                  10                  15

Val Thr Ile Thr Cys Arg Ala Ser Gln Gly Ile Ser Ser Tyr Leu Ala
                 20                  25                  30

Trp Tyr Gln Gln Lys Pro Gly Lys Ala Pro Lys Leu Leu Ile Tyr Ala
             35                  40                  45

Ala Ser Thr Leu Gln Ser Gly Val Pro Ser Arg Phe Ser Gly Ser Gly
         50                  55                  60

Ser Gly Thr Asp Phe Thr Leu Thr Ile Ser Ser Leu Gln Pro Glu Asp
 65                  70                  75                  80

Phe Ala Thr Tyr Tyr Cys Gln Gln Leu Asn Ser Tyr Pro Leu Thr Phe
                     85                  90                  95

Gly Gly Gly Thr Lys Val Glu Ile Lys
                100                 105

<210> SEQ ID NO 966
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 966

Gln Ser Val Leu Thr Gln Pro Ala Ser Val Ser Gly Pro Pro Gly Gln
  1               5                  10                  15

Ser Ile Ala Ile Ser Cys Thr Gly Thr Asn Ser Asp Val Gly Ala Tyr
                 20                  25                  30

Asn Tyr Val Ser Trp Tyr Gln Gln His Pro Gly Lys Ala Pro Lys Leu
             35                  40                  45

Met Ile Tyr Glu Val Ser Asn Arg Pro Ser Gly Val Ser Asp Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asn Tyr Tyr Cys Ser Ser Tyr Thr Ser Ser
                     85                  90                  95

Ser Thr Trp Val Phe Gly Gly Gly Thr Lys Leu Thr Val Leu
                100                 105                 110

<210> SEQ ID NO 967
<211> LENGTH: 108
<212> TYPE: PRT
```

<213> ORGANISM: Artificial Sequence
<220> FEATURE:
<221> NAME/KEY: source
<223> OTHER INFORMATION: /note="VL V-J-Region sequence"

<400> SEQUENCE: 967

```
Gln Ser Val Leu Thr Gln Pro Pro Ser Val Ser Val Ala Pro Gly Lys
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Ile Tyr
        35                  40                  45
Tyr Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp His
                85                  90                  95
Tyr Val Phe Gly Thr Gly Thr Lys Val Thr Val Leu
            100                 105
```

<210> SEQ ID NO 968
<211> LENGTH: 105
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 968

```
Tyr Asp Pro Thr Ala Pro Val Thr Leu Ser Ala Ser Val Gly Asp Arg
1               5                   10                  15
Val Thr Ile Thr Cys Arg Ala Ser Gln Ser Ile Ser Ser Tyr Leu Asn
            20                  25                  30
Trp Tyr Gln Gln Lys Pro Gly Lys Ala Pro Lys Leu Leu Ile Tyr Ala
        35                  40                  45
Ala Ser Ser Leu Gln Ser Gly Val Pro Ser Arg Phe Ser Gly Ser Gly
    50                  55                  60
Ser Gly Thr Asp Phe Thr Leu Thr Ile Ser Ser Leu Gln Pro Glu Asp
65                  70                  75                  80
Phe Ala Thr Tyr Tyr Cys Gln Gln Ser Tyr Ser Thr Pro Tyr Thr Phe
                85                  90                  95
Gly Gln Gly Thr Lys Leu Glu Ile Lys
            100                 105
```

<210> SEQ ID NO 969
<211> LENGTH: 104
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 969

```
Pro Pro Ala Pro Leu Thr Leu Ser Val Ser Pro Gly Glu Arg Ala Thr
1               5                   10                  15
Leu Ser Cys Arg Ala Ser Gln Ser Val Ser Ser Asn Leu Ala Trp Tyr
            20                  25                  30
Gln Gln Lys Pro Gly Gln Ala Pro Arg Leu Leu Ile Tyr Gly Ala Ser
        35                  40                  45
```

Thr Arg Ala Thr Gly Ile Pro Ala Arg Phe Ser Gly Ser Gly Ser Gly
 50                  55                  60

Thr Glu Phe Thr Leu Thr Ile Ser Ser Leu Gln Ser Glu Asp Phe Ala
 65                  70                  75                  80

Val Tyr Tyr Cys Gln Gln Tyr Asn Asn Trp Pro Leu Trp Thr Phe Gly
             85                  90                  95

Gln Gly Thr Lys Leu Glu Ile Lys
            100

<210> SEQ ID NO 970
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 970

Lys Ile Val Met Ala Gln Ser Pro Ala Thr Leu Ser Leu Ser Pro Gly
 1               5                   10                  15

Glu Arg Thr Thr Leu Ser Gly Arg Ala Ser Gln Ser Val His Asn Ile
                 20                  25                  30

Tyr Leu Pro Trp Tyr Gln Gln Lys Pro Gly Gln Ala Ala Arg Leu Leu
             35                  40                  45

Ile Tyr Gly Thr Ser Ser Arg Ser Thr Gly Val Thr Asp Arg Phe Ser
 50                  55                  60

Gly Ser Gly Ser Gly Thr Asp Phe Thr Leu Thr Ile Ser Arg Leu Glu
 65                  70                  75                  80

Ser Glu Asp Phe Ala Val Tyr Phe Cys Gln His Tyr Glu Ser Ser Pro
             85                  90                  95

Pro Val Phe Thr Phe Gly Pro Gly Thr Lys Val Asp Ile Lys
            100                 105                 110

<210> SEQ ID NO 971
<211> LENGTH: 111
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 971

Gln Ser Val Leu Thr Gln Ser Pro Ser Ala Ser Ala Ser Leu Gly Ala
 1               5                   10                  15

Ser Val Lys Leu Thr Cys Thr Leu Thr Ser Gly His Ser Asn Tyr Ala
                 20                  25                  30

Ile Ala Trp His Gln Gln Gln Pro Glu Arg Gly Pro Arg Tyr Leu Met
             35                  40                  45

Lys Val Asn Ser Asp Gly Ser His Asn Lys Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Asp Asp Glu Ala Asp Tyr Tyr Cys Gln Thr Trp Asp
             85                  90                  95

Thr Gly Ile Gln Val Phe Gly Pro Gly Thr Lys Val Thr Val Leu
            100                 105                 110

<210> SEQ ID NO 972

-continued

```
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 972

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Tyr Val Phe Gly Thr Gly Thr Lys Val Thr Val Leu
            100                 105                 110

<210> SEQ ID NO 973
<211> LENGTH: 111
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 973

Gln Ser Val Leu Thr Gln Ser Pro Ser Ala Ser Ala Ser Leu Gly Ala
1               5                   10                  15

Ser Val Lys Leu Thr Cys Thr Leu Thr Ser Gly His Ser Asn Tyr Ala
            20                  25                  30

Ile Ala Trp His Gln Gln Gln Pro Glu Arg Gly Pro Arg Tyr Leu Met
        35                  40                  45

Lys Val Asn Ser Asp Gly Ser His Asn Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Asp Asp Glu Ala Asp Tyr Tyr Cys Gln Thr Trp Asp
                85                  90                  95

Thr Gly Ile Gln Val Phe Gly Pro Gly Thr Lys Val Thr Val Leu
            100                 105                 110

<210> SEQ ID NO 974
<211> LENGTH: 112
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 974

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30
```

```
Asn His Val Ser Trp Tyr Gln Gln His Pro Gly Lys Ala Pro Lys Leu
             35                  40                  45

Met Ile Tyr Asp Val Asn Asn Arg Pro Ser Gly Val Ser His Arg Phe
 50                      55                  60

Ser Gly Ser Lys Ser Gly Asn Arg Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Ser Leu Leu Tyr Val Phe Gly Ser Gly Thr Lys Val Thr Val Leu
                100                 105                 110
```

<210> SEQ ID NO 975
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 975

```
Gln Ser Val Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Asp Tyr
                 20                  25                  30

Lys Tyr Val Ser Trp Tyr Gln Gln Tyr Pro Gly Lys Ala Pro Arg Leu
             35                  40                  45

Met Ile Tyr Asp Val Ile Lys Arg Pro Ser Gly Val Pro Asp Arg Phe
 50                      55                  60

Ser Gly Ser Lys Ser Asp Asn Thr Ala Ser Leu Thr Ile Ser Gly Leu
 65                  70                  75                  80

Gln Ala Glu Asp Glu Ala Asp Tyr Tyr Cys Cys Ser Tyr Val Gly Ser
                 85                  90                  95

Tyr Thr Val Ala Phe Gly Gly Gly Thr Lys Leu Thr Val Leu
                100                 105                 110
```

<210> SEQ ID NO 976
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 976

```
Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                 20                  25                  30

Ser Leu Val Ser Trp Phe Gln Gln His Pro Gly Arg Ala Pro Lys Leu
             35                  40                  45

Ile Ile Tyr Glu Gly Ser Gln Arg Pro Ser Gly Val Ser Asn Arg Phe
 50                      55                  60

Ser Gly Ser Lys Ser Gly Asn Thr Ala Ser Leu Thr Ile Ser Gly Leu
 65                  70                  75                  80

Gln Thr Glu Asp Glu Ala His Tyr Tyr Cys Cys Ser Tyr Ala Ala Gly
                 85                  90                  95

Asn Thr Arg Val Phe Gly Gly Gly Thr Lys Leu Thr Val Leu
                100                 105                 110
```

```
<210> SEQ ID NO 977
<211> LENGTH: 104
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 977

Leu Met Thr Gln Ala Pro Val Thr Leu Ser Val Ser Pro Gly Glu Arg
1               5                   10                  15

Ala Thr Leu Ser Cys Arg Ala Ser Gln Ser Val Ser Ser Asn Leu Ala
            20                  25                  30

Trp Tyr Gln Gln Lys Pro Gly Gln Ala Pro Arg Leu Leu Ile Tyr Gly
        35                  40                  45

Ala Ser Thr Arg Ala Thr Gly Ile Pro Ala Arg Phe Ser Gly Ser Gly
    50                  55                  60

Ser Gly Thr Glu Phe Thr Leu Thr Ile Ser Ser Leu Gln Ser Glu Asp
65                  70                  75                  80

Phe Ala Val Tyr Tyr Cys Gln Gln Tyr Asn Asn Leu Tyr Thr Phe Gly
                85                  90                  95

Gln Gly Thr Lys Leu Glu Ile Lys
            100

<210> SEQ ID NO 978
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 978

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu
            100                 105                 110

<210> SEQ ID NO 979
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 979

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
```

```
                20                  25                  30

Tyr Val Ser Trp Tyr Gln Gln Leu Pro Gly Thr Ala Pro Lys Leu Leu
         35                  40                  45

Ile Tyr Asp Asn Asn Gln Arg Pro Ser Gly Ile Pro Asp Arg Phe Ser
         50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Val Val Phe Gly Gly Gly Thr Lys Leu Thr Val Leu
            100                 105                 110

<210> SEQ ID NO 980
<211> LENGTH: 104
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 980

Ser Pro Gln Ala Pro Val Thr Leu Ser Leu Ser Pro Gly Glu Arg Ala
 1               5                  10                  15

Thr Leu Ser Cys Arg Ala Ser Gln Ser Val Ser Ser Tyr Leu Ala Trp
             20                  25                  30

Tyr Gln Gln Lys Pro Gly Gln Ala Pro Arg Leu Leu Ile Tyr Asp Ala
         35                  40                  45

Ser Asn Arg Ala Thr Gly Ile Pro Ala Arg Phe Ser Gly Ser Gly Ser
     50                  55                  60

Gly Thr Asp Phe Thr Leu Thr Ile Thr Asn Leu Glu Pro Glu Asp Phe
 65                  70                  75                  80

Ala Val Tyr Tyr Cys Gln Gln Arg Ser Asn Trp Pro Pro Thr Phe Gly
                 85                  90                  95

Gln Gly Thr Lys Val Glu Ile Lys
            100

<210> SEQ ID NO 981
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 981

Gln Phe Val Leu Thr Gln Ser Leu Ser Val Ser Val Ala Leu Gly Gln
 1               5                  10                  15

Thr Ala Asn Ile Thr Cys Gly Gly His Asn Ile Val Ala Lys Thr Val
             20                  25                  30

His Trp Tyr Gln Gln Lys Ser Gly Gln Ala Pro Val Leu Val Ile Tyr
         35                  40                  45

Arg Asp Thr Asn Arg Pro Ser Arg Ile Pro Glu Arg Phe Ser Gly Ser
     50                  55                  60

Thr Ser Gly Asn Thr Ala Thr Leu Thr Ile Arg Thr Ala Gln Ala Gly
 65                  70                  75                  80

Asp Glu Ala Asp Tyr Tyr Cys Gln Val Trp Asp Ile Ser Ser Val Val
                 85                  90                  95

Phe Gly Gly Gly Thr Lys Leu Thr Val Leu
```

<210> SEQ ID NO 982
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 982

```
Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu
            100                 105                 110
```

<210> SEQ ID NO 983
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 983

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Ile Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110
```

<210> SEQ ID NO 984
<211> LENGTH: 103
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 984

```
Pro Gln Ala Pro Val Thr Leu Ser Ala Ser Val Gly Asp Arg Ile Thr
1               5                   10                  15
```

```
Ile Thr Cys Arg Ala Ser Gln Ser Ile Ser Arg Tyr Leu Asn Trp Tyr
            20                  25                  30

Gln Gln Lys Pro Gly Arg Ala Pro Asn Leu Leu Ile Tyr Ala Ala Ser
        35                  40                  45

Ala Leu Gln Ser Gly Val Pro Ser Arg Phe Ser Gly Ser Gly Ser Gly
    50                  55                  60

Thr Asp Phe Thr Leu Thr Ile Ser Ser Leu Gln Pro Glu Asp Phe Ala
65                  70                  75                  80

Thr Tyr Tyr Cys Gln Gln Ser Ser Thr Thr Pro Leu Thr Phe Gly Gly
                85                  90                  95

Gly Thr Lys Val Glu Ile Asn
            100

<210> SEQ ID NO 985
<211> LENGTH: 104
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 985

Asp Asp Pro Lys Ala Pro Ala Thr Leu Ser Leu Ser Pro Gly Asp Arg
1               5                   10                  15

Ala Thr Leu Ser Cys Arg Ala Ser Gln Ser Val Ser Ser Tyr Leu Ala
            20                  25                  30

Trp Tyr Gln Gln Lys Pro Gly Gln Pro Pro Arg Leu Leu Ile Phe Asp
        35                  40                  45

Ala Ser Thr Arg Ala Thr Gly Ile Pro Ala Arg Phe Ser Gly Ser Gly
    50                  55                  60

Ser Gly Thr Asp Phe Thr Leu Thr Ile Ser Ser Leu Glu Pro Glu Asp
65                  70                  75                  80

Phe Ala His Tyr Tyr Cys Gln Leu Arg Ser Asn Trp Arg Thr Phe Gly
                85                  90                  95

Gly Gly Thr Lys Val Glu Ile Lys
            100

<210> SEQ ID NO 986
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 986

Leu Asp Asp Pro Gln Asp Pro Val Ser Leu Ser Ala Ser Val Gly Asp
1               5                   10                  15

Lys Val Thr Ile Thr Cys Arg Ala Ser Gln Ser Ile Ser Ser His Leu
            20                  25                  30

Asn Trp Tyr Gln Gln Gln Pro Gly Lys Ala Pro Asn Leu Leu Ile Tyr
        35                  40                  45

Ala Ala Ser Thr Leu Gln Tyr Gly Val Pro Ser Arg Phe Ser Gly Ser
    50                  55                  60

Gly Ser Gly Thr Asp Phe Ile Leu Thr Ile Ser Asn Leu Gln Pro Glu
65                  70                  75                  80

Asp Phe Ala Thr Tyr Tyr Cys Gln Gln Ser Phe Ser Met Pro Phe Thr
                85                  90                  95
```

```
Phe Gly Pro Gly Thr Lys Val Asp Val Lys
            100                 105
```

<210> SEQ ID NO 987
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 987

```
Met Ile Gln Ser Pro Val Cys Leu Ala Val Ser Leu Gly Glu Arg Ala
1               5                   10                  15

Thr Ile Asn Cys Lys Ser Ser Gln Ser Val Tyr Ser Ser Asn Asn
            20                  25                  30

Lys Asp His Leu Ala Trp Tyr Leu Gln Arg Ser Gly Gln Pro Pro Gln
            35                  40                  45

Leu Leu Ile Tyr Trp Ala Ser Thr Arg Lys Ser Gly Val Pro Asp Arg
50                  55                  60

Phe Ser Gly Ser Gly Ser Gly Thr Asp Phe Thr Leu Thr Ile Ser Ser
65                  70                  75                  80

Leu Gln Ala Glu Asp Val Ala Val Tyr Tyr Cys Gln Gln Tyr Tyr Ile
                85                  90                  95

Thr Pro Pro Thr Phe Gly Gln Gly Thr Lys Val Glu Ile Lys
            100                 105                 110
```

<210> SEQ ID NO 988
<211> LENGTH: 105
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 988

```
Met Thr Pro Gln Ala Pro Val Thr Leu Ser Leu Ser Pro Gly Glu Arg
1               5                   10                  15

Ala Thr Leu Ser Cys Arg Ala Ser Gln Ser Val Asn Tyr Tyr Leu Ala
            20                  25                  30

Trp Tyr Gln Gln Lys Pro Gly Arg Ala Pro Arg Leu Leu Ile Tyr Asp
            35                  40                  45

Ala Ser Asn Arg Ala Thr Gly Val Pro Ala Arg Phe Ser Gly Arg Gly
        50                  55                  60

Ser Gly Thr Asp Phe Thr Leu Thr Ile Ser Ser Leu Glu Pro Glu Asp
65                  70                  75                  80

Phe Ala Val Tyr Tyr Cys Gln Leu Arg Ser Asn Trp Leu Leu Thr Phe
                85                  90                  95

Gly Gly Gly Thr Asn Val Glu Ile Lys
            100                 105
```

<210> SEQ ID NO 989
<211> LENGTH: 108
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 989

```
Gln Ser Val Leu Thr Gln Pro Ala Ser Val Ser Gly Ser Pro Gly Gln
1               5                   10                  15

Ser Ile Thr Ile Ser Cys Ala Gly Thr Ser Asp Leu Gly Thr Tyr
            20                  25                  30

His Leu Val Ser Trp Tyr Gln Gln His Pro Gly Lys Ala Pro Lys Leu
            35                  40                  45

Leu Ile Tyr Glu Gly Ser Arg Arg Pro Ser Gly Ile Ser Asp Arg Phe
        50                  55                  60

Ser Gly Ser Lys Ser Gly Asp Thr Ala Ala Leu Thr Ile Ser Gly Leu
65                  70                  75                  80

Gln Ala Glu Asp Glu Ala Asp Tyr Tyr Cys Cys Ser Tyr Ala Gly Thr
                85                  90                  95

Trp Val Phe Gly Gly Gly Thr Lys Val Thr Val Leu
            100                 105
```

<210> SEQ ID NO 990
<211> LENGTH: 120
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 990

```
Gln Ser Gln Leu Thr Gln Pro Glu Ser Ala Ser Gly Ser Arg Gly Gln
1               5                   10                  15

Trp Ile Thr Ile Ser Ile Thr Gly Thr Ser Asp Ser Gly Gly Tyr
            20                  25                  30

Ser Tyr Val Ser Gly Ser Gln Gln Gln Pro Gly Lys Ala Pro Lys Leu
            35                  40                  45

Ile Ile Phe Glu Val Asp Ile Arg Pro Ser Gly Ala Trp Asp Cys Phe
        50                  55                  60

Cys Gly Ser Lys Ser Asp Tyr Thr Ala Ser Ala Thr Met Ser Arg Phe
65                  70                  75                  80

Gln Ala Gln Asp Glu Ala Glu Tyr Asp Cys Asn Ser Ile Ser Ser Thr
                85                  90                  95

Ser Thr Asn Asn Val Phe Gly Arg Arg Thr Thr Gly Arg Pro Ser Ile
            100                 105                 110

Arg Gln Leu Arg Arg Leu Gly Asp
        115                 120
```

<210> SEQ ID NO 991
<211> LENGTH: 103
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 991

```
Pro Gln Ala Pro Ala Thr Leu Ser Ala Ser Val Gly Asp Arg Val Thr
1               5                   10                  15

Ile Thr Cys Arg Ala Ser Gln Val Ile Arg Asn Asp Leu Gly Trp Tyr
            20                  25                  30

Gln Gln Lys Pro Gly Asn Ala Pro Lys Arg Leu Ile Tyr Ala Ala Ser
            35                  40                  45

Ile Leu Gln Ser Gly Val Pro Ser Arg Phe Ser Gly Ser Gly Phe Gly
        50                  55                  60
```

```
Thr Glu Phe Thr Leu Thr Ile Ser Ser Leu Gln Pro Glu Asp Phe Ala
 65                  70                  75                  80

Thr Tyr Tyr Cys Leu Gln His Asn Ser Phe Pro Trp Thr Phe Gly Gln
                 85                  90                  95

Gly Thr Lys Val Glu Ile Lys
            100

<210> SEQ ID NO 992
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 992

Tyr Asp Pro Lys Ala Pro Leu Thr Leu Ser Leu Ser Pro Gly Glu Arg
  1               5                  10                  15

Ala Thr Leu Ser Cys Arg Ala Ser Gln Thr Val Ser Ser Ser Ser Leu
             20                  25                  30

Ala Trp Tyr Gln Gln Lys Pro Gly Gln Ala Pro Arg Leu Leu Ile Tyr
         35                  40                  45

Ser Ala Ser Ser Arg Ala Thr Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Ser Ala Val Tyr His Cys Gln Gln Tyr Gly Ser Ser Pro Gly Thr
                 85                  90                  95

Phe Gly Gln Gly Thr Lys Leu Glu Ile Lys
            100                 105

<210> SEQ ID NO 993
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 993

His Asp Pro Gln Ala Pro Val Thr Leu Ser Val Ser Pro Gly Glu Arg
  1               5                  10                  15

Val Thr Leu Ser Cys Arg Ala Ser Gln Ser Val Tyr Ser Asn Leu Ala
             20                  25                  30

Trp Tyr Gln Leu Lys Pro Gly Gln Gly Pro Arg Leu Leu Ile Tyr Ser
         35                  40                  45

Ala Ser Thr Arg Ala Thr Gly Ile Pro Val Arg Phe Ser Gly Ser Gly
 50                  55                  60

Ser Gly Thr Glu Phe Thr Leu Ser Ile Ser Ser Leu Gln Ser Glu Asp
 65                  70                  75                  80

Phe Ala Val Tyr Leu Cys Gln Gln Tyr Tyr Asn Trp Pro Pro Ile Thr
                 85                  90                  95

Phe Gly Gln Gly Thr Arg Leu Glu Ser Lys
            100                 105

<210> SEQ ID NO 994
<211> LENGTH: 105
<212> TYPE: PRT
<213> ORGANISM: Artificial Sequence
<220> FEATURE:
```

<221> NAME/KEY: source
<223> OTHER INFORMATION: /note="VL V-J-Region sequence"

<400> SEQUENCE: 994

```
Leu Thr Pro Gln Asp Pro Val Thr Leu Ser Ala Ser Val Gly Asp Arg
1               5                   10                  15

Val Thr Ile Thr Cys Gln Ala Ser Gln Asp Ile Ser Asn Tyr Leu Asn
            20                  25                  30

Trp Tyr Gln Gln Lys Pro Gly Lys Ala Pro Lys Leu Leu Ile Tyr Asp
        35                  40                  45

Ala Ser Asn Leu Glu Thr Gly Val Pro Ser Arg Phe Ser Gly Ser Gly
    50                  55                  60

Ser Gly Thr Asp Phe Thr Phe Thr Ile Ser Ser Leu Gln Pro Glu Asp
65                  70                  75                  80

Ile Ala Thr Tyr Tyr Cys Gln Gln Tyr Asp Asn Leu Pro Tyr Thr Phe
                85                  90                  95

Gly Gln Gly Thr Lys Leu Glu Ile Lys
            100                 105
```

<210> SEQ ID NO 995
<211> LENGTH: 107
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 995

```
Tyr Asp Pro Thr Ala Pro Val Thr Leu Ser Ala Ser Val Gly Asp Arg
1               5                   10                  15

Val Thr Ile Thr Cys Arg Ala Ser Gln Ser Ile Ser Ser Tyr Leu Asn
            20                  25                  30

Trp Tyr Gln Gln Lys Pro Gly Lys Ala Pro Lys Leu Leu Ile Tyr Ala
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Ser Thr Pro Pro Leu Ser
                85                  90                  95

Thr Phe Gly Pro Gly Thr Lys Val Asp Ile Lys
            100                 105
```

<210> SEQ ID NO 996
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 996

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
```

-continued

```
                    50                  55                  60
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                     85                  90                  95

Asn Gly Val Val Phe Gly Gly Gly Thr Lys Leu Thr Val Leu
                100                 105                 110
```

<210> SEQ ID NO 997
<211> LENGTH: 107
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 997

```
Pro Ala Leu Phe Phe Ser Pro Ala Thr Leu Ser Leu Ser Ser Gly Glu
 1               5                  10                  15

Arg Ala Thr Leu Ser Cys Arg Ala Ser Gln Ser Val Ile Ser Ser Tyr
                20                  25                  30

Leu Ala Trp Tyr Gln Gln Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln His Gly Ser Ser Pro Tyr
                 85                  90                  95

Thr Phe Gly Gln Gly Thr Lys Leu Glu Ile Lys
                100                 105
```

<210> SEQ ID NO 998
<211> LENGTH: 101
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 998

```
Pro Gln Ala Pro Ala Thr Leu Ser Ala Ser Val Gly Asp Arg Val Thr
 1               5                  10                  15

Ile Thr Cys Arg Ala Ser Gln Ser Ile Ser Ser Trp Leu Ala Trp Tyr
                20                  25                  30

Gln Gln Lys Pro Gly Lys Ala Pro Lys Leu Leu Ile Tyr Lys Ala Ser
             35                  40                  45

Ser Leu Glu Ser Gly Val Pro Ser Arg Phe Ser Gly Ser Gly Ser Gly
 50                  55                  60

Thr Glu Phe Thr Leu Thr Ile Ser Ser Leu Gln Pro Asp Asp Phe Ala
 65                  70                  75                  80

Thr Tyr Tyr Cys Gln Gln Tyr Asn Ser Tyr Pro Trp Thr Phe Gly Arg
                 85                  90                  95

Arg Asp Gln Arg Trp
                100
```

<210> SEQ ID NO 999
<211> LENGTH: 104
<212> TYPE: PRT

```
<213> ORGANISM: Artificial Sequence
<220> FEATURE:
<221> NAME/KEY: source
<223> OTHER INFORMATION: /note="VL V-J-Region sequence"

<400> SEQUENCE: 999
```

Cys Ser Met Thr Ser Asp Ser Ser His Pro Ala Ser Thr Gly Asp Arg
1               5                   10                  15

Val Thr Ile Thr Cys Arg Ala Ser Gln Gly Ile Ser Ser Tyr Leu Ala
            20                  25                  30

Trp Tyr Gln Gln Lys Pro Gly Lys Ala Pro Lys Leu Leu Ile Tyr Ala
        35                  40                  45

Ala Ser Thr Leu Gln Ser Gly Val Pro Ser Arg Phe Ser Gly Ser Gly
    50                  55                  60

Ser Gly Thr Asp Phe Thr Leu Thr Ile Ser Cys Leu Gln Ser Glu Asp
65                  70                  75                  80

Phe Ala Thr Tyr Tyr Cys Gln Gln Tyr Tyr Ser Tyr Pro Thr Phe Gly
                85                  90                  95

Pro Gly Thr Lys Val Asp Ile Lys
            100

```
<210> SEQ ID NO 1000
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1000
```

Gln Ser Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Leu Val
                85                  90                  95

Phe Gly Gly Gly Thr Lys Leu Thr Val Leu
            100                 105

```
<210> SEQ ID NO 1001
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1001
```

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

```
Ile Tyr Ser Asn Asn Gln Arg Pro Ser Gly Val Pro Asp Arg Phe Ser
         50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Arg Thr Lys Leu Thr Val Leu
            100                 105                 110

<210> SEQ ID NO 1002
<211> LENGTH: 104
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1002

Thr Pro Gln Tyr Pro Leu Thr Leu Ser Ala Ser Val Gly Asp Arg Val
  1               5                  10                  15

Thr Ile Thr Cys Gln Ala Ser Gln Asp Ile Ser Asn Tyr Leu Asn Trp
             20                  25                  30

Tyr Gln Gln Lys Pro Gly Lys Ala Pro Lys Leu Leu Ile Tyr Asp Ala
         35                  40                  45

Ser Asn Leu Glu Thr Gly Val Pro Ser Arg Phe Ser Gly Ser Gly Ser
 50                  55                  60

Gly Thr Asp Phe Thr Phe Thr Ile Ser Ser Leu Gln Pro Glu Asp Ile
 65                  70                  75                  80

Ala Thr Tyr Tyr Cys Gln Gln Tyr Asp Asn Leu Pro Leu Thr Phe Gly
                 85                  90                  95

Gln Gly Thr Lys Leu Glu Ile Lys
            100

<210> SEQ ID NO 1003
<211> LENGTH: 109
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1003

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Ser
            100                 105

<210> SEQ ID NO 1004
```

```
<211> LENGTH: 109
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1004

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu Phe Gly Gly Gly Thr Lys Leu Thr Val Leu
            100                 105

<210> SEQ ID NO 1005
<211> LENGTH: 111
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1005

Tyr Glu Pro Pro Ile Pro Val Thr Leu Ala Val Ser Leu Gly Glu Arg
1               5                   10                  15

Ala Thr Ile Asn Cys Lys Ser Ser Gln Ser Val Leu Tyr Ser Ser Asn
            20                  25                  30

Asn Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Ser Thr Pro Leu Thr Phe Gly Gly Gly Thr Lys Val Glu Ile Lys
            100                 105                 110

<210> SEQ ID NO 1006
<211> LENGTH: 107
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1006

Tyr Asp Pro Pro Ala Pro Val Thr Leu Ser Leu Ser Pro Gly Glu Arg
1               5                   10                  15

Ala Thr Leu Ser Cys Arg Ala Ser Gln Ser Val Ser Ser Ser Tyr Leu
            20                  25                  30
```

```
Ala Trp Tyr Gln Gln Lys Pro Gly Gln Ala Pro Arg Leu Leu Ile Tyr
            35                  40                  45

Gly Ala Ser Ser Arg Ala Thr Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Tyr Gly Ser Ser Pro Pro Tyr
                 85                  90                  95

Thr Phe Gly Gln Gly Thr Lys Leu Glu Ile Lys
            100                 105

<210> SEQ ID NO 1007
<211> LENGTH: 108
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1007

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Pro Val Phe Gly Gly Gly Thr Lys Leu Thr Val Leu
            100                 105

<210> SEQ ID NO 1008
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1008

Ile Glu Pro Thr Ala Pro Val Thr Leu Ser Leu Ser Pro Gly Glu Arg
1               5                   10                  15

Ala Thr Leu Ser Cys Arg Ala Ser Gln Ser Val Ser Ser Ser Tyr Leu
            20                  25                  30

Ala Trp Tyr Gln Gln Lys Pro Gly Gln Ala Pro Arg Leu Leu Ile Tyr
        35                  40                  45

Gly Ala Ser Ser Arg Ala Thr Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Tyr Gly Ser Ser Pro Leu Thr
                 85                  90                  95

Phe Gly Gly Gly Thr Lys Val Glu Ile Lys
            100                 105
```

<210> SEQ ID NO 1009
<211> LENGTH: 107
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1009

His Asp Pro Gln Ala Pro Phe Thr Leu Ser Leu Ser Pro Gly Glu Arg
1               5                   10                  15

Ala Thr Met Ser Cys Arg Ala Ser Leu Ser Val Ser Ser Asn Tyr Leu
            20                  25                  30

Ala Trp Tyr Gln Gln Lys Pro Gly Gln Ala Pro Arg Leu Leu Ile Tyr
        35                  40                  45

Gly Ala Ser Ser Arg Ala Thr Gly Ile Pro Asp Arg Phe Ser Gly Gly
    50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Tyr Gly Ser Ser Pro Val Tyr
                85                  90                  95

Ser Phe Gly Gln Gly Thr Lys Leu Glu Ile Lys
            100                 105

<210> SEQ ID NO 1010
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1010

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Thr Val Asn Trp Tyr Arg Gln Leu Pro Gly Thr Ala Pro Lys Leu Leu
        35                  40                  45

Ile Tyr Ser Asn Asp Gln Arg Pro Ser Gly Val Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Asn Ser Leu
                85                  90                  95

Asn Gly Tyr Phe Phe Gly Pro Gly Thr Lys Val Thr Val Leu
            100                 105                 110

<210> SEQ ID NO 1011
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1011

Gln Ser Val Leu Thr Gln Pro His Ser Val Ser Gly Ser Pro Gly Lys
1               5                   10                  15

Thr Val Thr Ile Ser Cys Thr Arg Ser Ser Gly Ser Ile Ala Ser Ser

```
                  20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
    50                  55                  60

Gly Ser Ile Asp Ser Ser Asn Ser Ala Ser Leu Thr Ile Thr Gly
65                  70                  75                  80

Leu Lys Thr Glu Asp Glu Ala Asp Tyr Tyr Cys Trp Ser Tyr Asp Asn
                85                  90                  95

Tyr Gln Glu Ile Phe Gly Ser Gly Thr Thr Val Thr Val Leu
                100                 105                 110
```

<210> SEQ ID NO 1012
<211> LENGTH: 108
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1012

```
Ser Cys Ser Ile Phe Gln Thr Pro Ala Thr Leu Ser Leu Ser Pro Gly
1               5                   10                  15

Glu Arg Asp Thr Leu Ser Cys Arg Ala Ser Gln Ser Val Ser Ser Asn
                20                  25                  30

Tyr Leu Ser Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Trp Thr Phe Gly Gln Gly Thr Lys Val Glu Ile Lys
                100                 105
```

<210> SEQ ID NO 1013
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1013

```
Gln Ser Val Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
                20                  25                  30

Asp Tyr Val Ser Trp Tyr Gln Gln His Pro Gly Lys Ala Pro Lys Leu
            35                  40                  45

Met Ile Phe Glu Val Ser Asn Arg Pro Ser Gly Val Ser Asn Arg Phe
    50                  55                  60

Ile Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Ser Asp Leu Val Phe Gly Gly Gly Thr Lys Leu Thr Val Leu
```

100                 105                 110

<210> SEQ ID NO 1014
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1014

Gln Ser Val Leu Thr Gln Pro Pro Ser Lys Ser Gly Thr Pro Gly Gln
1               5                   10                  15

Arg Val Thr Ile Ser Cys Tyr Gly Ser Arg Ser Asn Ile Gly Ser Thr
            20                  25                  30

Thr Val Asn Trp Phe Gln Gln Leu Pro Glu Ser Ala Pro Lys Leu Leu
        35                  40                  45

Ile His Ser Asn Asp Gln Arg Pro Ser Gly Val Pro Asp Arg Phe Ser
    50                  55                  60

Gly Ser Lys Ser Asp Thr Ser Ala Ser Leu Ala Ile Ser Gly Leu Gln
65                  70                  75                  80

Ser Glu Asp Glu Ala Asp Tyr Tyr Cys Ala Ala Trp Asp Ala Ser Leu
                85                  90                  95

Lys Val Phe Leu Leu Gly Thr Gly Thr Lys Val Thr Val Leu
            100                 105                 110

<210> SEQ ID NO 1015
<211> LENGTH: 107
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1015

Pro Ala Ser Pro Lys Ser Pro Val Thr Leu Ser Leu Ser Pro Gly Glu
1               5                   10                  15

Arg Ala Thr Leu Ser Cys Arg Ala Ser Gln Ser Val Gly Asn Ser Phe
            20                  25                  30

Leu Ala Trp Tyr Gln Gln Lys Pro Gly Gln Thr Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Arg
65                  70                  75                  80

Glu Asp Phe Ala Val Tyr Tyr Cys Gln Gln Tyr Gly Ser Ser Pro Gly
                85                  90                  95

Thr Phe Gly Gln Gly Thr Lys Val Glu Val Lys
            100                 105

<210> SEQ ID NO 1016
<211> LENGTH: 111
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1016

Gln Ser Val Leu Thr Gln Pro Ala Ser Val Ser Gly Ser Pro Gly Gln
1               5                   10                  15

```
Ser Ile Thr Ile Ser Cys Thr Gly Thr Ser Gly Asp Val Glu Asn Tyr
            20                  25                  30

Asn Val Val Ser Trp Tyr Gln Gln His Pro Gly Lys Ala Pro Lys Leu
        35                  40                  45

Ile Ile Tyr Glu Val Thr Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Ser Ala Ser Phe
                85                  90                  95

Thr Ile Ser Trp Val Phe Gly Gly Gly Thr Lys Leu Thr Val Leu
            100                 105                 110
```

<210> SEQ ID NO 1017
<211> LENGTH: 107
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1017

```
Cys Cys Ser Met Thr Gln Ser Pro Ala Thr Leu Ser Ala Ser Val Gly
 1               5                  10                  15

Asp Arg Val Thr Ile Ser Cys Gln Ala Asn Gln Asp Ile Lys Lys Ser
            20                  25                  30

Phe Asn Trp Tyr His Gln Lys Pro Gly Arg Ala Pro Lys Val Leu Ile
        35                  40                  45

Tyr Asp Ser Val Ile Leu Glu Thr Gly Val Pro Ser Arg Phe Ser Gly
 50                  55                  60

Ser Gly Ser Gly Thr His Phe Thr Leu Thr Ile Ser Ser Leu Gln Pro
 65                  70                  75                  80

Glu Asp Ile Gly Thr Tyr Tyr Cys Gln Gln Tyr Glu His Leu Pro Leu
                85                  90                  95

Thr Phe Gly Gly Gly Thr Lys Val Glu Leu Lys
            100                 105
```

<210> SEQ ID NO 1018
<211> LENGTH: 108
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1018

```
Ser Cys Ser Met Thr Gln Ser Pro Val Thr Leu Ser Ala Ser Val Gly
 1               5                  10                  15

Asp Arg Val Thr Ile Thr Cys Arg Ala Ser Gln Thr Ile Tyr Ser Trp
            20                  25                  30

Leu Ala Trp Tyr Gln Gln Lys Pro Gly Lys Ala Pro Lys Leu Leu Ile
        35                  40                  45

Tyr Gln Ala Ser Asn Leu Glu Ile Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Ser Thr Asp Ser Leu
                85                  90                  95
```

Tyr Thr Phe Gly Gln Gly Thr Lys Leu Glu Ile Lys
            100                 105

<210> SEQ ID NO 1019
<211> LENGTH: 106
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1019

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Val Val
                85                  90                  95

Phe Gly Gly Gly Thr Lys Leu Thr Val Leu
            100                 105

<210> SEQ ID NO 1020
<211> LENGTH: 108
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1020

Cys Arg Ala Met Thr Gln Ser Pro Val Thr Leu Ser Val Ser Pro Gly
1               5                   10                  15

Glu Arg Ala Thr Leu Ser Cys Arg Ala Ser Gln Arg Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Asp Ile Gln Ser
65                  70                  75                  80

Glu Asp Phe Ala Tyr Tyr Cys Gln His Tyr Asn Asn Trp Pro Pro
                85                  90                  95

Trp Thr Phe Gly Gln Gly Thr Lys Val Glu Ile Lys
            100                 105

<210> SEQ ID NO 1021
<211> LENGTH: 107
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1021

```
Cys Cys Ser Met Thr Gln Thr Pro Ala Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Leu
                85                  90                  95

Ala Phe Gly Gln Gly Thr Lys Val Glu Ile Lys
            100                 105
```

<210> SEQ ID NO 1022
<211> LENGTH: 107
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1022

```
Val Trp Ser Met Thr Gln Thr Pro Gly Thr Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Ala Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 1023
<211> LENGTH: 105
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1023

```
Ala Met Thr Gln Ser Pro Val Thr Leu Ser Ala Ser Val Gly Asp Arg
1               5                   10                  15

Val Thr Ile Thr Cys Arg Ala Ser Gln Phe Ile Ser Ser Ala Leu Ala
            20                  25                  30

Trp Tyr Gln Gln Lys Pro Gly Lys Ala Pro Lys Leu Leu Ile Tyr Asp
        35                  40                  45

Ala Ser Ser Leu Glu Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80
```

```
Phe Ala Thr Tyr Tyr Cys Gln Gln Phe Asn Ser Tyr Pro Ser Thr Phe
                85                  90                  95

Gly Pro Gly Thr Lys Val Asp Ile Lys
            100                 105
```

<210> SEQ ID NO 1024
<211> LENGTH: 108
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1024

```
Val Cys Ser Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
                20                  25                  30

Tyr Leu Ala Trp Tyr Gln Gln Lys Pro Gly Gln Ala Pro Arg Leu Leu
            35                  40                  45

Met Tyr Gly Ala Ser Arg Arg Ala Ala Gly Ile Ser Asp Arg Phe Ser
        50                  55                  60

Gly Ser Gly Ser Gly Thr Asp Phe Ala Leu Thr Ile Ser Arg Leu Glu
65                  70                  75                  80

Pro Glu Asp Phe Ala Val Tyr Tyr Cys Gln Glu Tyr Gly Ser Ser Pro
                85                  90                  95

Gly Thr Phe Gly Gln Gly Thr Lys Leu Glu Ile Lys
            100                 105
```

<210> SEQ ID NO 1025
<211> LENGTH: 107
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1025

```
Ser Trp Ser Met Thr Gln Ser Pro Ala Thr Leu Ser Leu Ser Ala Gly
1               5                   10                  15

Glu Arg Ala Thr Leu Ser Cys Arg Ala Ser Gln Ser Val Thr Thr Phe
                20                  25                  30

Leu Ala Trp Tyr Gln Gln Lys Pro Gly Gln Ala Pro Arg Leu Leu Ile
            35                  40                  45

Tyr Asp Ala Thr Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Tyr Gly Trp Pro Pro
                85                  90                  95

Gly Phe Gly Gly Gly Thr Lys Val Glu Ile Lys
            100                 105
```

<210> SEQ ID NO 1026
<211> LENGTH: 108
<212> TYPE: PRT
<213> ORGANISM: Artificial Sequence
<220> FEATURE:
<221> NAME/KEY: source
<223> OTHER INFORMATION: /note="VL V-J-Region sequence"

-continued

<400> SEQUENCE: 1026

Val Cys Ser Met Thr Gln Thr Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Asn Thr Phe Gly Gly Gly Thr Lys Val Glu Ile Lys
            100                 105

<210> SEQ ID NO 1027
<211> LENGTH: 109
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1027

Val Trp Phe Met Asp Gln Ser Pro Gly Ala Leu Cys Leu Ser Ala Gly
1               5                   10                  15

Glu Arg Ala Thr Leu Ser Cys Arg Ala Ser Gln Ser Val Ser Ser Ser
            20                  25                  30

Tyr Leu Ala Trp Cys Gln Gln Lys Pro Phe Gln Ala Pro Arg Leu Leu
        35                  40                  45

Met Glu Trp Cys Ile Gln Gln Gly His Trp His Pro Arg Gln Val Gln
    50                  55                  60

Trp Gln Trp Val Trp Asp Lys Thr Ser Leu Ser Pro Ser Ala Asp Trp
65                  70                  75                  80

Ser Leu Lys Ile Leu His Cys Ile Thr Val Ser Ser Met Val Ala His
                85                  90                  95

Leu Ser Leu Ser Ala Glu Gly Pro Arg Trp Arg Ser Asn
            100                 105

<210> SEQ ID NO 1028
<211> LENGTH: 113
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1028

Cys Cys Ser Met Thr Gln Ser Pro Val Thr Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Tyr Cys Met Gln Gly
                    85                  90                  95

Thr His Trp Pro Pro Trp Thr Phe Gly Gln Gly Thr Lys Val Glu Ile
                    100                 105                 110

Lys

<210> SEQ ID NO 1029
<211> LENGTH: 111
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1029

Cys Trp Ser Met Thr Gln Thr Pro Val Thr Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Trp Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                    85                  90                  95

Thr Leu His Arg Phe Phe Gly Gly Gly Thr Lys Val Glu Ile Lys
                    100                 105                 110

<210> SEQ ID NO 1030
<211> LENGTH: 110
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1030

Gln Ser Val Leu Thr Gln Pro Pro Ser Val Ser Gly Ser Pro Gly Gln
1               5                   10                  15

Ser Val Thr Ile Ser Cys Thr Gly Thr Asn Ser Asp Val Gly Thr Tyr
                20                  25                  30

Asp Arg Val Ser Trp Tyr Gln Gln Pro Pro Gly Thr Ala Pro Lys Leu
            35                  40                  45

Ile Ile Tyr Glu Val Asn Asn Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Arg Ser Gly
                    85                  90                  95

Arg Thr Phe Val Phe Gly Thr Gly Thr Lys Val Thr Val Leu
                    100                 105                 110

<210> SEQ ID NO 1031
<211> LENGTH: 108
<212> TYPE: PRT
<213> ORGANISM: Artificial Sequence
```

<220> FEATURE:
<221> NAME/KEY: source
<223> OTHER INFORMATION: /note="VL V-J-Region sequence"

<400> SEQUENCE: 1031

```
Cys Cys Ser Met Thr Gln Thr Pro Gly Val Leu Gly Leu Ser Pro Gly
1               5                   10                  15

Glu Arg Ala Thr Leu Ser Cys Arg Val Ser Gln Arg Lys Thr Ser Thr
            20                  25                  30

Ser Leu Val Arg Tyr Gln Gln Arg Pro Gly Gln Ala Pro Thr Leu Leu
        35                  40                  45

Met Tyr Gly Thr Ser Asn Arg Ala Thr Gly Ile Pro Asp Arg Phe Ser
50                  55                  60

Gly Ser Gly Ser Gly Thr Asp Phe Thr Val Thr Ile Ser Arg Leu Glu
65                  70                  75                  80

Pro Glu Asp Phe Ala Met Tyr Tyr Cys Gln Gln Phe Asp Ser Ser Pro
                85                  90                  95

Trp Thr Phe Gly Gln Gly Thr Lys Val Glu Phe Thr
            100                 105
```

<210> SEQ ID NO 1032
<211> LENGTH: 112
<212> TYPE: PRT
<213> ORGANISM: Artificial Sequence
<220> FEATURE:
<221> NAME/KEY: source
<223> OTHER INFORMATION: /note="VL V-J-Region sequence"

<400> SEQUENCE: 1032

```
Cys Cys Ala Leu Thr Gln Ser Pro Ala Thr Leu Pro Val Thr Pro Gly
1               5                   10                  15

Glu Pro Ala Ser Ile Ser Cys Lys Ser Ser Gln Ser Leu Leu His Ser
            20                  25                  30

Asn Gly Tyr Asn Tyr Leu Ala Trp Tyr Leu Gln Lys Pro Gly Gln Ser
        35                  40                  45

Pro Gln Leu Leu Phe Tyr Leu Gly Ser Asp Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Pro Glu Asp Val Gly Val Tyr Tyr Cys Met Gln Gly
                85                  90                  95

Leu His Thr Pro Leu Thr Phe Gly Gly Gly Thr Lys Val Glu Ile Lys
            100                 105                 110
```

<210> SEQ ID NO 1033
<211> LENGTH: 16
<212> TYPE: PRT
<213> ORGANISM: Artificial Sequence
<220> FEATURE:
<221> NAME/KEY: source
<223> OTHER INFORMATION: /note="CDR3 sequence"

<400> SEQUENCE: 1033

```
Val Thr Glu Ile Val Gly Ala Asn Arg Trp Val Pro Val Gly Pro Trp
1               5                   10                  15
```

<210> SEQ ID NO 1034
<211> LENGTH: 11
<212> TYPE: PRT
<213> ORGANISM: Artificial Sequence
<220> FEATURE:

```
<221> NAME/KEY: source
<223> OTHER INFORMATION: /note="CDR3 sequence"

<400> SEQUENCE: 1034

Gln Gln Tyr Asn Asn Trp Pro Gln Ser Thr Phe
1               5                   10

<210> SEQ ID NO 1035
<211> LENGTH: 14
<212> TYPE: PRT
<213> ORGANISM: Artificial Sequence
<220> FEATURE:
<221> NAME/KEY: source
<223> OTHER INFORMATION: /note="CDR3 sequence"

<400> SEQUENCE: 1035

Ala Arg Trp Arg Ala Gly Val Pro Ser Tyr Phe Asp Tyr Trp
1               5                   10

<210> SEQ ID NO 1036
<211> LENGTH: 9
<212> TYPE: PRT
<213> ORGANISM: Artificial Sequence
<220> FEATURE:
<221> NAME/KEY: source
<223> OTHER INFORMATION: /note="CDR3 sequence"

<400> SEQUENCE: 1036

Gln Gln Tyr Ala Asn Val Phe Thr Phe
1               5

<210> SEQ ID NO 1037
<211> LENGTH: 13
<212> TYPE: PRT
<213> ORGANISM: Artificial Sequence
<220> FEATURE:
<221> NAME/KEY: source
<223> OTHER INFORMATION: /note="CDR3 sequence"

<400> SEQUENCE: 1037

Ala Arg Ala Ala Gly Val Gly Val Ala Leu Asp Tyr Trp
1               5                   10

<210> SEQ ID NO 1038
<211> LENGTH: 12
<212> TYPE: PRT
<213> ORGANISM: Artificial Sequence
<220> FEATURE:
<221> NAME/KEY: source
<223> OTHER INFORMATION: /note="CDR3 sequence"

<400> SEQUENCE: 1038

Gln His Tyr Glu Ser Ser Pro Pro Val Phe Thr Phe
1               5                   10

<210> SEQ ID NO 1039
<211> LENGTH: 11
<212> TYPE: PRT
<213> ORGANISM: Artificial Sequence
<220> FEATURE:
<221> NAME/KEY: source
<223> OTHER INFORMATION: /note="CDR3 sequence"

<400> SEQUENCE: 1039

Arg His Ile Gly Arg His Tyr Tyr Phe Asp Tyr
1               5                   10
```